US012449730B2

(12) United States Patent
Hatakeyama

(10) Patent No.: US 12,449,730 B2
(45) Date of Patent: Oct. 21, 2025

(54) RESIST COMPOSITION AND PATTERNING PROCESS

(71) Applicant: Shin-Etsu Chemical Co., Ltd., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 581 days.

(21) Appl. No.: 17/965,175

(22) Filed: Oct. 13, 2022

(65) Prior Publication Data

US 2023/0129578 A1 Apr. 27, 2023

(30) Foreign Application Priority Data

Oct. 20, 2021 (JP) ................................ 2021-171611

(51) Int. Cl.

| | |
|---|---|
| ***G03F 7/004*** | (2006.01) |
| ***C07C 211/62*** | (2006.01) |
| ***C07C 211/63*** | (2006.01) |
| ***C07C 211/64*** | (2006.01) |
| ***C08F 212/14*** | (2006.01) |
| ***C08F 220/18*** | (2006.01) |
| ***C08F 220/22*** | (2006.01) |
| ***C08F 220/28*** | (2006.01) |
| ***C08F 220/38*** | (2006.01) |
| ***G03F 7/038*** | (2006.01) |
| ***G03F 7/039*** | (2006.01) |

(52) U.S. Cl.

CPC .......... *G03F 7/0045* (2013.01); *C07C 211/62* (2013.01); *C07C 211/63* (2013.01); *C07C 211/64* (2013.01); *C08F 212/24* (2020.02); *C08F 220/1806* (2020.02); *C08F 220/1811* (2020.02); *C08F 220/22* (2013.01); *C08F 220/281* (2020.02); *C08F 220/382* (2020.02); *G03F 7/0382* (2013.01); *G03F 7/0392* (2013.01)

(58) Field of Classification Search

None

See application file for complete search history.

(56) References Cited

U.S. PATENT DOCUMENTS

| | | | | |
|---|---|---|---|---|
| 9,360,753 B2 * | 6/2016 | Hatakeyama | ......... | G03F 7/0392 |
| 11,187,980 B2 * | 11/2021 | Hatakeyama | ......... | G03F 7/0045 |
| 11,281,101 B2 * | 3/2022 | Hatakeyama | ......... | G03F 7/0382 |
| 2016/0122292 A1 * | 5/2016 | Sakai | .................. | C07D 311/86 549/392 |
| 2022/0026805 A1 * | 1/2022 | Hatakeyama | ......... | G03F 7/0046 |
| 2023/0152692 A1 * | 5/2023 | Hatakeyama | ......... | G03F 7/0045 430/270.1 |

FOREIGN PATENT DOCUMENTS

| | | | | |
|---|---|---|---|---|
| JP | 2000191934 | A | * | 7/2000 |
| JP | 2001-194776 | A | | 7/2001 |
| JP | 2002-226470 | A | | 8/2002 |
| JP | 2002-363148 | A | | 12/2002 |
| JP | 2008074922 | A | * | 4/2008 |
| JP | 2013-83957 | A | | 5/2013 |
| JP | 2018-97356 | A | | 6/2018 |
| WO | 2008/066011 | A1 | | 6/2008 |

OTHER PUBLICATIONS

Japanese search report for related JP application (no date) (Year: 0000).*

Hutchinson, "The Shot Noise Impact on Resist Roughness in EUV Lithography", SPIE, 1998, vol. 3331, pp. 531-536, cited in Specification (7 pages).

Lio, "EUV Resists: What's Next?", SPIE, 2016, vol. 9776, pp. 97760V-1-97760V-14, cited in Specification (14 pages).

* cited by examiner

*Primary Examiner* — Amanda C. Walke

(74) *Attorney, Agent, or Firm* — WHDA, LLP

(57) ABSTRACT

A resist composition comprising a base polymer and a quencher is provided. The quencher is a salt compound obtained from a nitrogen-containing compound having an iodine-substituted aromatic ring bonded to the nitrogen atom via a $C_1$-$C_{20}$ hydrocarbon group which may contain an ester bond and/or an ether bond and a fluorinated 1,3-diketone compound, fluorinated β-keto ester compound or fluorinated imide compound. The resist composition has a high sensitivity and forms a pattern with improved LWR or CDU, independent of whether it is of positive or negative tone.

12 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2021-171611 filed in Japan on Oct. 20, 2021, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of 7-nm node devices by double patterning of the ArF immersion lithography and 5-nm node devices by the EUV lithography is implemented in a mass scale.

As the pattern feature size is reduced, approaching to the diffraction limit of light, light contrast lowers. In the case of positive resist film, a lowering of light contrast leads to reductions of resolution and focus margin of hole and trench patterns. For preventing any influence of a reduction of resolution of resist pattern due to a lowering of light contrast, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

With respect to the acid labile group used in (meth) acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 4 discloses a resist material comprising a sulfonium or iodonium salt capable of generating carboxylic acid as a quencher.

Like photoacid generators, quenchers of sulfonium and iodonium salt type are photo-decomposable. Thus, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

Patent Documents 5 and 6 disclose resist compositions comprising iodine-substituted aniline compounds. Since the aniline compounds have a low basicity and a low acid-capturing capability, their acid diffusion control is not enough. There is a need for a quencher having improved acid diffusion control, high absorbance, and high sensitizing effect.

It is believed that the number of photons absorbed in a resist film upon EUV exposure is 1/14 of that of ArF excimer laser exposure. Non-Patent Document 1 points out that a variation in number of photons, i.e., shot noise causes a variation in size. It is also believed that not only a variation in photon number, but also the uneven distribution of components in a resist film causes a variation in size. Non-Patent Document 2 proposes to develop a resist material comprising uniform components.

CITATION LIST

Patent Document 1: JP-A 2001-194776
Patent Document 2: JP-A 2002-226470
Patent Document 3: JP-A 2002-363148
Patent Document 4: WO 2008/066011
Patent Document 5: JP-A 2013-083957
Patent Document 6: JP-A 2018-097356
Non-Patent Document 1: SPIE Vol. 3331, p531 (1998)
Non-Patent Document 2: SPIE Vol. 9776, p97760V-1 (2016)

DISCLOSURE OF INVENTION

For the resist material, it is desired to develop a quencher capable of reducing the LWR of line patterns or improving the CDU of hole patterns and increasing sensitivity.

An object of the invention is to provide a resist composition which exhibits a high sensitivity and a reduced LWR or improved CDU, independent of whether it is of positive tone or negative tone; and a pattern forming process using the same.

The inventor has found that using a salt compound obtained from a specific nitrogen-containing compound having an iodine-substituted aromatic ring and a fluorinated 1,3-diketone compound, fluorinated β3-keto ester compound or fluorinated imide compound as the quencher, a resist material having a reduced LWR, improved CDU, high contrast, improved resolution, and wide process margin is obtainable.

In one aspect, the invention provides a resist composition comprising a base polymer and a quencher. The quencher comprises a salt compound which is obtained from a nitrogen-containing compound having an iodine-substituted aromatic ring bonded to the nitrogen atom via a $C_1$-$C_{20}$ hydrocarbon group which may contain at least one bond selected from an ester bond and an ether bond and at least one compound selected from a fluorinated 1,3-diketone compound, fluorinated β-keto ester compound, and fluorinated imide compound.

In a preferred embodiment, the salt compound has the formula (A).

(A)

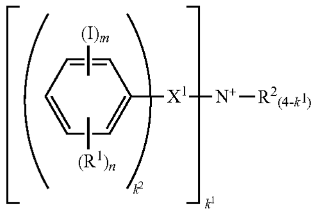

Herein m is an integer of 1 to 5, n is an integer of 0 to 4, m+n is from 1 to 5, $k^1$ is an integer of 1 to 3, $k^2$ is 1 or 2, $X^1$ is a $C_1$-$C_{20}$ ($k^2$+1)-valent hydrocarbon group which may contain at least one bond selected from an ester bond and an ether bond, $R^1$ is hydroxy, a $C_1$-$C_6$ saturated hydrocarbyl group, $C_1$-$C_6$ saturated hydrocarbyloxy group, $C_2$-$C_6$ saturated hydrocarbylcarbonyloxy group, fluorine, chlorine, bromine, amino, —N($R^{1A}$)—C(═O)—$R^{1B}$ or —N($R^{1A}$)—C(═O)—O—$R^{1B}$, $R^{1A}$ is hydrogen or a $C_1$-$C_6$ saturated hydrocarbyl group, $R^{1B}$ is a $C_1$-$C_6$ saturated hydrocarbyl group, $C_2$-$C_8$ unsaturated aliphatic hydrocarbyl group, $C_6$-$C_{12}$ aryl group or $C_7$-$C_{13}$ aralkyl group, $R^2$ is hydrogen, nitro, or a $C_1$-$C_{20}$ hydrocarbyl group which may contain at least one moiety selected from hydroxy, carboxy, thiol, ether bond, ester bond, nitro, cyano, halogen and amino, in case of $k^1$=1 or 2, two groups $R^2$ may bond together to form a ring with the nitrogen atom to which they are attached, the ring optionally containing a double bond, oxygen, sulfur or nitrogen, or $R^2$ and $X^1$ may bond together to form a ring with the nitrogen atom to which they are attached, the ring optionally containing a double bond, oxygen, sulfur or nitrogen, $R^3$ and $R^4$ are each independently a $C_1$-$C_{16}$ hydrocarbyl group, $C_1$-$C_{16}$ fluorinated hydrocarbyl group, $C_1$-$C_{16}$ hydrocarbyloxy group or $C_1$-$C_{16}$ fluorinated hydrocarbyloxy group, at least one of $R^3$ and $R^4$ being a $C_1$-$C_{16}$ fluorinated hydrocarbyl group or $C_1$-$C^{16}$ fluorinated hydrocarbyloxy group, and in the foregoing groups, some or all of the hydrogen atoms may be substituted by at least one moiety selected from cyano, nitro, hydroxy, and halogen other than fluorine, and some constituent —$CH_2$— may be replaced by at least one moiety selected from an ether bond, ester bond and thioether bond, and $X^2$ is —C(H)═ or —N═.

The resist composition may further comprise an acid generator capable of generating a sulfonic acid, imide acid or methide acid, an organic solvent, and/or a surfactant.

In a preferred embodiment, the base polymer comprises repeat units having the formula (a1) or repeat units having the formula (a2).

(a1)

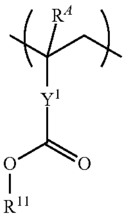

(a2)

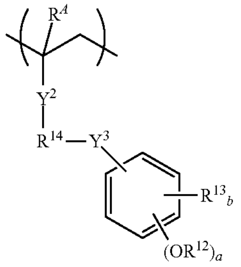

Herein $R^A$ is each independently hydrogen or methyl. $Y^1$ is a single bond, phenylene, naphthylene, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ are each independently an acid labile group. $R^{13}$ is fluorine, trifluoromethyl, cyano, a $C_1$-$C_6$ saturated hydrocarbyl group, $C_1$-$C_6$ saturated hydrocarbyloxy group, $C_2$-$C_7$ saturated hydrocarbylcarbonyl group, $C_2$-$C_7$ saturated hydrocarbylcarbonyloxy group, or $C_2$-$C_7$ saturated hydrocarbyloxycarbonyl group. $R^{14}$ is a single bond or a $C_1$-$C_6$ alkanediyl group in which some constituent —$CH_2$— may be replaced by an ether bond or ester bond; a is 1 or 2, b is an integer of 0 to 4, and a+b is from 1 to 5.

Typically, the resist composition is a chemically amplified positive resist composition.

In another preferred embodiment, the base polymer is free of an acid labile group. Typically, the resist composition is a chemically amplified negative resist composition.

In a preferred embodiment, the base polymer comprises repeat units of at least one type selected from repeat units having the formulae (f1) to (f3).

(f1)

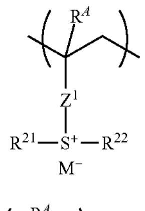

(f2)

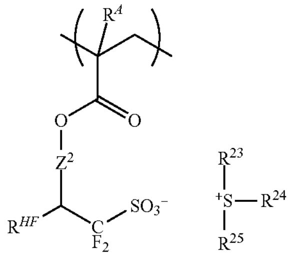

-continued (f3)

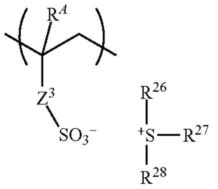

Herein $R^A$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—. —C(=O)—O—$Z^{11}$— or —C(=O)—N—H—$Z^{11}$—. $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety. $Z^2$ is a single bond, —$Z^{21}$—C(=O)—O—, —$Z^{21}$—O— or —$Z^{21}$—O—C(=O)—. $Z^{21}$ is a $C_1$-$C_{12}$ saturated hydrocarbylene group which may contain a carbonyl moiety, ester bond or ether bond. $Z^3$ is a single bond, methylene, ethylene, phenylene, fluorinated phenylene, trifluoromethyl-substituted phenylene group, —O—$Z^{31}$—, —C(=O)—O—$Z^{31}$—, or —C(=O)—NH—$Z^{31}$—. $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety. $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached. $R^{HF}$ is hydrogen or trifluoromethyl. $M^-$ is a non-nucleophilic counter ion.

In another aspect, the invention provides a pattern forming process comprising the steps of applying the resist composition defined herein to form a resist film on a substrate, exposing the resist film to high-energy radiation, and developing the exposed resist film in a developer. Typically, the high-energy radiation is ArF excimer laser of wavelength 193 nm, KrF excimer laser of wavelength 248 nm. EB, or EUV of wavelength 3 to 15 nm.

Advantageous Effects of Invention

Since iodine is contained, the salt compound having formula (A) is highly absorptive to EUV and has a sensitizing effect. Since iodine has a large atomic weight, the salt compound is highly effective for suppressing acid diffusion. Because of the lack of photosensitivity, the salt compound is not decomposed even in the exposed region. Therefore, the acid diffusion control ability is high in the exposed region, and a pattern film thickness loss in alkaline developer is suppressed. By virtue of the repulsive effect of fluorine, the quencher in the form of a salt containing an anion derived from a fluorinated 1,3-diketone compound, fluorinated β-keto ester compound or fluorinated imide compound is uniformly distributed in the resist film. A resist composition having a high sensitivity, low LWR and improved CDU is thus designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. The term "group" and "moiety" are interchangeable. The iodine-substituted compound is also referred to as iodized compound. In chemical formulae, the broken line designates a valence bond, and Me stands for methyl and Ac for acetyl.

The abbreviations and acronyms have the following meaning.

| | |
|---|---|
| EB: | electron beam |
| EUV: | extreme ultraviolet |
| Mw: | weight average molecular weight |
| Mn: | number average molecular weight |
| Mw/Mn: | molecular weight dispersity |
| GPC: | gel permeation chromatography |
| PEB: | post-exposure bake |
| PAG: | photoacid generator |
| LWR: | line width roughness |
| CDU: | critical dimension uniformity |

Resist Composition

The resist composition of the invention is defined as comprising a base polymer and a quencher, the quencher comprising a salt compound which is obtained from a nitrogen-containing compound having an iodized aromatic ring bonded to the nitrogen atom via a $C_1$-$C_{20}$ hydrocarbon group which may contain at least one bond selected from an ester bond and an ether bond and at least one compound selected from a fluorinated 1,3-diketone compound, fluorinated β-keto ester compound and fluorinated imide compound. The salt compound is referred to as "salt compound A," hereinafter.

Salt Compound A

The salt compound A preferably has the following formula (A).

(A)

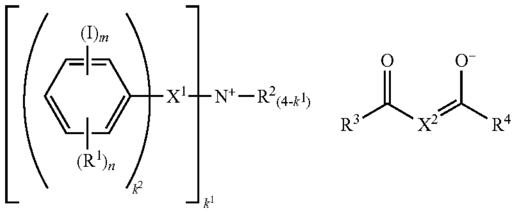

In formula (A), m is an integer of 1 to 5, n is an integer of 0 to 4, m+n is from 1 to 5, $k^1$ is an integer of 1 to 3, and $k^2$ is 1 or 2.

$X^1$ is a $C_1$-$C_{20}$ ($k^2$+1)-valent hydrocarbon group which may contain at least one bond selected from an ester bond and an ether bond. The hydrocarbon group may be saturated or unsaturated and straight, branched or cyclic. Examples thereof include $C_1$-$C_{20}$ hydrocarbylene groups and trivalent groups obtained by removing one hydrogen from the hydrocarbylene groups. Suitable hydrocarbylene groups include alkanediyl groups such as methylene, ethylene, propane-1,2-diyl, propane-1,3-diyl, butane-1,2-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ cyclic saturated hydrocarbylene groups such as cyclopentanediyl, cyclohexanediyl, norbornanediyl, and adamantanediyl; $C_2$-$C_{20}$ unsaturated aliphatic hydrocarbylene groups such as vinylene and propene-1,3-diyl; $C_6$-$C_{20}$ arylene groups such as phenylene and naphthylene; and combinations thereof.

In formula (A), $R^1$ is hydroxy, a $C_1$-$C_6$ saturated hydrocarbyl group, $C_1$-$C_6$ saturated hydrocarbyloxy group, $C_2$-$C_6$ saturated hydrocarbylcarbonyloxy group, fluorine, chlorine, bromine, amino, —N($R^{1A}$)—C(═O)—$R^{1B}$ or N($R^{1A}$)—C(═O)—O—$R^{1B}$. $R^{1A}$ is hydrogen or a $C_1$-$C_6$ saturated hydrocarbyl group. $R^{1B}$ is a $C_1$-$C_6$ saturated hydrocarbyl group, $C_2$-$C_8$ unsaturated aliphatic hydrocarbyl group, $C_6$-$C_{12}$ aryl group or $C_7$-$C_{13}$ aralkyl group.

The $C_1$-$C_6$ saturated hydrocarbyl group may be straight, branched or cyclic and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, and cyclohexyl. Examples of the saturated hydrocarbyl moiety in the $C_1$-$C_6$ saturated hydrocarbyloxy group and $C_2$-$C_6$ saturated hydrocarbylcarbonyloxy group are as exemplified above for the saturated hydrocarbyl group.

The $C_2$-$C_8$ unsaturated aliphatic hydrocarbyl group may be straight, branched or cyclic and examples thereof include vinyl, 1-propenyl, 2-propenyl, butenyl, hexenyl and cyclohexenyl.

Suitable $C_6$-$C_{12}$ aryl groups include phenyl, tolyl, xylyl, 1-naphthyl and 2-naphthyl. Suitable $C_7$-$C_{13}$ aralkyl groups include benzyl and phenethyl.

Of these, $R^1$ is preferably fluorine, chlorine, bromine, hydroxy, amino, $C_1$-$C_3$ saturated hydrocarbyl group, $C_1$-$C_3$ saturated hydrocarbyloxy group, $C_2$-$C_4$ saturated hydrocarbylcarbonyloxy group, —N($R^{1A}$)—C(═O)—$R^{1B}$ or —N($R^{1A}$)—C(═O)—O—$R^{1B}$. When n is 2 or more, groups $R^1$ may be the same or different.

In formula (A), $R^2$ is hydrogen, nitro, or a $C_1$-$C_{20}$ hydrocarbyl group. The $C_1$-$C_{20}$ hydrocarbyl group may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{20}$ alkenyl groups such as vinyl, propenyl, butenyl and hexenyl; $C_2$-$C_{20}$ cyclic unsaturated aliphatic hydrocarbyl groups such as cyclohexenyl and norbornenyl; $C_2$-$C_{20}$ alkynyl groups such as ethynyl, propynyl and butynyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutyinaphthyl, sec-butyinaphthyl, tert-butyinaphthyl; $C_7$-$C_{20}$ aralkyl groups such as benzyl and phenethyl; and combinations thereof such as 2-cyclohexylethynyl and 2-phenylethynyl. The hydrocarbyl group may contain at least one moiety selected from hydroxy, carboxy, thiol, ether bond, ester bond, nitro, cyano, halogen, and amino.

Incase of $k^1$=1 or 2, groups $R^2$ may be the same or different. Also, in case of $k^1$=1 or 2, two groups $R^2$ may bond together to form a ring with the nitrogen atom to which they are attached, the ring may contain a double bond, oxygen, sulfur or nitrogen; or $R^2$ and $X^1$ may bond together to form a ring with the nitrogen atom to which they are attached, the ring may contain a double bond, oxygen, sulfur or nitrogen.

Examples of the cation (derived from the nitrogen-containing compound) of salt compound A are shown below, but not limited thereto.

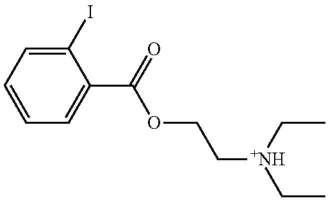

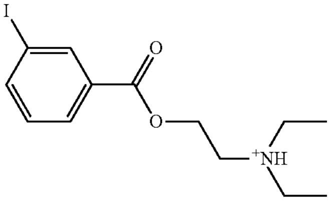

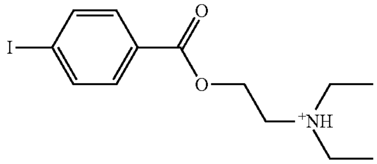

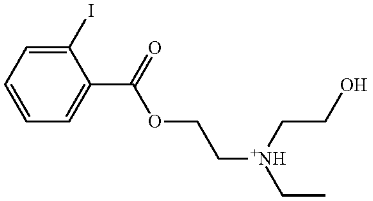

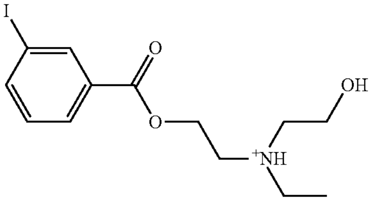

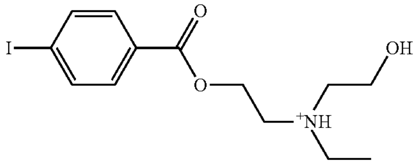

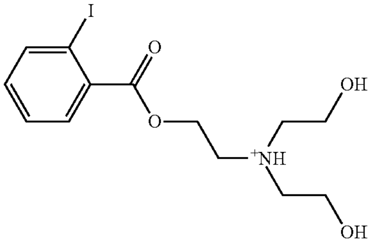

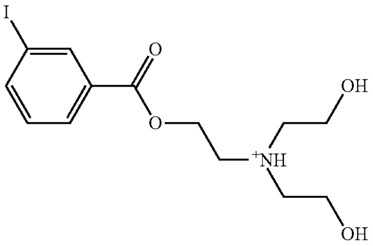

-continued
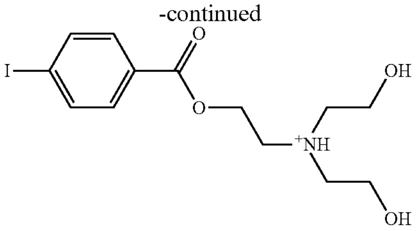
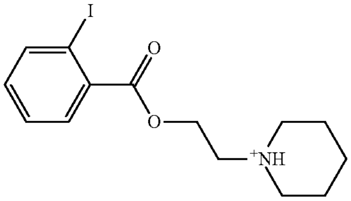
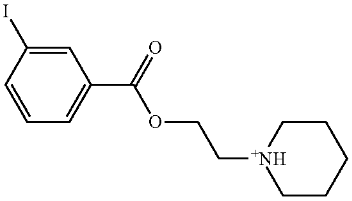
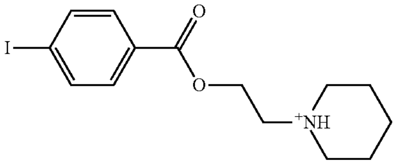
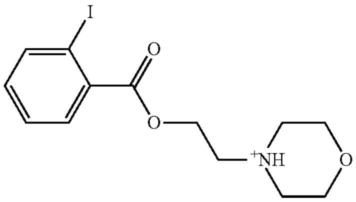
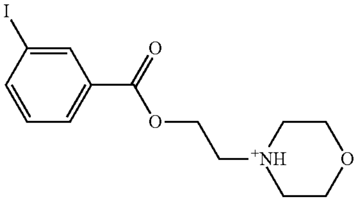
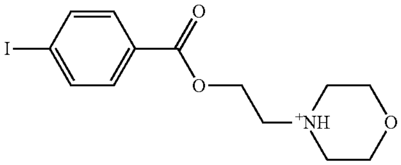
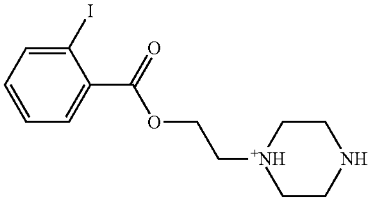
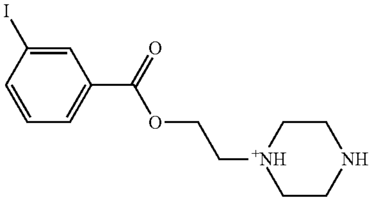
-continued
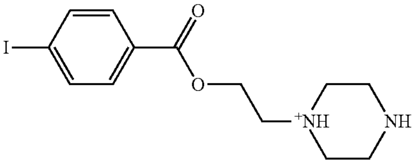
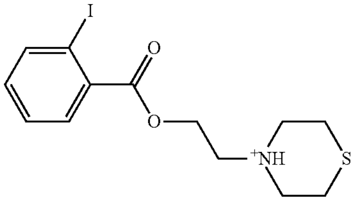
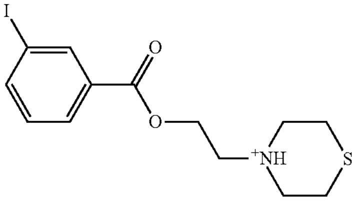
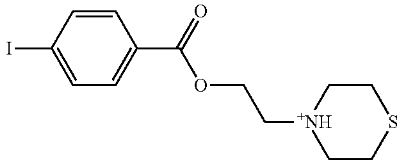
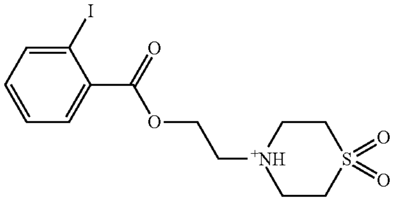
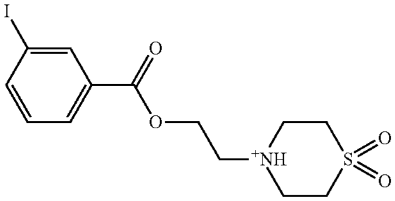
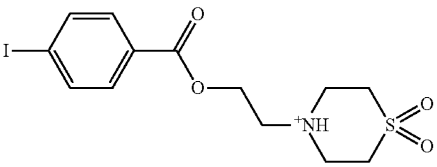
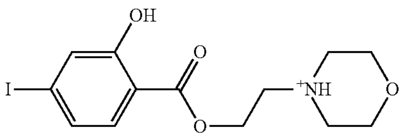
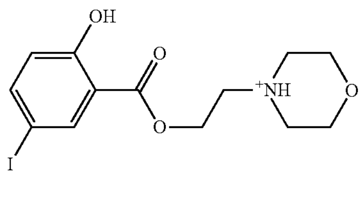

-continued
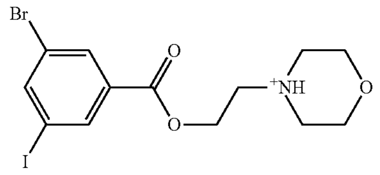
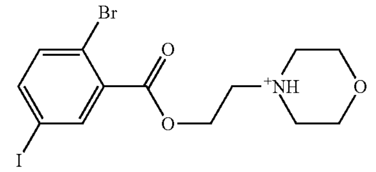
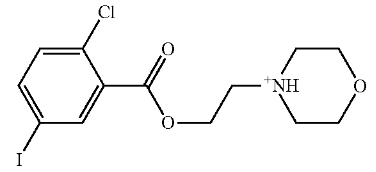
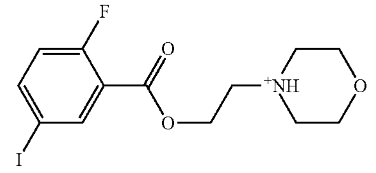
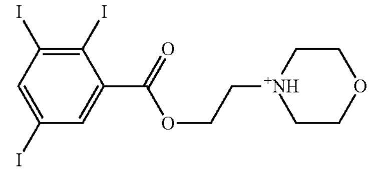
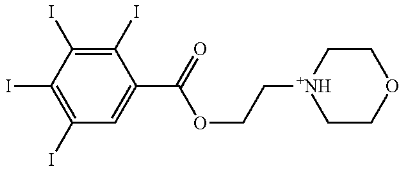
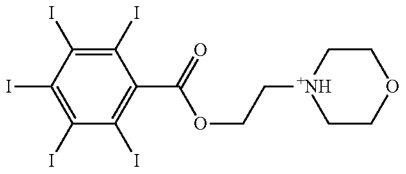
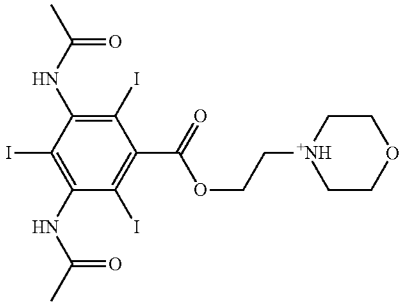
-continued
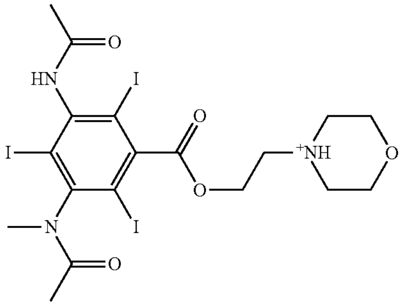
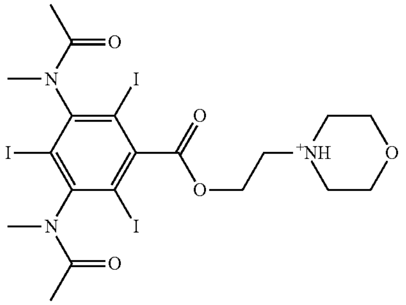
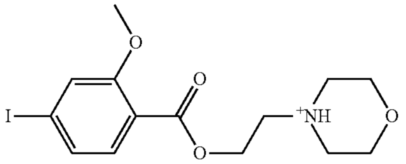
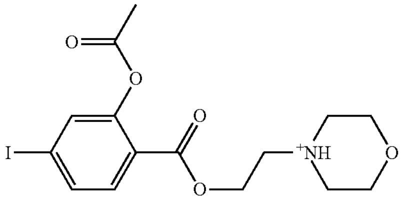
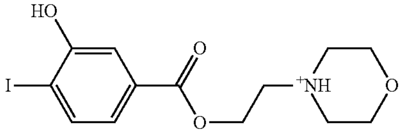
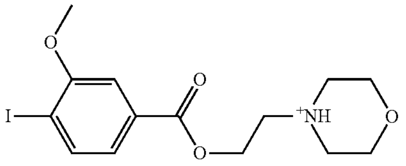
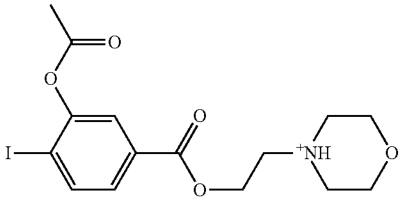
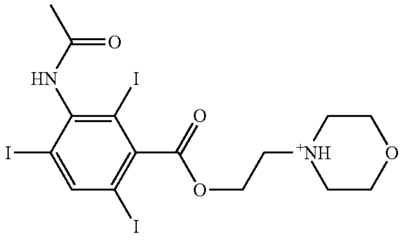

-continued
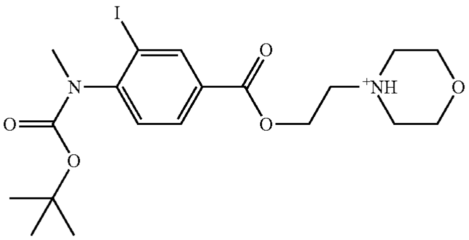
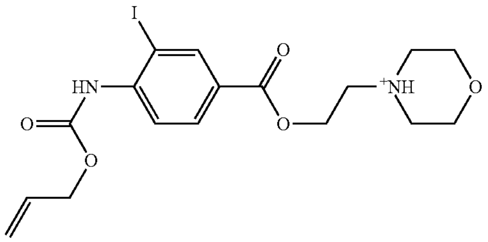
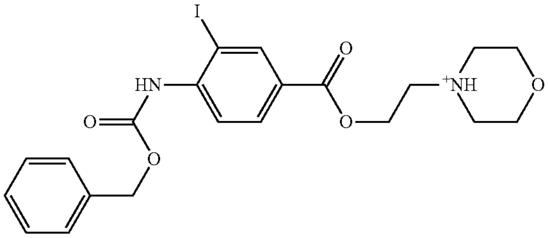
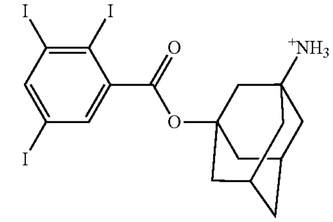
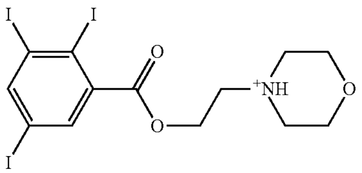
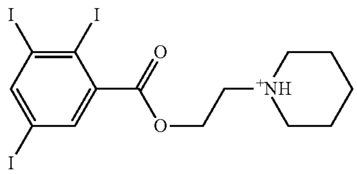
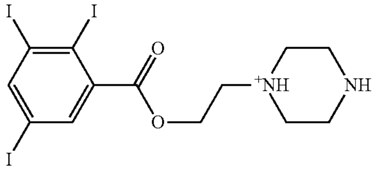
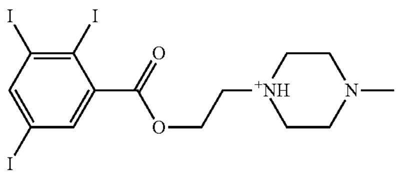
-continued
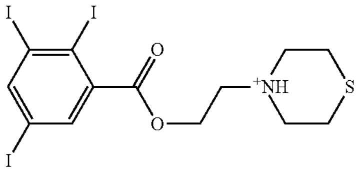
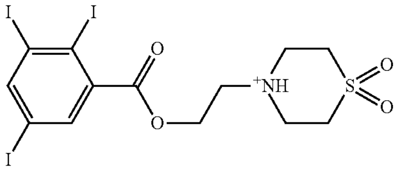
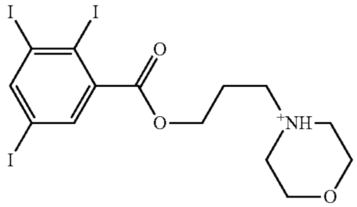
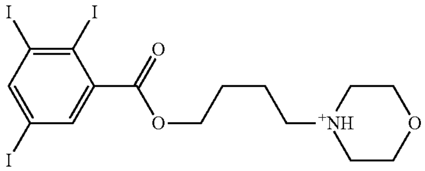
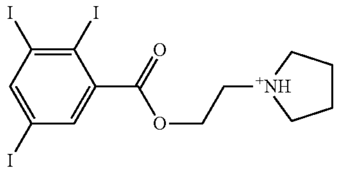
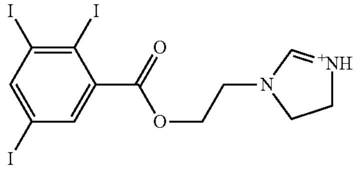
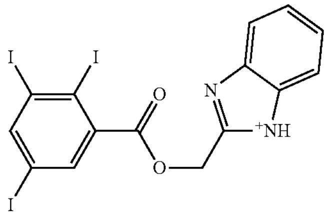
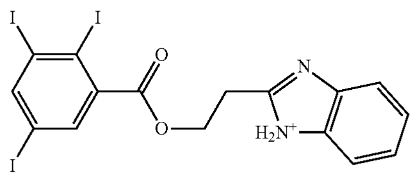
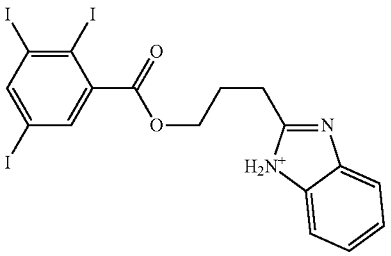

-continued
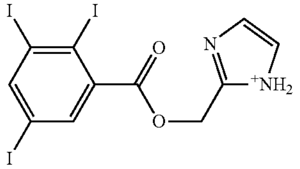
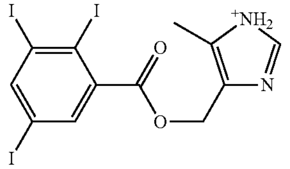
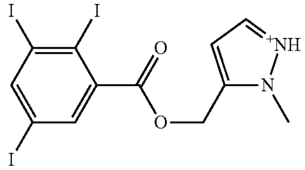
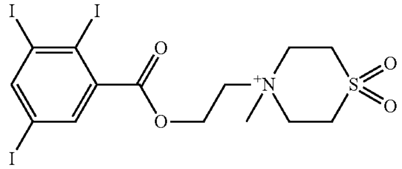
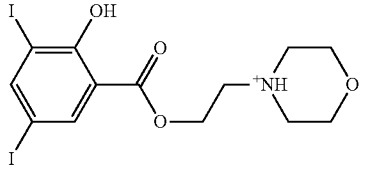
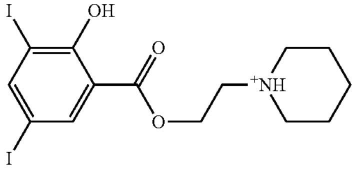
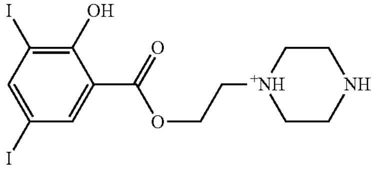
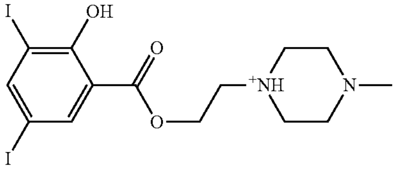
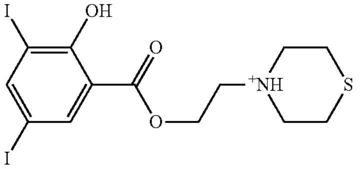
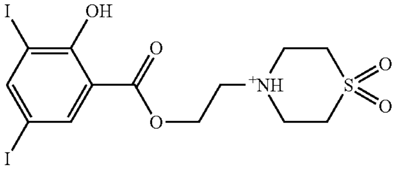
-continued
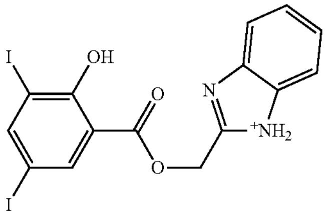
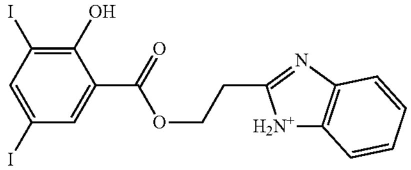
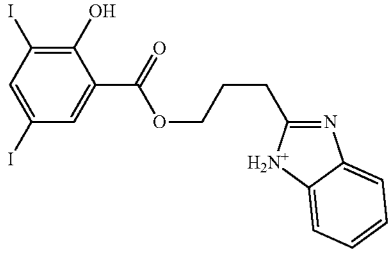
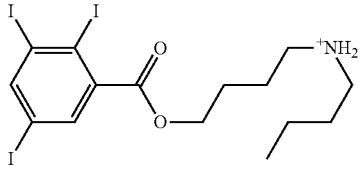
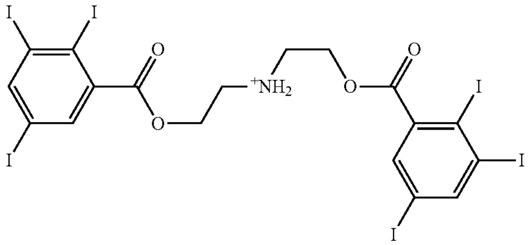
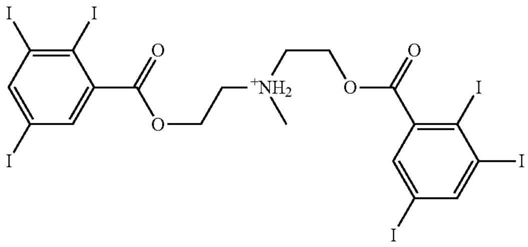
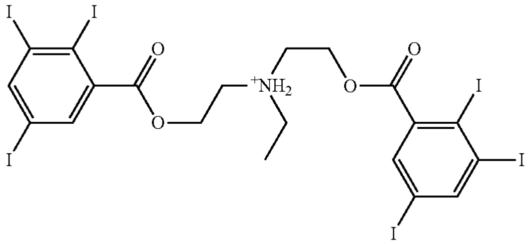

-continued
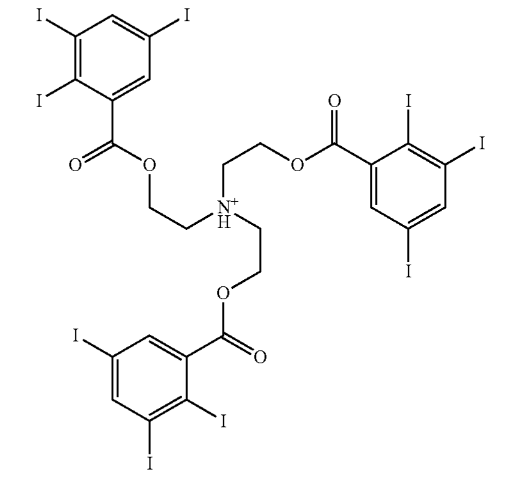
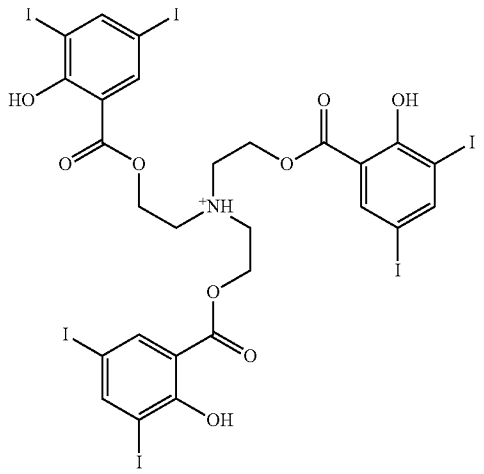
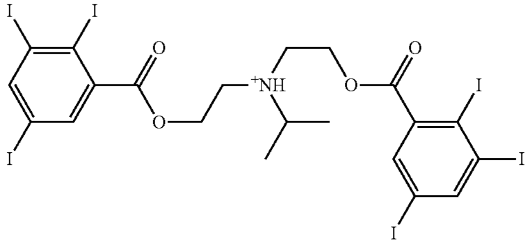
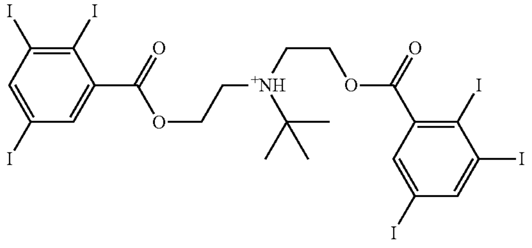
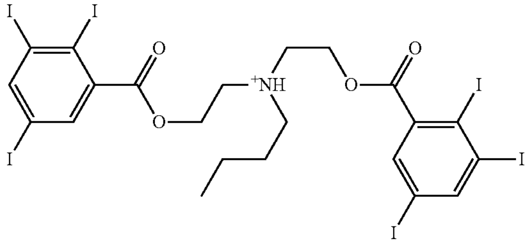
-continued
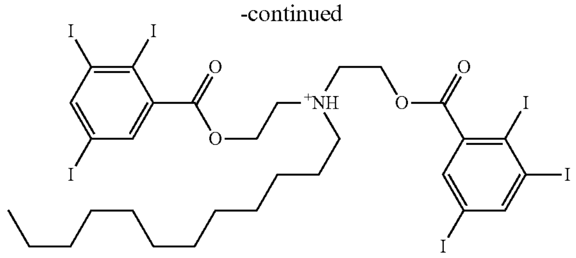
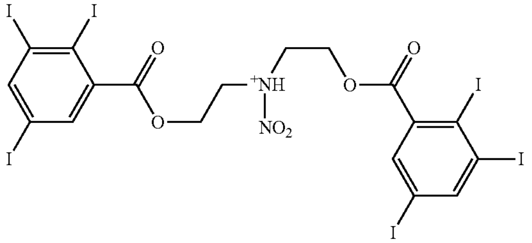
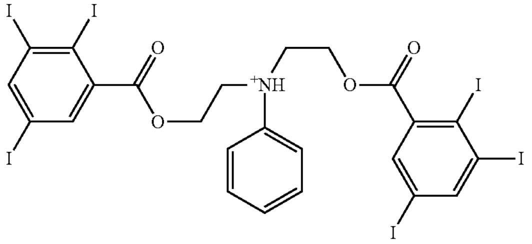
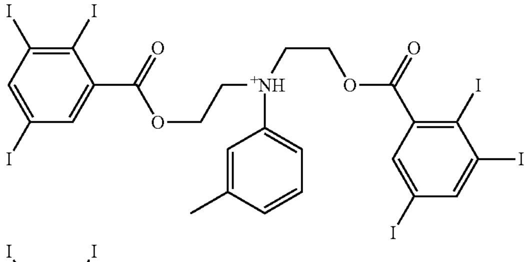
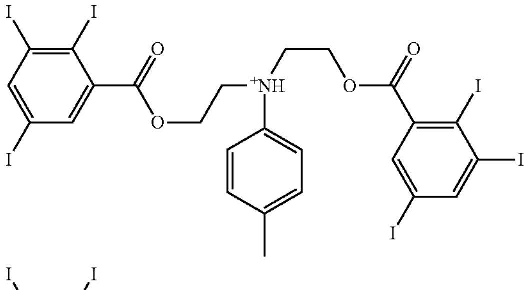
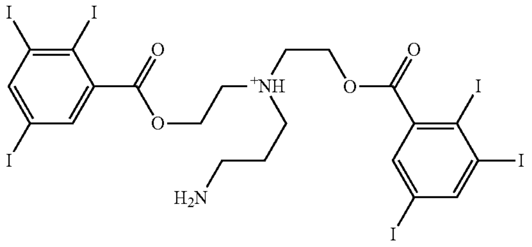
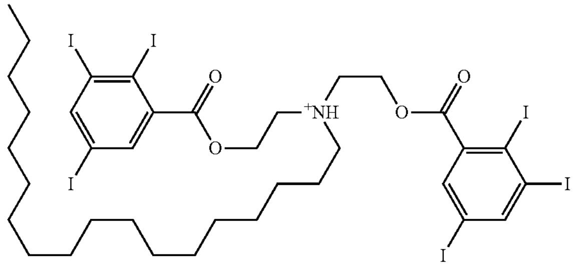

-continued
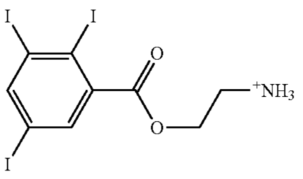
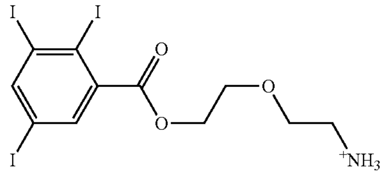
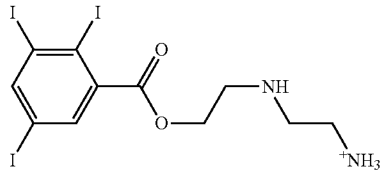
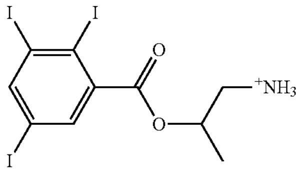
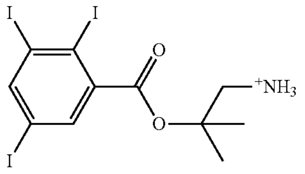
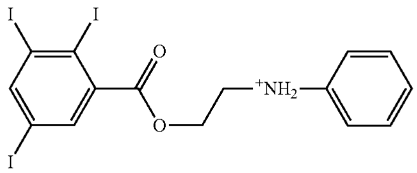
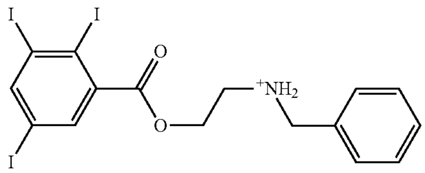
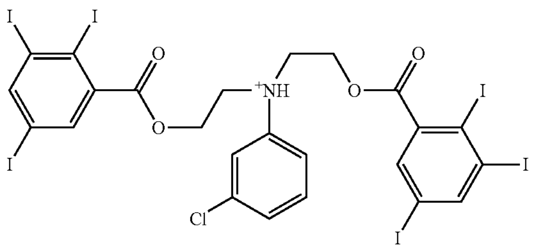
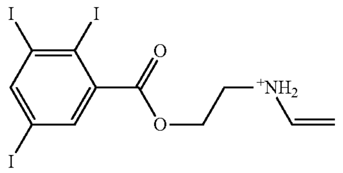
-continued
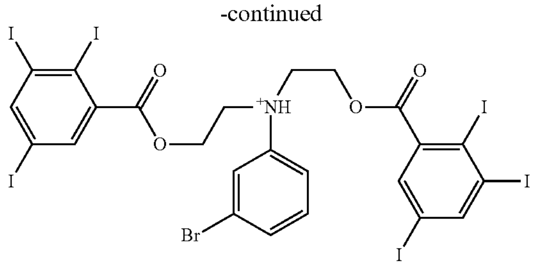
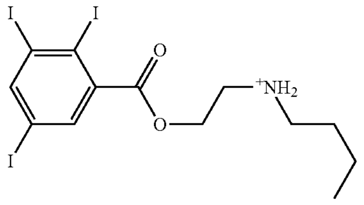
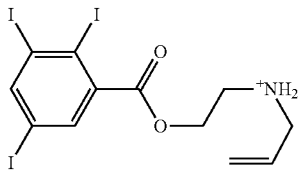
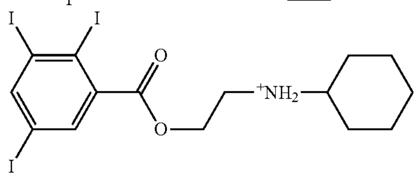
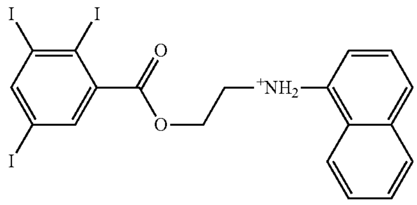
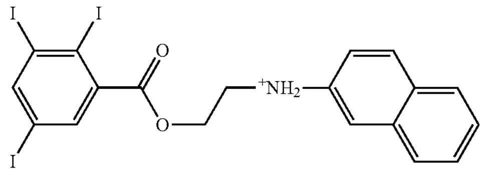
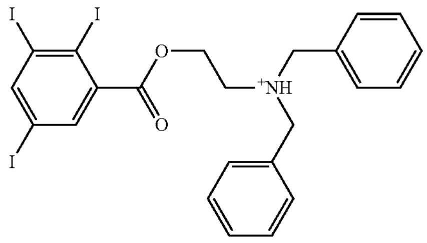
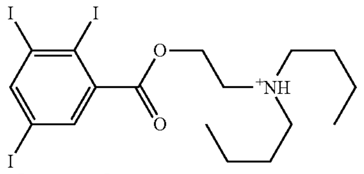
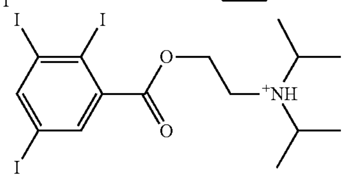

-continued
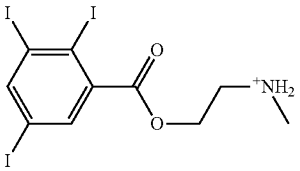
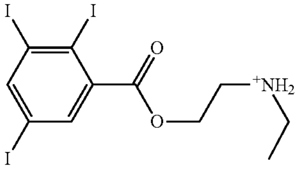
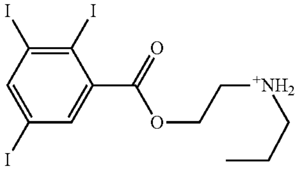
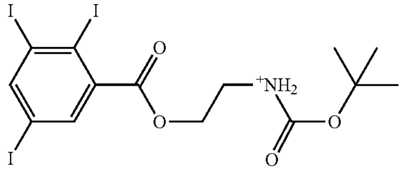
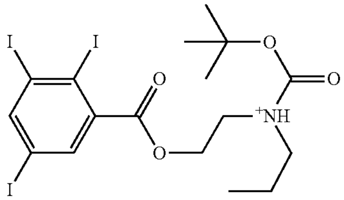
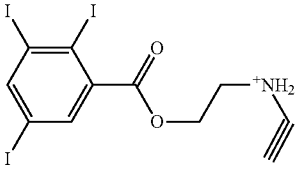
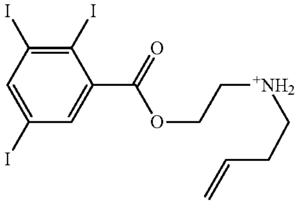
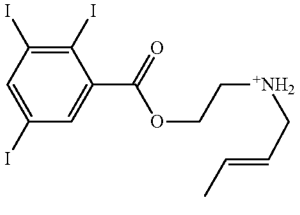
-continued
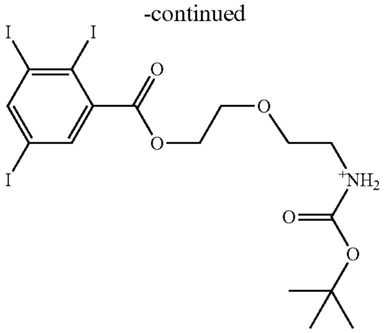
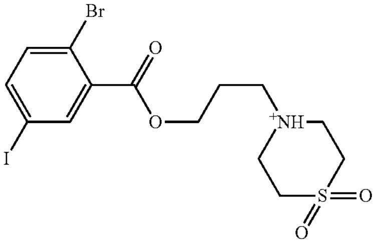
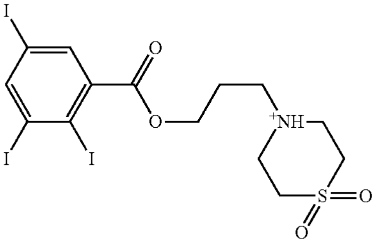
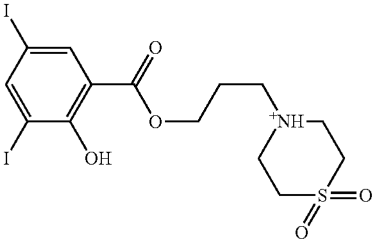
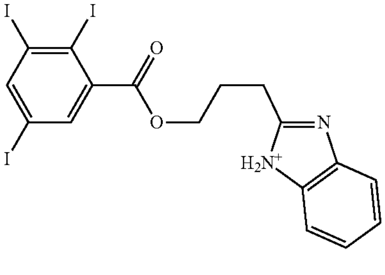
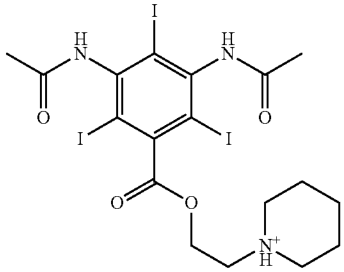

-continued
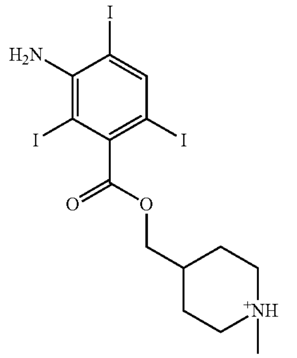
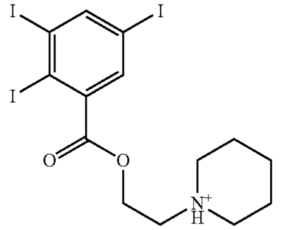
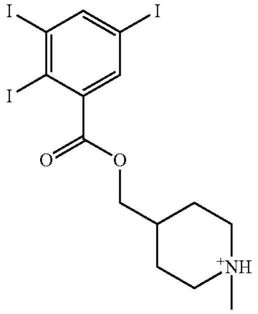
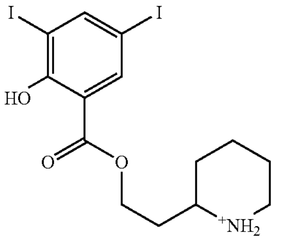
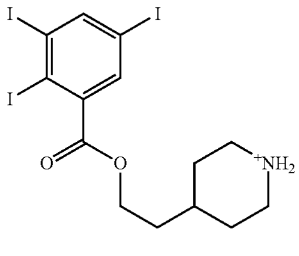
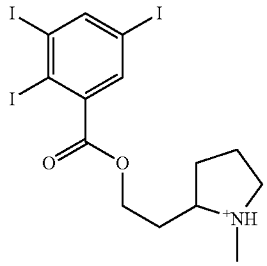
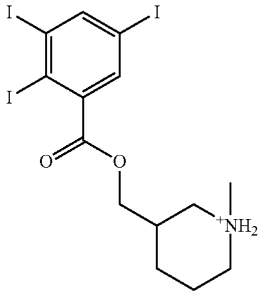
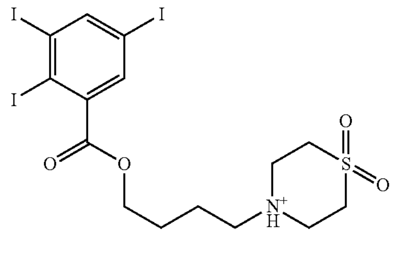
-continued
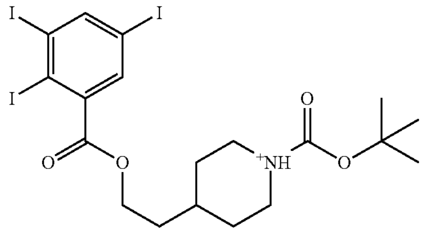
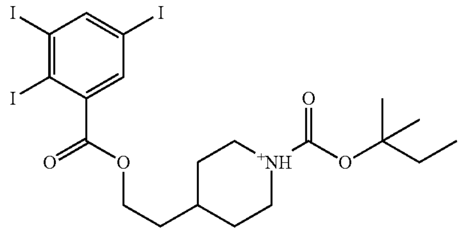
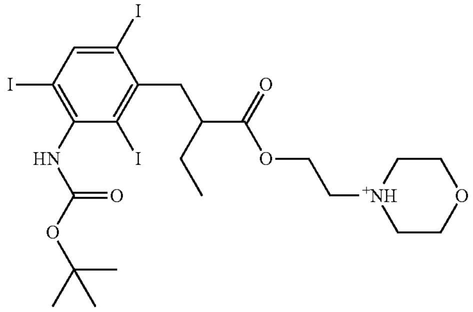
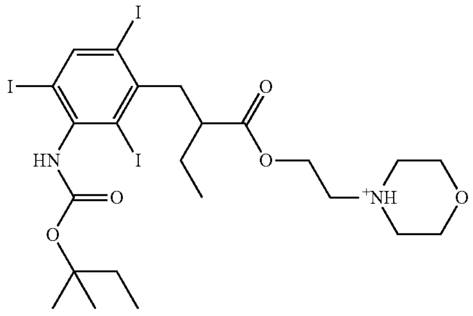
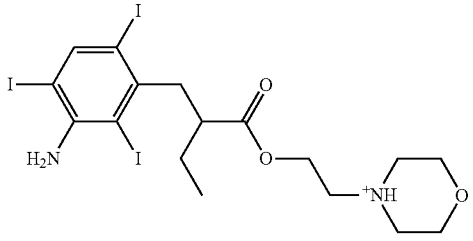
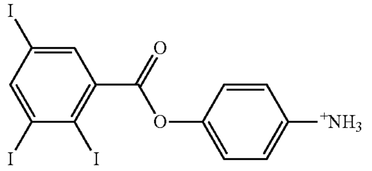
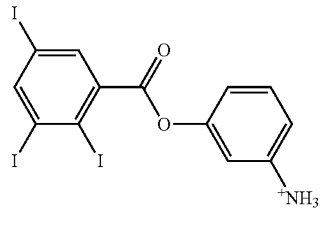

-continued
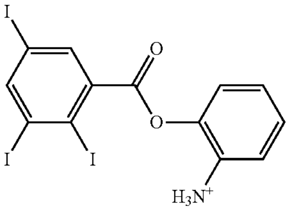
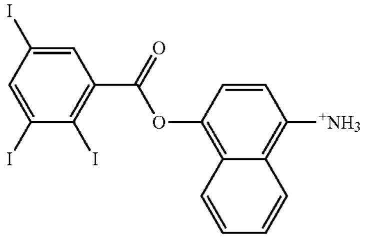
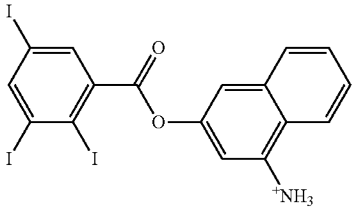
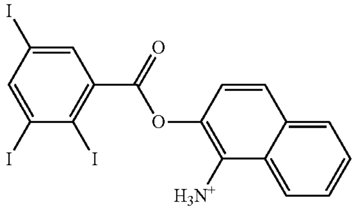
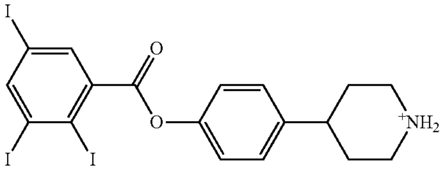
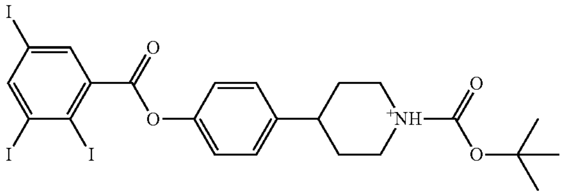
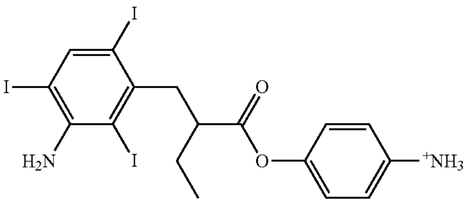
-continued
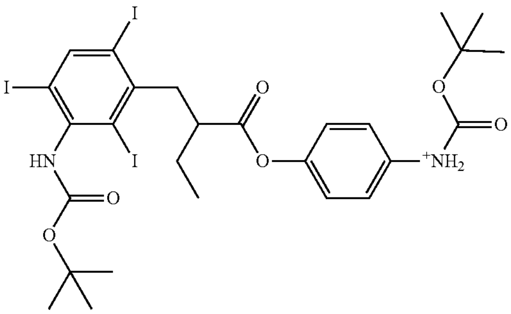
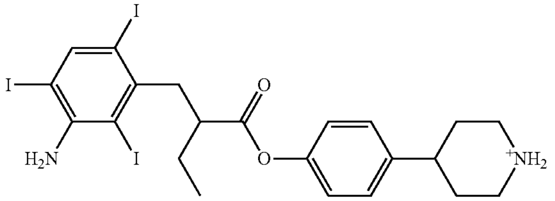
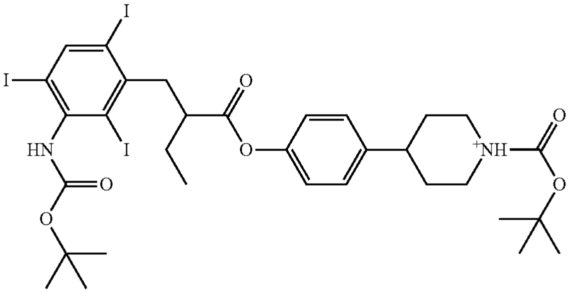
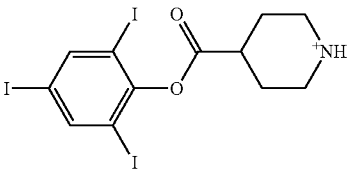
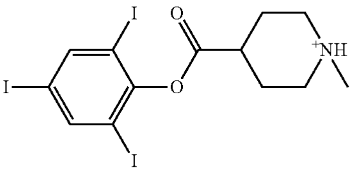
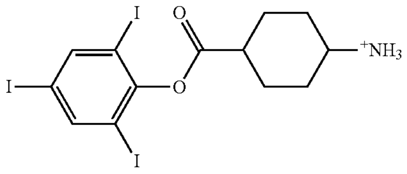
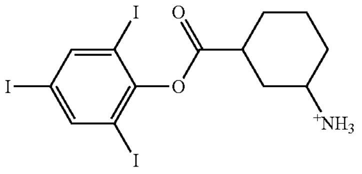
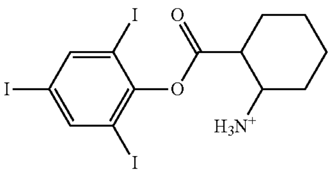

-continued
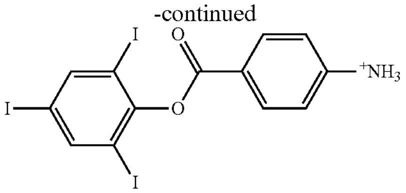
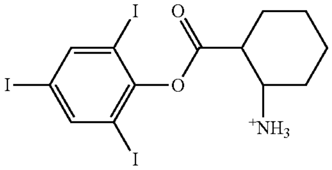
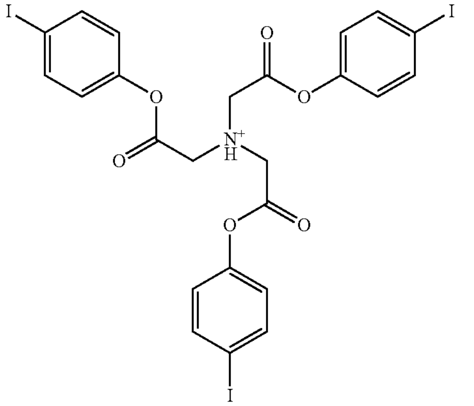
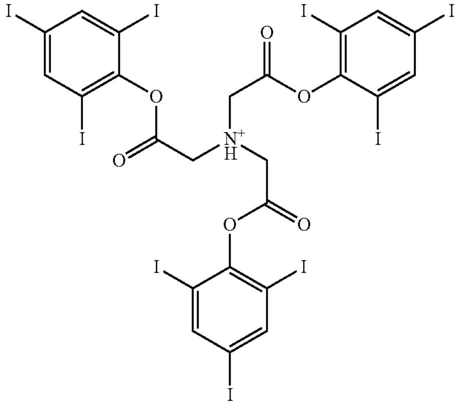
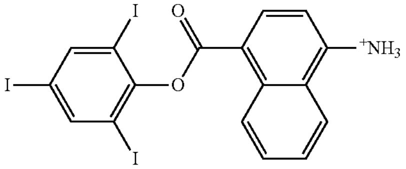
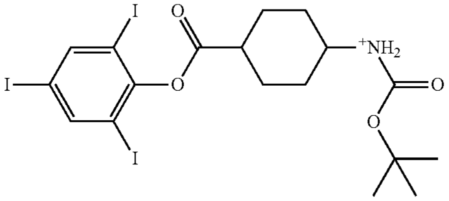
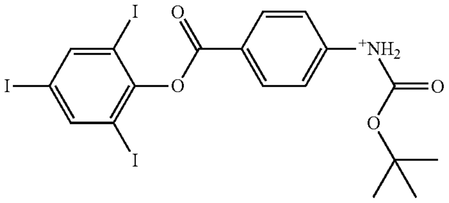
-continued
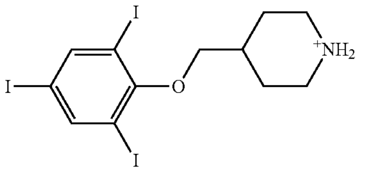
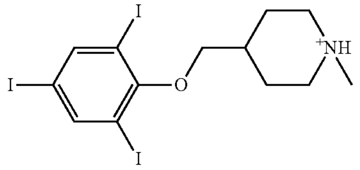
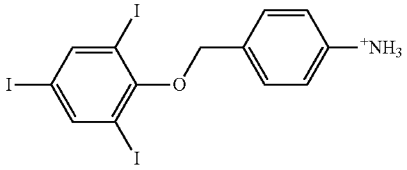
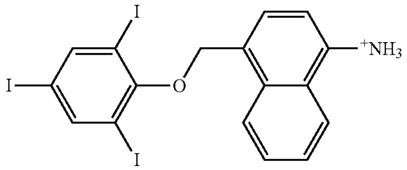
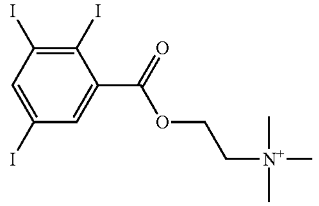
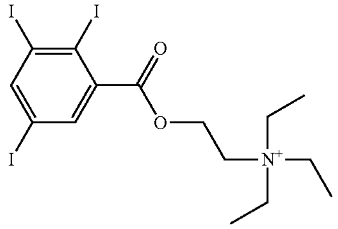
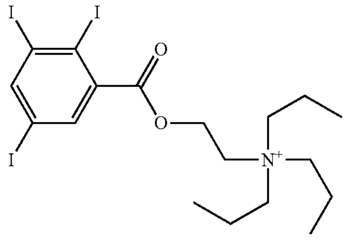
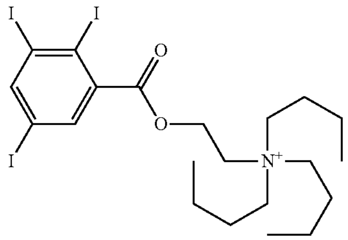

-continued
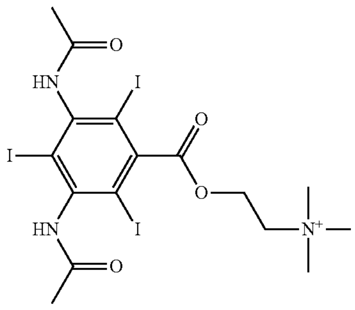
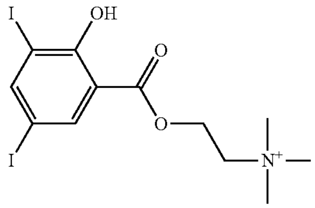
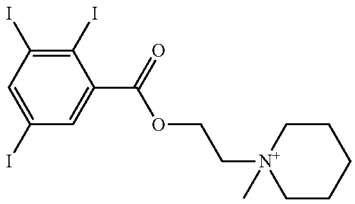
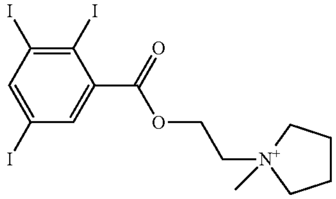
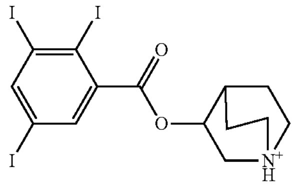
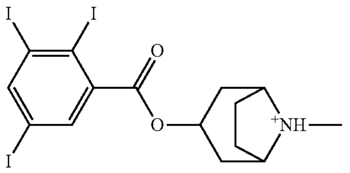
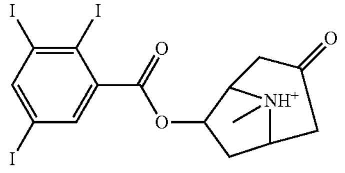
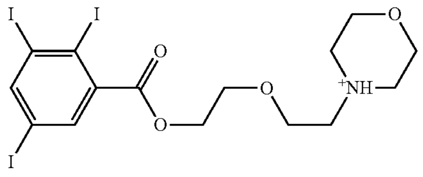
-continued
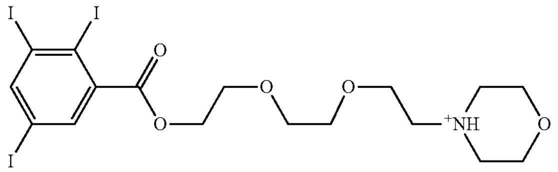
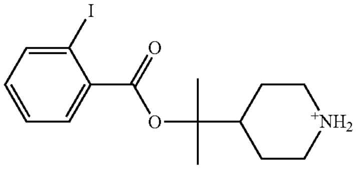
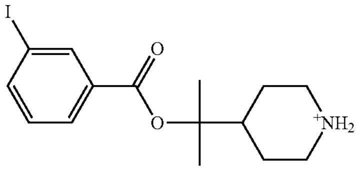
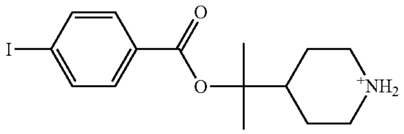
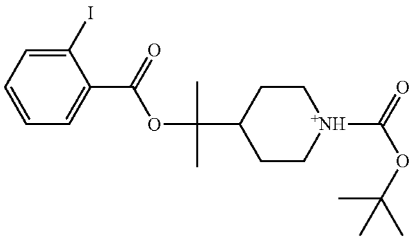
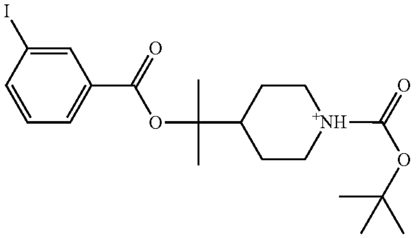
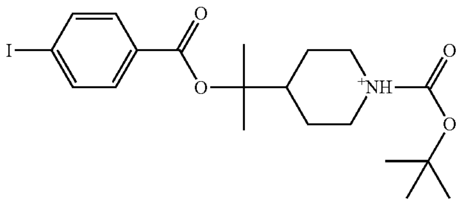
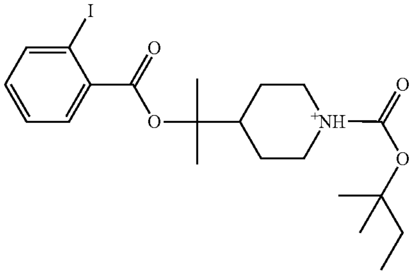

-continued
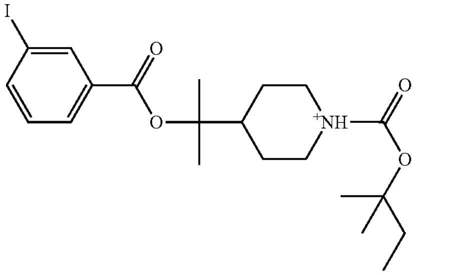
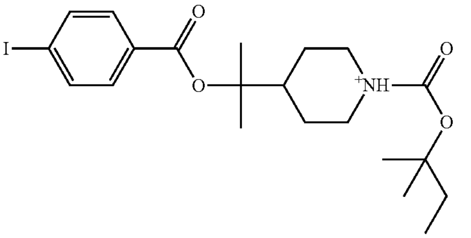
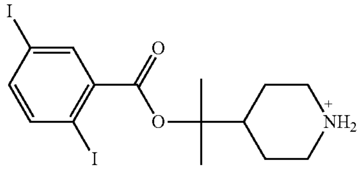
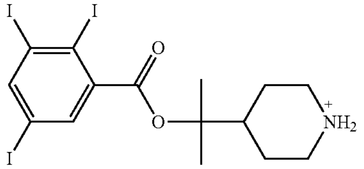
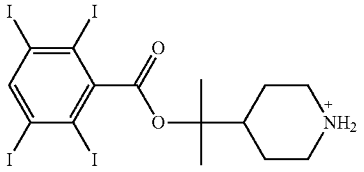
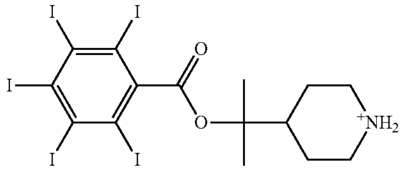
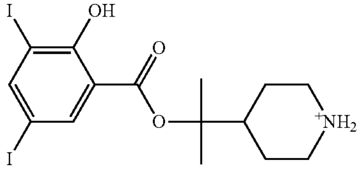
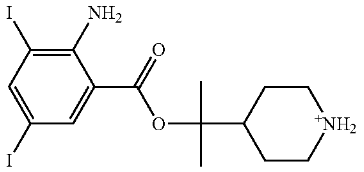
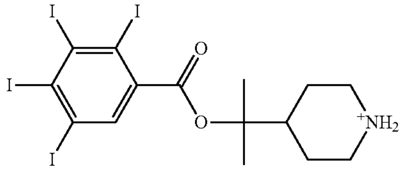
-continued
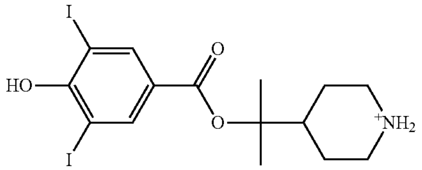
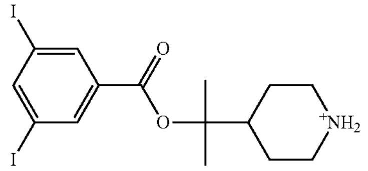
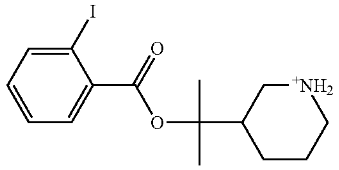
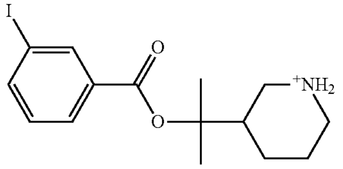
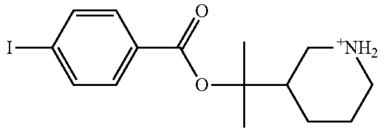
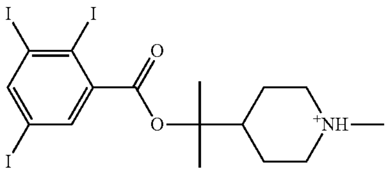
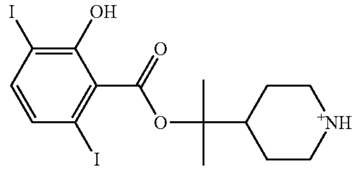
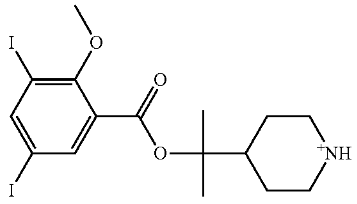
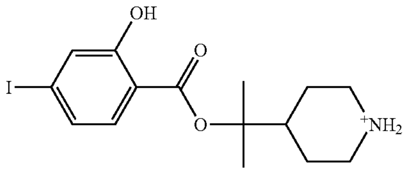

-continued
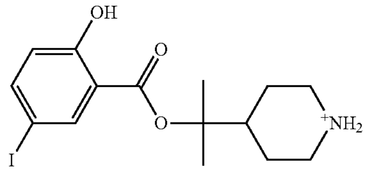
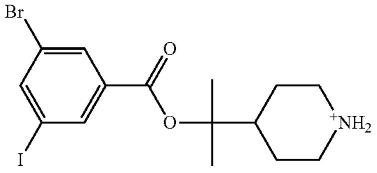
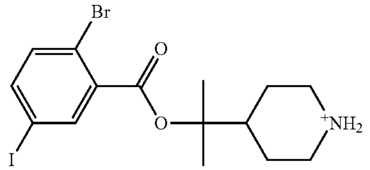
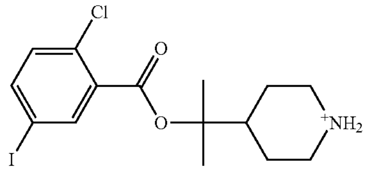
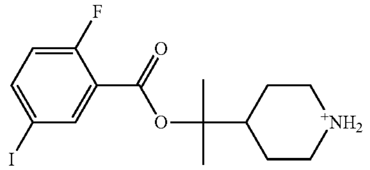
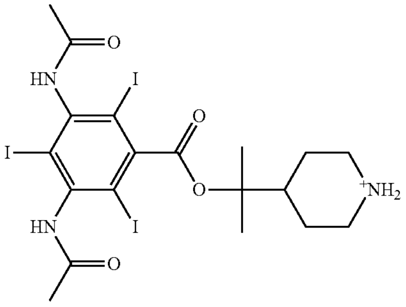
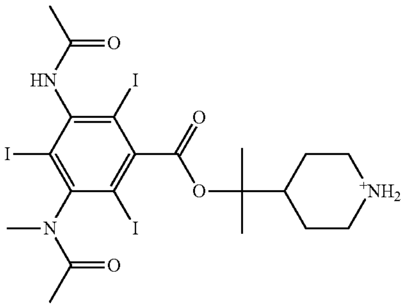
-continued
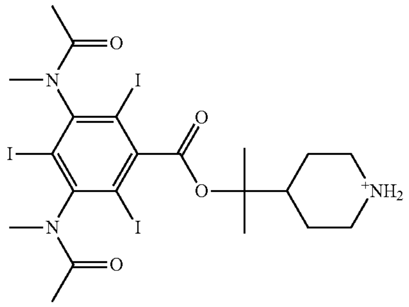
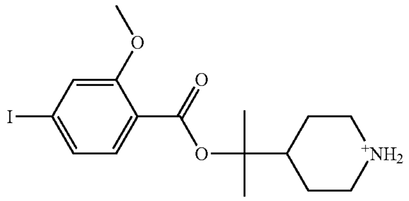
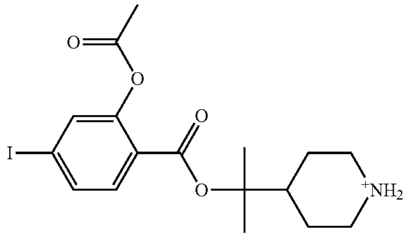
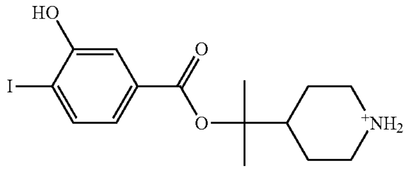
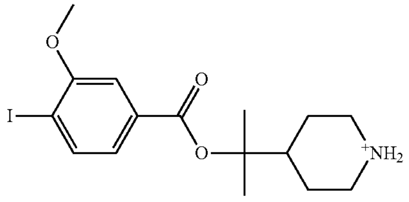
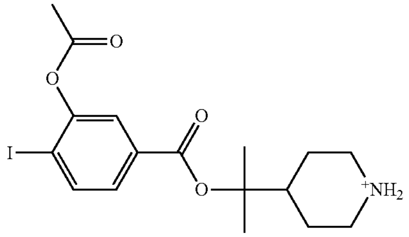
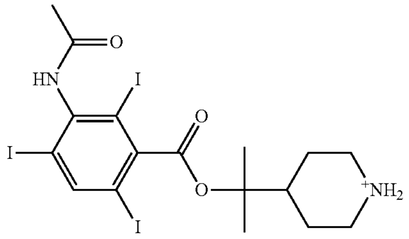

-continued
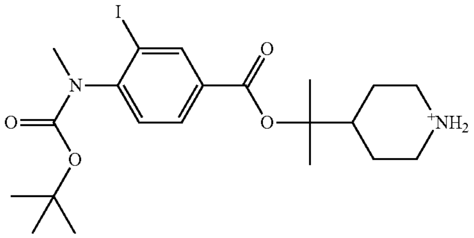
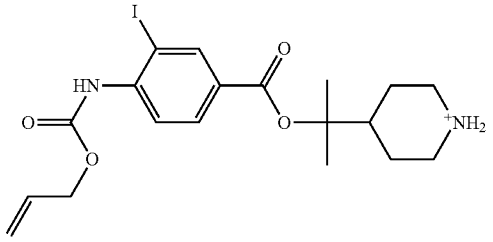
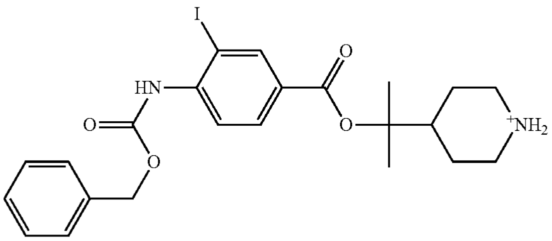
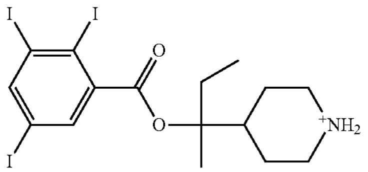
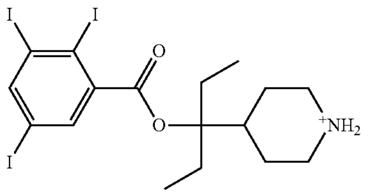
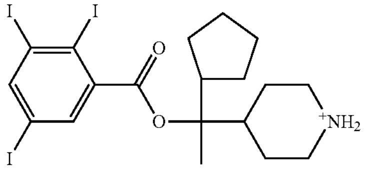
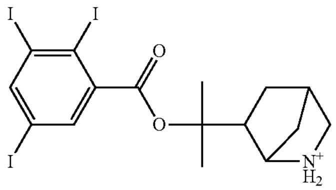
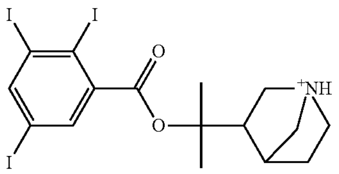
-continued
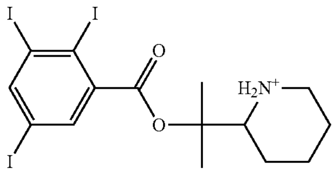
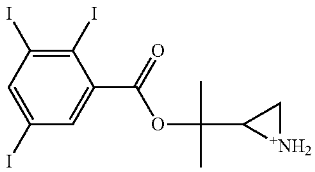
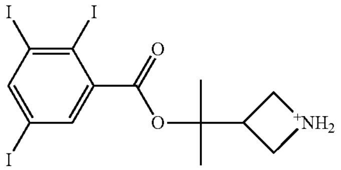
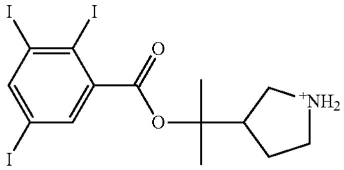
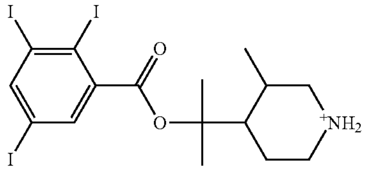
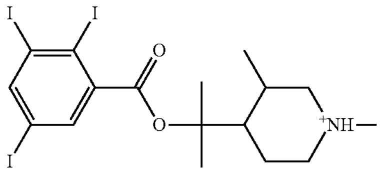
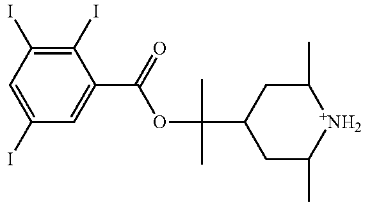
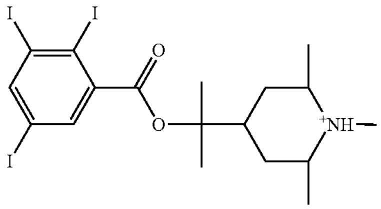
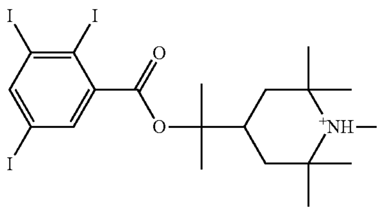

-continued
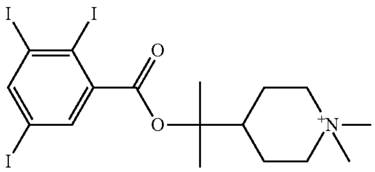
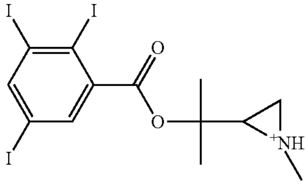
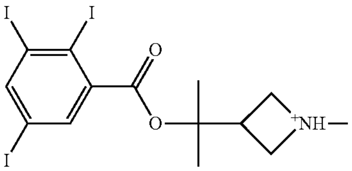
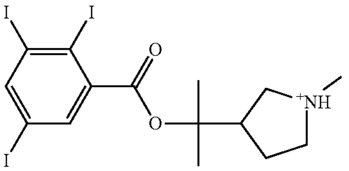
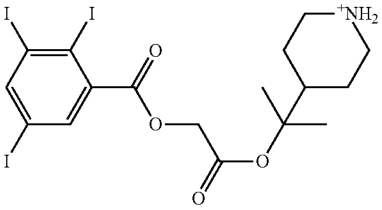
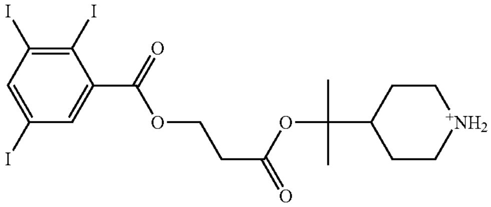
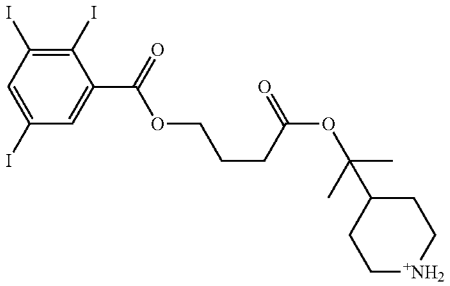
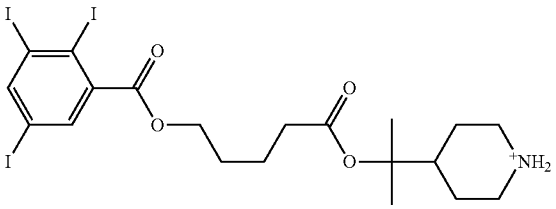
-continued
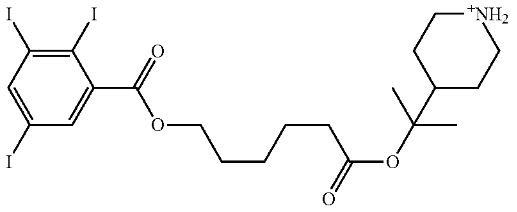
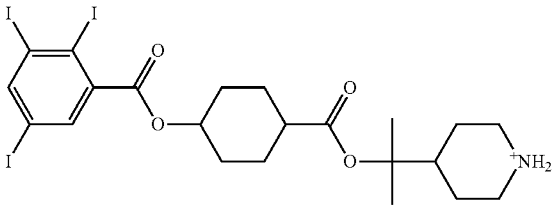
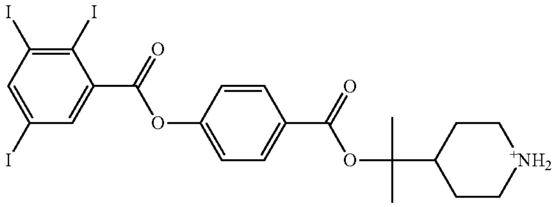
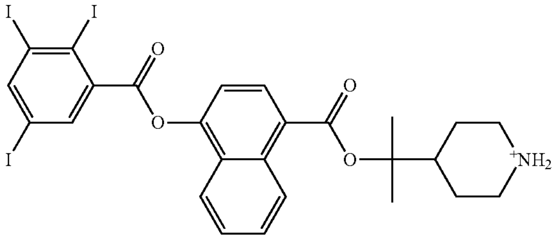
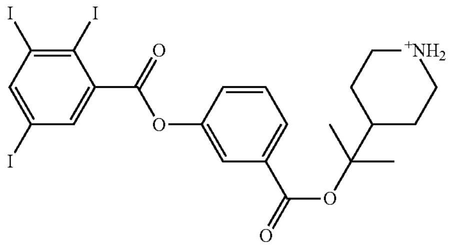
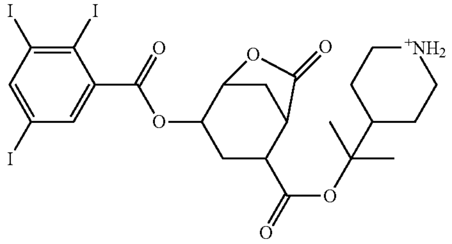
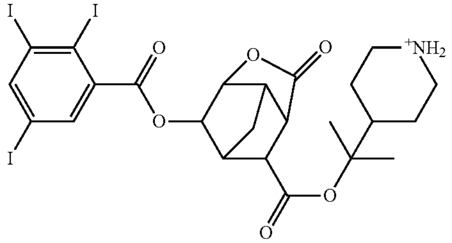

-continued
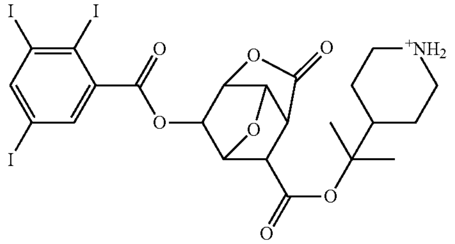
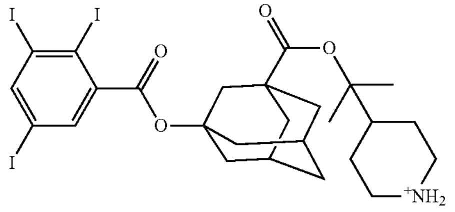
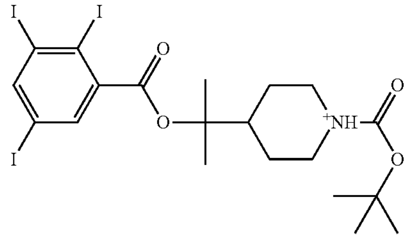
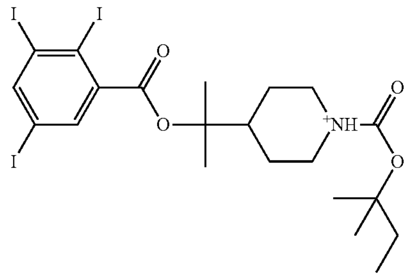
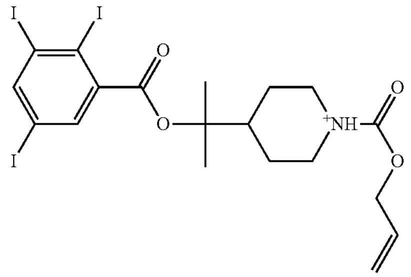
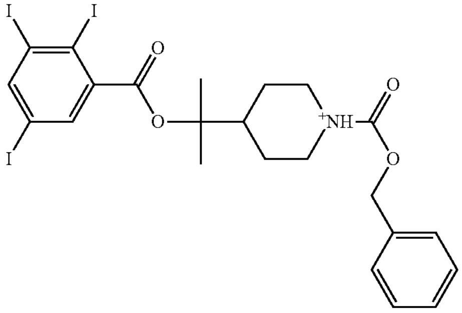
-continued
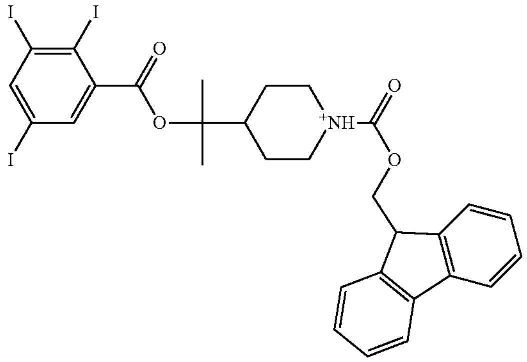
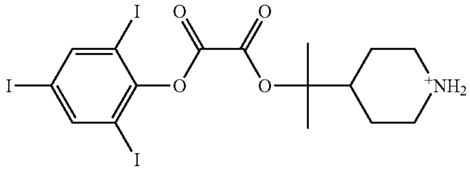
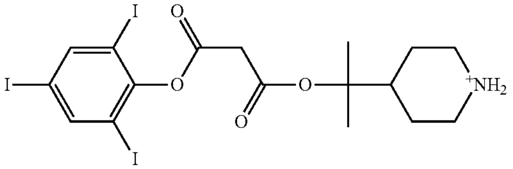
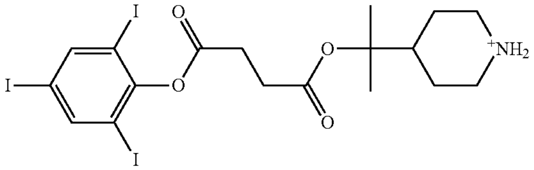
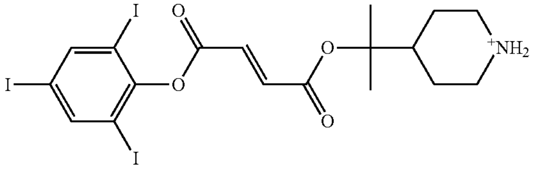
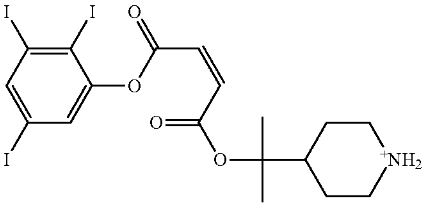
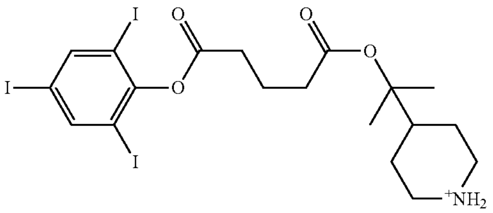
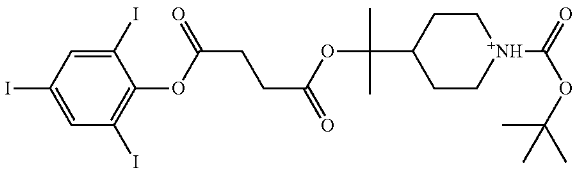

-continued
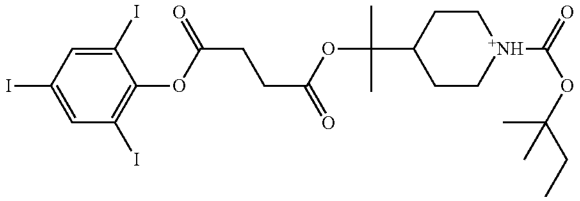
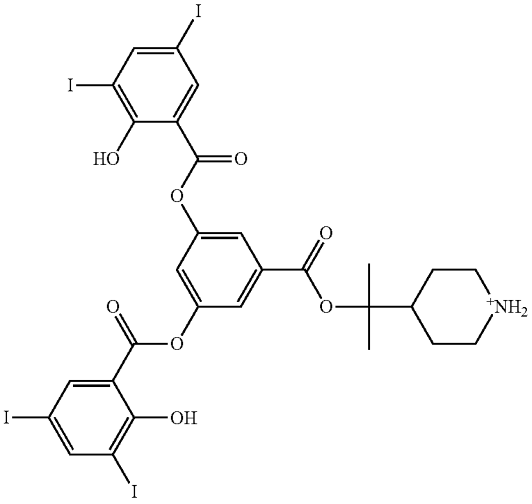
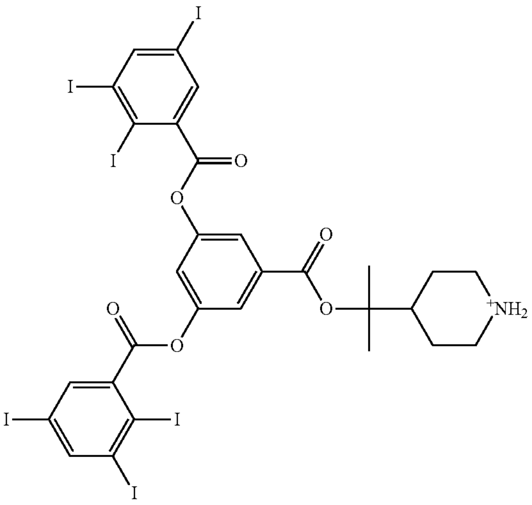
-continued
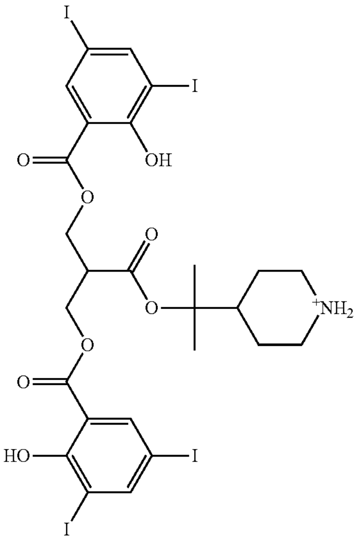
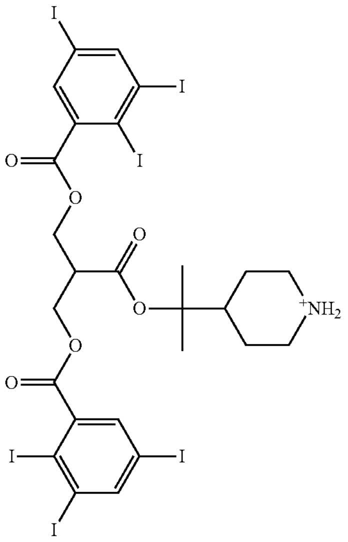
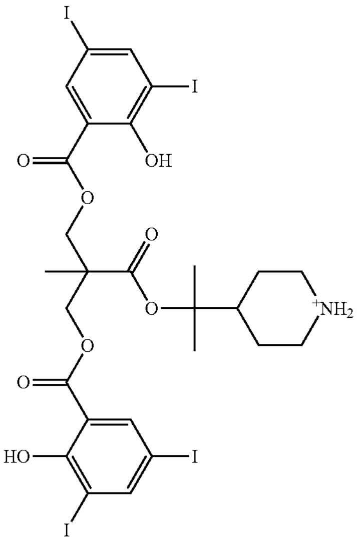

-continued
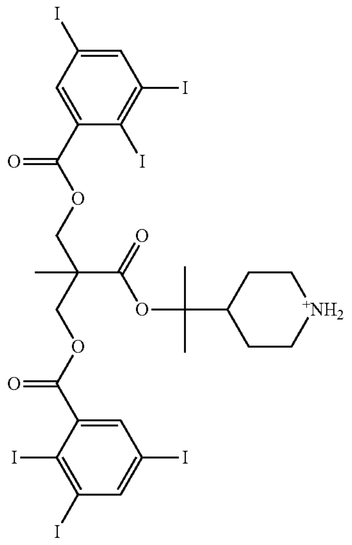
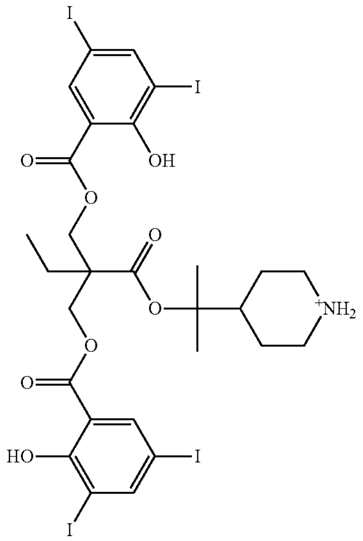
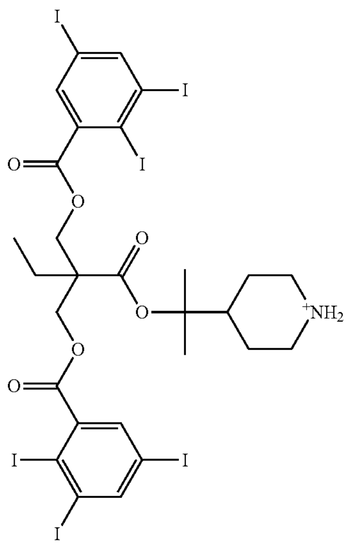
-continued
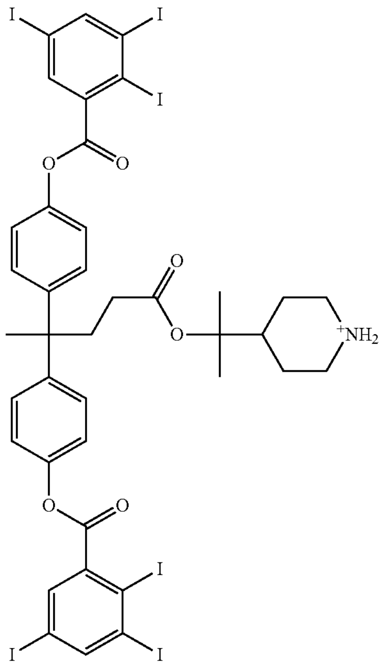
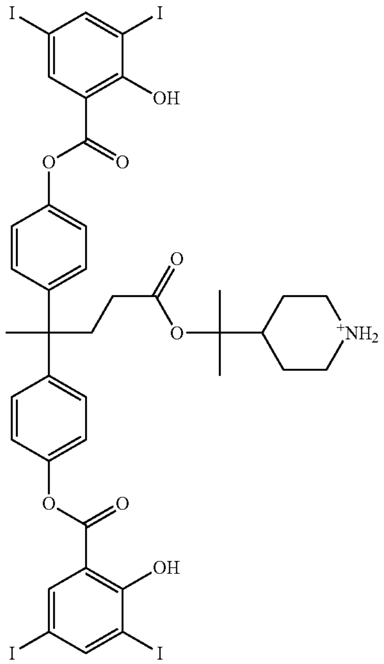
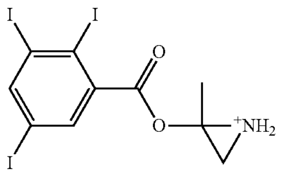
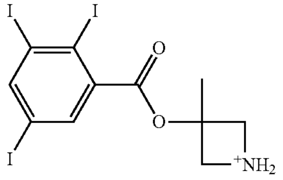

-continued
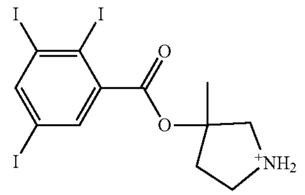
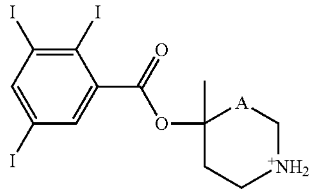
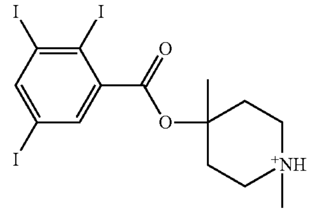
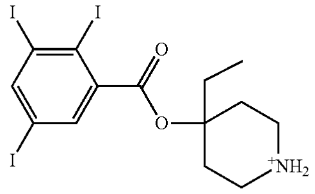
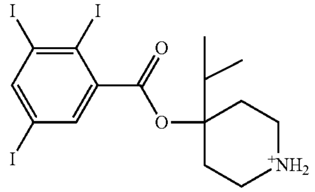
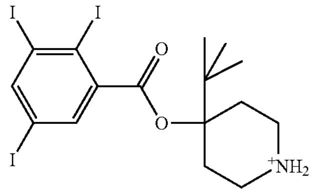
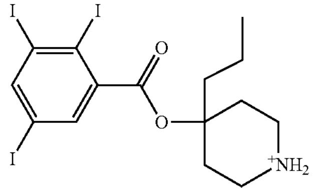
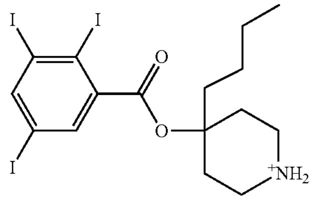
-continued
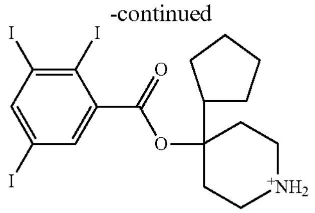
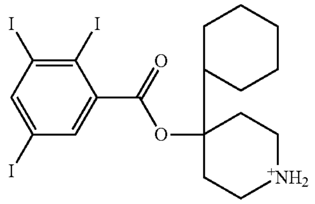
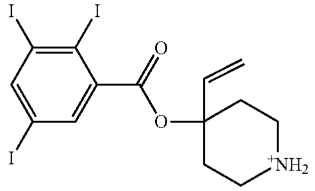
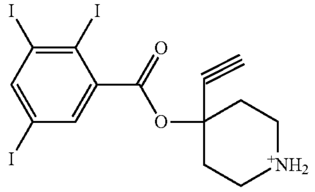
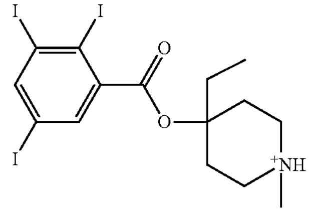
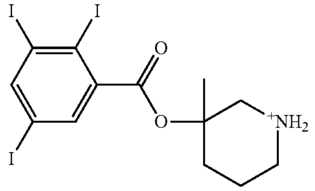
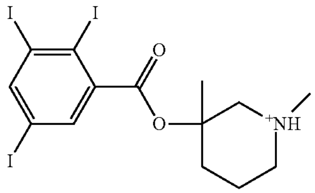
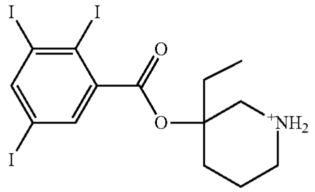
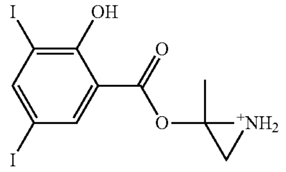

-continued
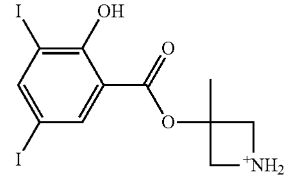
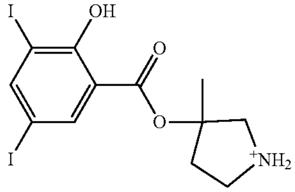
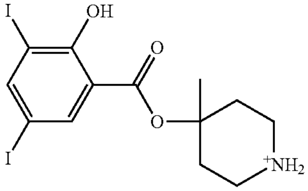
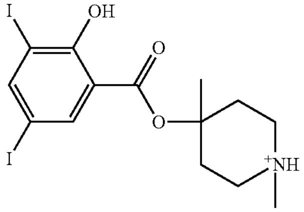
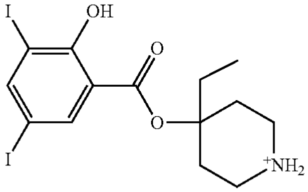
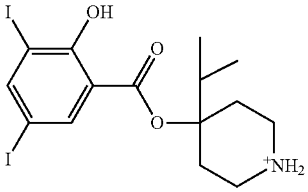
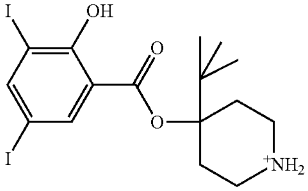
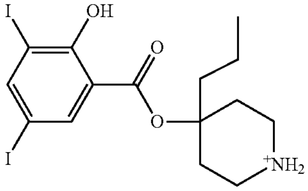
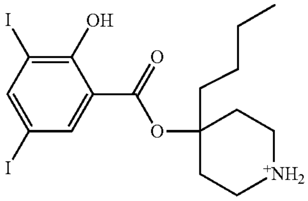
-continued
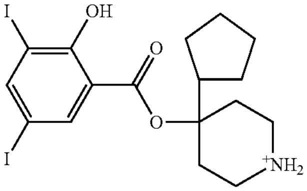
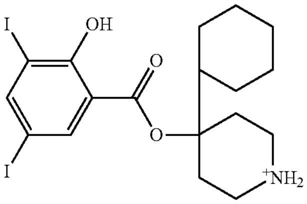
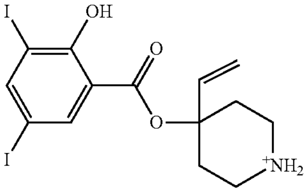
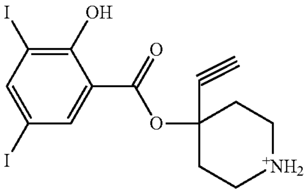
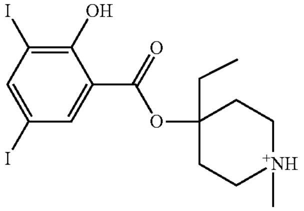
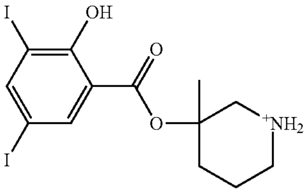
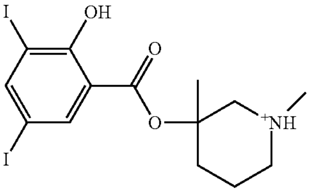
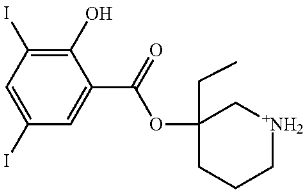

-continued
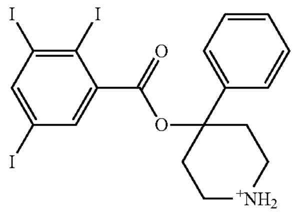
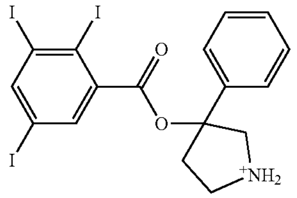
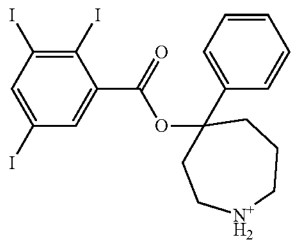
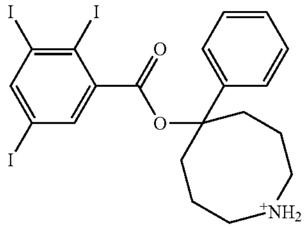
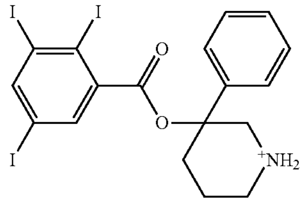
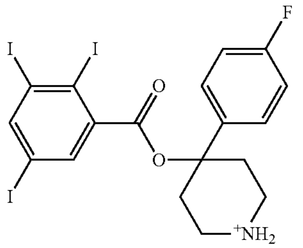
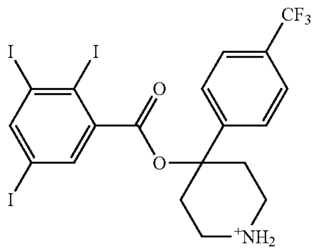
-continued
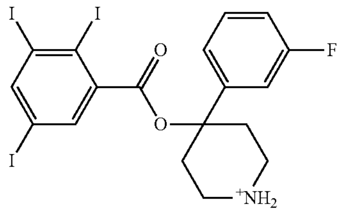
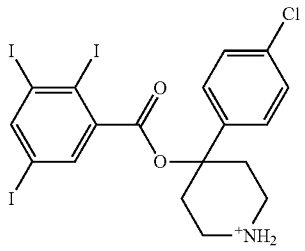
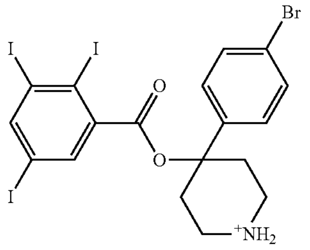
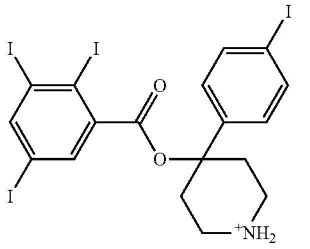
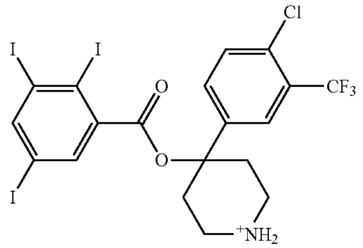
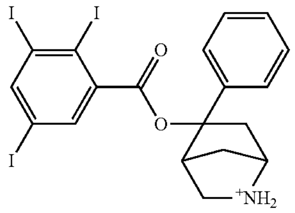
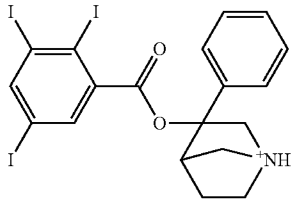

-continued
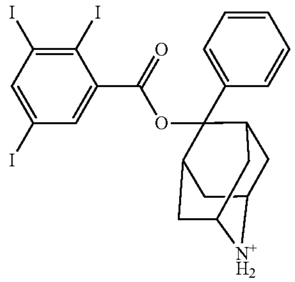
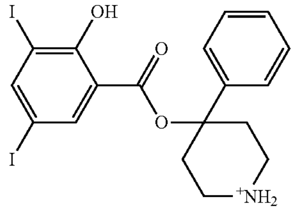
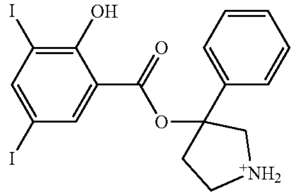
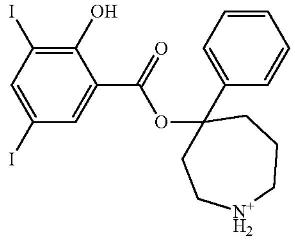
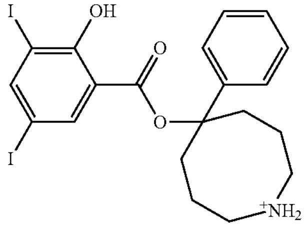
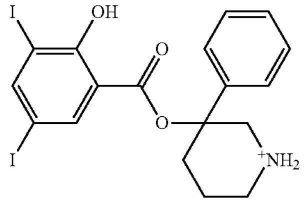
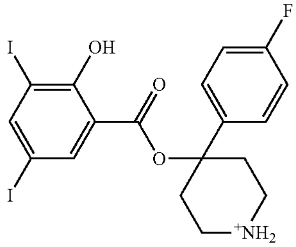
-continued
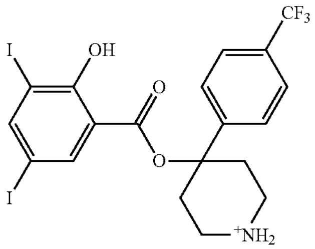
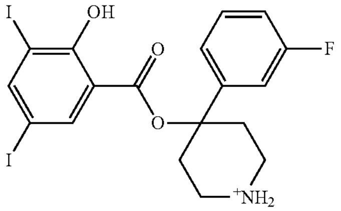
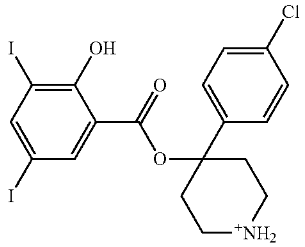
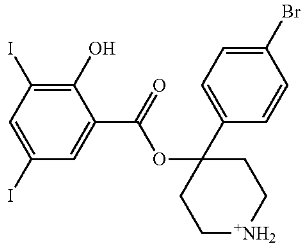
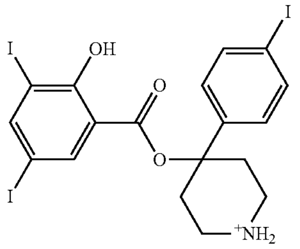
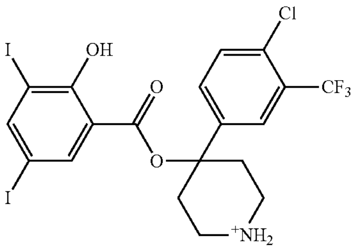
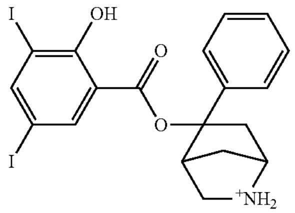

-continued
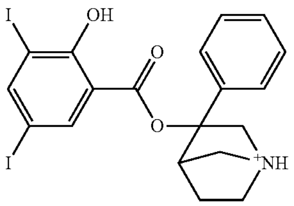
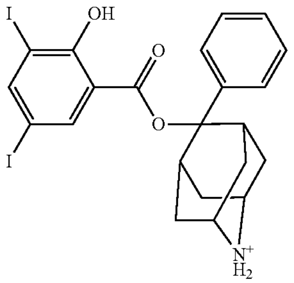
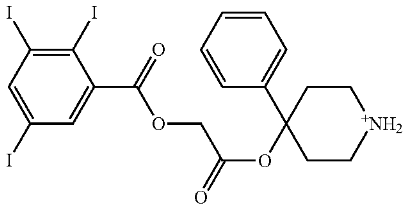
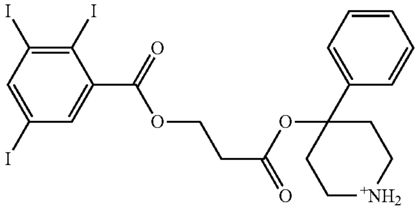
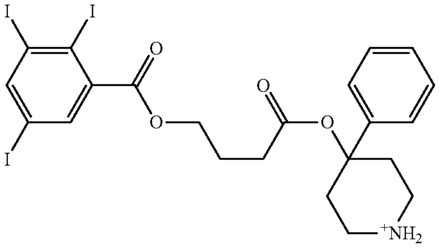
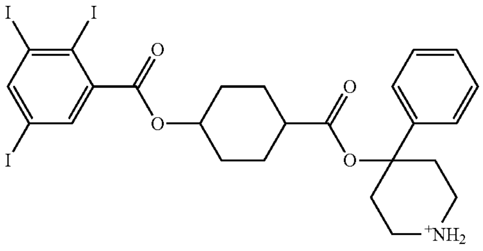
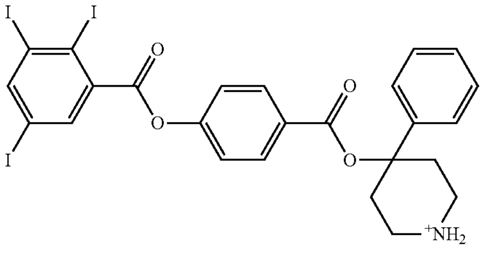
-continued
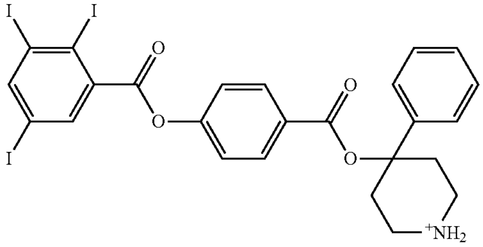
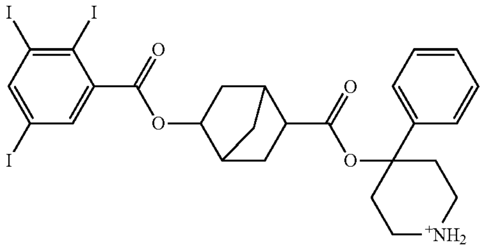
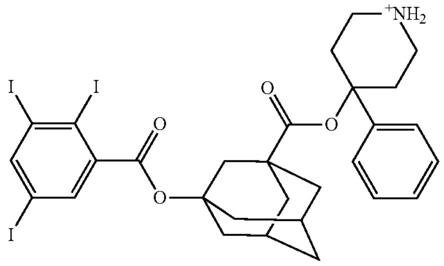
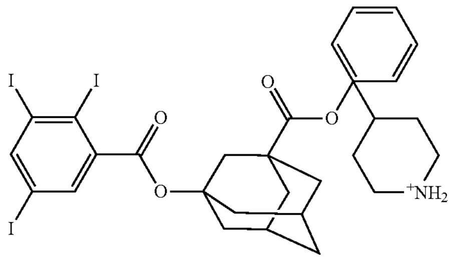
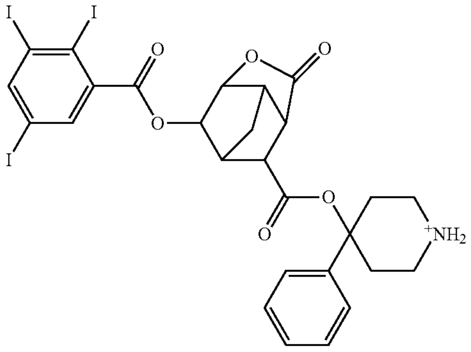
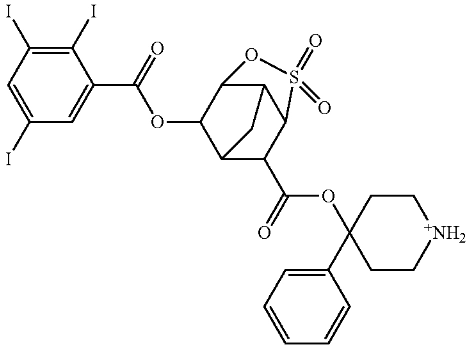

-continued
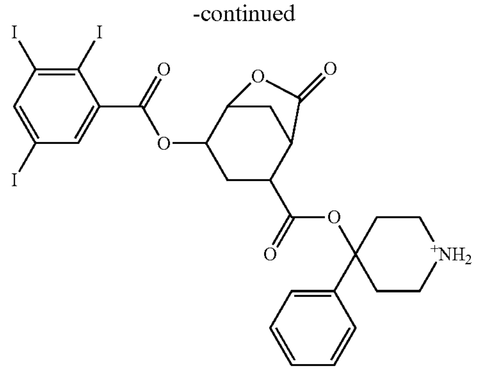
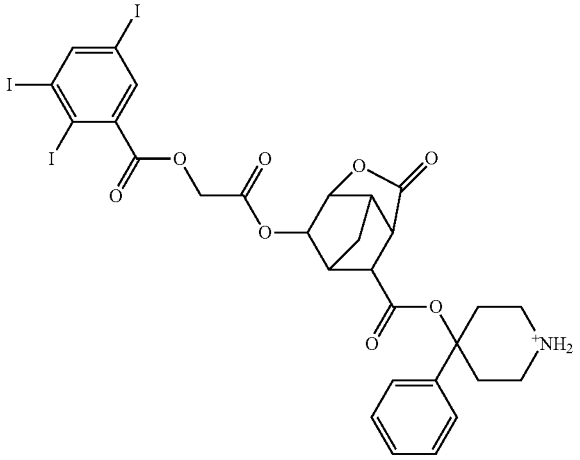
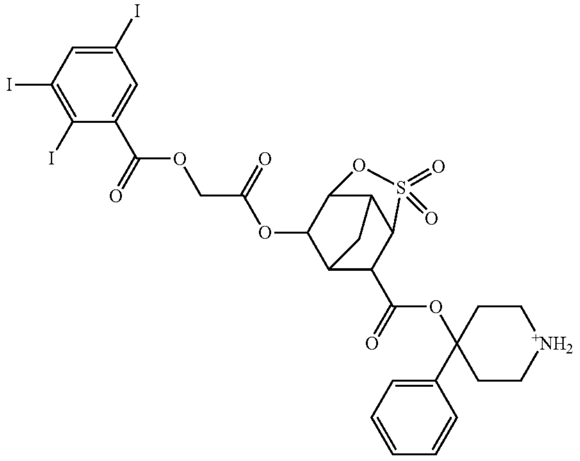
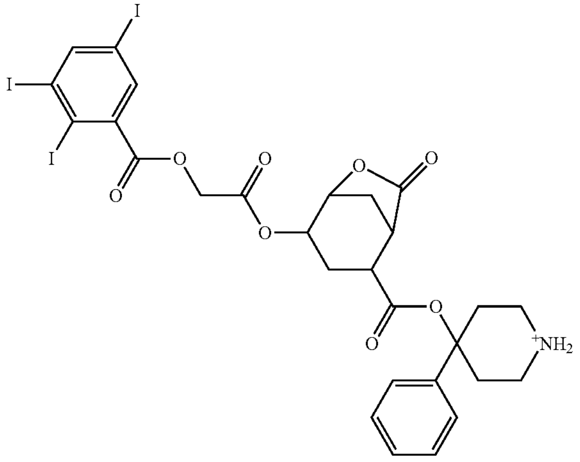
-continued
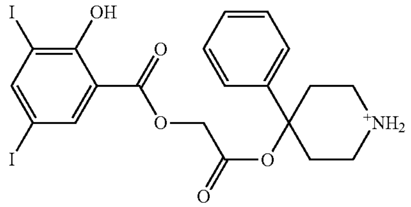
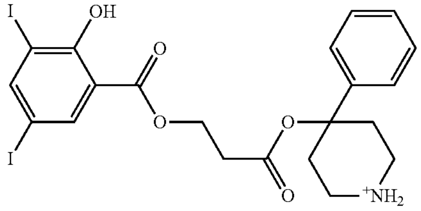
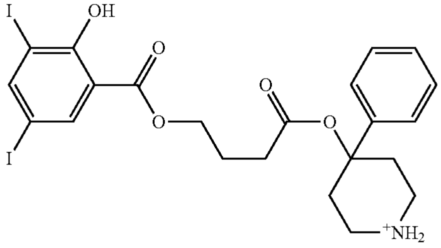
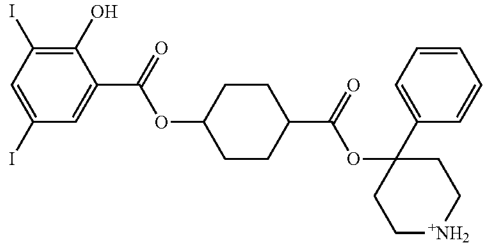
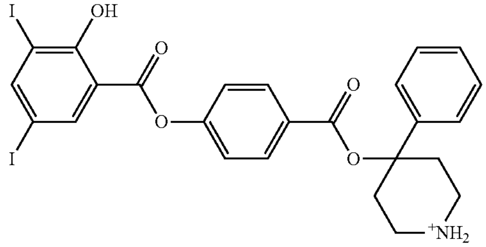
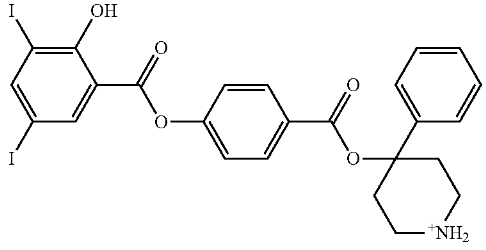
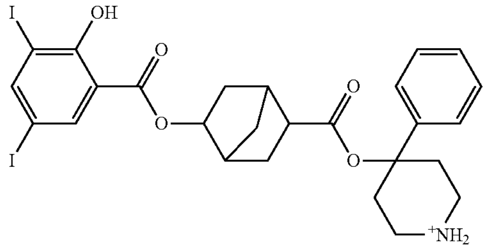

-continued

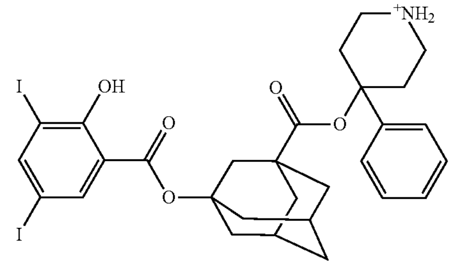

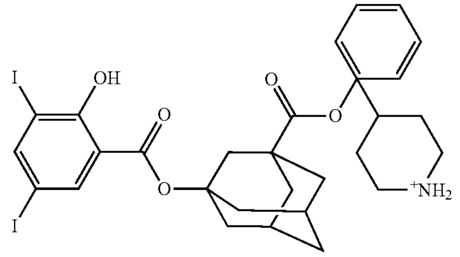

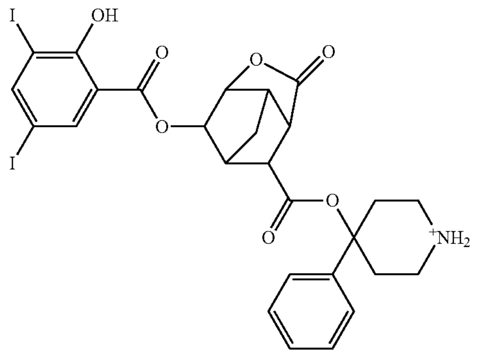

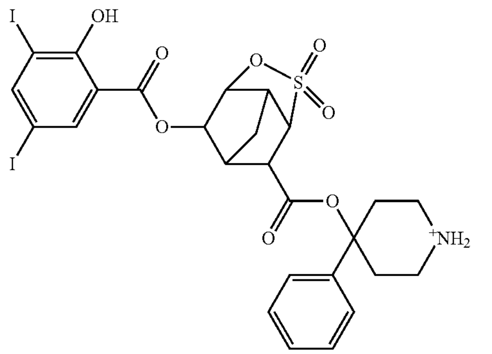

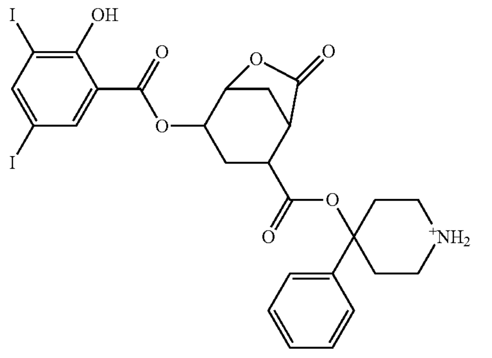

-continued

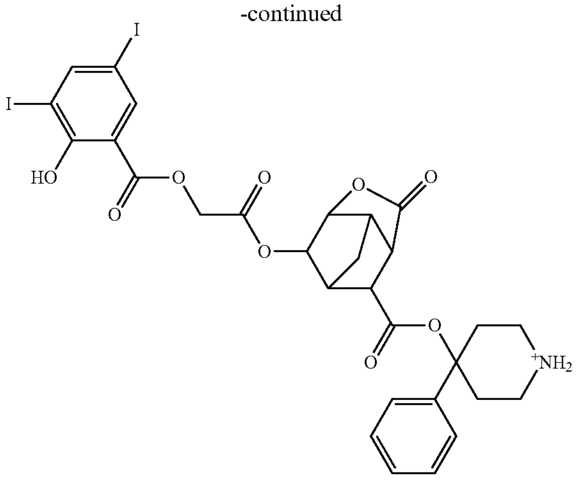

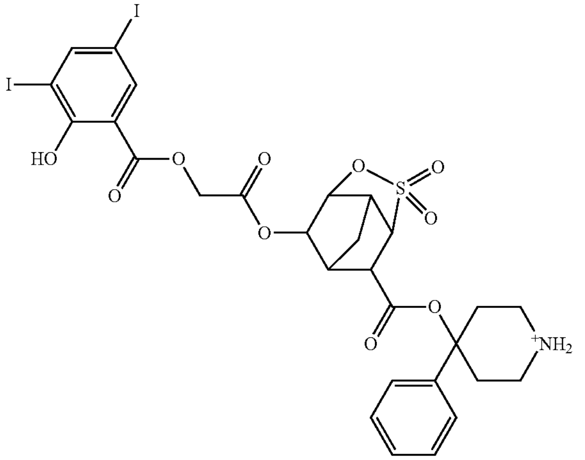

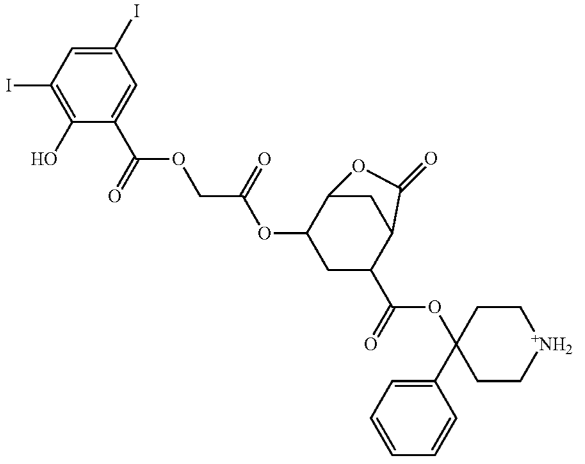

In formula (A), $R^3$ and $R^4$ are each independently a $C_1$-$C_{16}$ hydrocarbyl group, $C_1$-$C_{16}$ fluorinated hydrocarbyl group, $C_1$-$C_{16}$ hydrocarbyloxy group or $C_1$-$C_{16}$ fluorinated hydrocarbyloxy group. At least one of $R^3$ and $R^4$ is a $C_1$-$C_{16}$ fluorinated hydrocarbyl group or $C_1$-$C_{16}$ fluorinated hydrocarbyloxy group. In the hydrocarbyl and hydrocarbyloxy groups, some or all of the hydrogen atoms may be substituted by at least one moiety selected from cyano, nitro, hydroxy, and halogen other than fluorine, and some constituent $—CH_2—$ may be replaced by at least one bond selected from an ether bond, ester bond and thioether bond.

The hydrocarbyl group and hydrocarbyl moiety of the hydrocarbyloxy group represented by $R^3$ and $R^4$ may be saturated or unsaturated and straight, branched or cyclic. Examples thereof include $C_1$-$C_{16}$ alkyl groups such as methyl, ethyl, n-propyl, isopropyl, n-butyl, isobutyl, sec-butyl, tert-butyl, n-pentyl, isopentyl, sec-pentyl, 3-pentyl, tert-pentyl, neopentyl, n-hexyl, n-octyl, n-nonyl, n-decyl, undecyl, dodecyl, tridecyl, tetradecyl, pentadecyl, and hexadecyl; $C_3$-$C_{16}$ cyclic saturated hydrocarbyl groups such as cyclopropyl, cyclobutyl, cyclopentyl, cyclohexyl, adamantyl, norbornyl, cyclopropylmethyl, cyclopropylethyl, cyclobutylmethyl, cyclobutylethyl, cyclopentylmethyl, cyclopentylethyl, cyclohexylmethyl, cyclohexylethyl, methylcyclopropyl, methylcyclobutyl, methylcyclopentyl, methylcyclohexyl, ethylcyclopropyl, ethylcyclobutyl, ethylcyclopentyl, and ethylcyclohexyl; $C_2$-$C_{16}$ alkenyl groups such as vinyl, 1-propenyl, 2-propenyl, butenyl, pentenyl, hexenyl, heptenyl, nonenyl, decenyl, undecenyl, dodecenyl, tridecenyl, tetradecenyl, pentadecenyl, and hexadecenyl; $C_2$-$C_{16}$ alkynyl groups such as ethynyl, propynyl, butynyl, pentynyl, hexynyl heptynyl, octynyl, nonynyl, decynyl, undecynyl, dodecynyl, tridecynyl, tetradecynyl, pentadecynyl, and hexadecynyl; $C_3$-$C_{16}$ cyclic unsaturated aliphatic hydrocarbyl groups such as cyclopentenyl, cyclohexenyl, methylcyclopentenyl, methylcyclohexenyl, ethylcyclopentenyl, ethylcyclohexenyl, norbornenyl; $C_6$-$C_{16}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl; $C_7$-$C_{16}$ aralkyl groups such as benzyl, phenethyl, phenylpropyl, phenylbutyl, 1-naphthylmethyl, 2-naphthylmethyl, 9-fluorenylmethyl, 1-naphthylethyl, 2-naphthylethyl, 9-fluorenylethyl; and combinations thereof.

The fluorinated hydrocarbyl group and fluorinated hydrocarbyl moiety of the fluorinated hydrocarbyloxy group represented by $R^3$ and $R^4$ may be saturated or unsaturated and straight, branched or cyclic. Examples thereof include the groups exemplified above for the hydrocarbyl group and hydrocarbyl moiety of the hydrocarbyloxy group represented by $R^3$ and $R^4$, in which at least one hydrogen is substituted by fluorine, for instance, monofluoromethyl, difluoromethyl, trifluoromethyl, 2,2,2-trifluoroethyl, 1,1,2,2,2-pentafluoroethyl, 1,1,1,3,3,3-hexafluoro-2-propyl, 1,1,2,2,3,3,3-heptafluoropropyl, 1,1,2,2,3,3,4,4,4-nonafluorobutyl, 2-fluorophenyl, 3-fluorophenyl, 4-fluorophenyl, 2,4-difluorophenyl, 2,3-difluorophenyl, 3,4-difluorophenyl, 3,5-difluorophenyl, 2,4,5-trifluorophenyl, 2,3,4-trifluorophenyl, 2,3,4,5-tetrafluorophenyl, 2,3,5,6-tetrafluorophenyl, 2,3,4,5,6-pentafluorophenyl, pentafluoromethylphenyl, 2-trifluoromethylphenyl, 3-trifluoromethylphenyl, 4-trifluoromethylphenyl, and 2,4,5-trifluorophenyl.

In formula (A), $X^2$ is —C(H)= or —N=.

Examples of the anion (derived from the fluorinated 1,3-diketone compound, fluorinated β-keto ester compound, or fluorinated imide compound) of salt compound A are shown below, but not limited thereto.

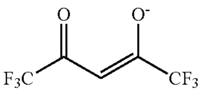
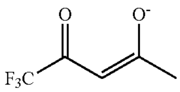
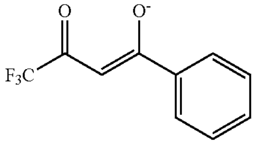
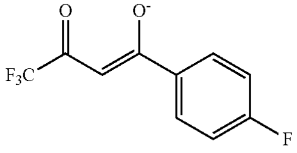

-continued

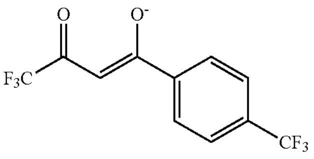
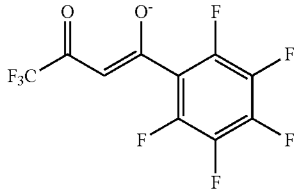
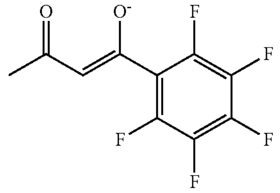
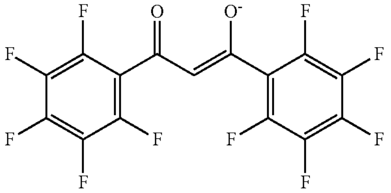
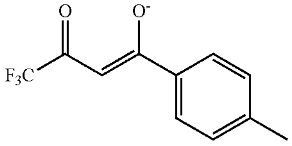
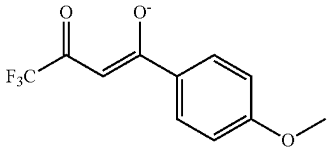
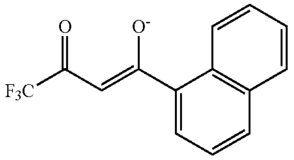
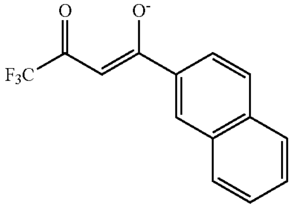
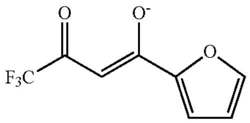
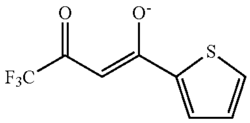
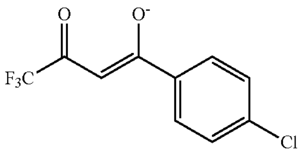

-continued
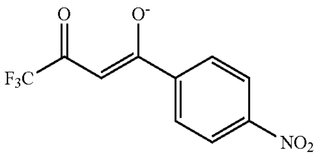
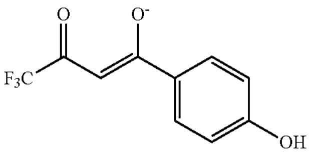
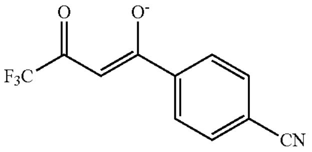
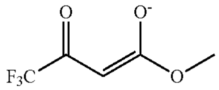
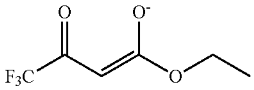
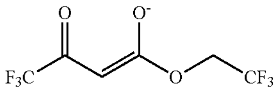
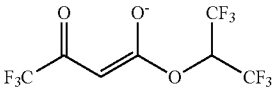
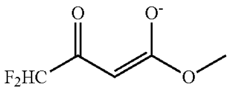
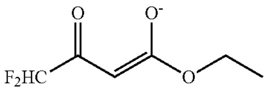
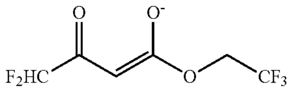
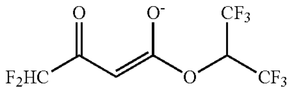
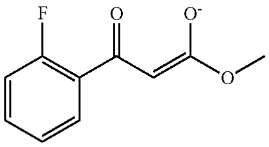
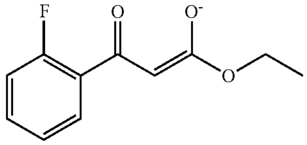
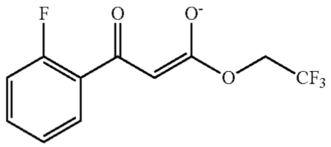
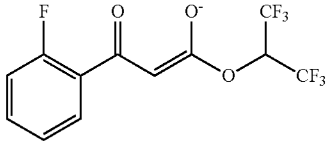
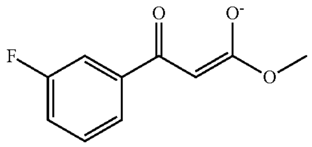
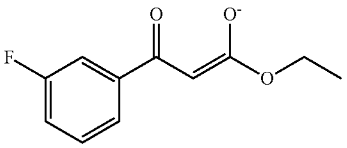
-continued
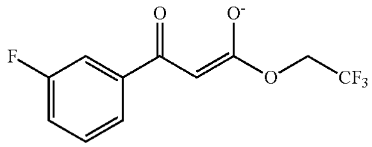
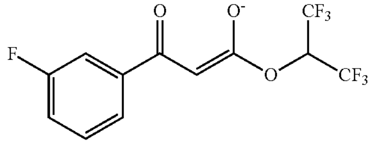
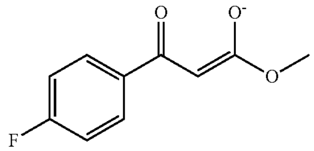
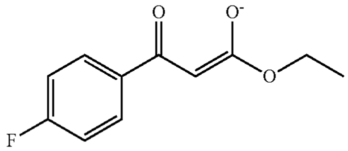
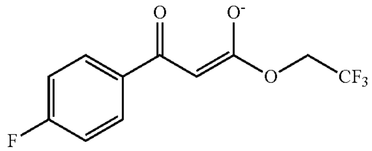
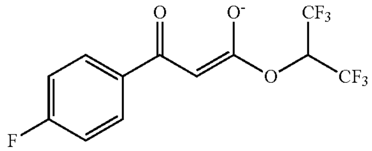
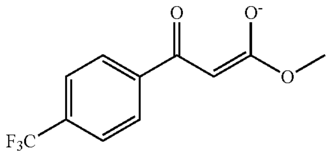
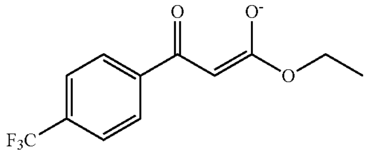
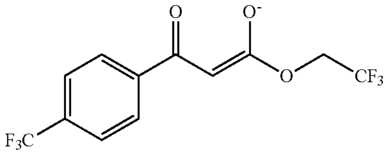
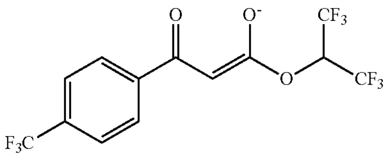
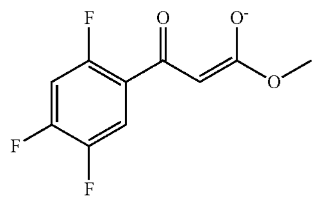

-continued

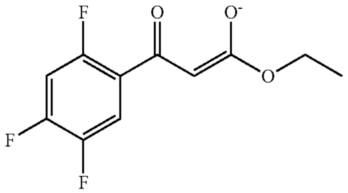

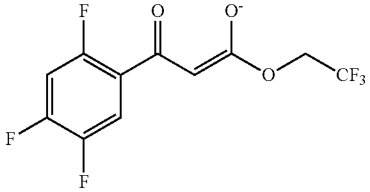

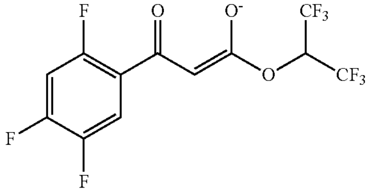

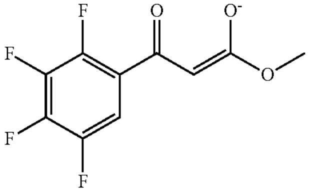

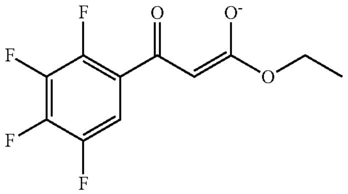

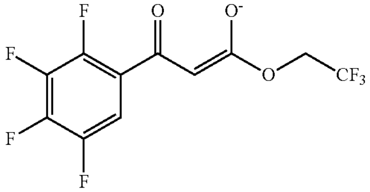

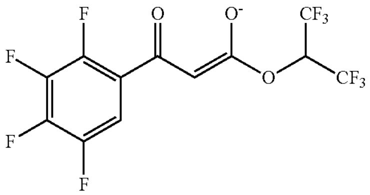

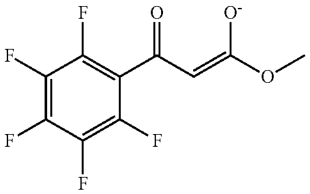

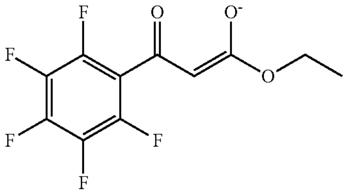

-continued

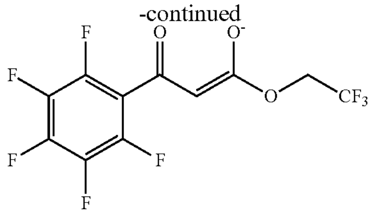

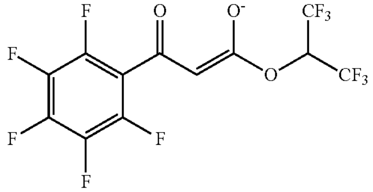

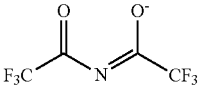

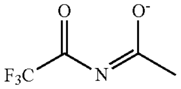

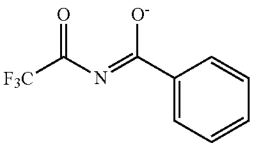

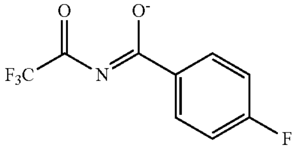

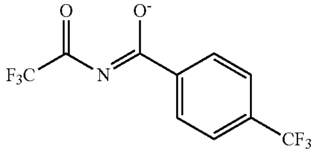

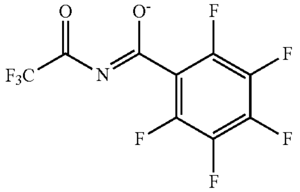

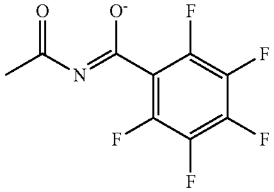

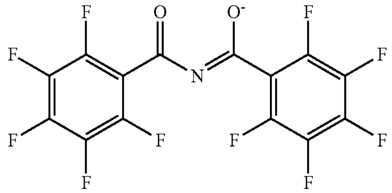 [SMILES: O=C(/N=C(\[O-])c1c(F)c(F)c(F)c(F)c1F)c1c(F)c(F)c(F)c(F)c1F]

The salt compound A may be synthesized, for example, by neutralization reaction of a nitrogen-containing compound having an iodized aromatic ring bonded to the nitrogen atom via a $C_1$-$C_{20}$ hydrocarbon group which may contain an ester bond and/or ether bond with a fluorinated 1,3-diketone compound, fluorinated β-keto ester compound, or fluorinated imide compound. It is acceptable that the nitrogen-containing compound and the fluorinated 1,3-diketone compound, fluorinated β-keto ester compound, or fluorinated imide compound are added along with other components during preparation of a resist composition and neutralization reaction takes place therein so that the resist composition may eventually contain salt compound A.

The salt compound A functions as a quencher having a sensitizing effect in a resist composition. While conventional quenchers serve to control acid diffusion to reduce sensitivity so that LWR and CDU are aggravated, salt compound A has an acid diffusion controlling effect due to the amino group and the iodine atom with a large atomic weight and a sensitivity-increasing effect due to the sensitizing effect of EUV-absorptive iodine atom. The repulsion effect of the fluorinated 1,3-diketone compound, fluorinated β-keto ester compound or fluorinated imide compound prevents the quencher from agglomerating together. This enables to distribute the quencher uniformly and to make the diffusion distance of acid uniform on a nanometer level, leading to improvements in LWR and CDU of resist patterns.

In the resist composition, salt compound A is preferably present in an amount of 0.001 to 50 parts by weight, more preferably 0.01 to 40 parts by weight per 100 parts by weight of the base polymer, as viewed from sensitivity and acid diffusion suppressing effect.

Because of the lack of photosensitivity, salt compound A is not decomposed upon exposure. It is thus effective for suppressing acid diffusion in the exposed region.

Base Polymer

Where the resist composition is of positive tone, the base polymer comprises repeat units containing an acid labile group, preferably repeat units having the formula (a1) or repeat units having the formula (a2). These units are simply referred to as repeat units (a1) and (a2).

(a1)

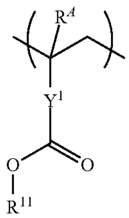

(a2)

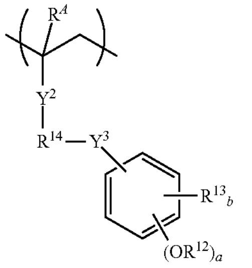

In formulae (a1) and (a2), $R^A$ is each independently hydrogen or methyl. $Y^1$ is a single bond, phenylene, naphthylene, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ are each independently an acid labile group. $R^{13}$ is fluorine, trifluoromethyl, cyano, $C_1$-$C_6$ saturated hydrocarbyl group, $C_1$-$C_6$ saturated hydrocarbyloxy group, $C_2$-$C_7$ saturated hydrocarbylcarbonyl group, $C_2$-$C_7$ saturated hydrocarbylcarbonyloxy group, or $C_2$-$C_7$ saturated hydrocarbyloxycarbonyl group. $R^{14}$ is a single bond or a $C_1$-$C_6$ alkanediyl group in which some constituent —$CH_2$— may be replaced by an ether bond or ester bond. The subscript "a" is 1 or 2, b is an integer of 0 to 4, and a+b is from 1 to 5.

Examples of the monomer from which the repeat units (a1) are derived are shown below, but not limited thereto. $R^A$ and $R^{11}$ are as defined above.

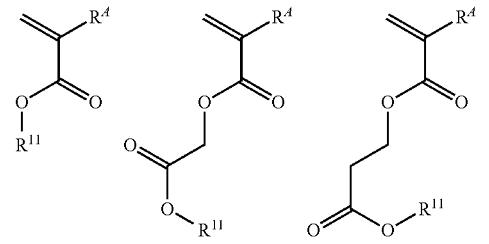

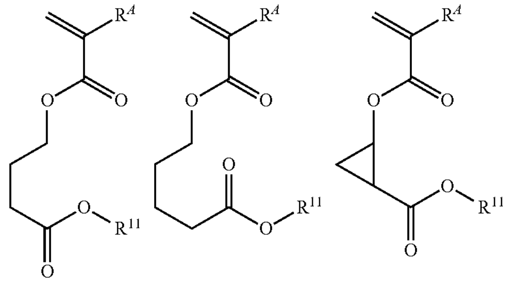

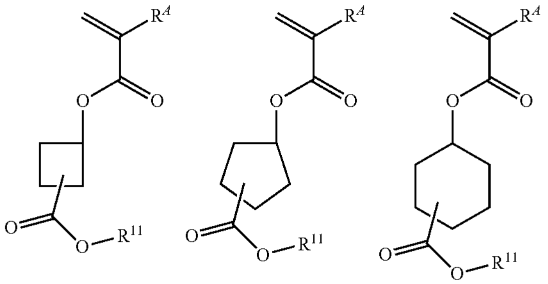

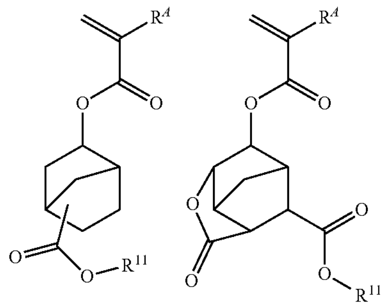

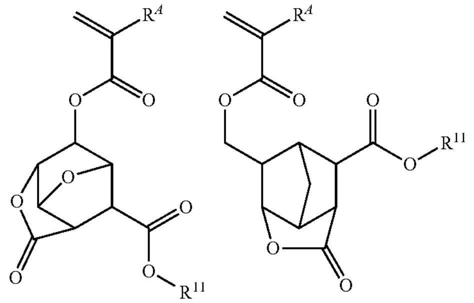

-continued
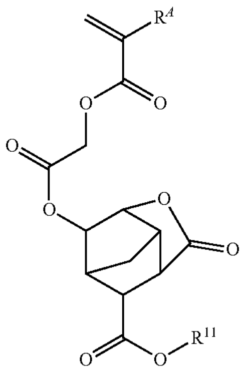
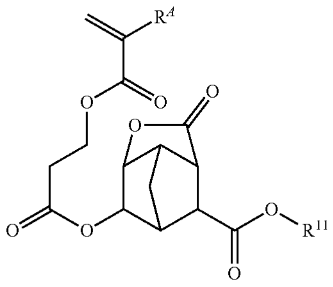
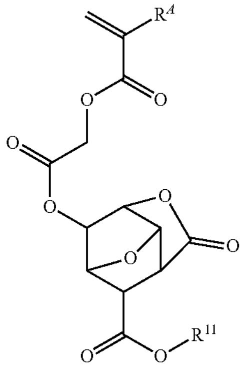
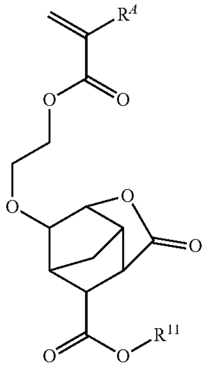
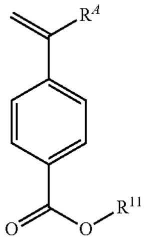
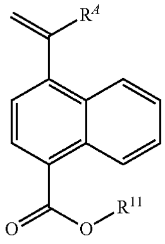
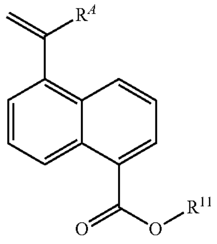
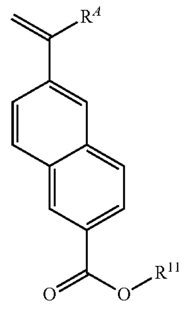
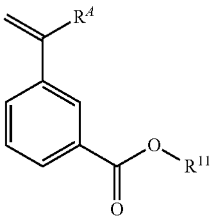
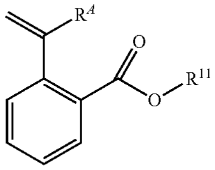
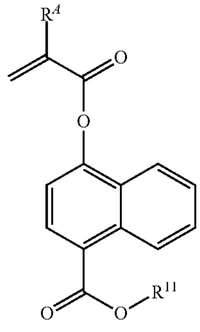
-continued
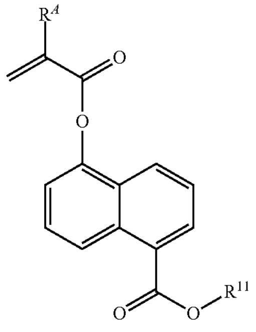
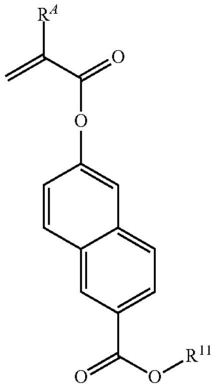
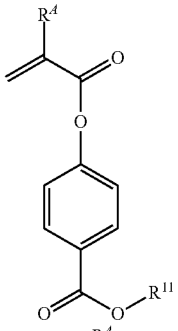
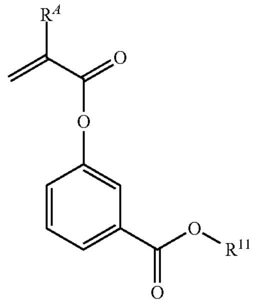
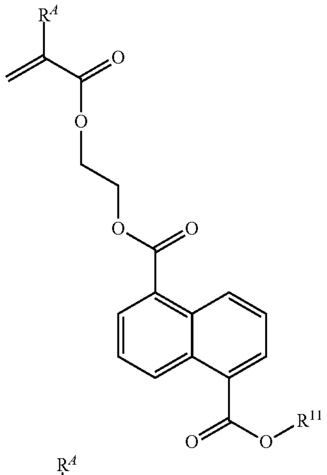
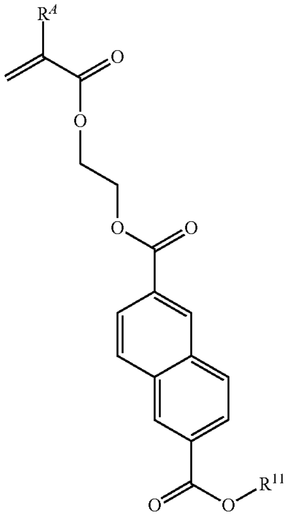

Examples of the monomer from which the repeat units (a2) are derived are shown below, but not limited thereto. $R^A$ and $R^{12}$ are as defined above.

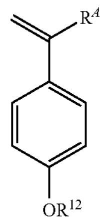
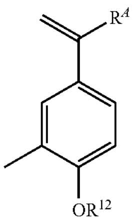
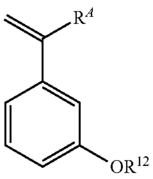
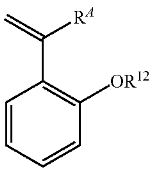

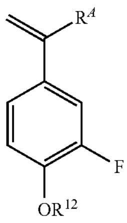
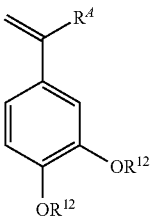
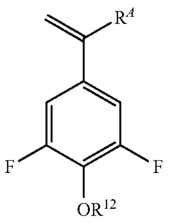

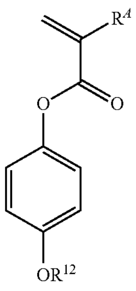
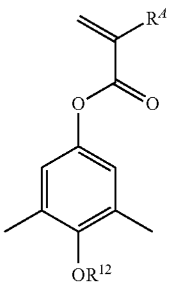
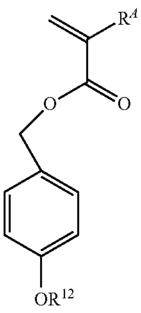

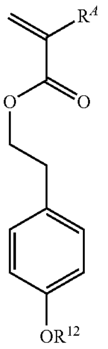
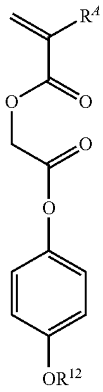
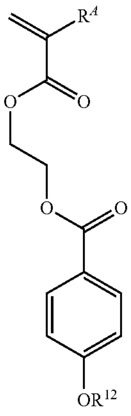

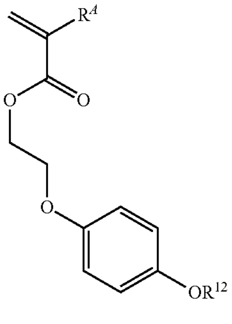
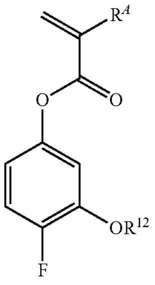
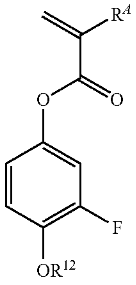

-continued

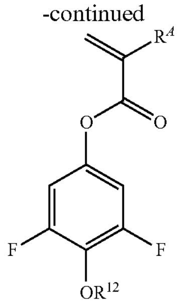

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

(AL-1)

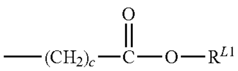

(AL-2)

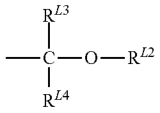

(AL-3)

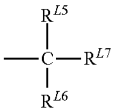

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ saturated hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached. The ring preferably contains 4 to 16 carbon atoms and is typically alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia. $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached. The ring preferably contains 4 to 16 carbon atoms and is typically alicyclic.

The base polymer may further comprise repeat units (b) having a phenolic hydroxy group as an adhesive group.

Examples of suitable monomers from which repeat units (b) are derived are given below, but not limited thereto. Herein $R^A$ is as defined above.

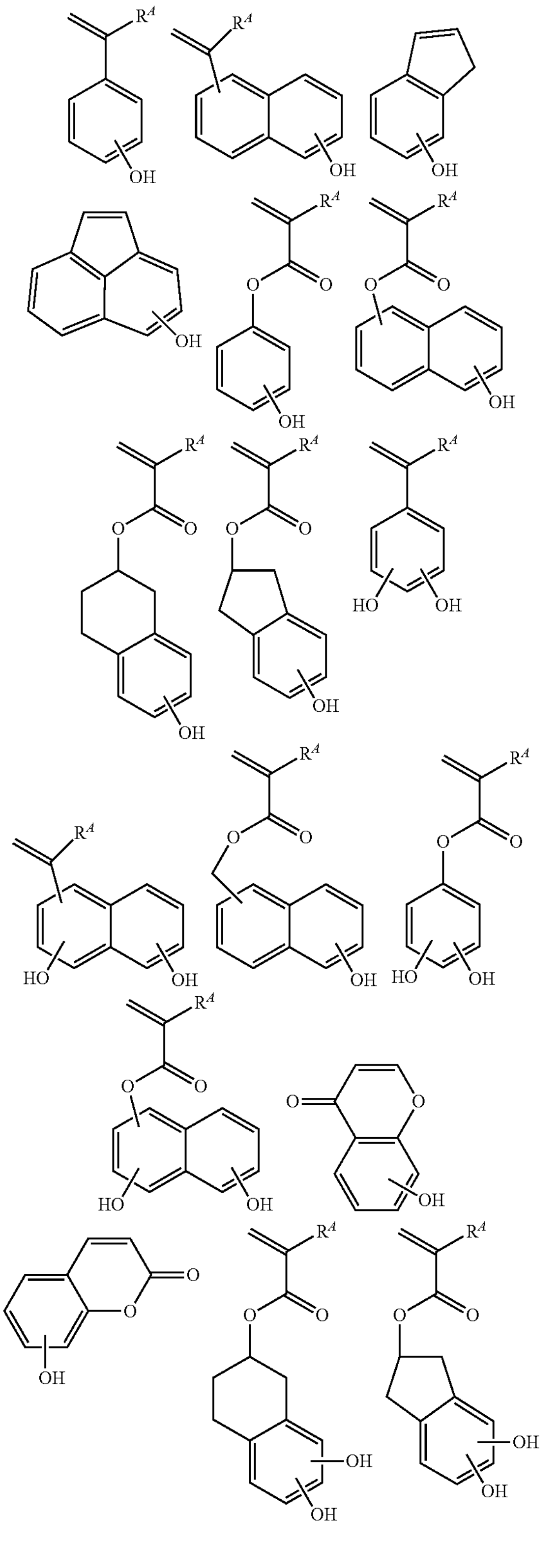

The base polymer may further contain repeat units (c) having another adhesive group selected from hydroxy group (other than the foregoing phenolic hydroxy), lactone ring, sultone ring, ether bond, ester bond, sulfonate bond, carbonyl group, sulfonyl group, cyano group, and carboxy group. Examples of suitable monomers from which repeat units (c) are derived are given below, but not limited thereto. Herein $R^A$ is as defined above.

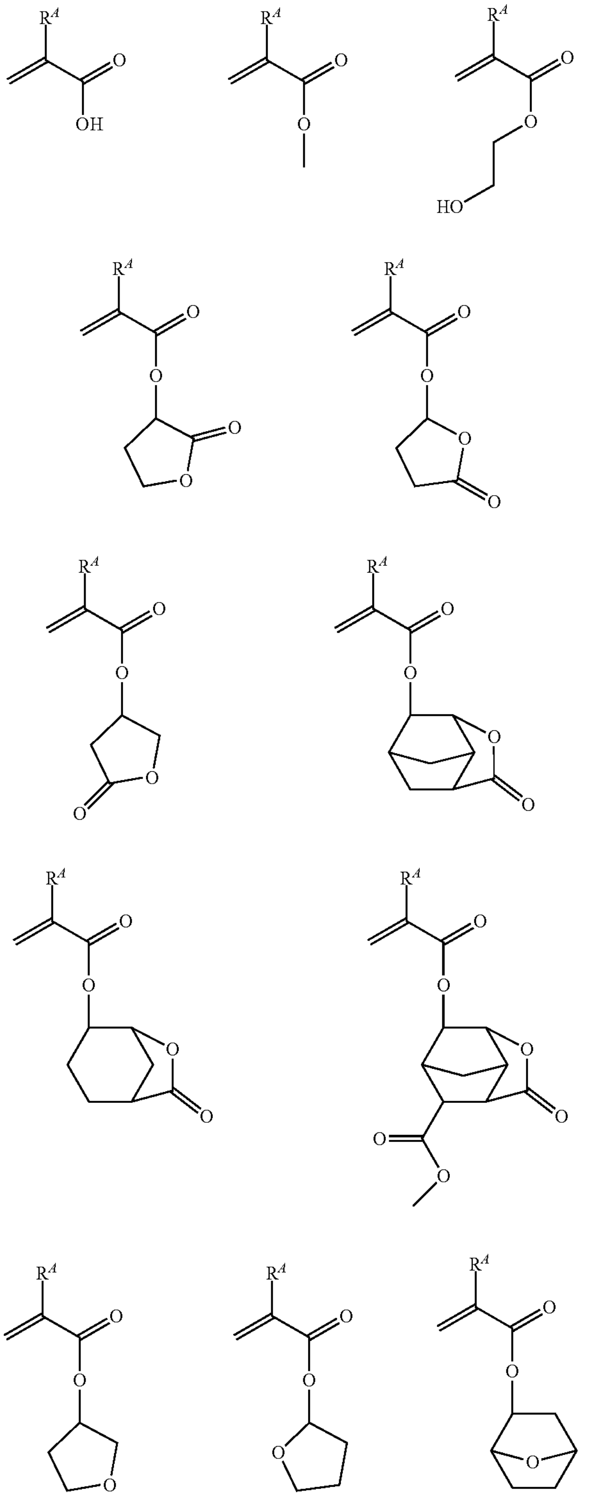

-continued
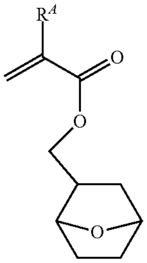
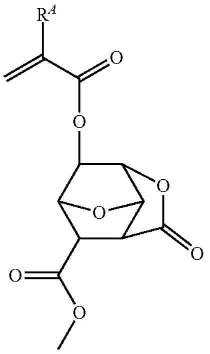
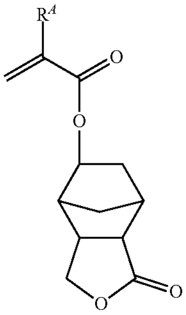
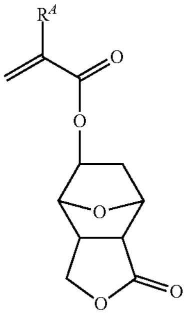
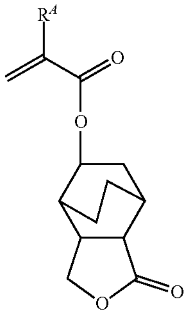
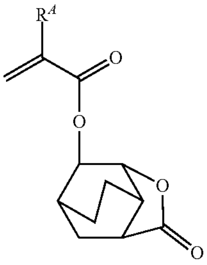
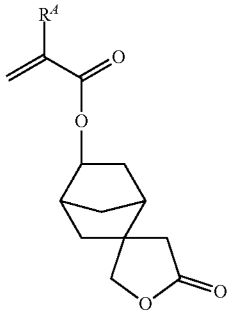
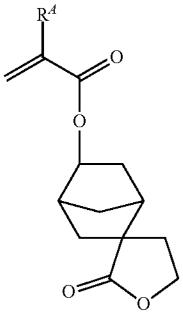
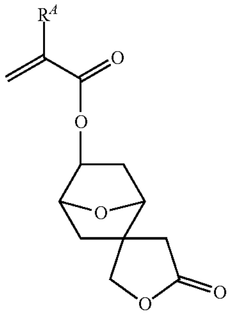
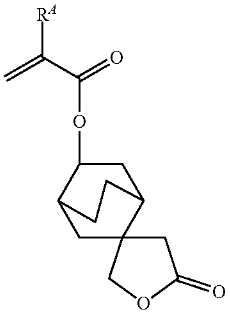
-continued
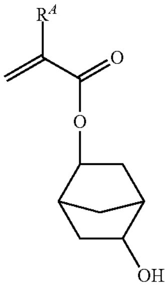
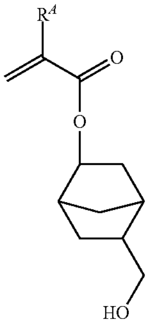
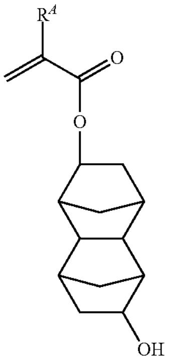
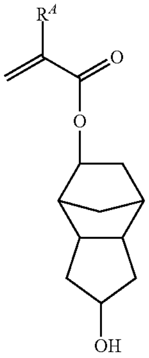
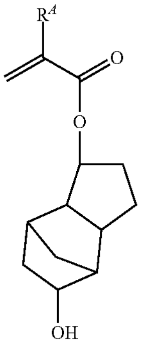
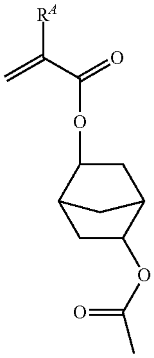
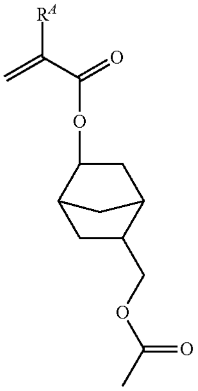
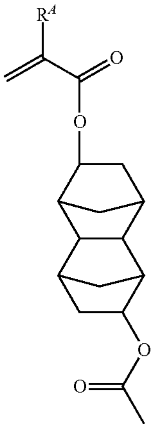

-continued
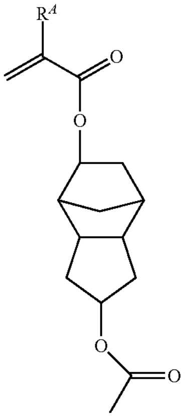
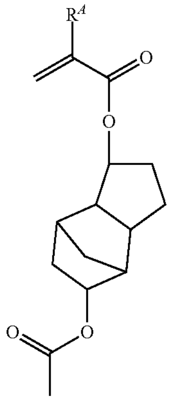
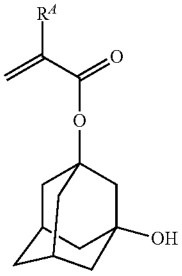
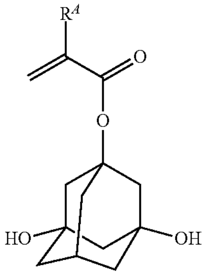
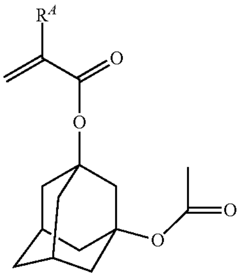
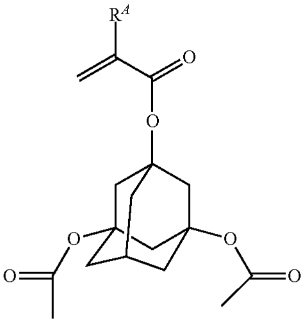
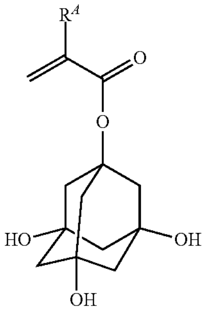
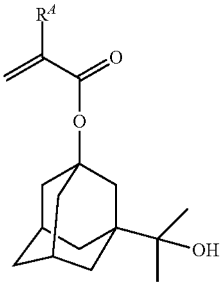
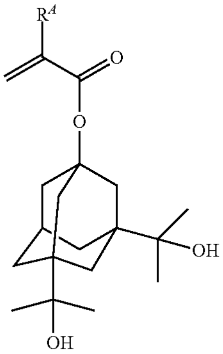
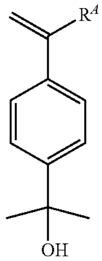
-continued
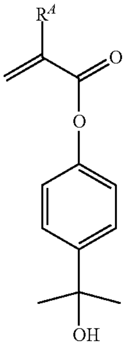
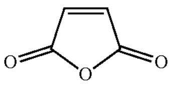
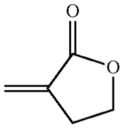
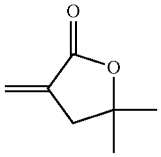
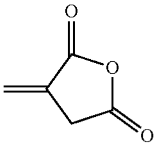
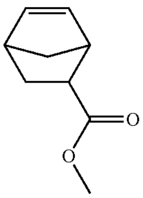
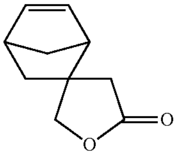
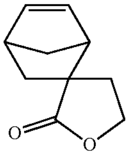
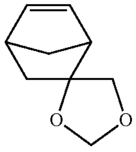
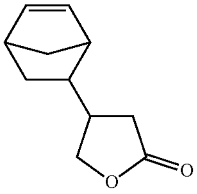
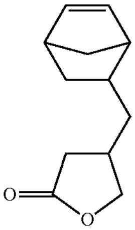
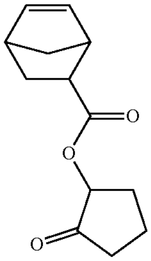
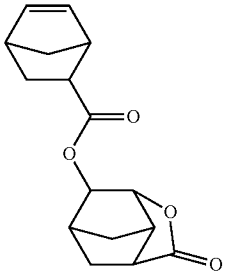
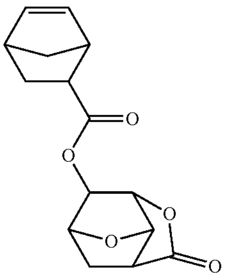
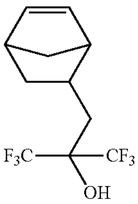
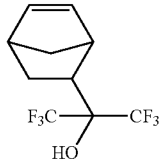
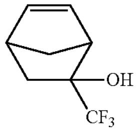
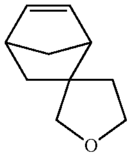

-continued
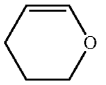
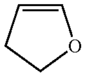
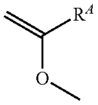
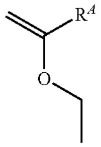
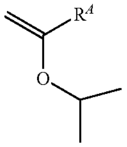
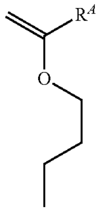
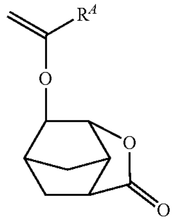
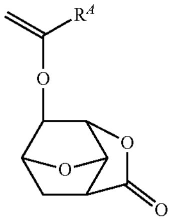
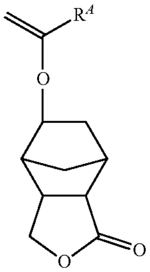
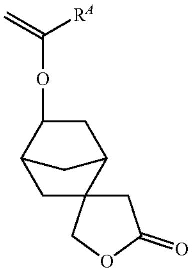
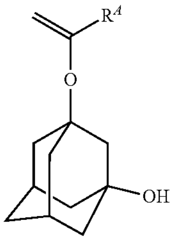
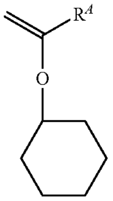
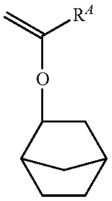
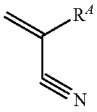
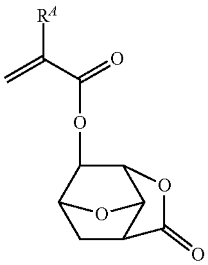
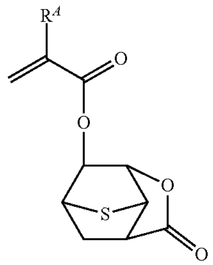
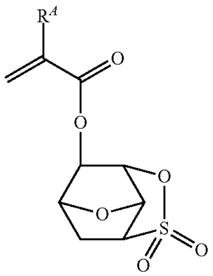
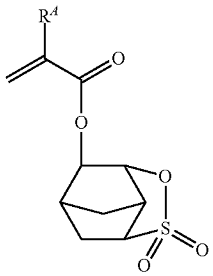
-continued
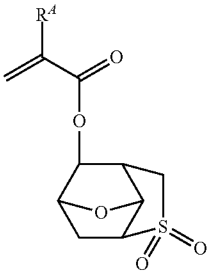
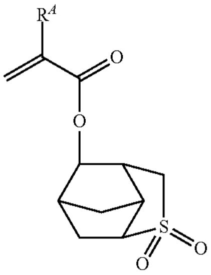
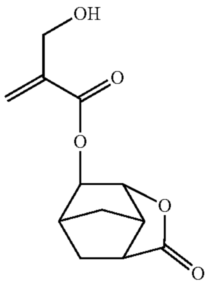
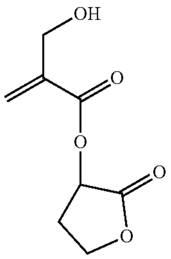
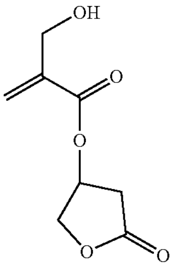
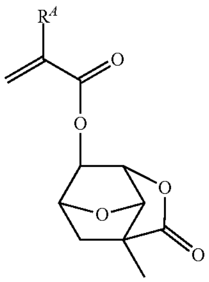
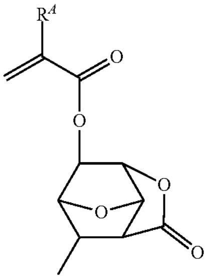
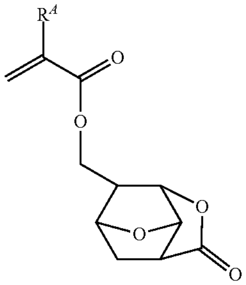
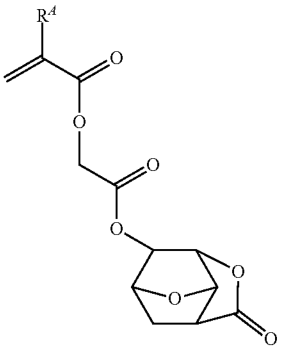
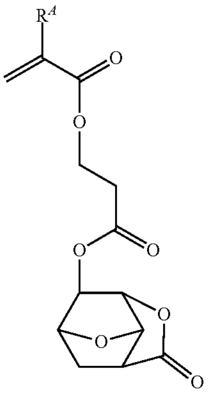

-continued
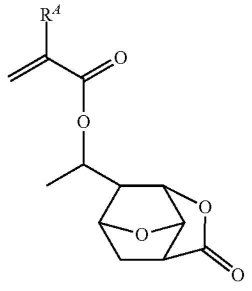
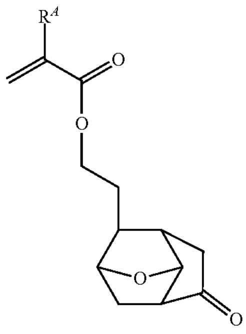
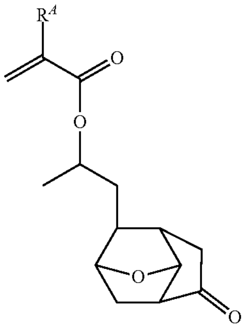
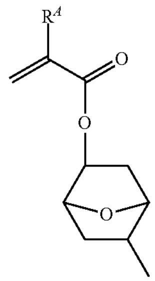
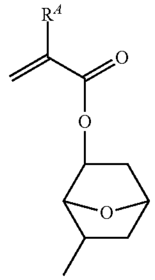
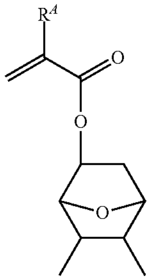
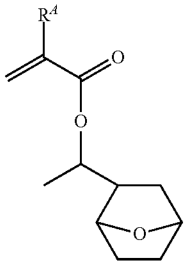
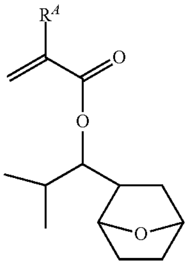
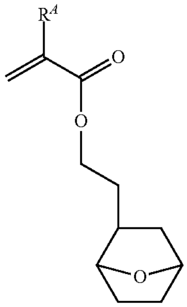
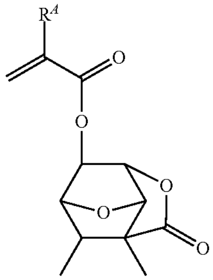
-continued
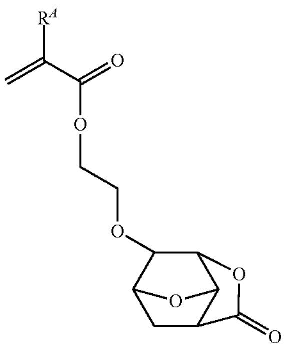
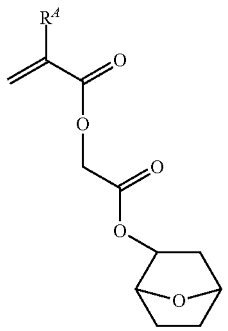
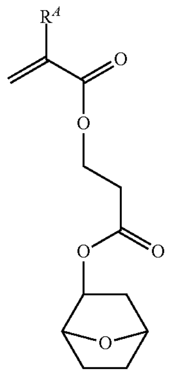
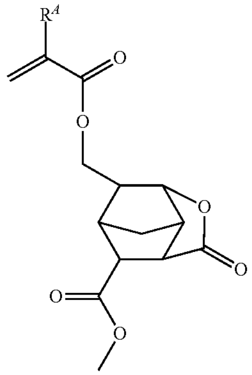
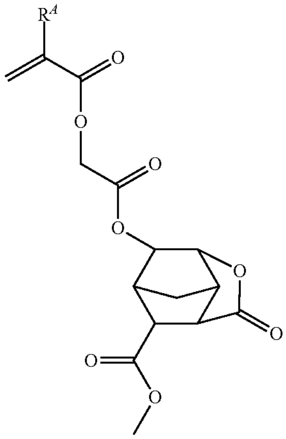
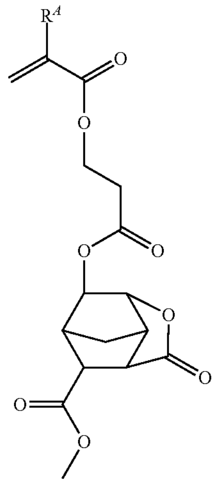
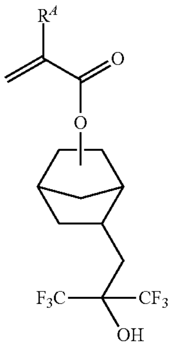
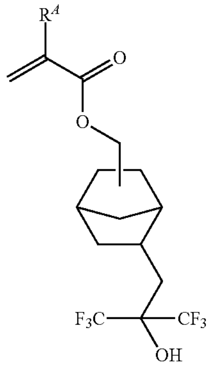

-continued
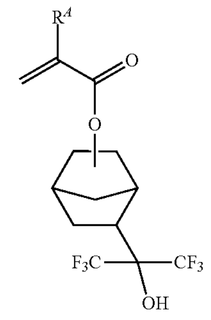
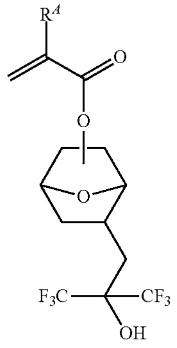
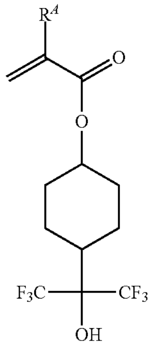
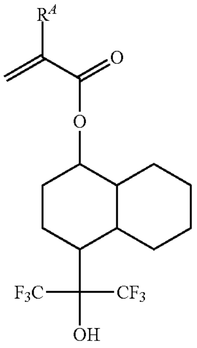
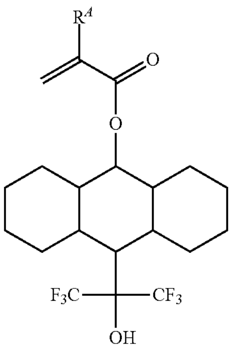
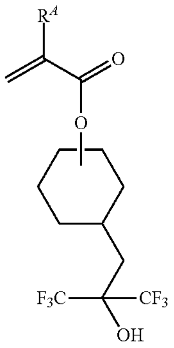
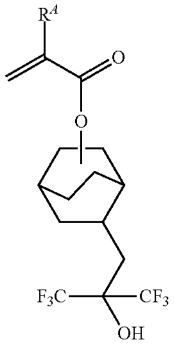
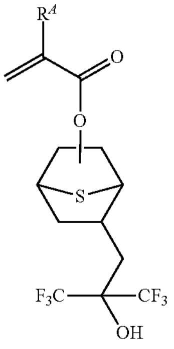
-continued
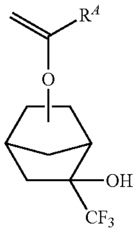
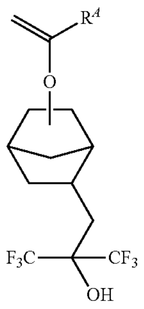
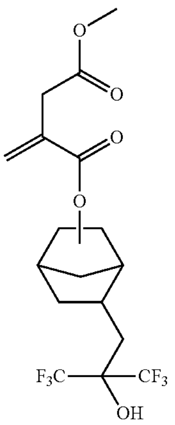
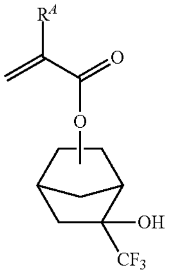
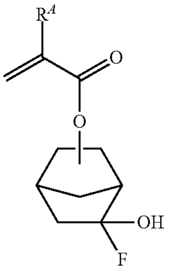
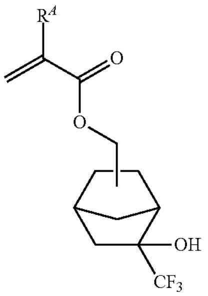
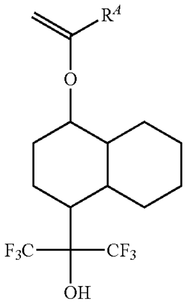
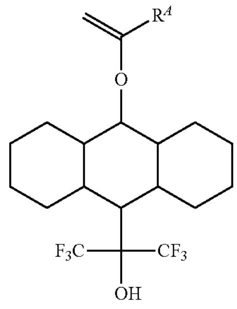
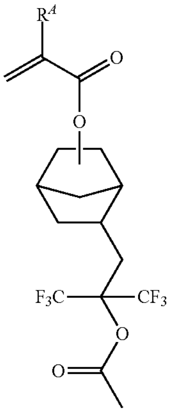
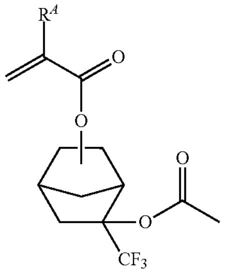
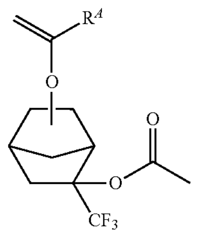

-continued
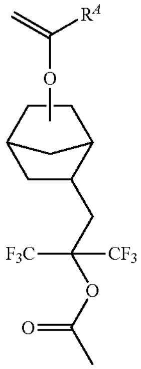
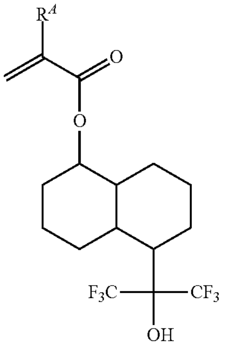
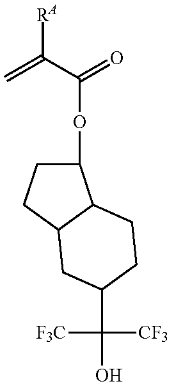
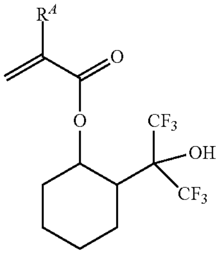
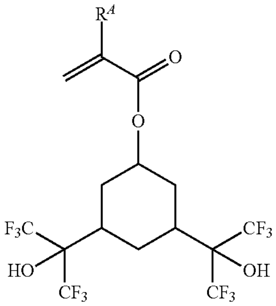
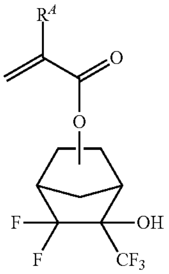
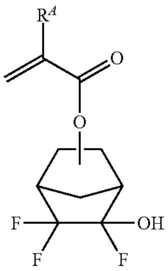
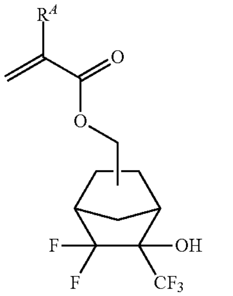
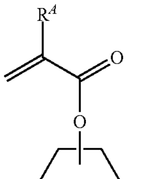
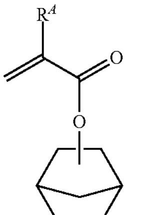
-continued
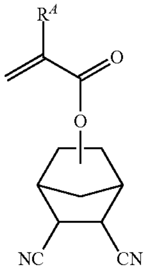
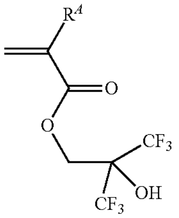
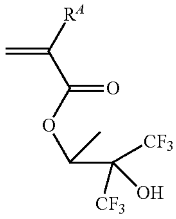
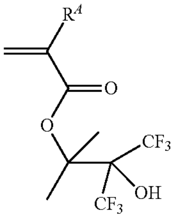
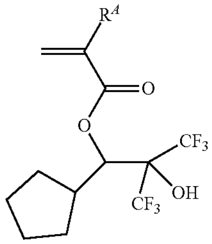
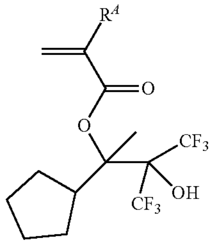
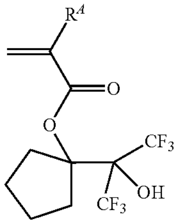
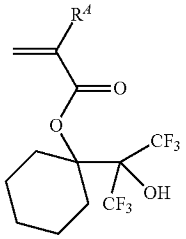
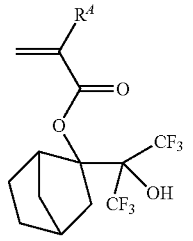
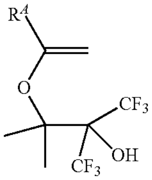
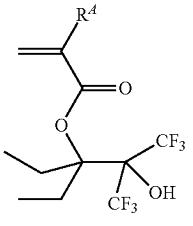
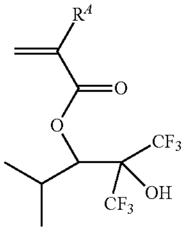
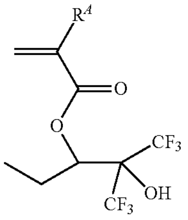
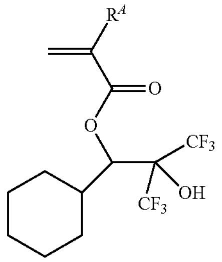

-continued
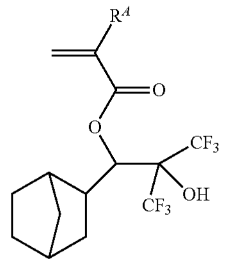
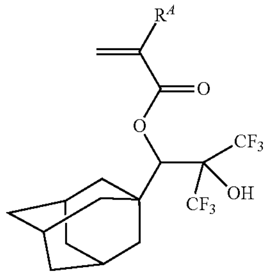
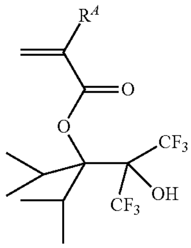
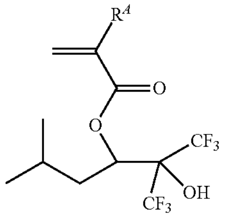
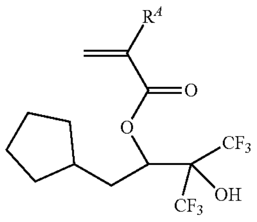
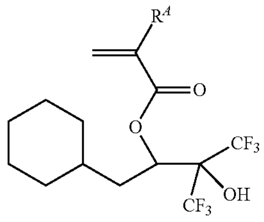
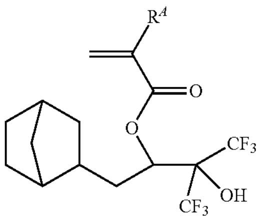
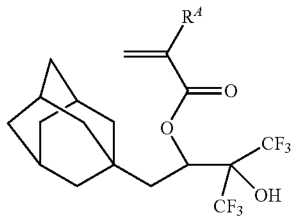
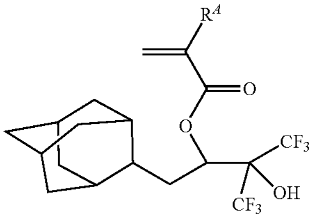
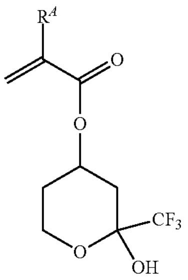
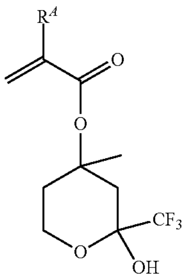
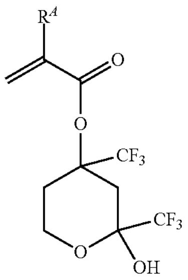
-continued
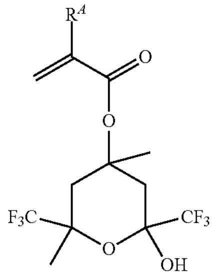
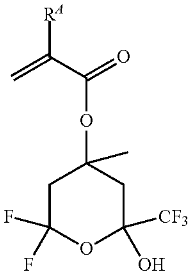
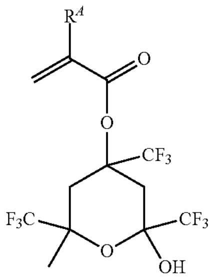
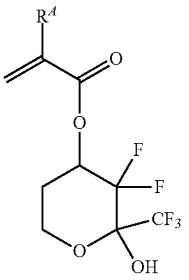
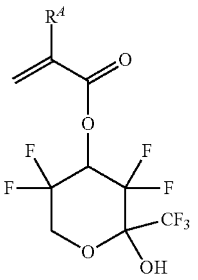
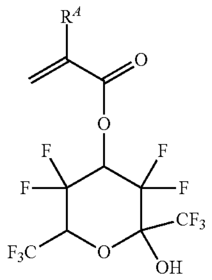
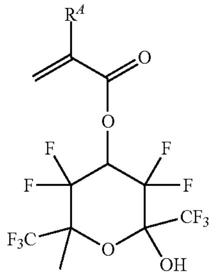
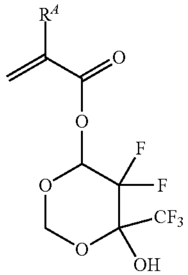
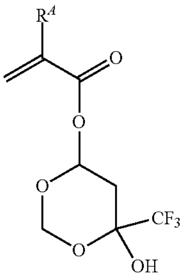
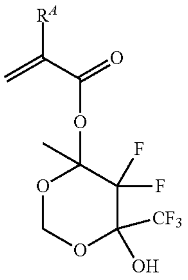
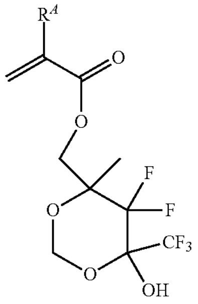
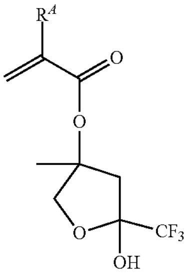
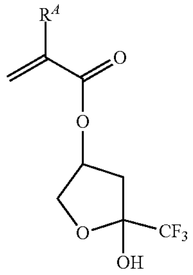
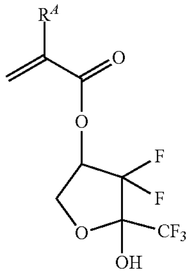

-continued
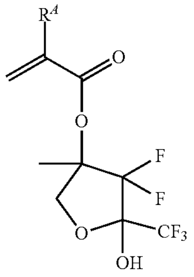 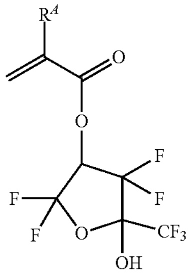 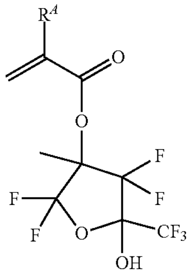
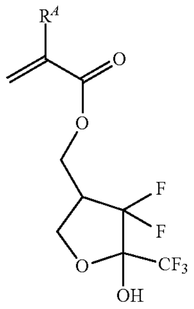 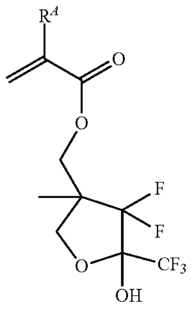 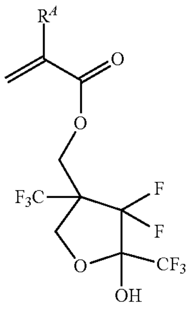
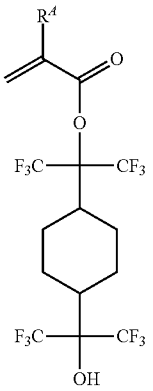 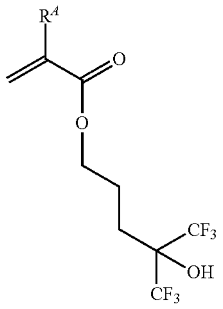 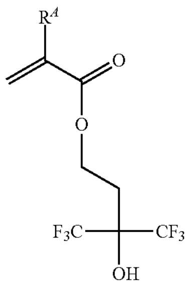
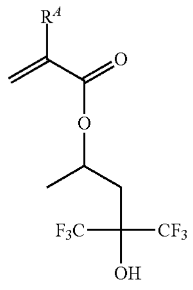 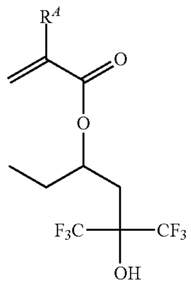
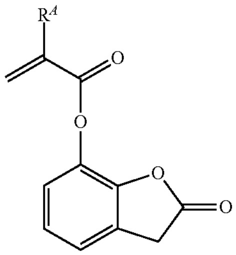 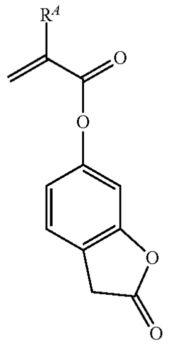
-continued
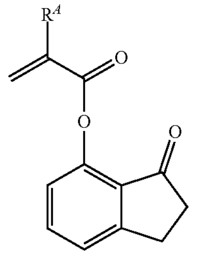 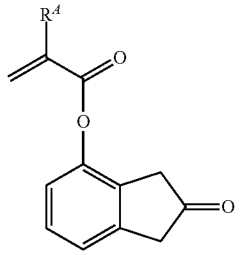
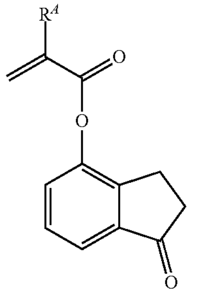 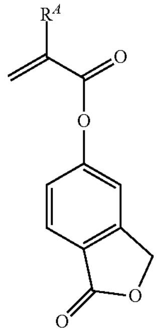 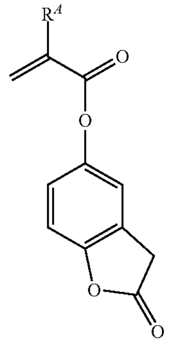
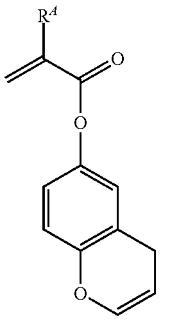 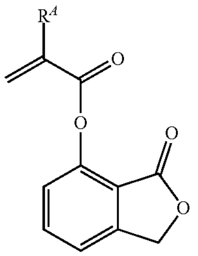 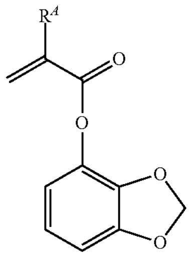
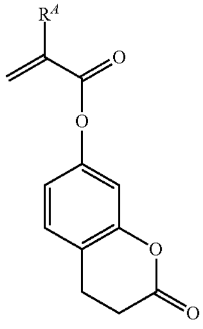 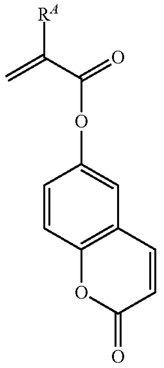 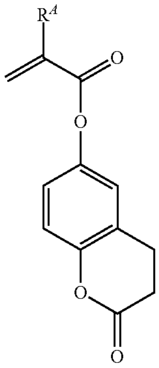
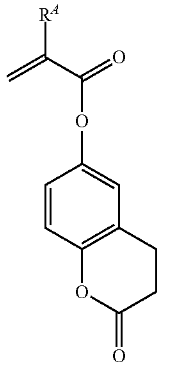 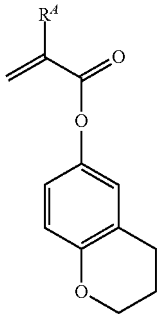 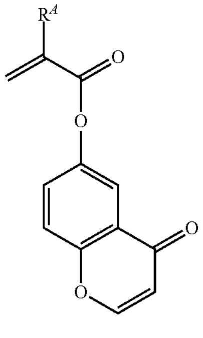

-continued
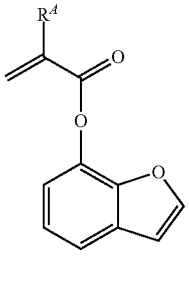
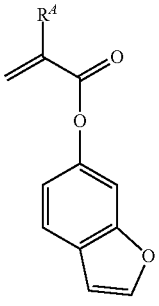
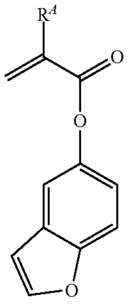
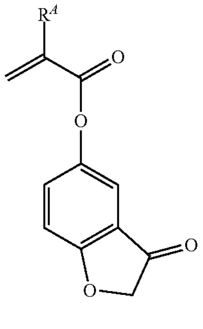
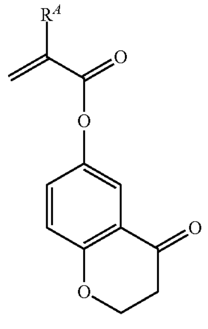
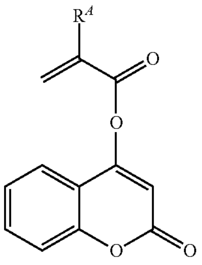
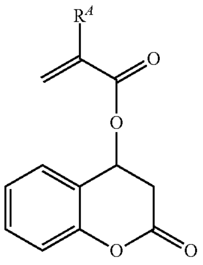
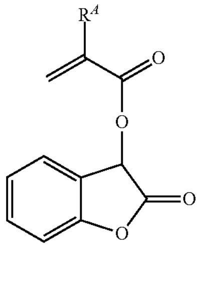
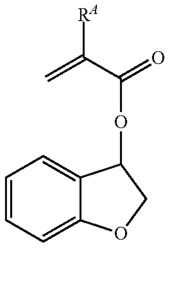
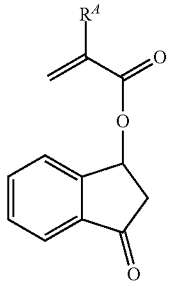
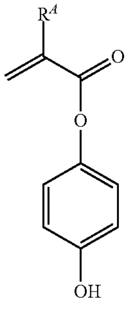
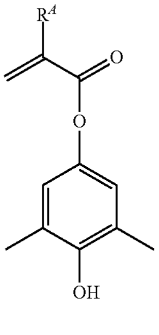
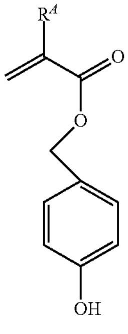
-continued
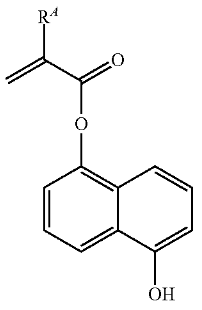
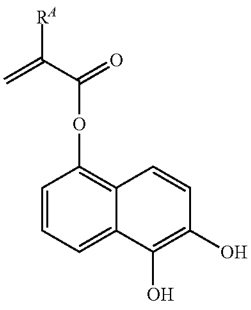
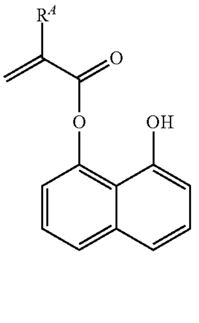
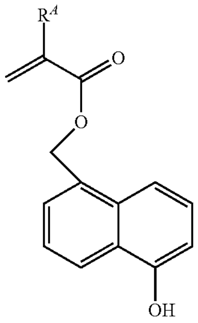
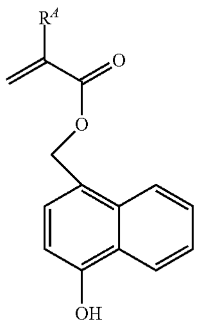
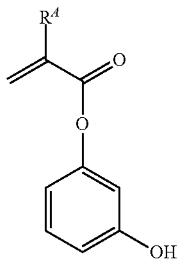
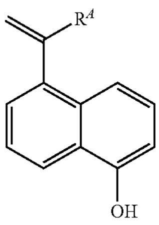
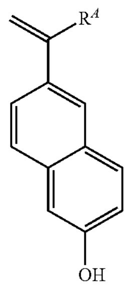
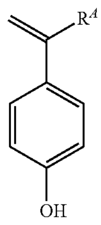
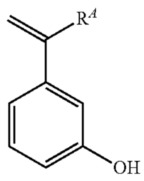
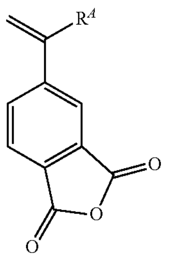
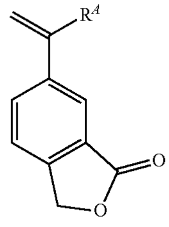
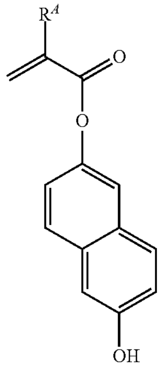
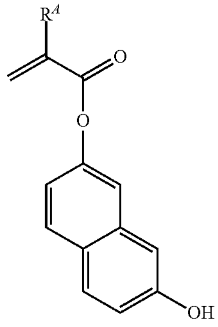

-continued
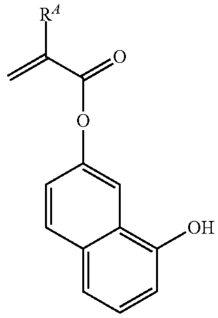
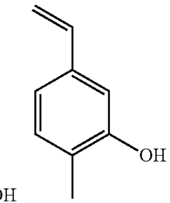
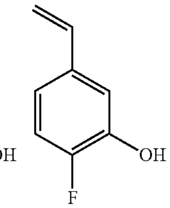
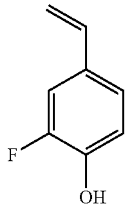
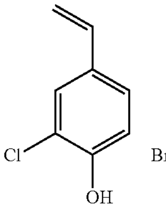
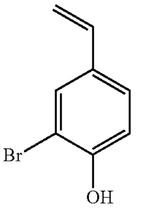
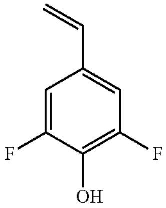
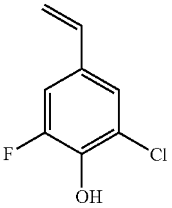
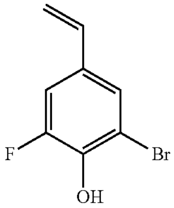
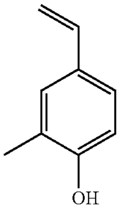
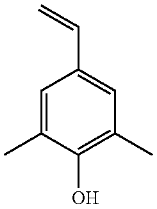
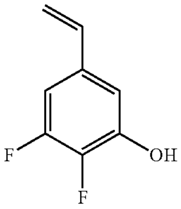
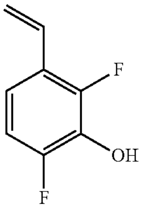
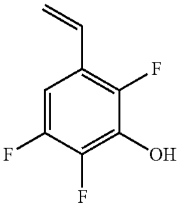
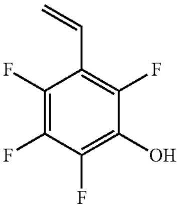
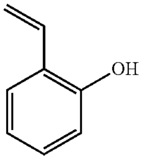
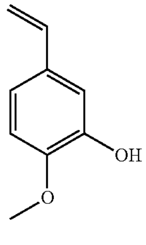
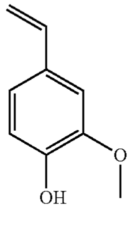
-continued
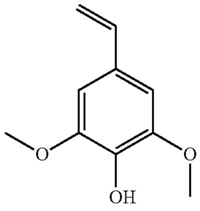
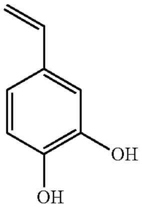
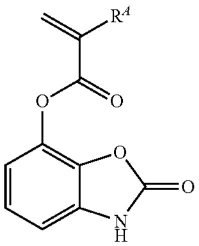
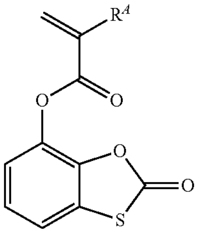
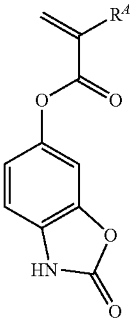
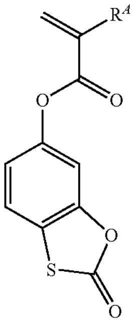
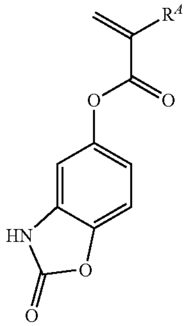
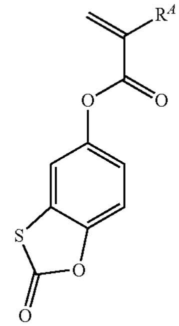
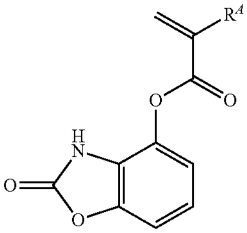
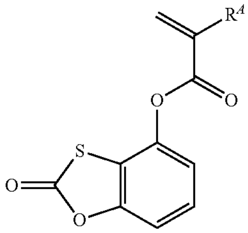
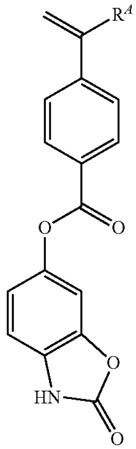
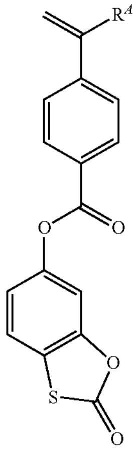
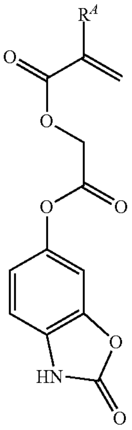

-continued

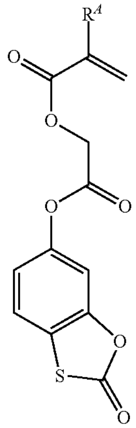
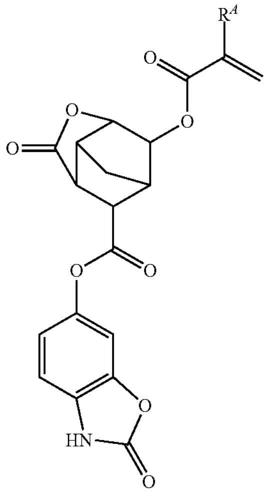
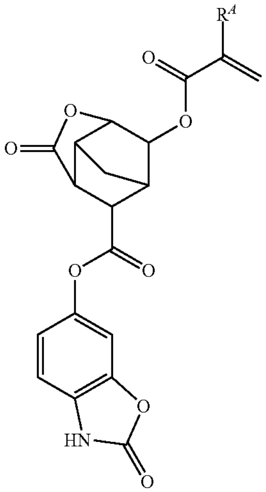
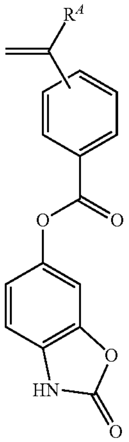
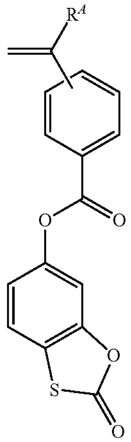
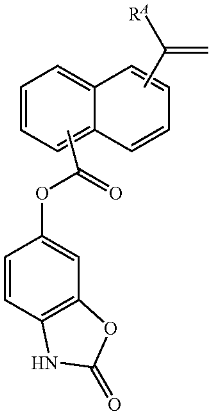
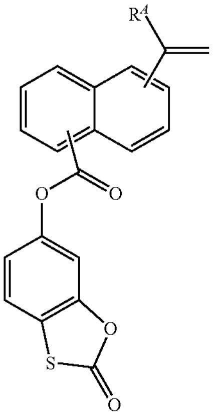
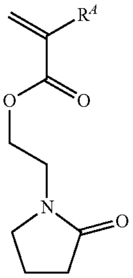
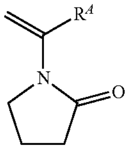
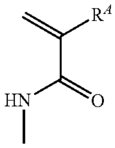
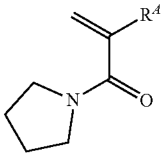

In another preferred embodiment, the base polymer may further comprise repeat units (d) derived from indene, benzofuran, benzothiophene, acenaphthylene, chromone, coumarin, norbornadiene, or derivatives thereof. Suitable monomers are exemplified below.

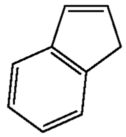
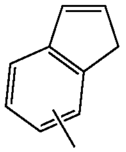
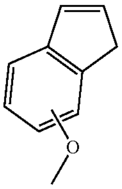
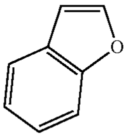
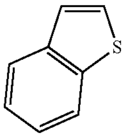
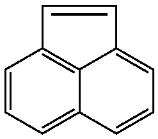
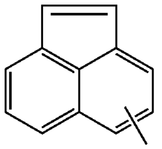
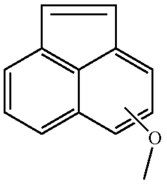
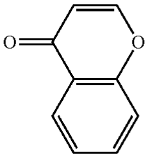
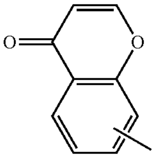
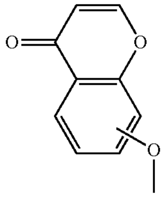
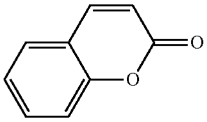
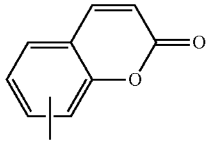
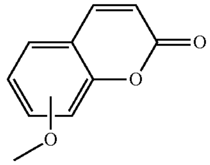
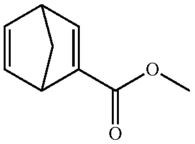

Furthermore, repeat units (e) may be incorporated in the base polymer, which are derived from styrene, vinylnaphthalene, vinylanthracene, vinylpyrene, methyleneindene, vinylpyridine, vinylcarbazole, or derivatives thereof.

In a further embodiment, repeat units (f) derived from an onium salt having a polymerizable unsaturated bond may be incorporated in the base polymer. Specifically, the base polymer may comprise repeat units of at least one type selected from repeat units having formulae (f1), (f2) and (f3). These units are simply referred to as repeat units (f1), (f2) and (f3) which may be used alone or in combination of two or more types.

(f1)

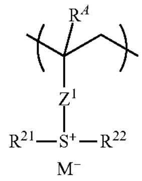

(f2)

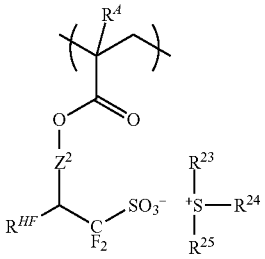

(f3)

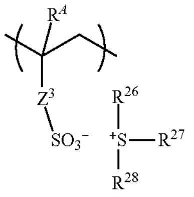

In formulae (f1) to (f3), $R^A$ is each independently hydrogen or methyl. $Z^1$ is a single bond, $C_1$-$C_6$ aliphatic hydrocarbylene group, phenylene group, naphthylene group, or $C_7$-$C_{18}$ group obtained by combining the foregoing, —O—$Z^{11}$—, —C(=O)—O—$Z^{11}$—, or —C(=O)NH—$Z^{11}$—. $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety. $Z^2$ is a single bond, —$Z^{21}$—C(=O)—O—, —$Z^{21}$—O— or —$Z^{21}$—O—C(=O)—. $Z^{21}$ is a $C_1$-$C_{12}$ saturated hydrocarbylene group which may contain a carbonyl moiety, ester bond or ether bond. $Z^3$ is a single bond, methylene group, ethylene group, phenylene group, fluorinated phenylene group, or trifluoromethyl-substituted phenylene group, —O—$Z^{31}$—, —C(=O)—$Z^{31}$—, or —C(=O)—NH—$Z^{31}$—. $Z^{31}$ is a $C_1$-$C_4$ aliphatic hydrocarbylene group, phenylene group, fluorinated phenylene group, or trifluoromethyl-substituted phenylene group, which may contain a carbonyl moiety, ester bond, ether bond or hydroxy moiety. The aliphatic hydrocarbylene groups $Z^{11}$ and $Z^{31}$ may be saturated or unsaturated and straight, branched or cyclic. The saturated hydrocarbylene group $Z^{21}$ may be straight, branched or cyclic.

In formulae (f1) to (f3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as will be exemplified later for $R^{101}$ to $R^{105}$ in formulae (1-1) and (1-2). In the hydrocarbyl group, some or all of the hydrogen atoms may be substituted by a moiety containing a heteroatom such as oxygen, sulfur, nitrogen or halogen, or some —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride (—C(=O)—O—C(=O)—) or haloalkyl moiety.

A pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In formula (f2), $R^{HF}$ is hydrogen or trifluoromethyl.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide: methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl at β-position as represented by the formula (f1-2).

$$R^{31}—CF_2—SO_3^- \quad (f1\text{-}1)$$

(f1-2)

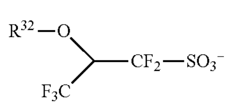

In formula (f1-1), $R^{31}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples of the hydrocarbyl group are as will be exemplified later for $R^{111}$ in formula (1A').

In formula (f1-2), $R^{32}$ is hydrogen, or a $C_1$-$C_{30}$ hydrocarbyl group or $C_2$-$C_{30}$ hydrocarbylcarbonyl group, which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic. Examples of the hydrocarbyl group are as will be exemplified later for $R^{111}$ in formula (1A').

Examples of the cation in the monomer from which repeat unit (f1) is derived are shown below, but not limited thereto. $R^A$ is as defined above.

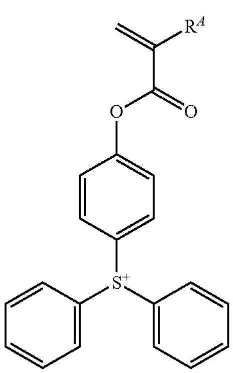
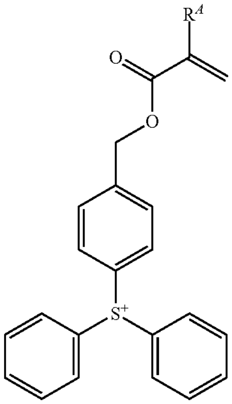
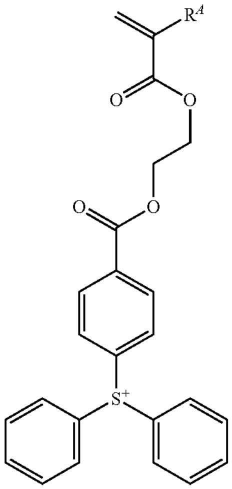
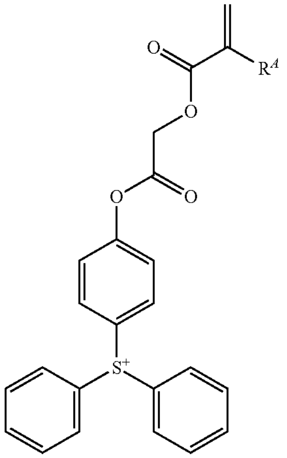
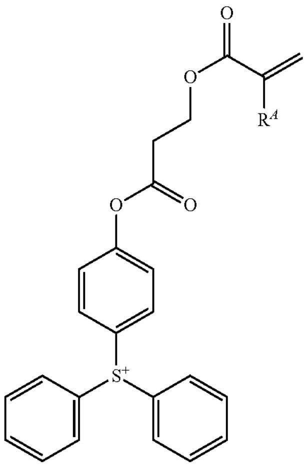
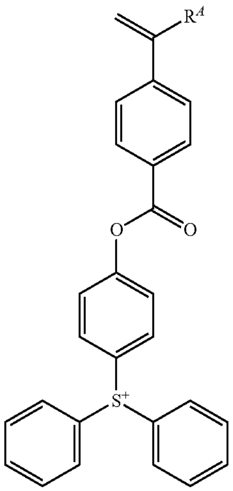
-continued
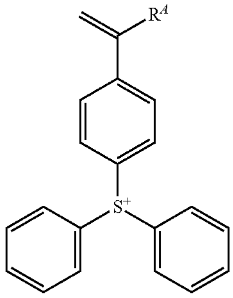
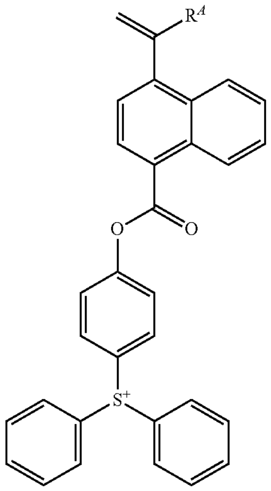
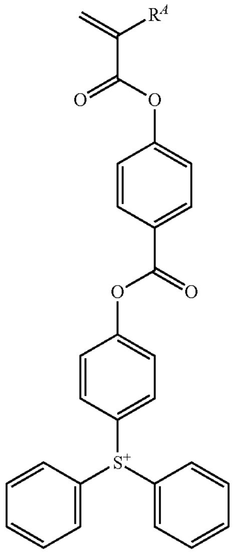
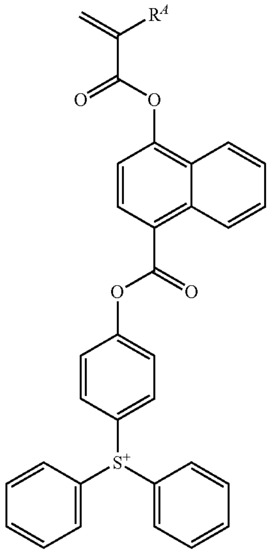
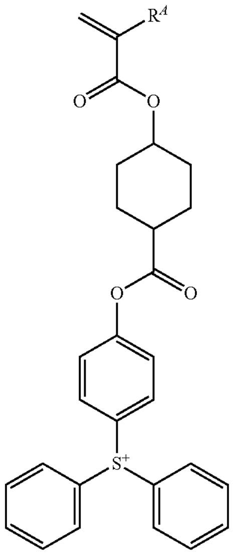
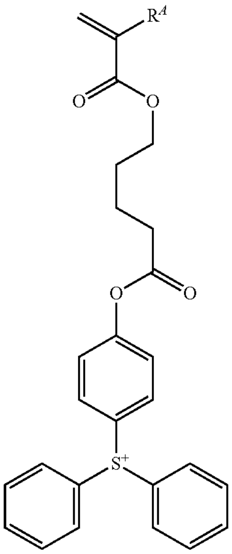

-continued
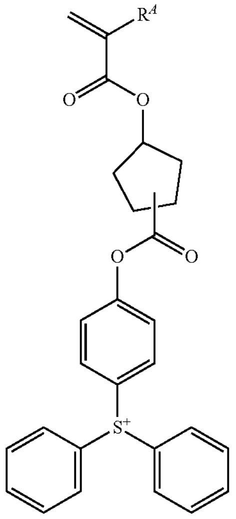
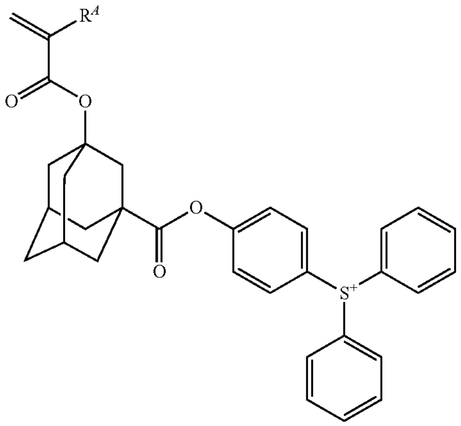
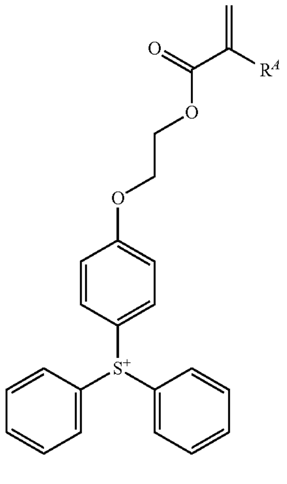
-continued
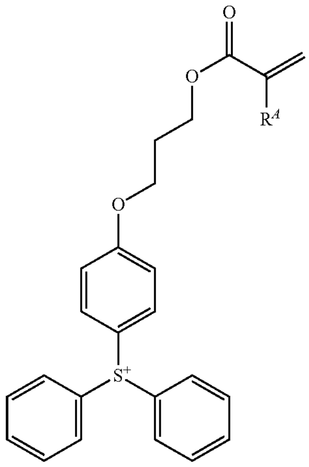
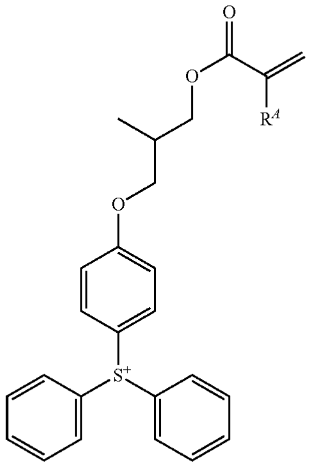
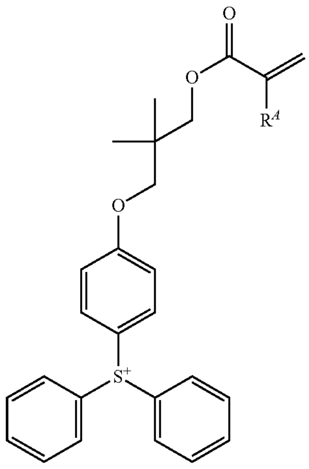
Examples of the cation in the monomer from which repeat unit (f2) or (f3) is derived are as will be exemplified later for the cation in the sulfonium salt having formula (1-1).
Examples of the anion in the monomer from which repeat unit (f2) is derived are shown below, but not limited thereto. $R^A$ is as defined above.

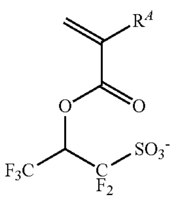
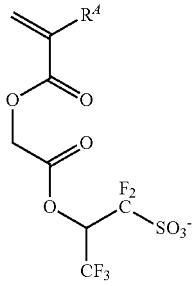
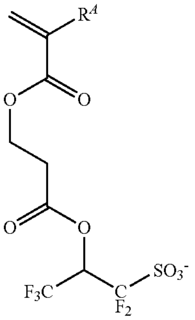
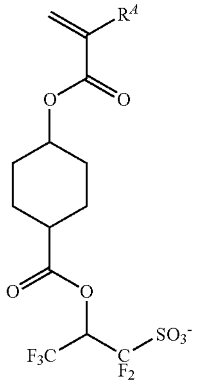
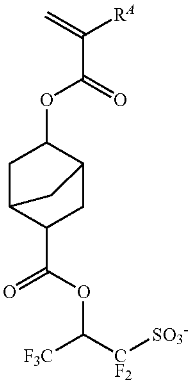
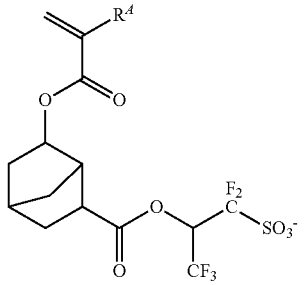
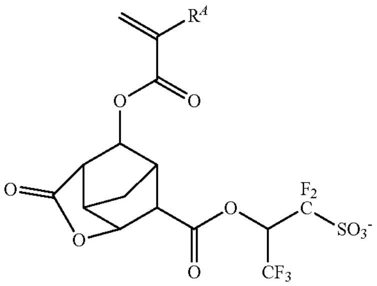
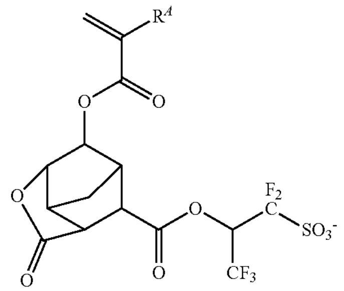
-continued
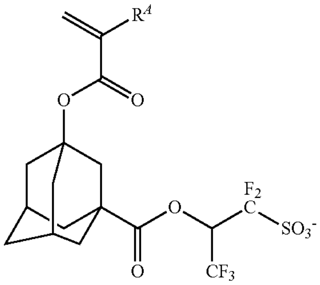
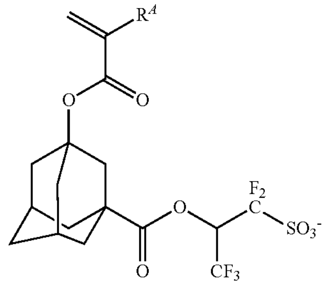
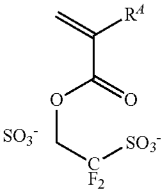
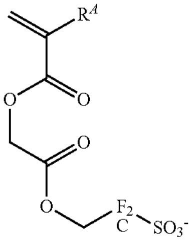
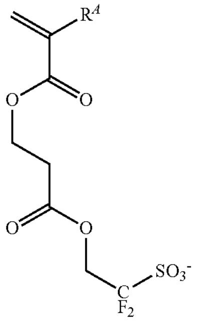
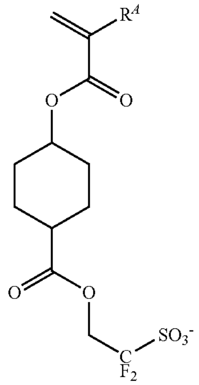
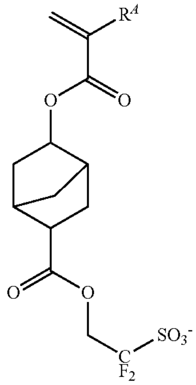
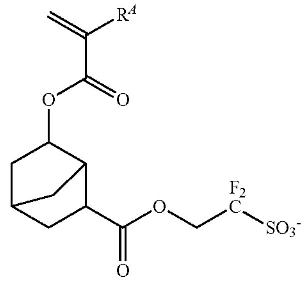

-continued
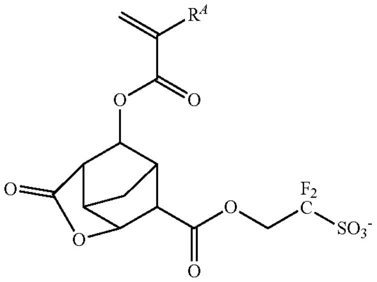
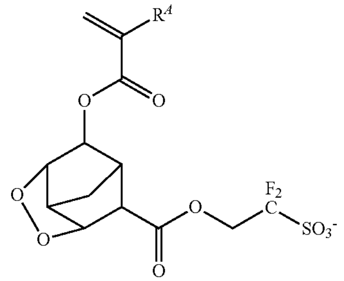
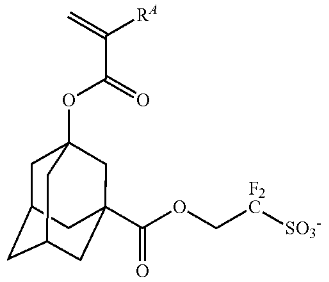
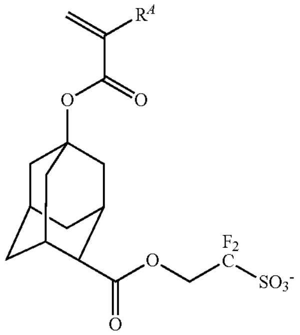
Examples of the anion in the monomer from which repeat unit (f3) is derived are shown below, but not limited thereto. $R^A$ is as defined above.
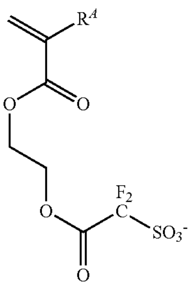
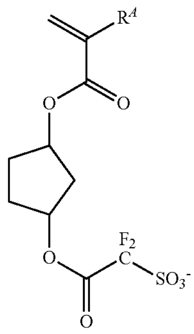
-continued
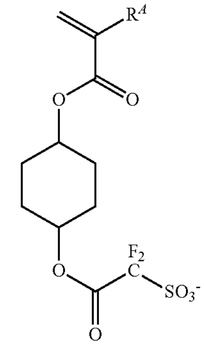
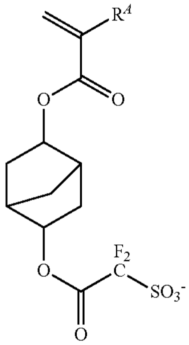
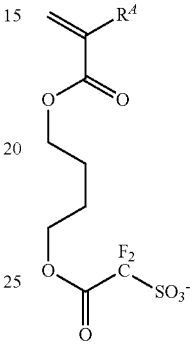
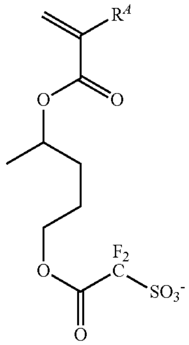
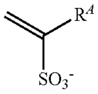
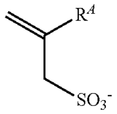
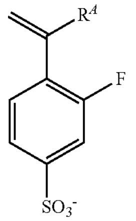
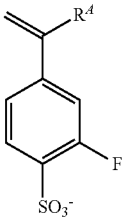
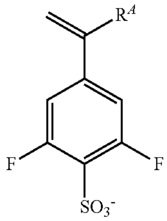
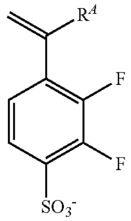
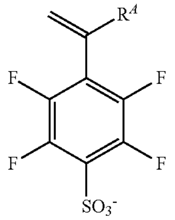
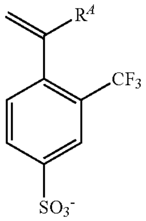
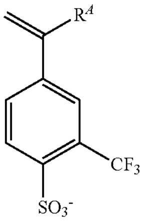
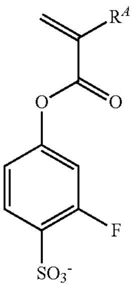
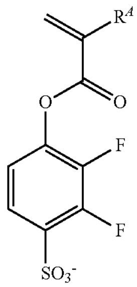
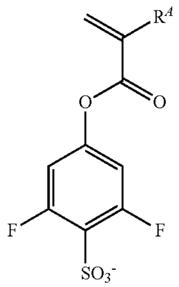
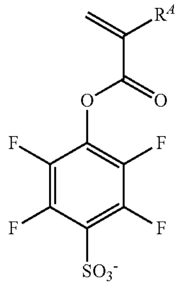
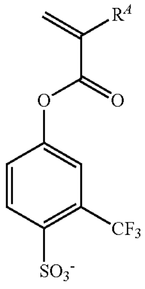
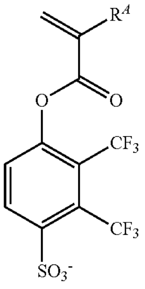

The attachment of an acid generator to the polymer main chain is effective in restraining acid diffusion, thereby preventing a reduction of resolution due to blur by acid diffusion. Also, LWR or CDU is improved since the acid generator is uniformly distributed. Where a base polymer containing repeat units (f), i.e., polymer-bound acid generator is used, the blending of an acid generator of addition type (to be described later) may be omitted.

The base polymer for formulating the positive resist composition comprises repeat units (a1) or (a2) having an acid labile group as essential component and additional repeat units (b), (c), (d), (e), and (f) as optional components. A fraction of units (a1), (a2), (b), (c), (d), (e), and (f) is: preferably 0≤a1<1.0, 0≤a2<1.0, 0<a1+a2<1.0, 0≤b≤0.9, 0≤c≤0.9, 0≤d≤0.8, 0≤e≤0.8, and 0≤f≤0.5; more preferably 0≤a1≤0.9, 0≤a2≤0.9, 0.1≤a1+a2≤0.9, 0≤b≤0.8, 0≤c≤0.8, 0≤d≤0.7, 0≤e≤0.7, and 0≤f≤0.4; and even more preferably 0≤a1≤0.8, 0≤a2≤0.8, 0.1≤a1+a2≤0.8, 0≤b≤0.75, 0≤c≤0.75, 0≤d≤0.6, 0≤e≤0.6, and 0≤f≤0.3. Notably, f=f1+f2+f3, meaning that unit (f) is at least one of units (f1) to (f3), and a1+a2+b+c+d+e+f=1.0.

For the base polymer for formulating the negative resist composition, an acid labile group is not necessarily essential. The base polymer comprises repeat units (b), and optionally repeat units (c), (d), (e), and/or (f). A fraction of these units is: preferably 0≤b≤1.0, 0≤c≤0.9, 0≤d≤0.8, 0≤e≤0.8, and 0≤f≤0.5; more preferably 0.2≤b≤1.0.0≤c≤0.8, 0≤d≤0.7, 0≤e≤0.7, and 0≤f≤0.4; and even more preferably 0.3≤b≤1.0, 0≤c≤0.75, 0≤d≤0.6, 0≤e≤0.6, and 0≤f≤0.3. Notably, f=f1+f2+f3, meaning that unit (f) is at least one of units (f1) to (f3), and b+c+d+e+f=1.0.

The base polymer may be synthesized by any desired methods, for example, by dissolving one or more monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxy group is copolymerized, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. A polymer having a Mw in the range ensures that a resist film has heat resistance and satisfactory solubility in alkaline developer.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that salt compound A functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane. N-sulfonyloxyimide, and oxime-O-sulfonate acid generators. Exemplary PAGs are described in JP-A 2008-111103, paragraphs[0122]-[0142] (U.S. Pat. No. 7,537,880).

As the PAG used herein, sulfonium salts having the formula (1-1) and iodonium salts having the formula (1-2) are also preferred.

(1-1)

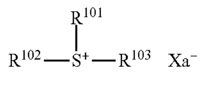

(1-2)

$$R^{104}—I^{+}—R^{105}\quad Xa^{-}$$

In formulae (1-1) and (1-2), $R^{101}$ to $R^{105}$ are each independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^{101}$ to $R^{105}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl and tert-butylnaphthyl; $C_7$-$C_{20}$ aralkyl groups such as benzyl and phenethyl; and combinations thereof.

Also included are substituted forms of the foregoing groups in which some or all of the hydrogen atoms are substituted by a moiety containing a heteroatom such as oxygen, sulfur, nitrogen or halogen, or some $—CH_2—$ is replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic ester bond, carbonate bond, lactone ring, sultone ring, carboxylic anhydride (—C(═O)—O—C(═O)—) or haloalkyl moiety.

A pair of $R^{101}$ and $R^{102}$ may bond together to form a ring with the sulfur atom to which they are attached. Preferred are those rings of the structure shown below.

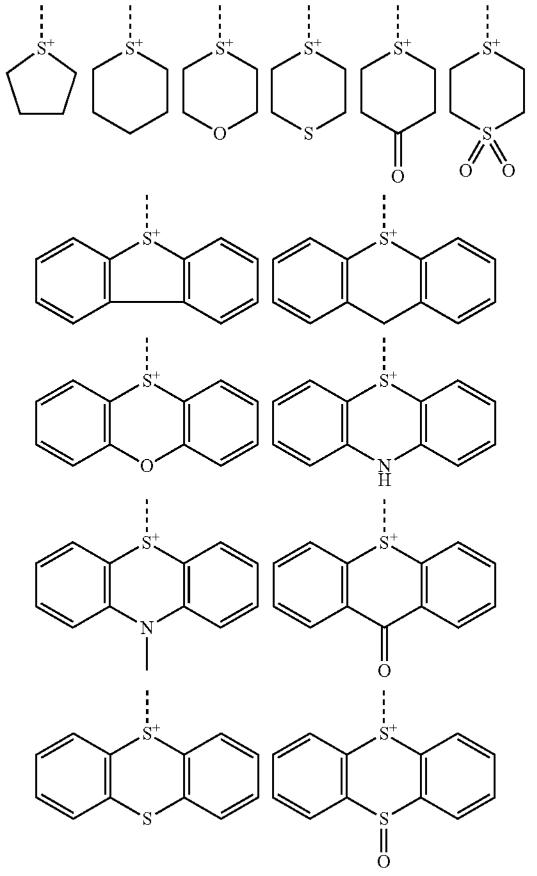

-continued

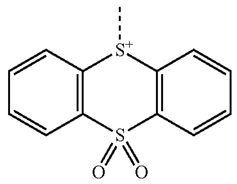

Herein, the broken line denotes a point of attachment to $R^{103}$.

Examples of the cation in the sulfonium salt having formula (1-1) are shown below, but not limited thereto.

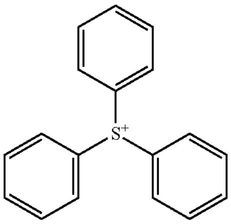

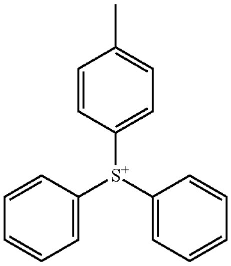

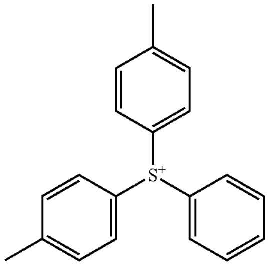

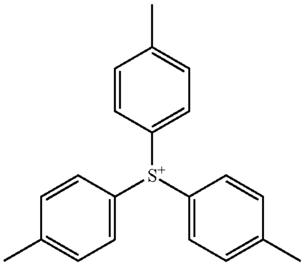

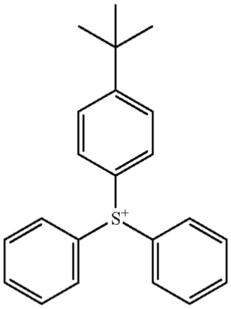

-continued
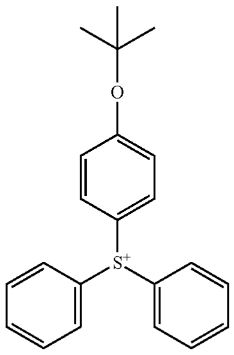
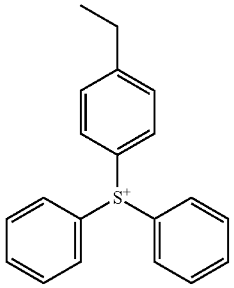
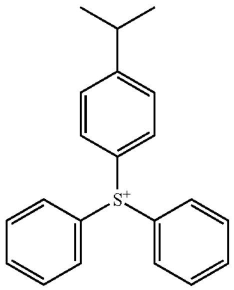
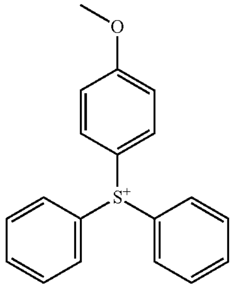
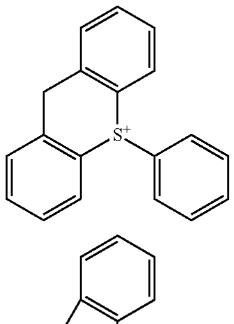
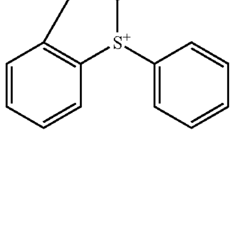
-continued
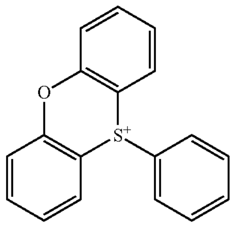
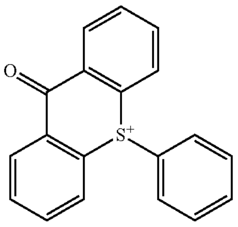
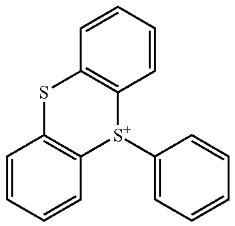
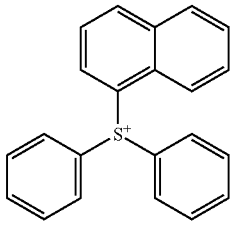
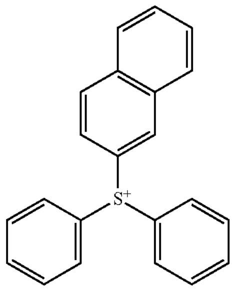
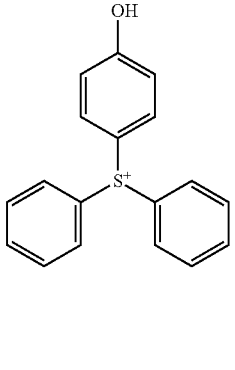

-continued
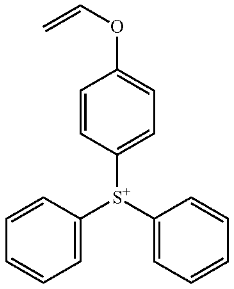
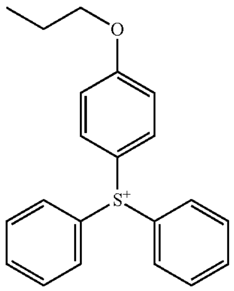
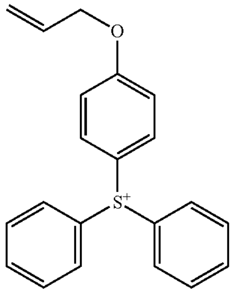
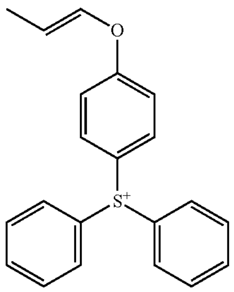
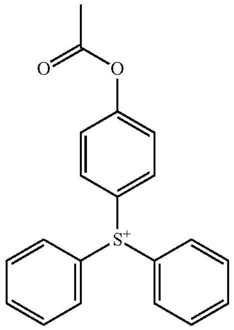
-continued
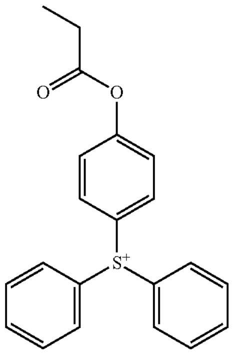
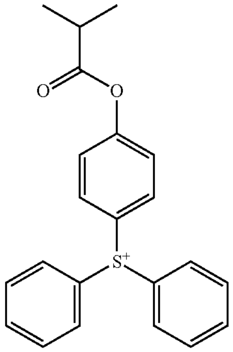
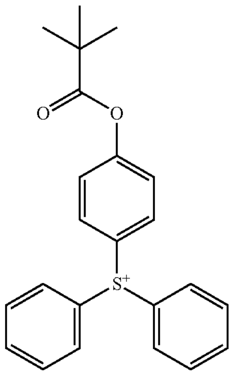
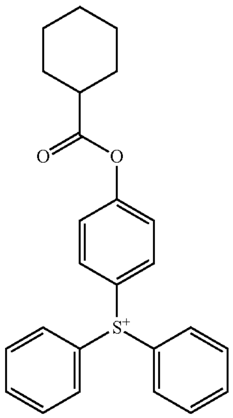

-continued
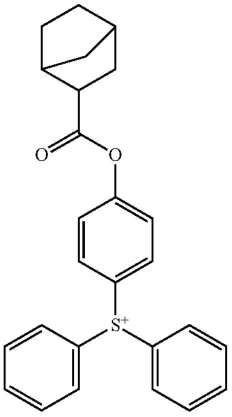
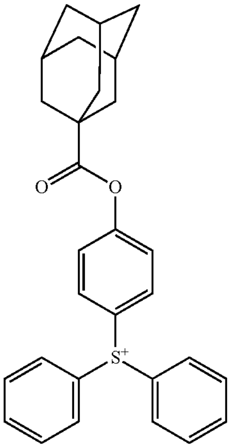
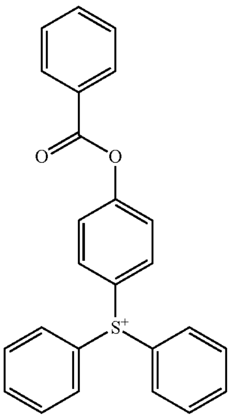
-continued
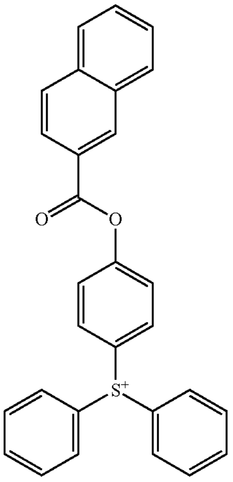
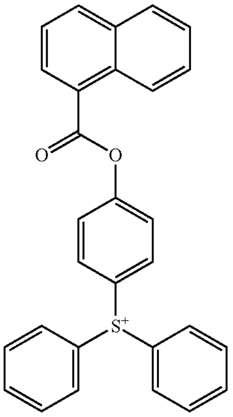
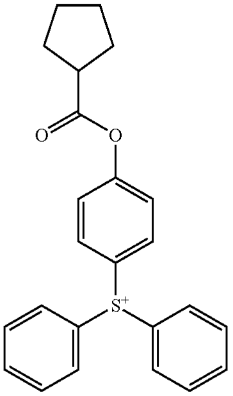

-continued
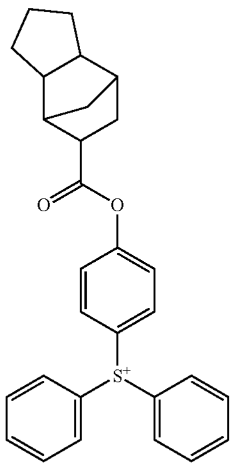
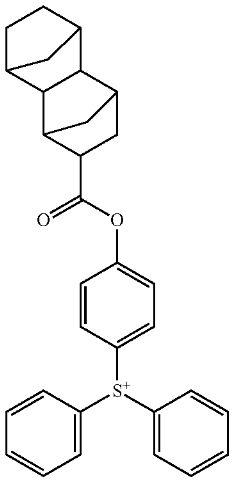
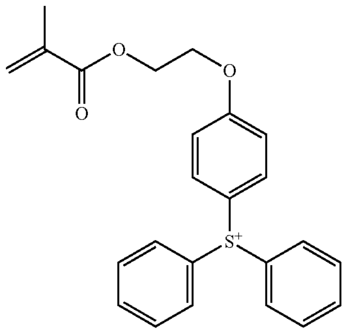
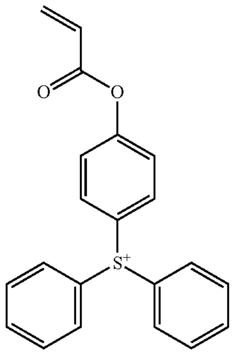
-continued
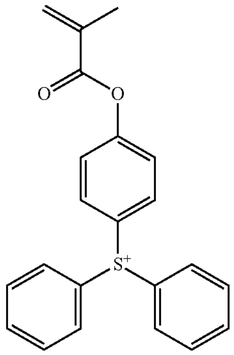
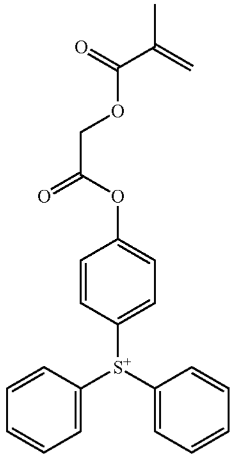
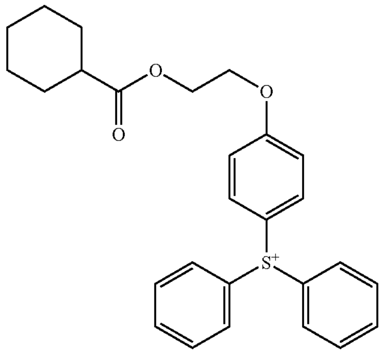
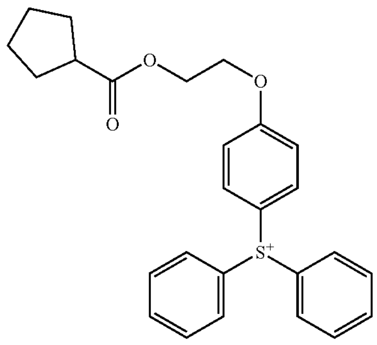

-continued
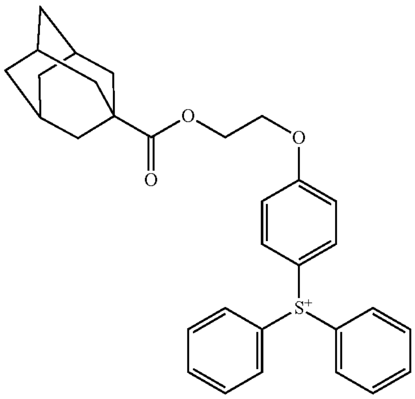
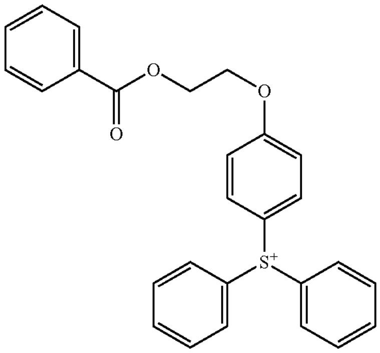
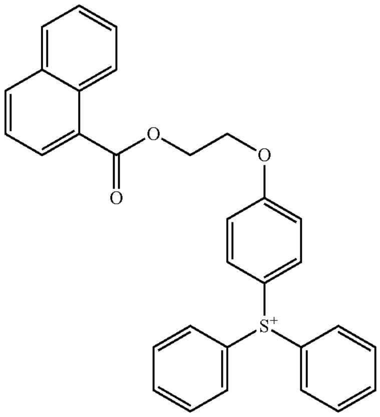
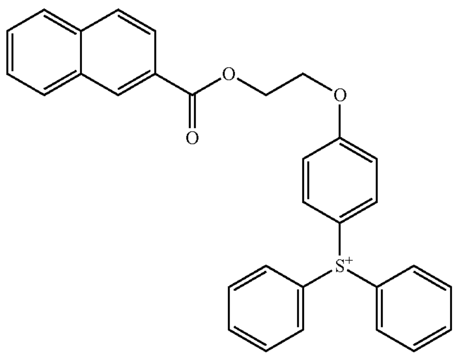
-continued
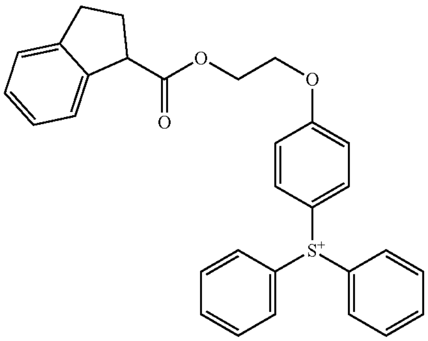
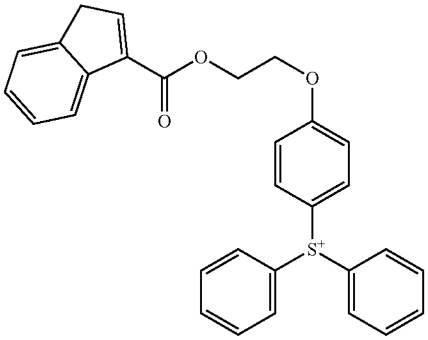
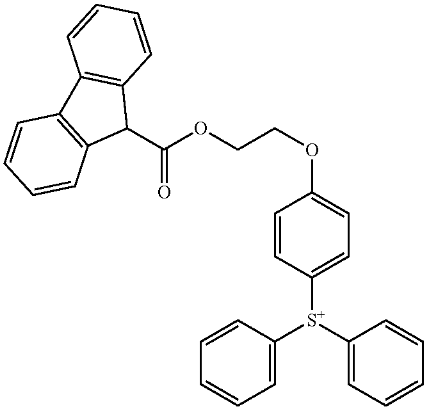
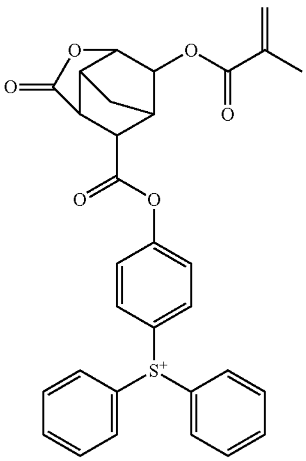

-continued
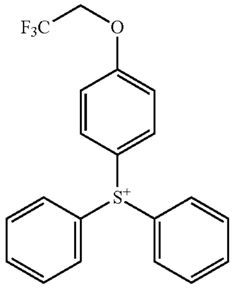
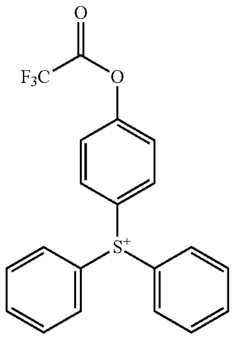
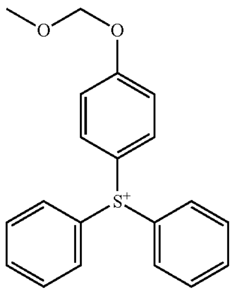
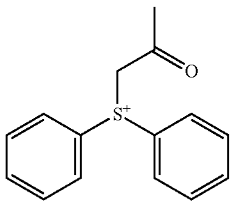
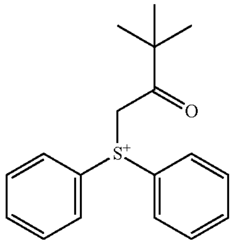
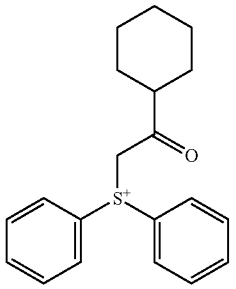
-continued
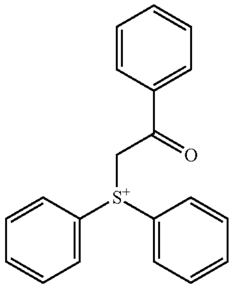
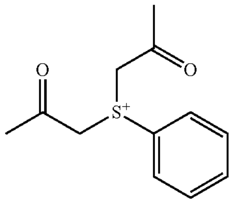
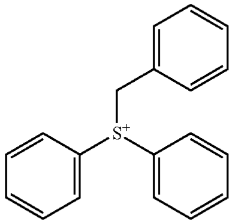
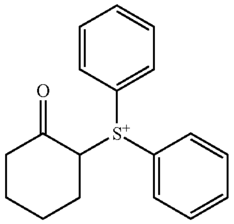
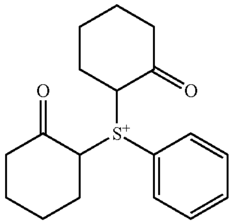
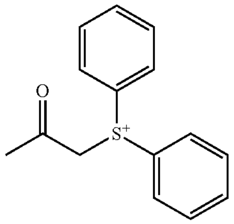
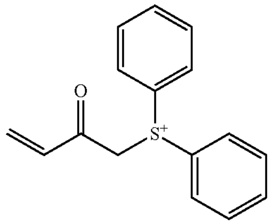

-continued
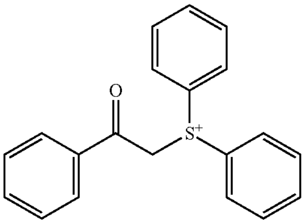
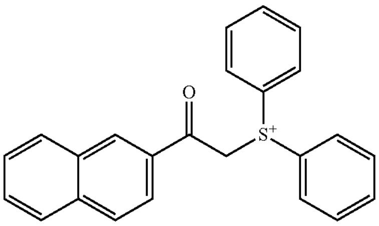
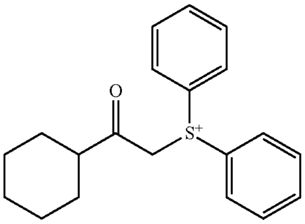
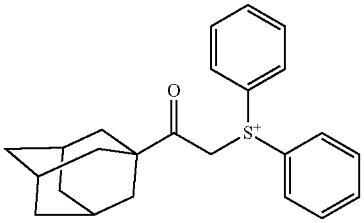
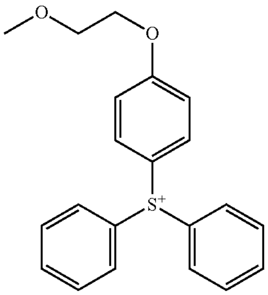
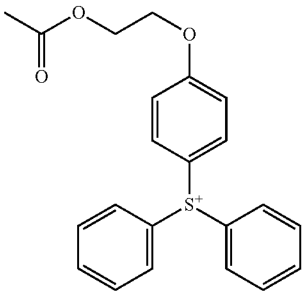
-continued
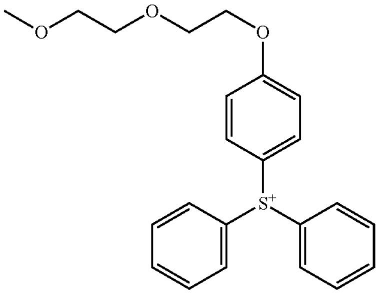
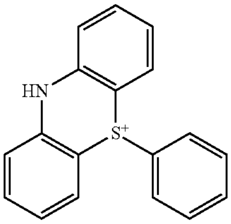
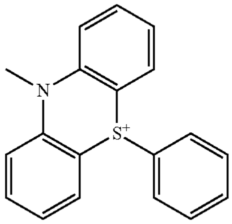
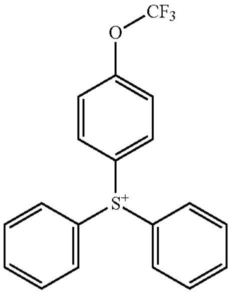
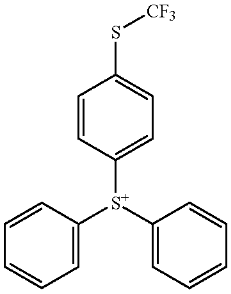
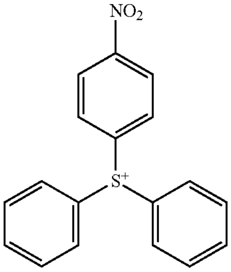

-continued
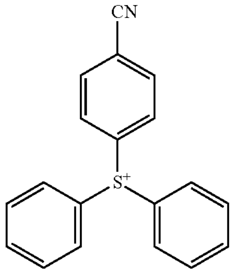
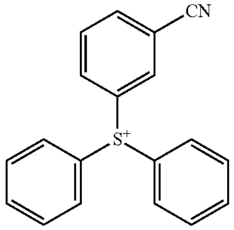
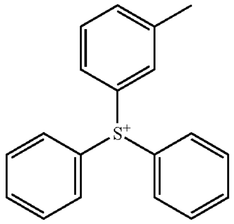
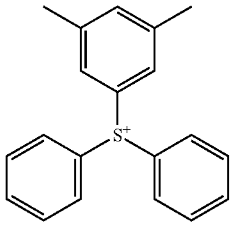
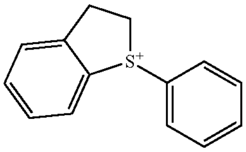
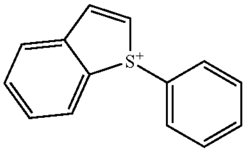
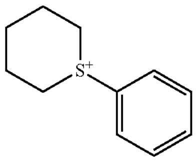
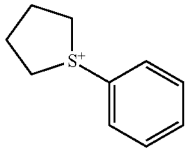
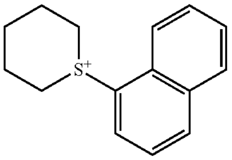
-continued
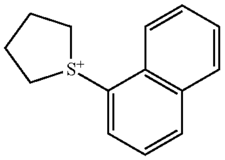
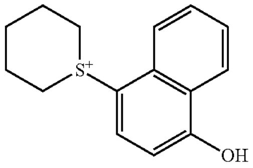
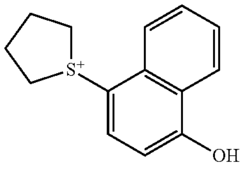
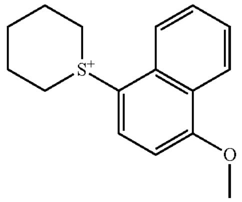
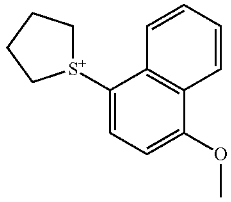
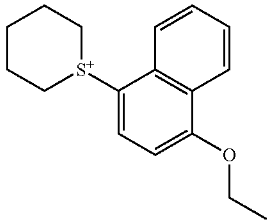
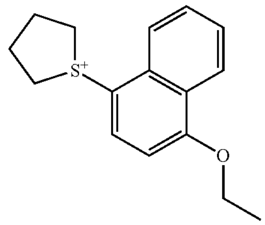
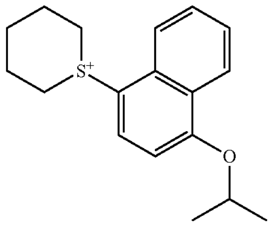

-continued
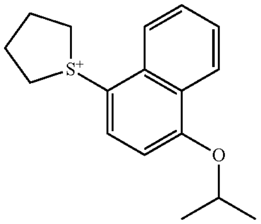
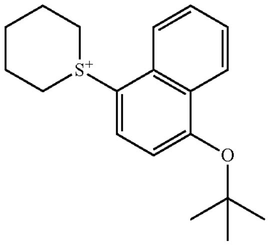
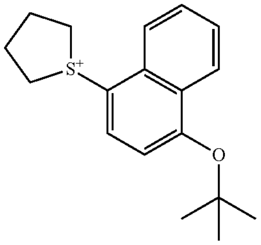
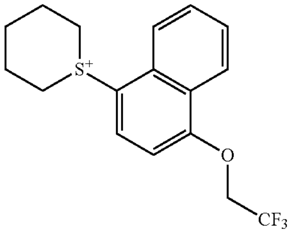
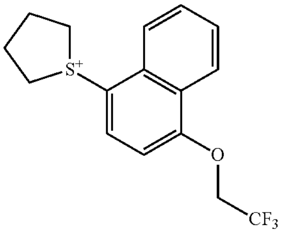
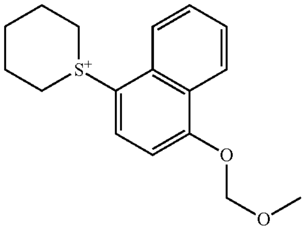
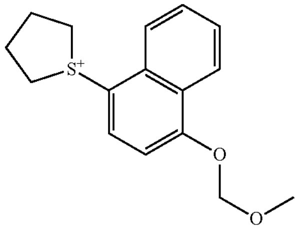
-continued
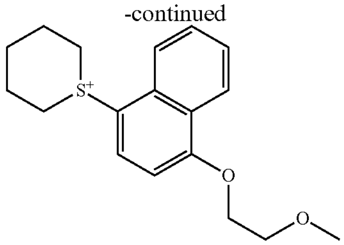
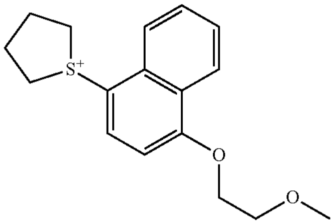
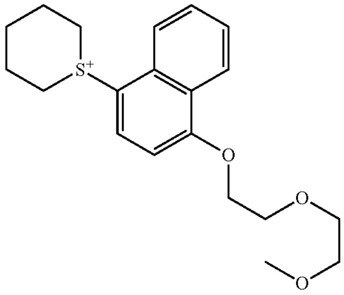
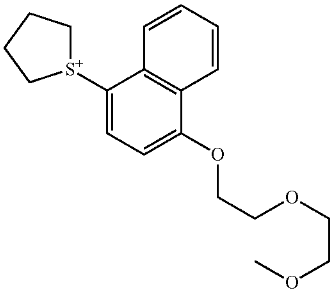
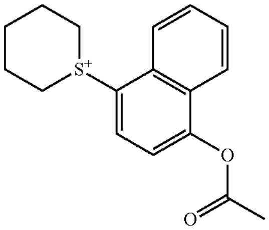
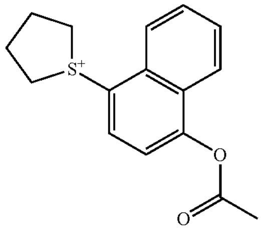
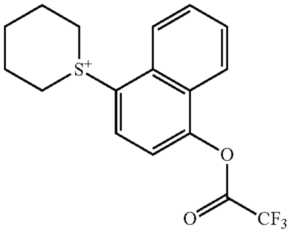

-continued
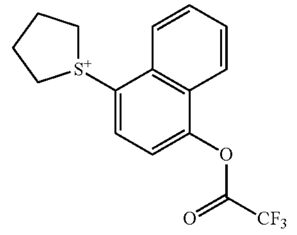
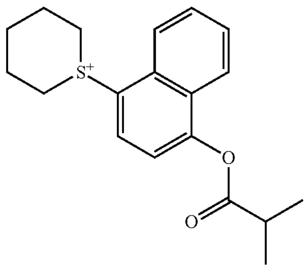
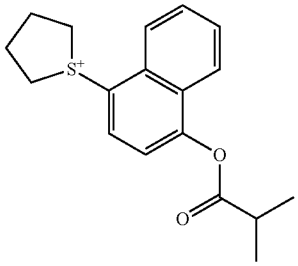
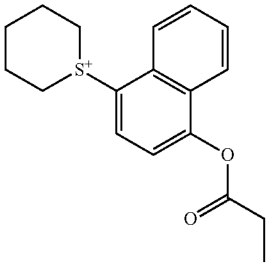
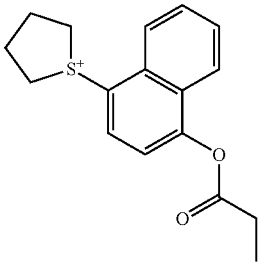
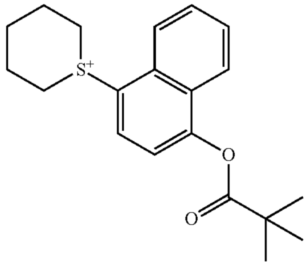
-continued
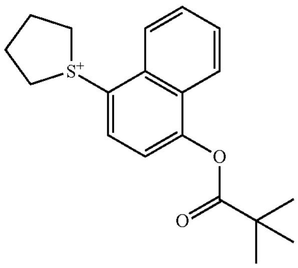
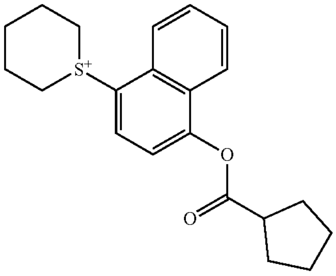
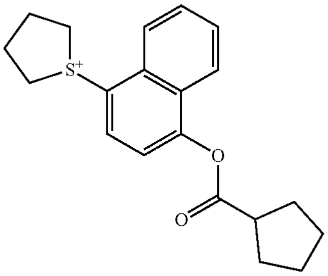
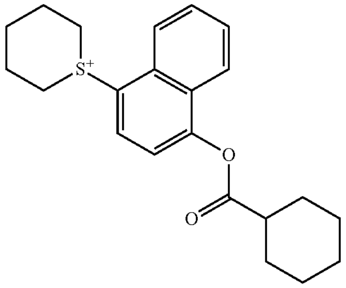
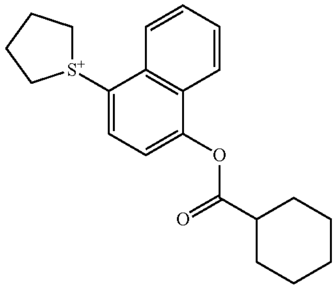
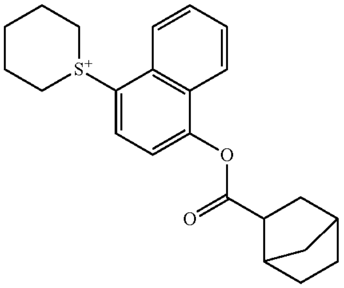

-continued
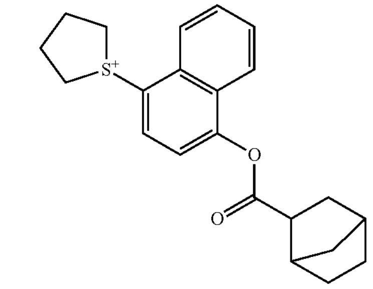
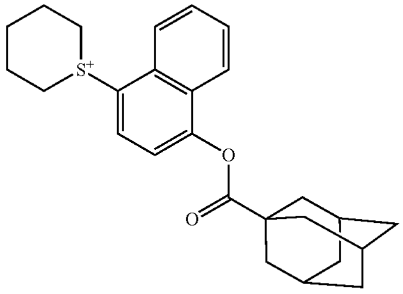
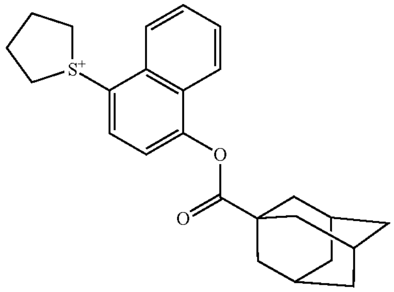
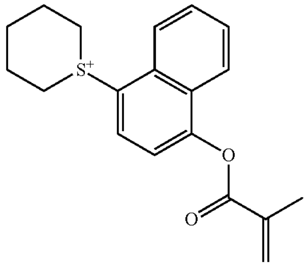
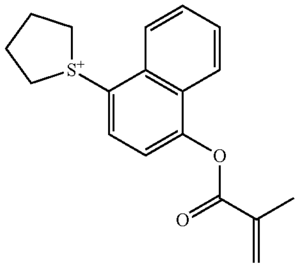
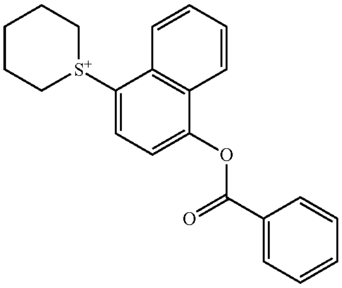
-continued
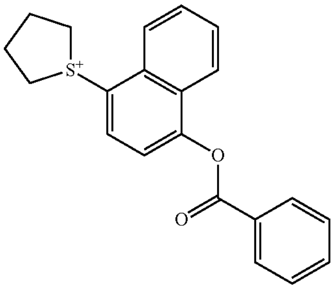
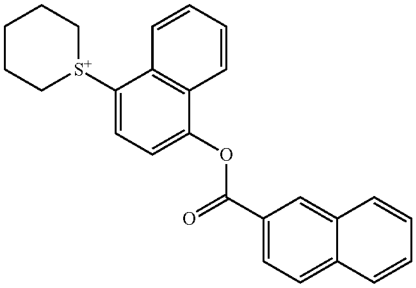
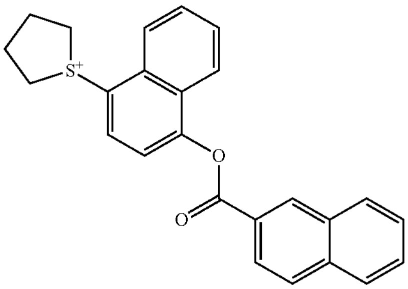
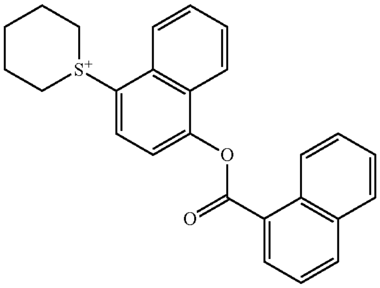
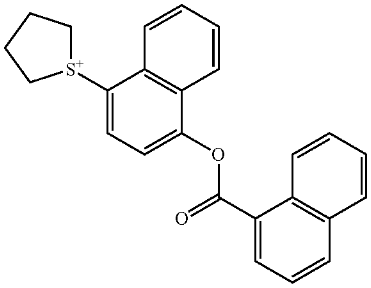

-continued
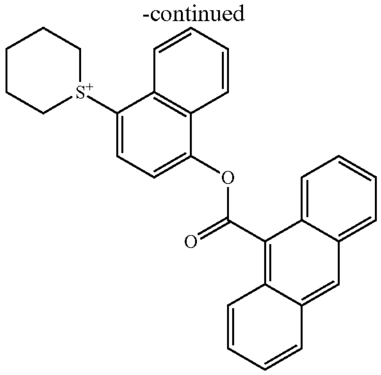
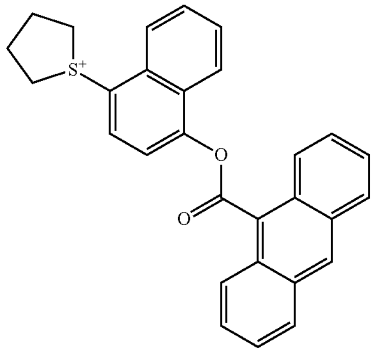
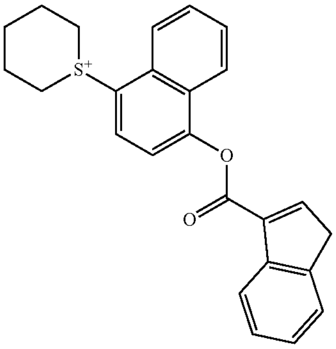
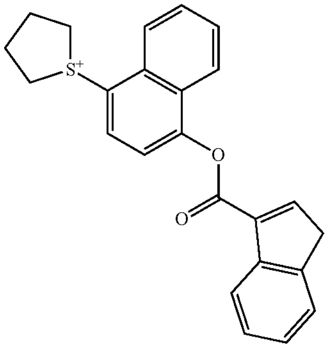
-continued
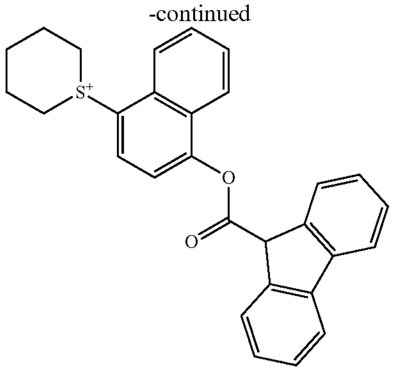
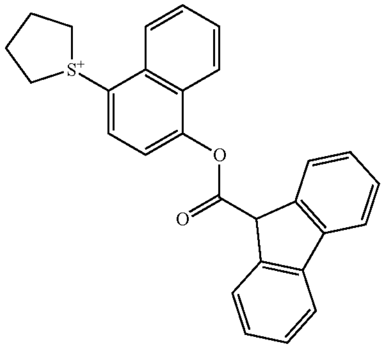
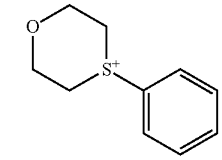
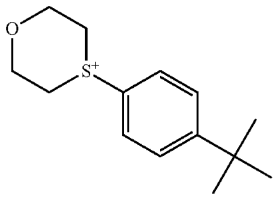
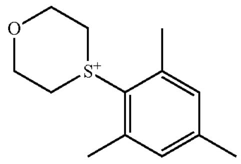
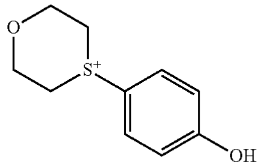
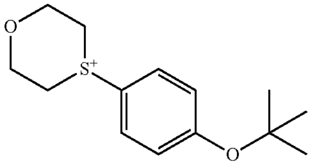
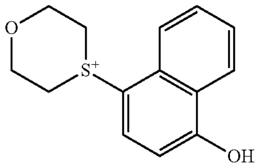

-continued
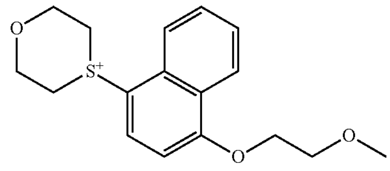
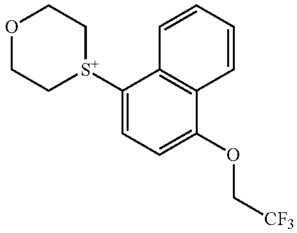
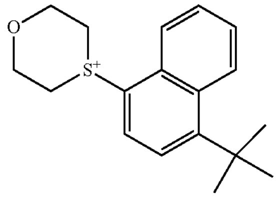
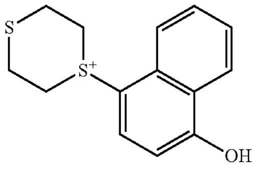
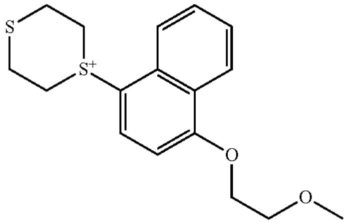
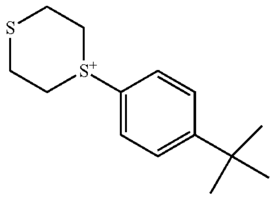
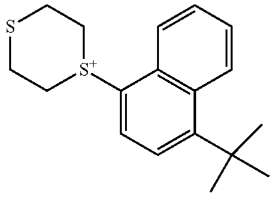
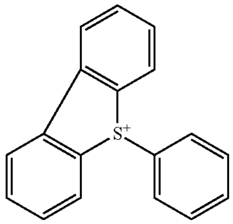
-continued
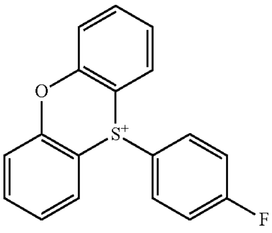
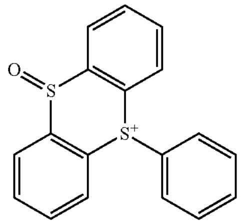
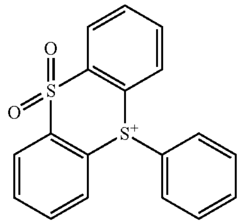
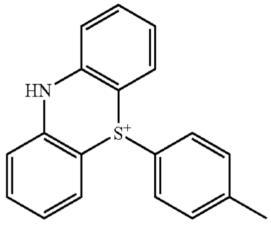
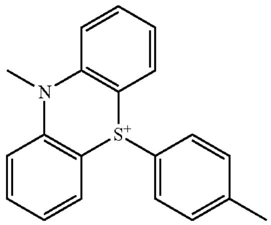
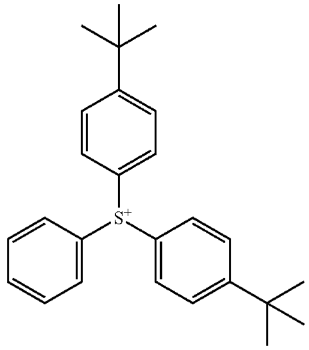

-continued
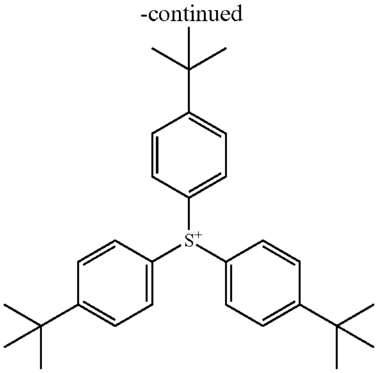
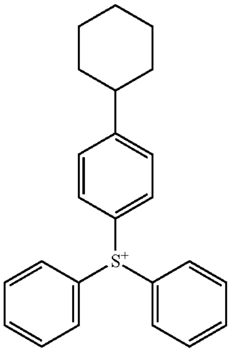
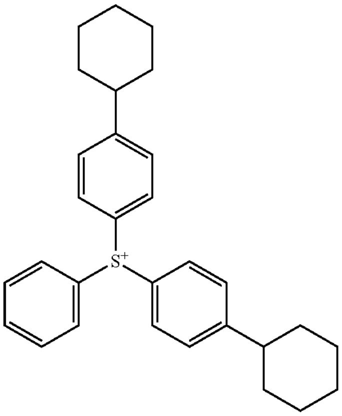
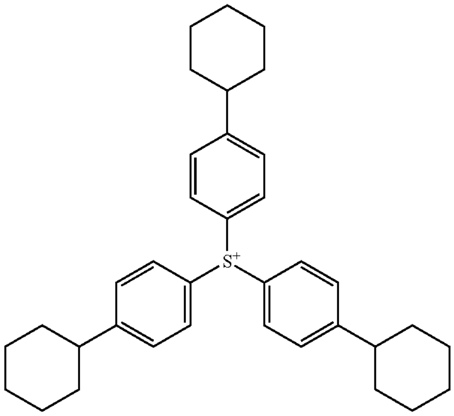
-continued
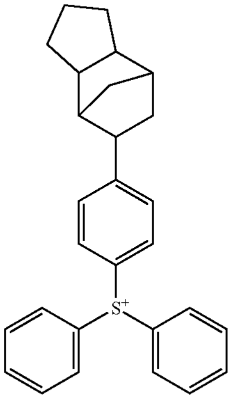
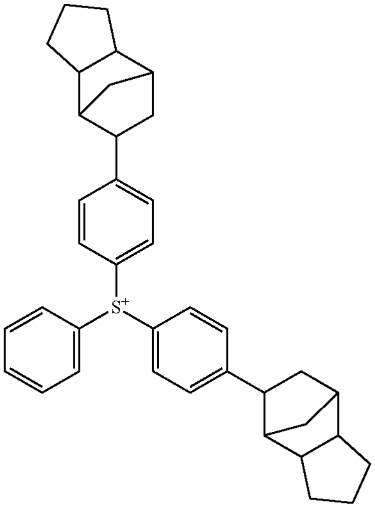
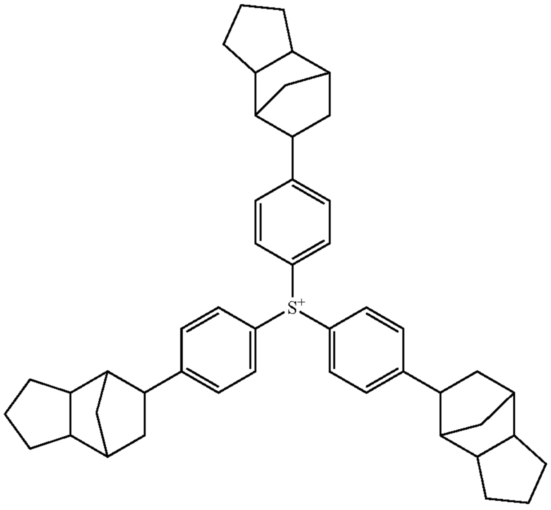

-continued
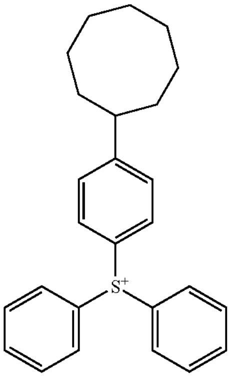
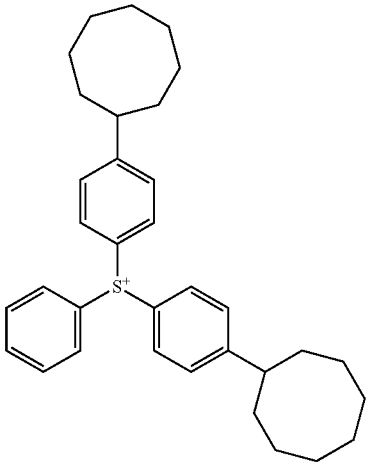
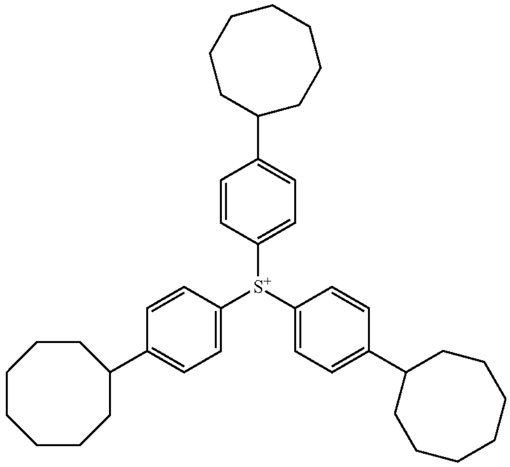
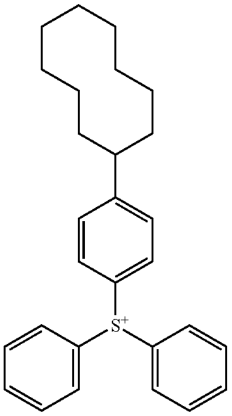
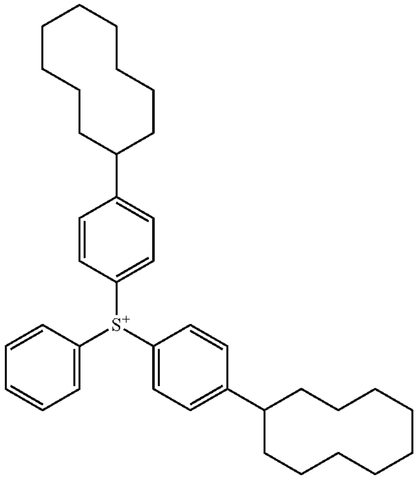
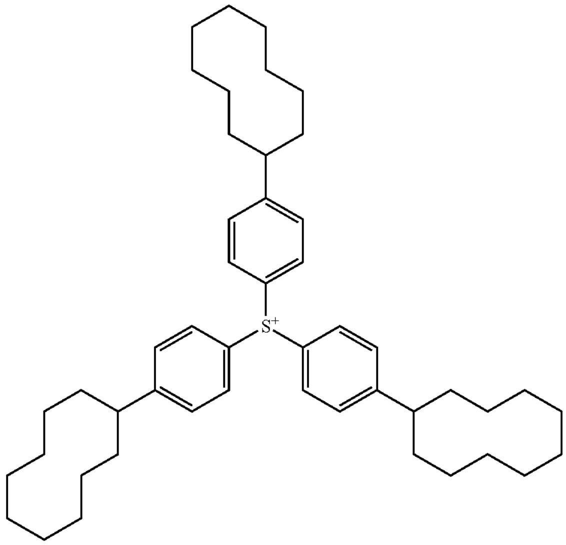
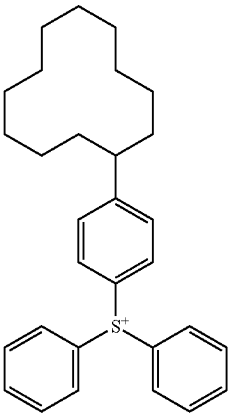

-continued
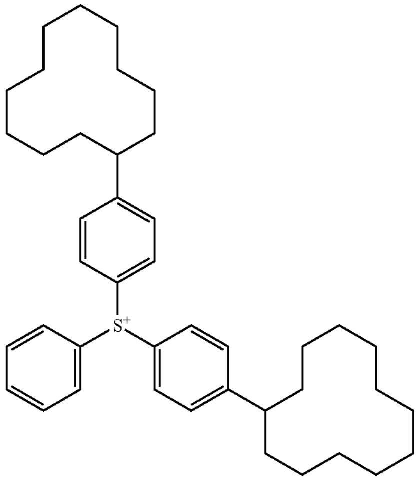
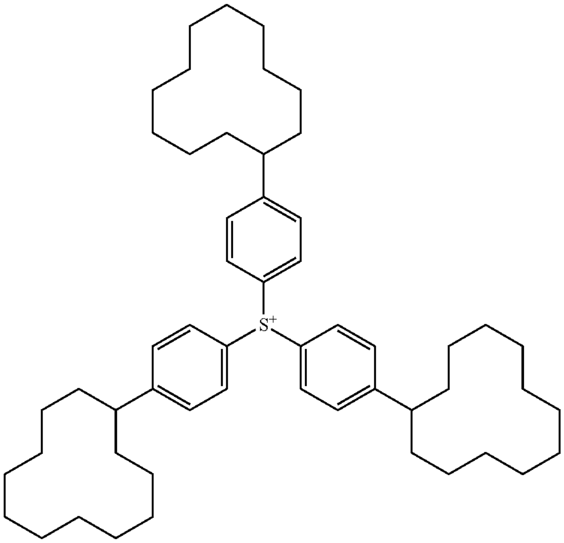
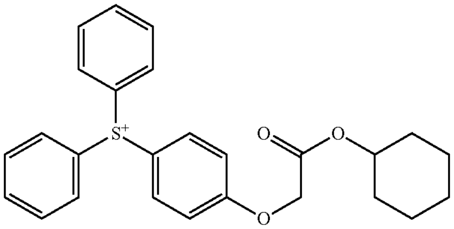
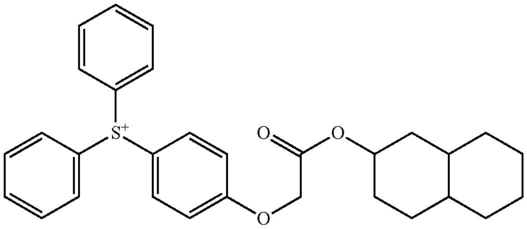
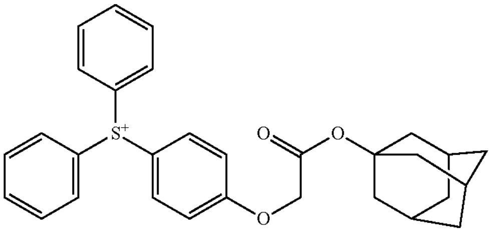
-continued
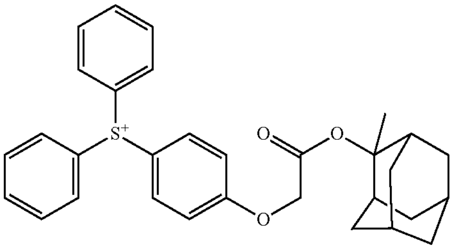
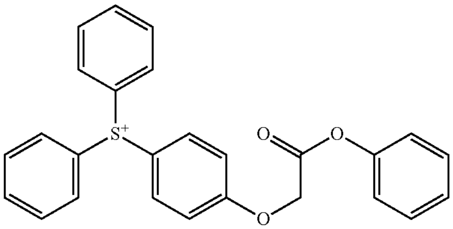
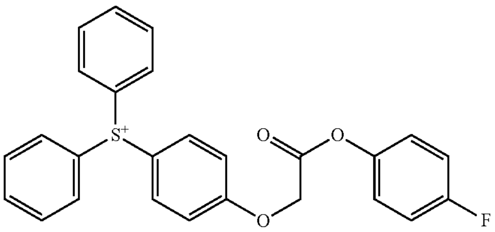
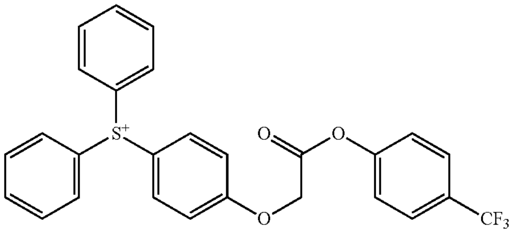
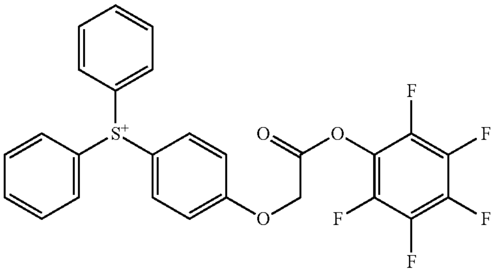
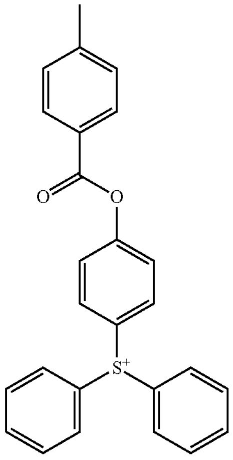

-continued
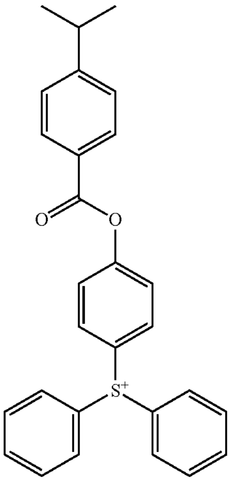
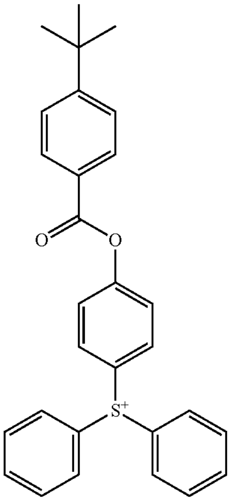
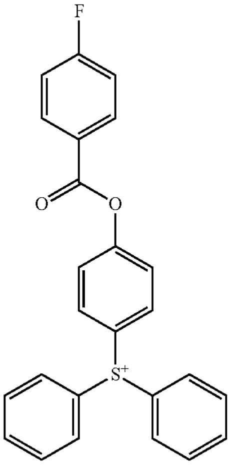
-continued
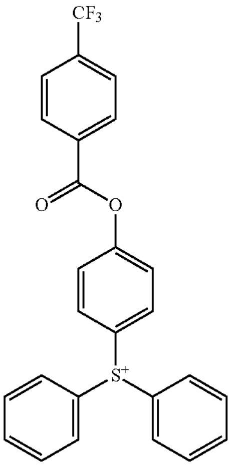
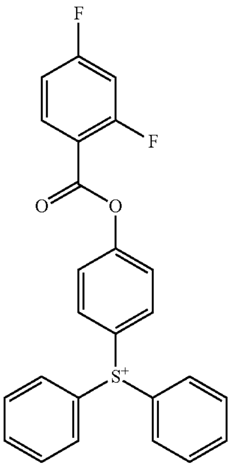
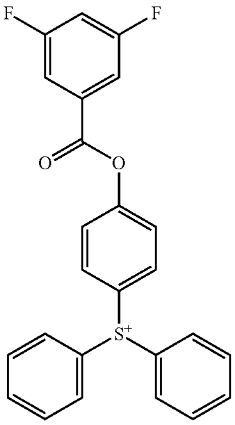

-continued
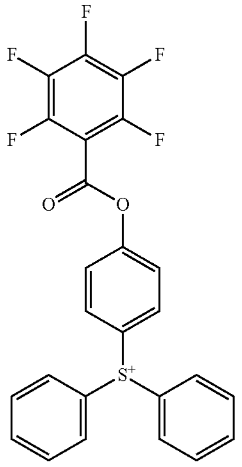
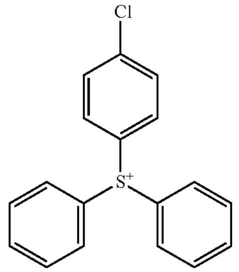
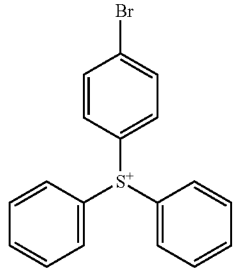
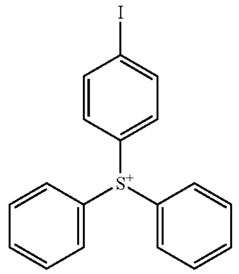
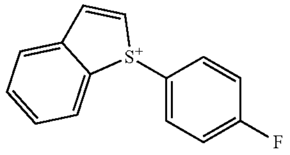
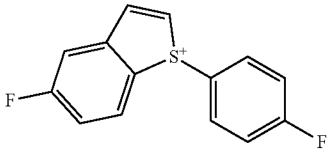
-continued
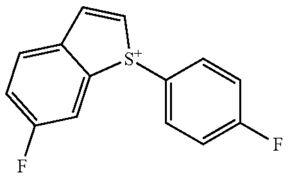
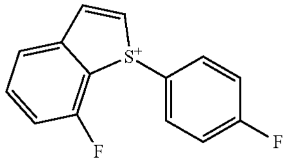
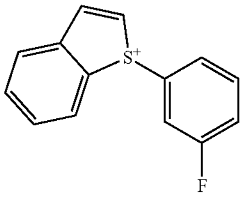
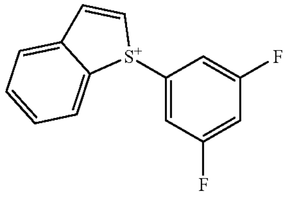
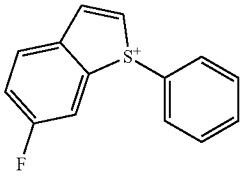
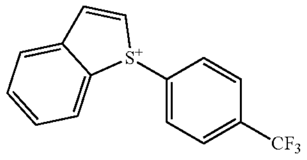
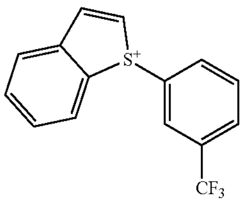
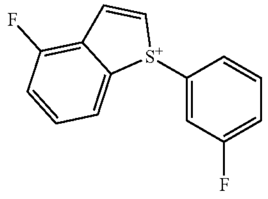
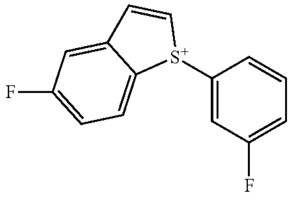

-continued
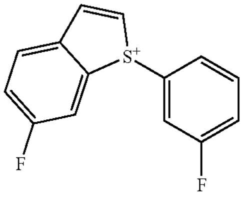
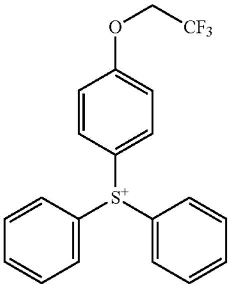
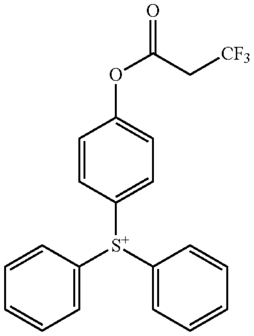
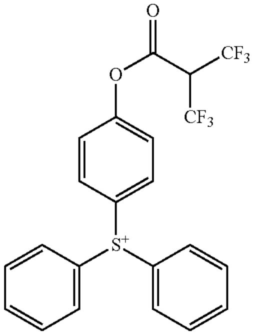
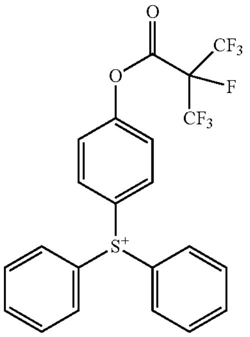
-continued
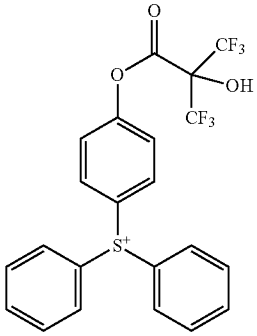
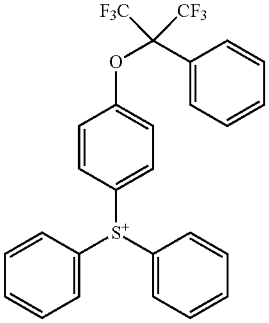
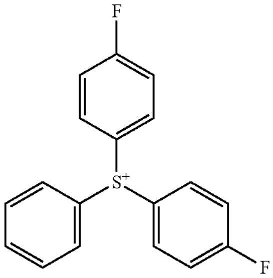
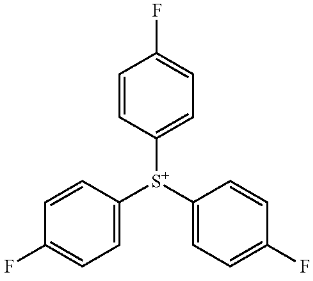
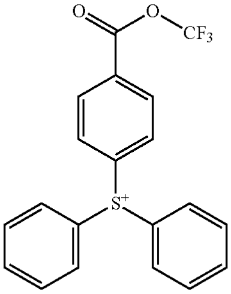

-continued
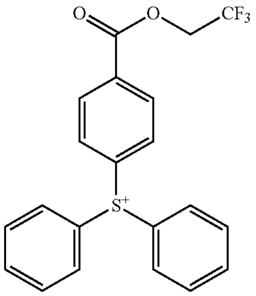
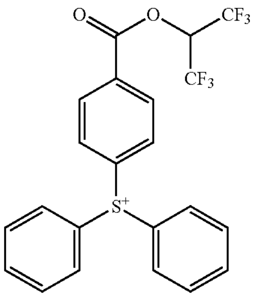
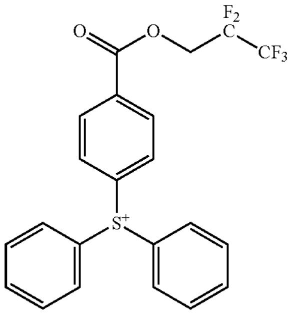
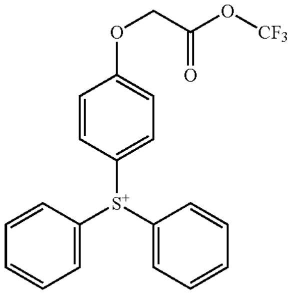
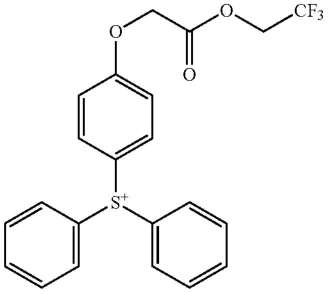
-continued
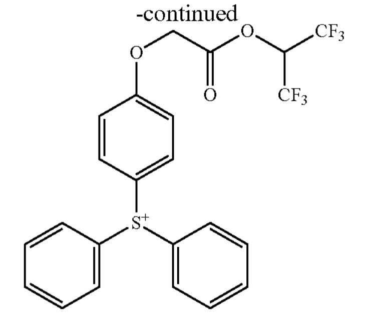
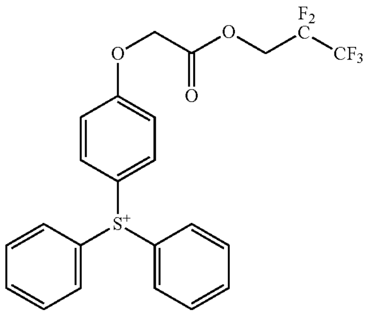
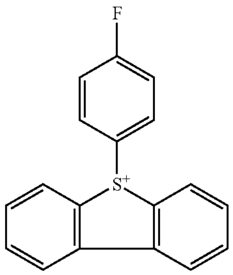
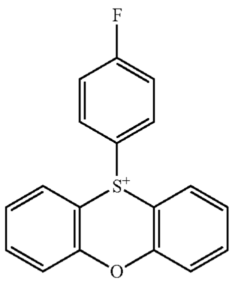
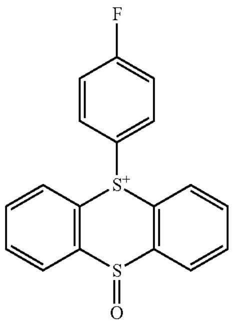

-continued
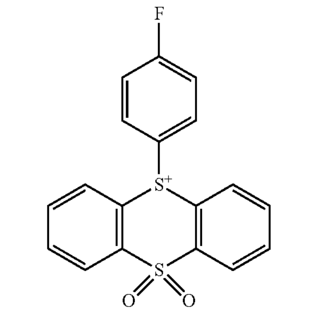
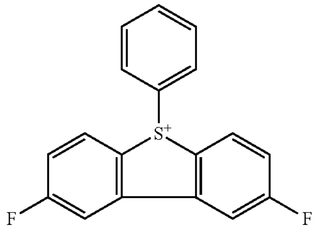
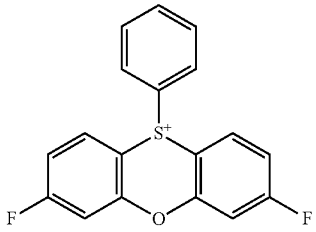
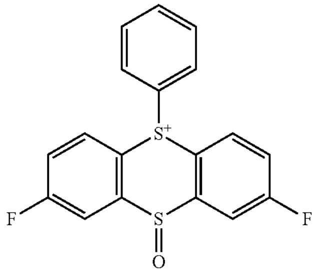
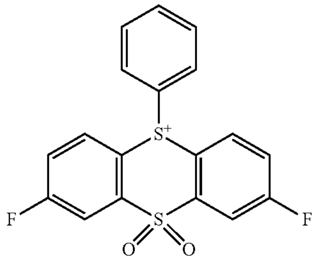
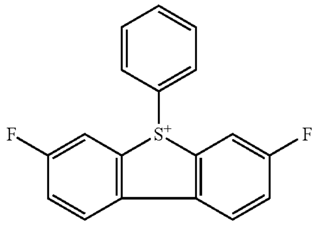
-continued
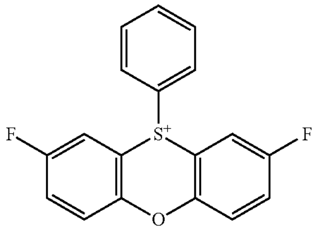
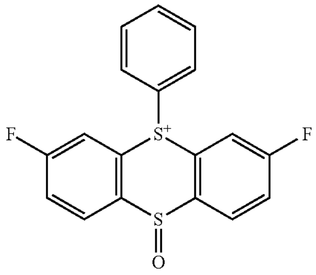
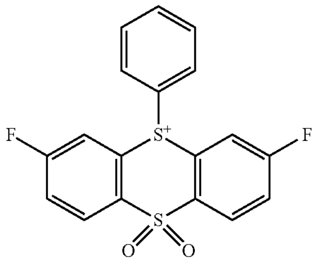
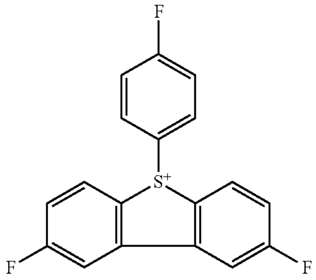
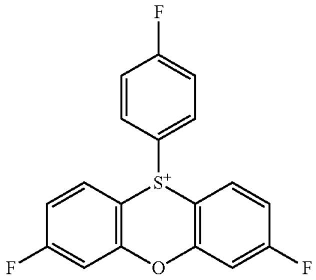
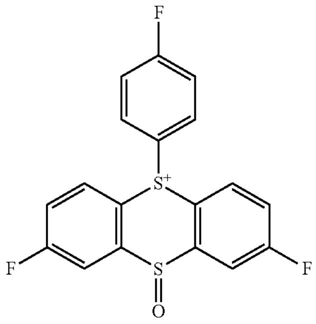

-continued
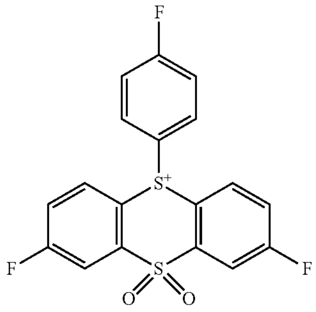
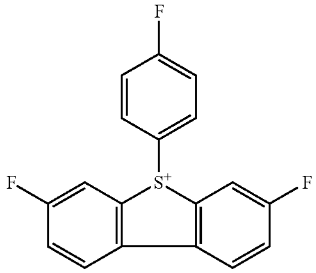
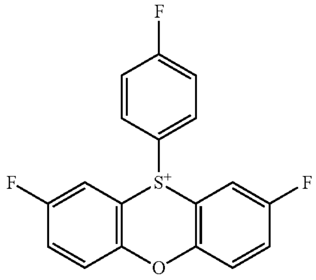
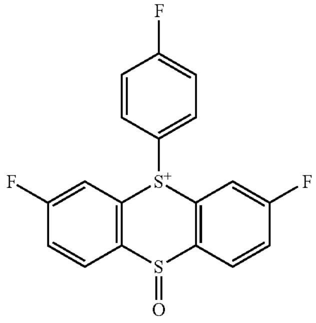
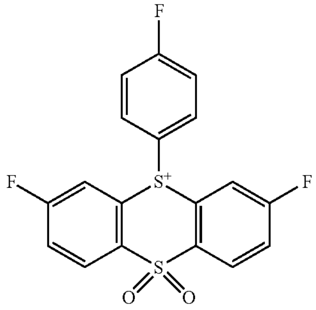
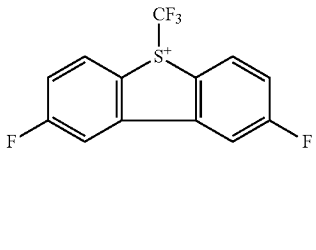
-continued
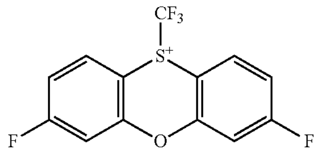
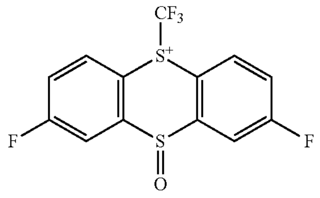
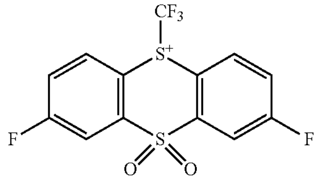
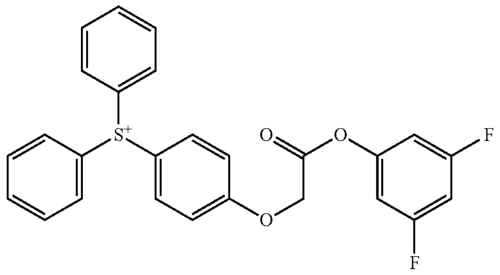
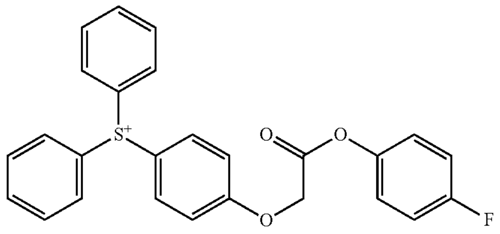
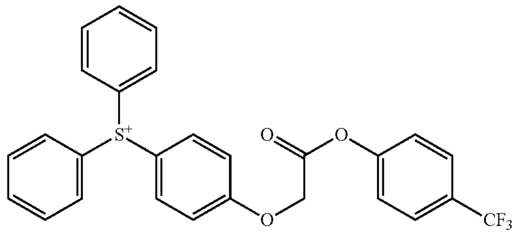
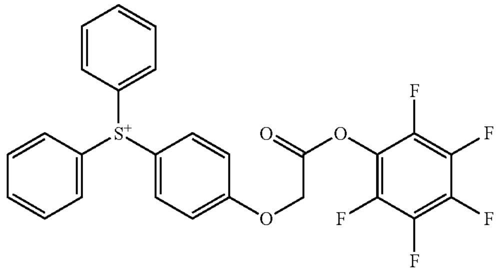

-continued
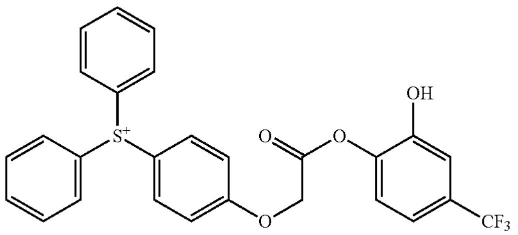
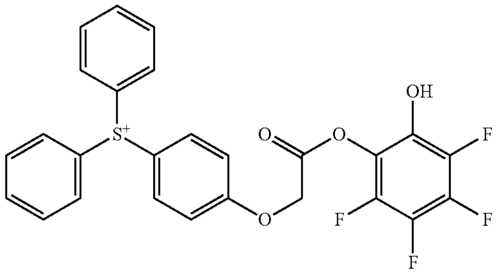
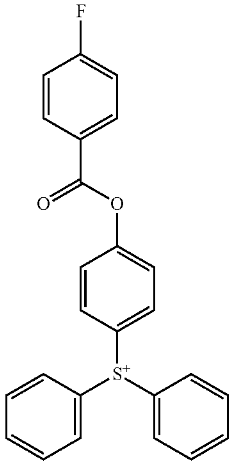
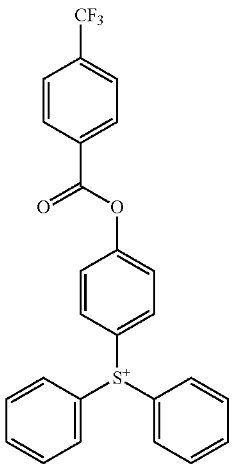
-continued
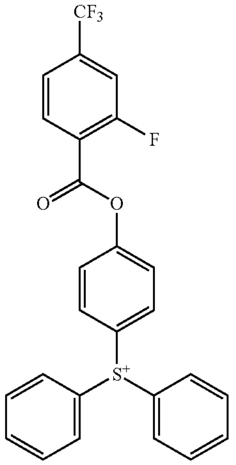
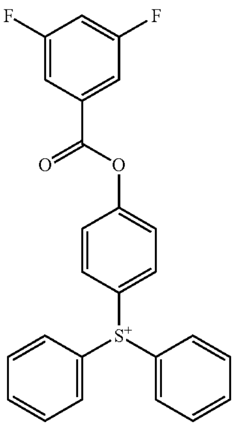
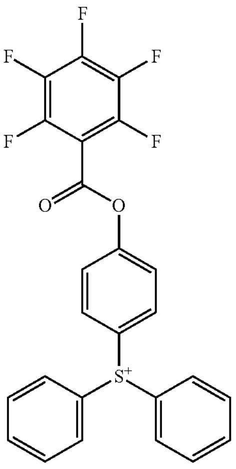

-continued
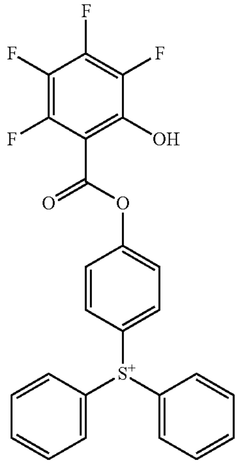
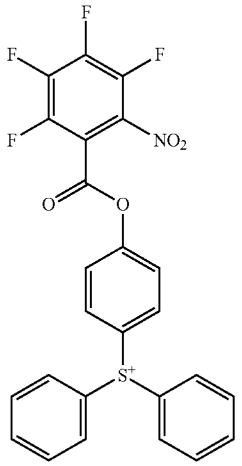
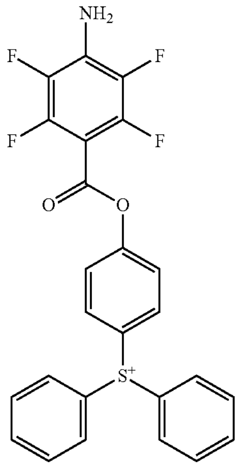
-continued
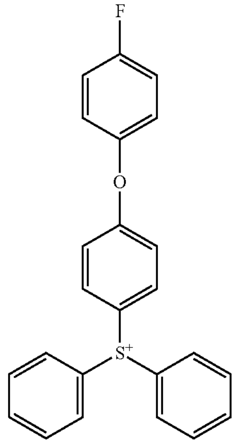
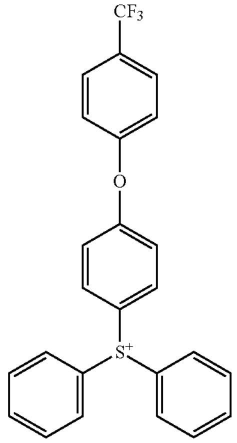
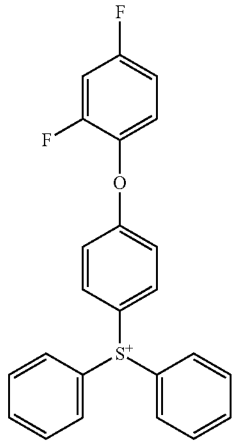

-continued
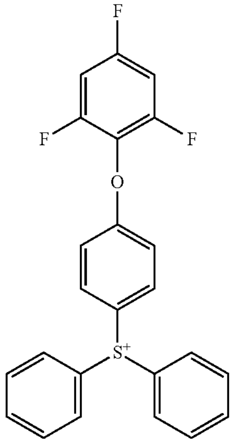
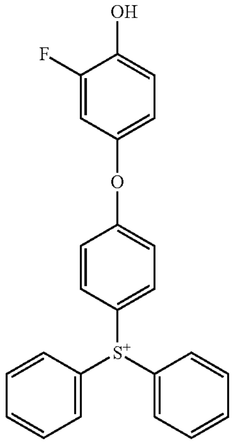
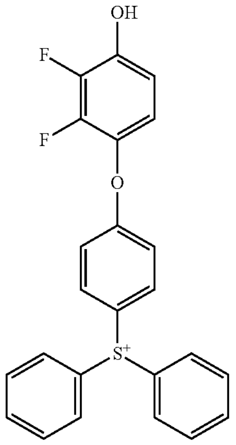
-continued
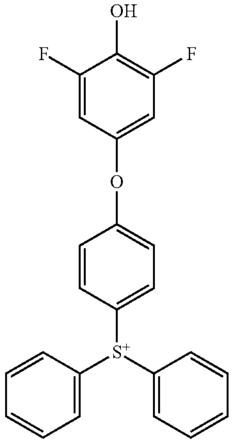
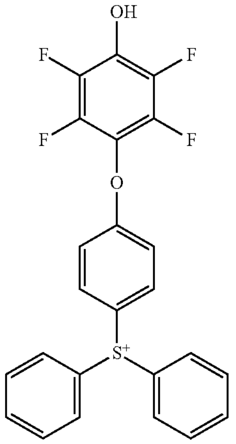
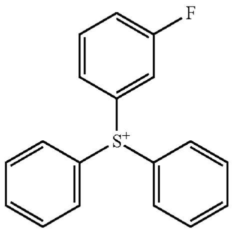
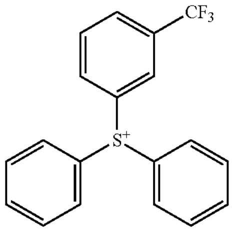
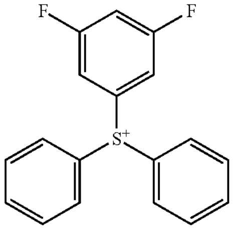
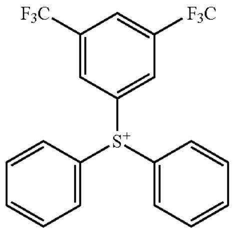
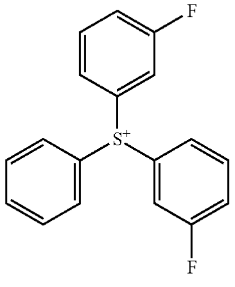
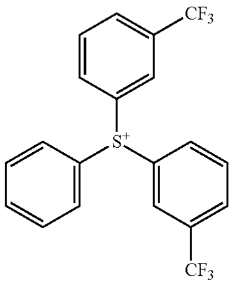

-continued
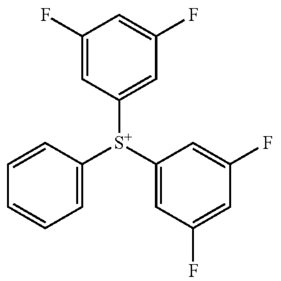
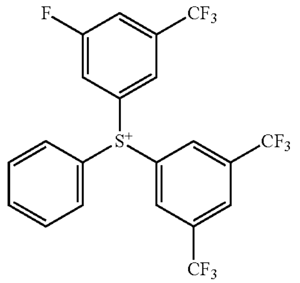
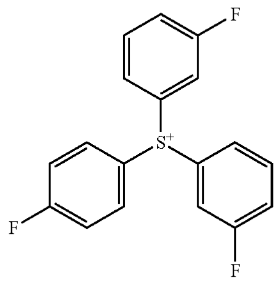
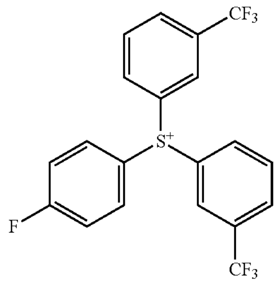
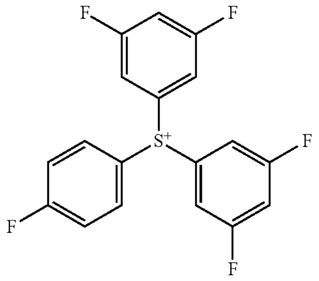
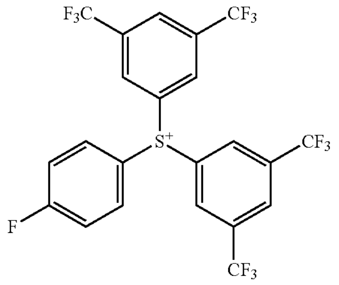
-continued
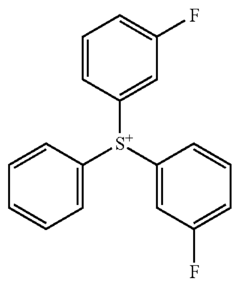
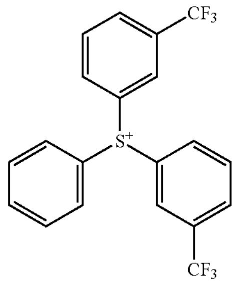
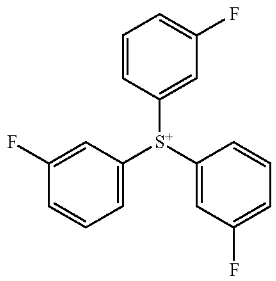
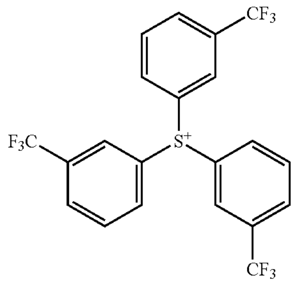
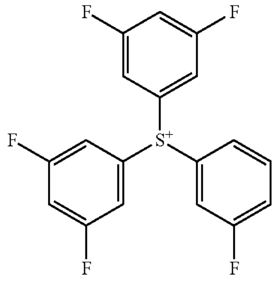
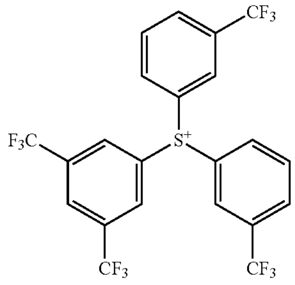

-continued
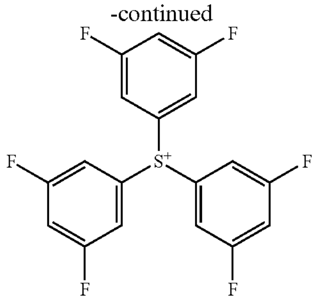
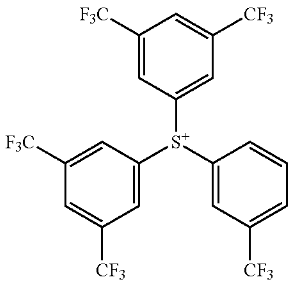
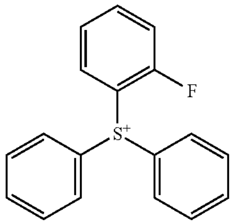
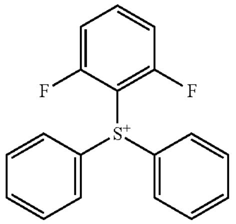
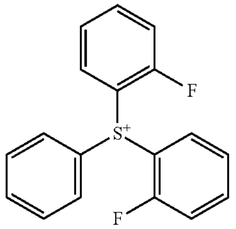
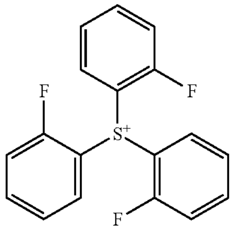
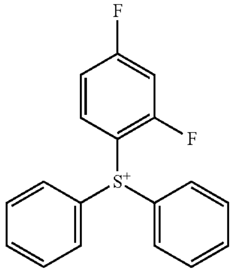
-continued
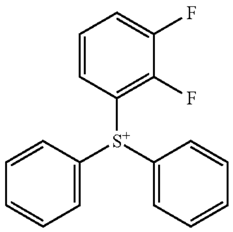
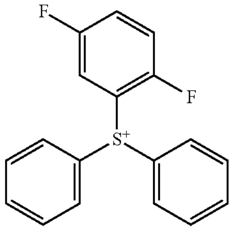
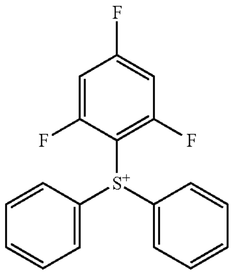
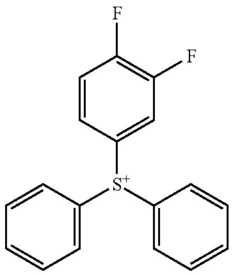
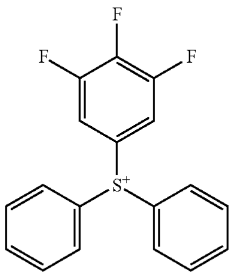
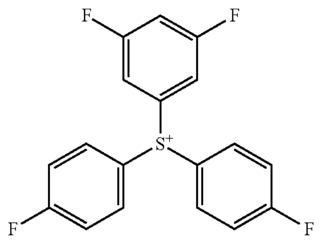

-continued
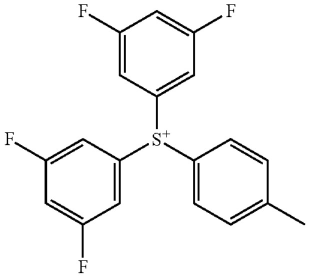
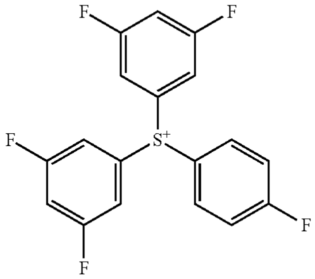
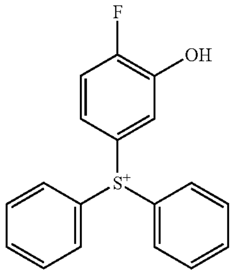
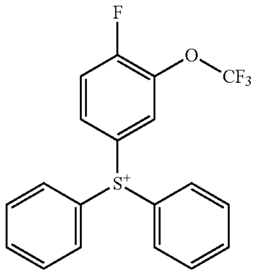
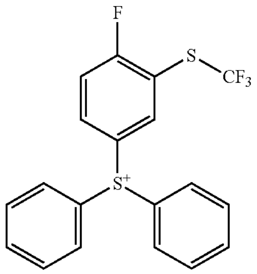
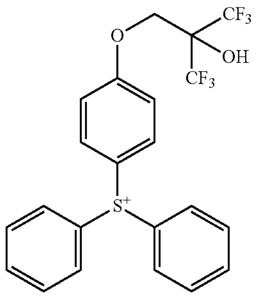
-continued
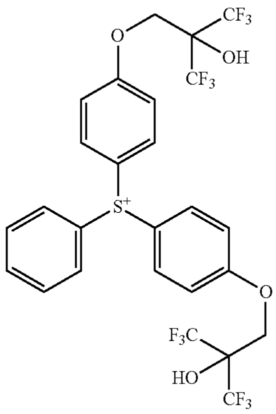
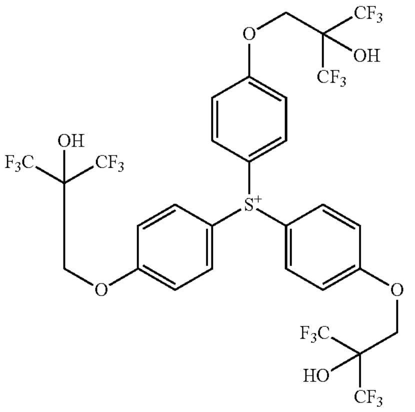
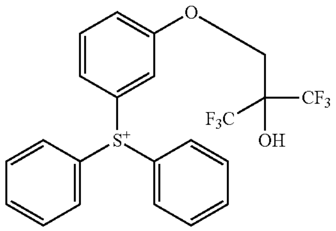
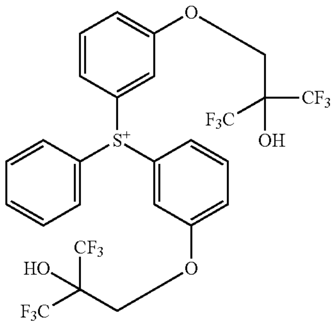
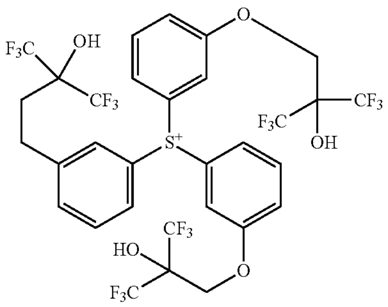

-continued
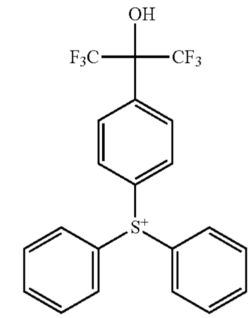
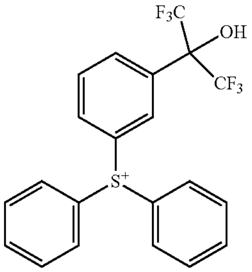
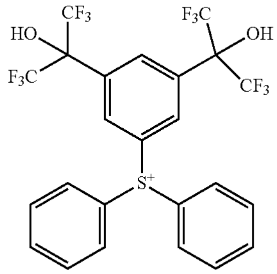
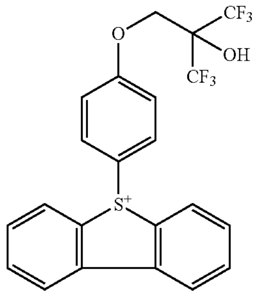
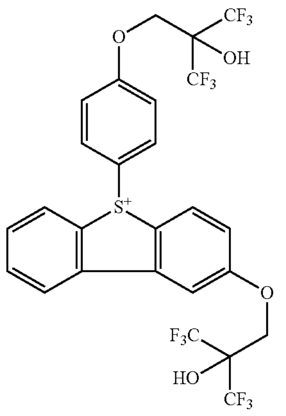
-continued
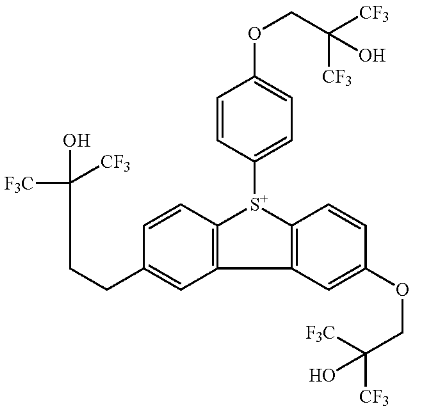
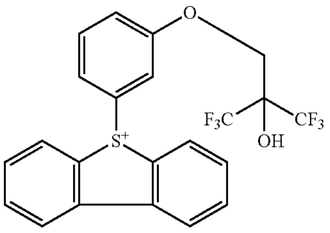
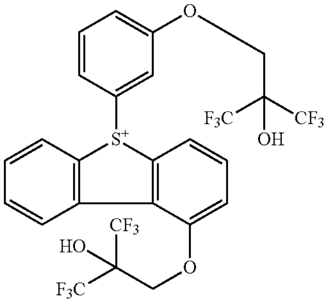
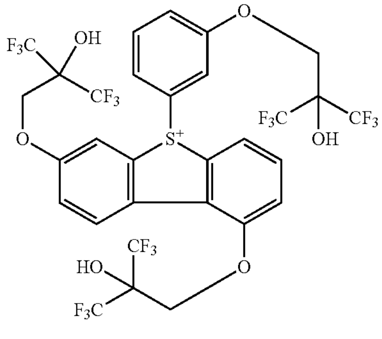
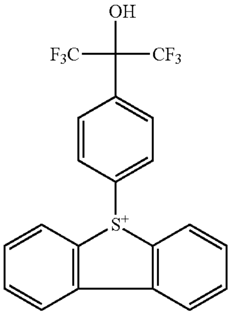

-continued
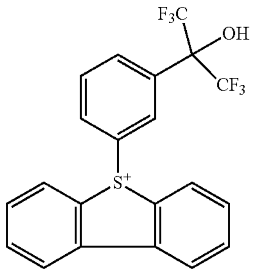
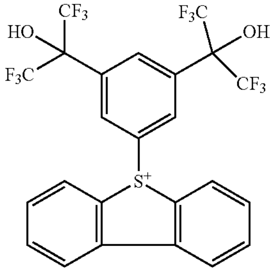
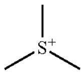
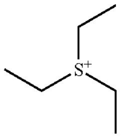
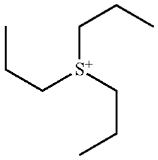
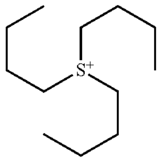
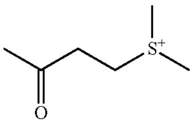
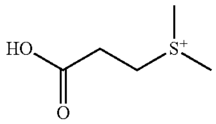
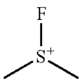
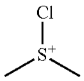
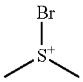
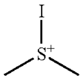
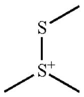
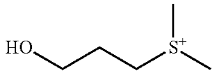
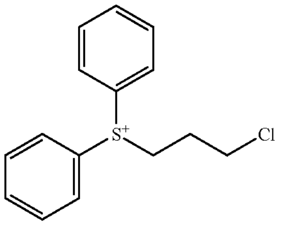
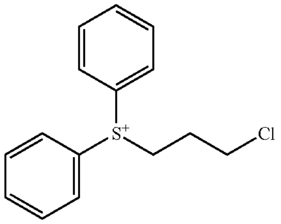
-continued
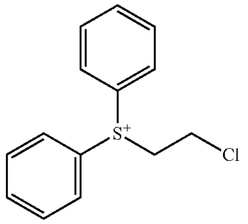
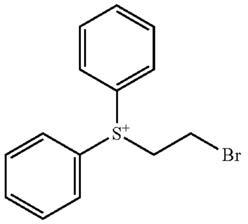
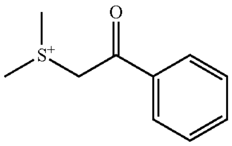
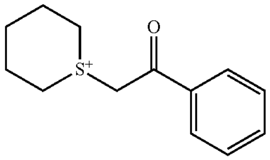
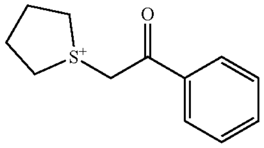
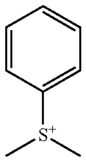
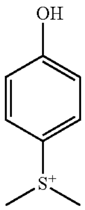
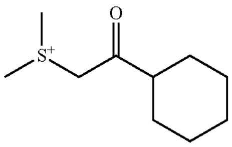
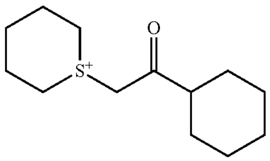
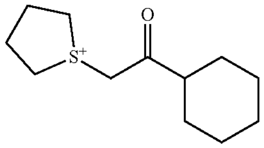

-continued
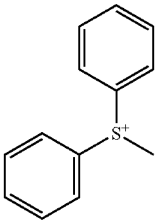
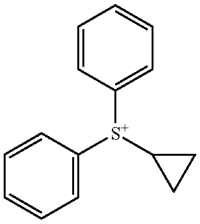
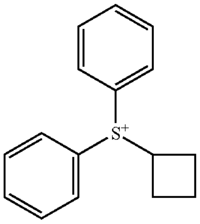
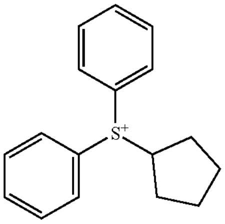
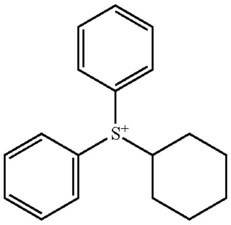
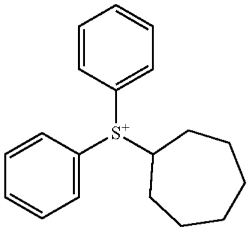
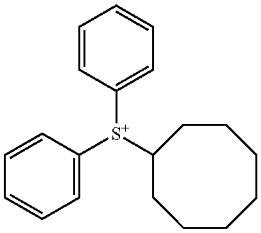
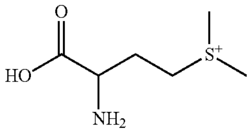
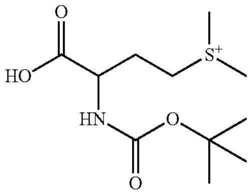
Examples of the cation in the iodonium salt having formula (1-2) are shown below, but not limited thereto.
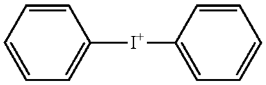
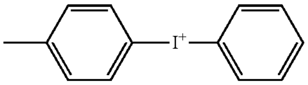
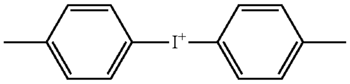
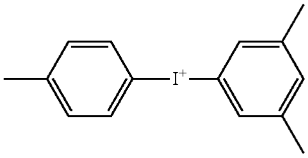
-continued
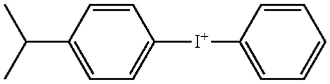
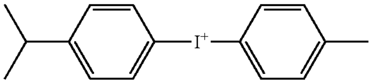
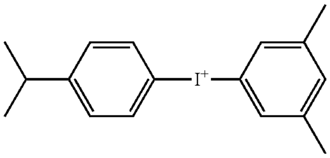
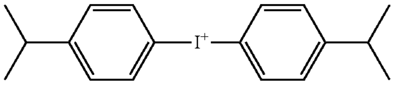
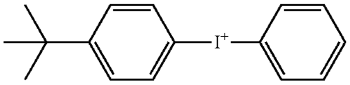
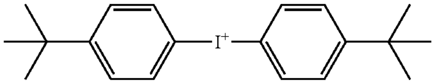
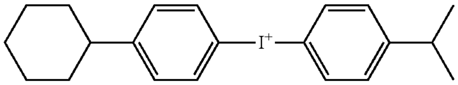
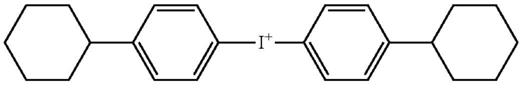
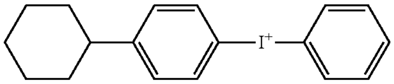
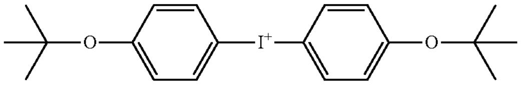
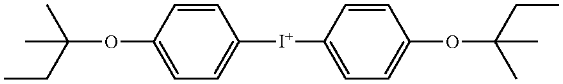
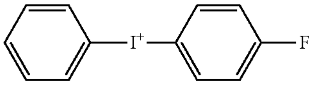
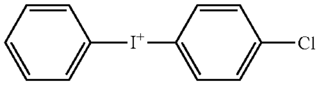
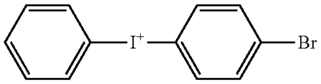
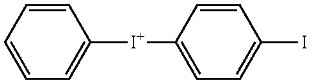
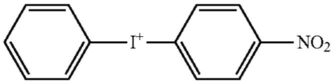
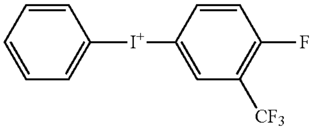
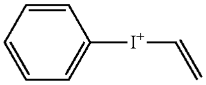
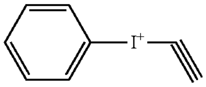
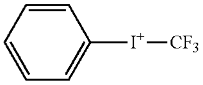

-continued

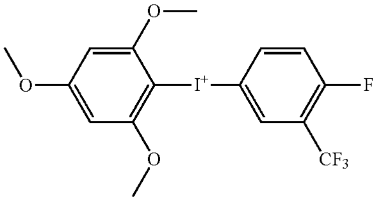

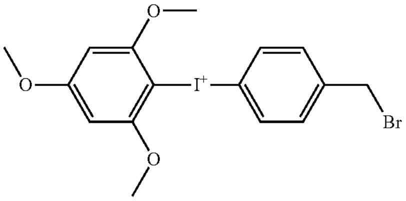

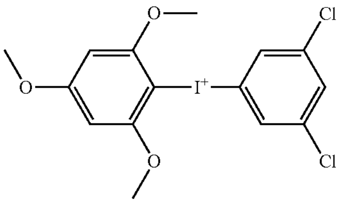

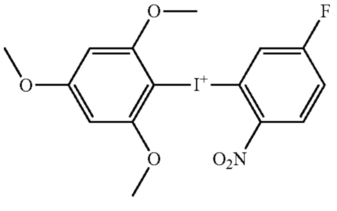

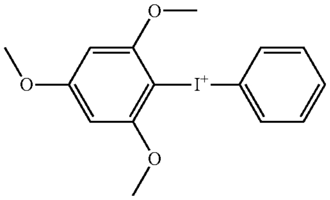

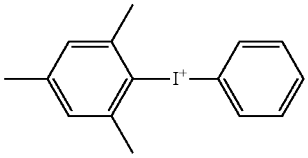

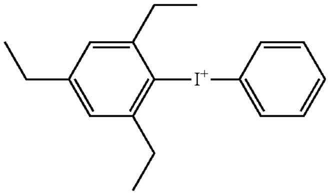

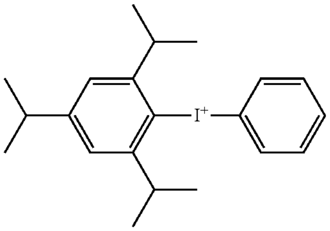

-continued

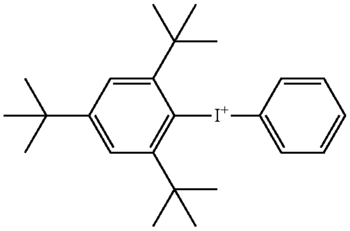

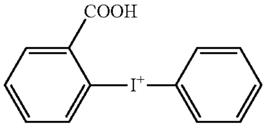

In formulae (1-1) and (1-2), $Xa^-$ is an anion of the following formula (1A), (1B), (1C) or (1D).

$$R^{fa}-CF_2-SO_3^- \quad (1A)$$

(1B)

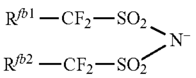

(1C)

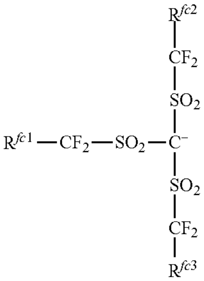

(1D)

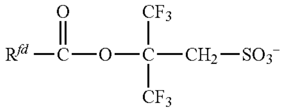

In formula (1A), $R^{fa}$ is fluorine or a $C_1$-$C_{40}$ hydrocarbyl group which may contain a heteroatom, the hydrocarbyl group may be saturated or unsaturated and straight, branched or cyclic. Examples thereof are as will be exemplified later for hydrocarbyl group $R^{111}$ in formula (1A').

Of the anions of formula (1A), a structure having formula (1A') is preferred.

(1A')

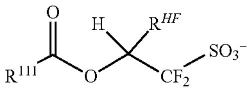

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic.

Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{39}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl; $C_7$-$C_{38}$ aralkyl groups such as benzyl and diphenylmethyl; and combinations thereof.

In the hydrocarbyl group, some or all of the hydrogen atoms may be substituted by a moiety containing a heteroatom such as oxygen, sulfur, nitrogen or halogen, or some —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride (—C(═O)—O—C(═O)—) or haloalkyl moiety. Examples of the heteroatom-containing hydrocarbyl group include tetrahydrofinyl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference is made to JP-A 2007-145797. JP-A 2008-106045, JP-A 2009-007327, and JP-A 2009-258695. Also useful are the sulfonium salts described in JP-A 2010-215608. JP-A 2012-041320. JP-A 2012-106986, and JP-A 2012-153644.

Examples of the anion having formula (1A) are as exemplified for the anion having formula (1A) in JP-A 2018-197853 (U.S. Pat. No. 11,022,883).

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$, $R^{fb2}$ and $R^{fb3}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—C—$SO_2$—$CF_2$—) to which they are attached, and the ring-forming pair is preferably a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are as exemplified for the anion having formula (1D) in JP-A 2018-197853.

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

(2)

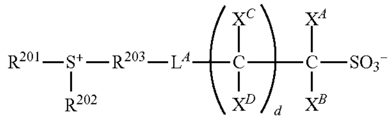

In formula (2), $R^{201}$ and $R^{202}$ are each independently halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, n-propyl, isopropyl, n-butyl, isobutyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[$5.2.1.0^{2,6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl: and combinations thereof. In the hydrocarbyl group, some or all of the hydrogen atoms may be substituted by a moiety containing a heteroatom such as oxygen, sulfur, nitrogen or halogen, or some —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride (—C(═O)—O—C(═O)—) or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene and tert-butylnaphthylene: and combinations thereof. In the hydrocarbylene group, some or all of the hydrogen atoms may be substituted by a moiety containing a heteroatom such as oxygen, sulfur, nitrogen or halogen, or some —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride (—C(═O)—O—C(═O)—) or haloalkyl moiety. Of the heteroatoms, oxygen is preferred.

In formula (2), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), d is an integer of 0 to 3.

Of the PAGs having formula (2), those having formula (2') are preferred.

(2')

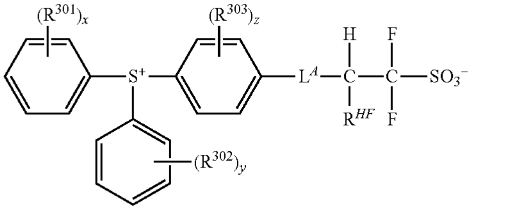

In formula (2'), $L^A$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the solvent. Also those having formula (2') are especially preferred because of extremely reduced acid diffusion.

Also sulfonium and iodonium salts having an anion containing an iodized or brominated aromatic ring are useful PAGs. These salts typically have the formulae (3-1) and (3-2).

(3-1)

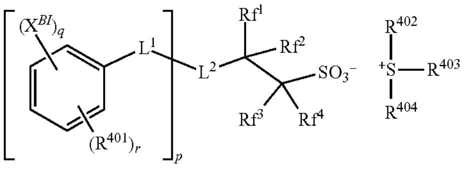

-continued (3-2)

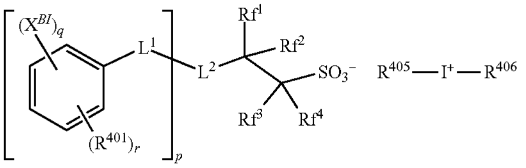

In formulae (3-1) and (3-2), p is an integer of 1 to 3; q is an integer of 1 to 5, and r is an integer of 0 to 3, meeting $1 \le q+r \le 5$. Preferably, q is 1, 2 or 3, more preferably 2 or 3, and r is 0, 1 or 2.

In formulae (3-1) and (3-2), $X^{BI}$ is iodine or bromine, and groups $X^{BI}$ may be identical or different when p and/or q is 2 or more.

$L^1$ is a single bond, ether bond, ester bond, or a $C_1$-$C_6$ saturated hydrocarbylene group which may contain an ether bond or ester bond. The saturated hydrocarbylene group may be straight, branched or cyclic.

$L^2$ is a single bond or a $C_1$-$C_{20}$ divalent linking group in case of p=1, and a $C_1$-$C_{20}$ (p+1)-valent linking group in case of p=2 or 3, the linking group optionally containing oxygen, sulfur or nitrogen.

$R^{401}$ is hydroxy, carboxy, fluorine, chlorine, bromine, amino or a $C_1$-$C_{20}$ saturated hydrocarbyl group. $C_1$-$C_{20}$ saturated hydrocarbyloxy group. $C_2$-$C_{20}$ saturated hydrocarbylcarbonyl, $C_2$-$C_{20}$ saturated hydrocarbyloxycarbonyl group, $C_2$-$C_{20}$ saturated hydrocarbylcarbonyloxy or $C_1$-$C_{20}$ saturated hydrocarbylsulfonyloxy group, which may contain fluorine, chlorine, bromine, hydroxy, amino or ether bond, or —$N(R^{401A})(R^{401B})$, —$N(R^{401C})$—C(═O)—$R^{401D}$ or —$N(R^{401C})$—C(═O)—O—$R^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain halogen, hydroxy, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. $R^{401D}$ is a $C_1$-$C_{16}$ aliphatic hydrocarbyl group. $C_6$-$C_{14}$ aryl group or $C_7$-$C_{15}$ aralkyl group, which may contain halogen, hydroxy, a $C_1$-$C_6$ saturated hydrocarbyloxy, $C_2$-$C_6$ saturated hydrocarbylcarbonyl, or $C_2$-$C_6$ saturated hydrocarbylcarbonyloxy moiety. The aliphatic hydrocarbyl group may be saturated or unsaturated and straight, branched or cyclic. The saturated hydrocarbyl, hydrocarbyloxy, hydrocarbyloxycarbonyl, hydrocarbylcarbonyl and hydrocarbylcarbonyloxy groups may be straight, branched or cyclic. When p and/or r is 2 or more, groups $R^{401}$ may be identical or different.

Inter alia, $R^{401}$ is preferably selected from hydroxy, —$N(R^{401C})$—C(═O)—$R^{401D}$, —$N(R^{401C})$—C(═O)—O—$R^{401D}$, fluorine, chlorine, bromine, methyl, and methoxy.

In formulae (3-1) and (3-2). $Rf^1$ to $Rf^4$ are each independently hydrogen, fluorine or trifluoromethyl, at least one thereof being fluorine or trifluoromethyl. Also $Rf^1$ and $Rf^2$, taken together, may form a carbonyl group. Most preferably both $Rf^3$ and $Rf^4$ are fluorine.

In formulae (3-1) and (3-2), $R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof are as exemplified above for the hydrocarbyl groups $R^{101}$ to $R^{105}$ in formulae (1-1) and (1-2). In the hydrocarbyl group, some or all of the hydrogen atoms may be substituted by hydroxy, carboxy, halogen, cyano, nitro, mercapto, sultone, sulfone, or sulfonium salt-containing moiety; or some —$CH_2$— may be replaced by an ether bond, ester bond, carbonyl, amide bond, carbonate or sulfonic ester bond. A pair of $R^{402}$ and $R^{403}$ may bond together to form a ring with the sulfur atom to which they are attached. Examples of the ring are as exemplified above for the ring that $R^{101}$ and $R^{102}$ in formula (1-1), taken together, form with the sulfur atom to which they are attached.

The cation in the sulfonium salt having formula (3-1) is as exemplified above for the cation in the sulfonium salt having formula (1-1). The cation in the iodonium salt having formula (3-2) is as exemplified above for the cation in the iodonium salt having formula (1-2).

Examples of the anion in the onium salt having formula (3-1) or (3-2) are shown below, but not limited thereto. Herein $X^{BI}$ is as defined above.

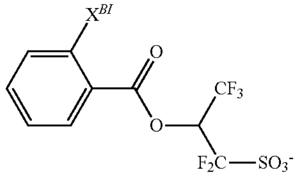

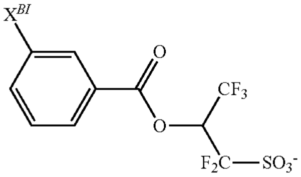

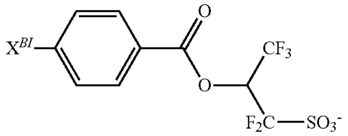

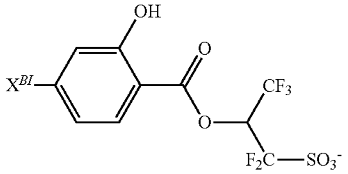

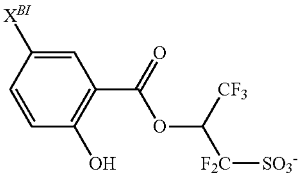

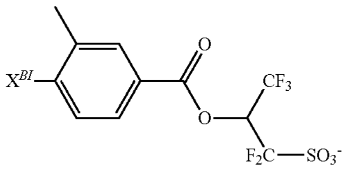

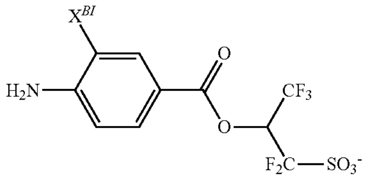

-continued

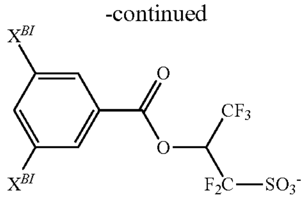

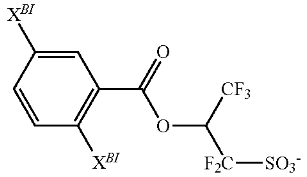

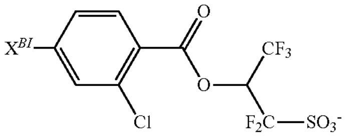

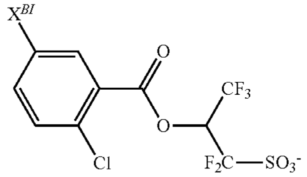

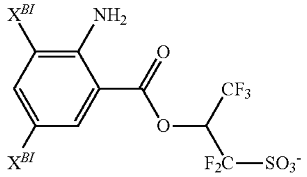

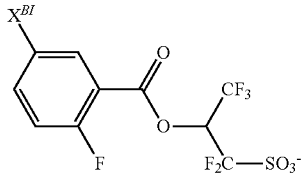

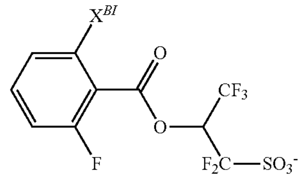

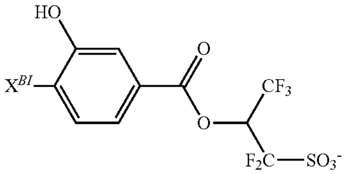

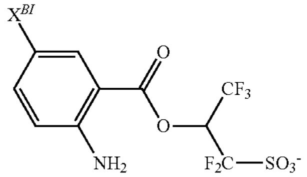

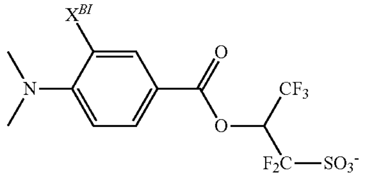

-continued
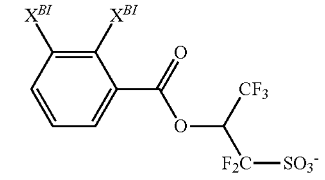
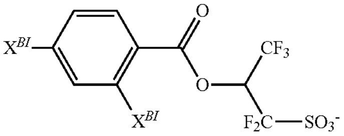
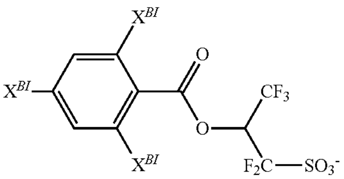
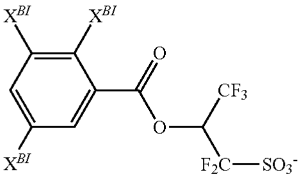
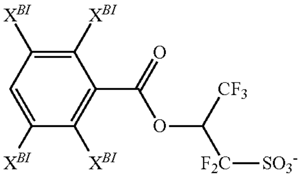
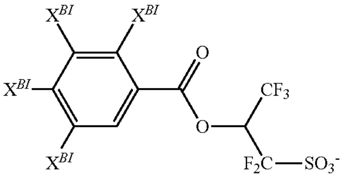
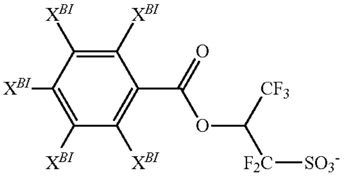
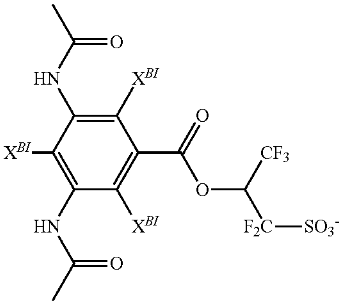
-continued
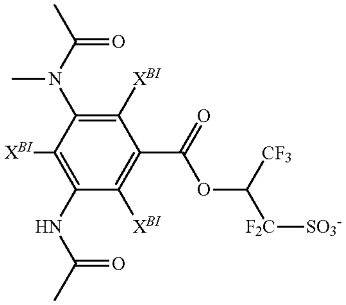
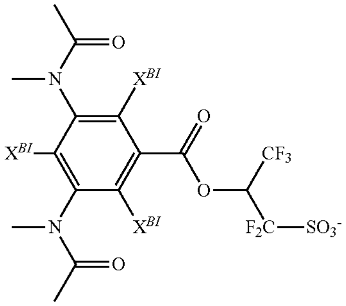
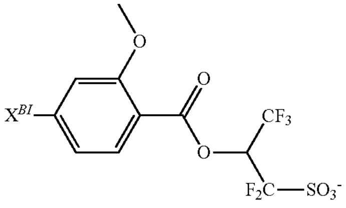
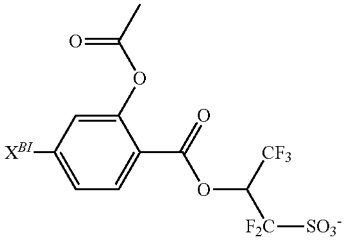
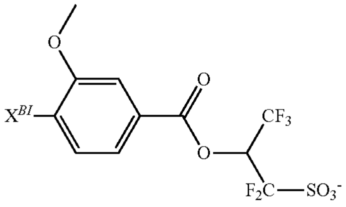
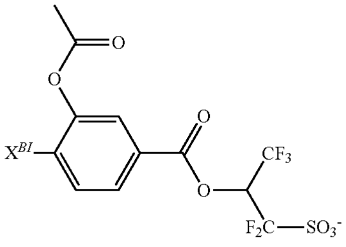

-continued
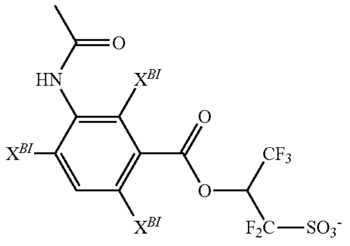
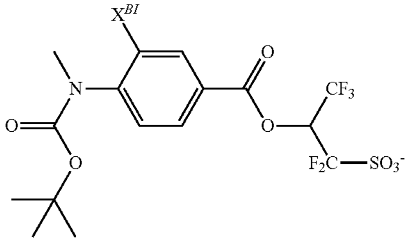
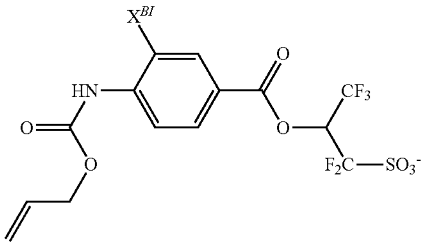
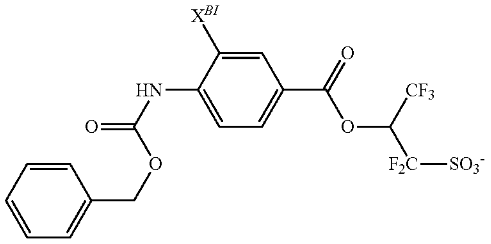
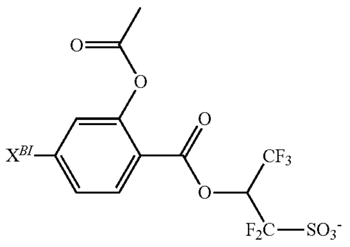
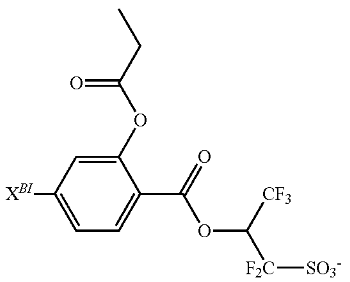
-continued
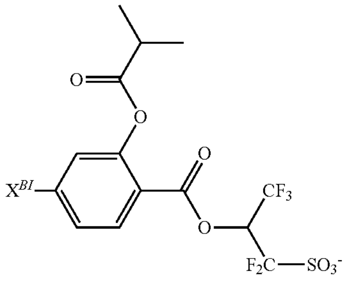
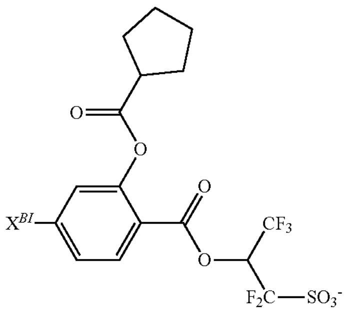
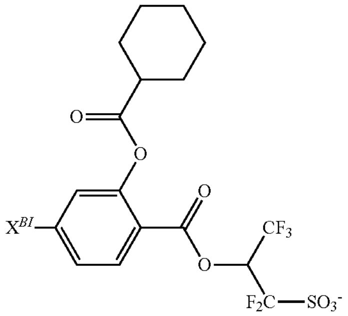
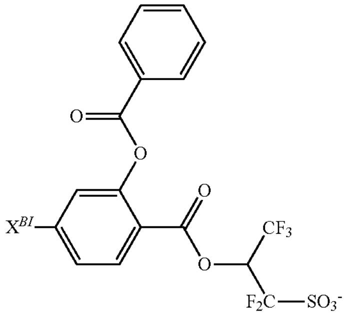
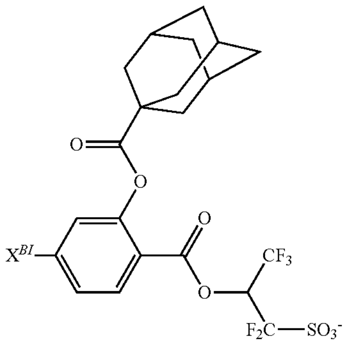

-continued
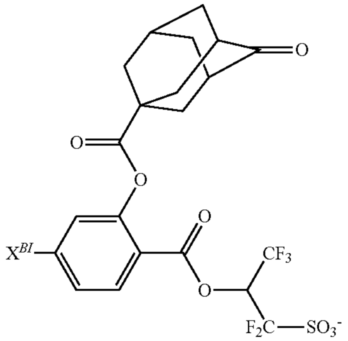
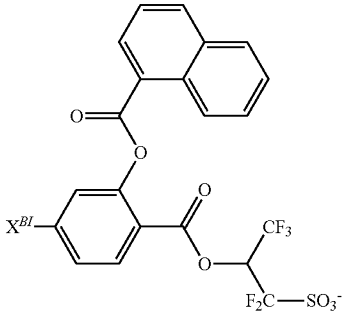
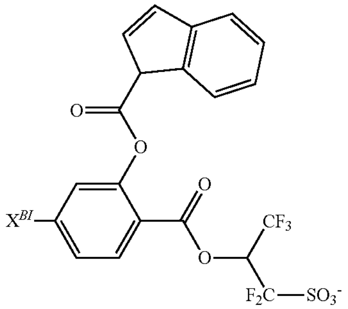
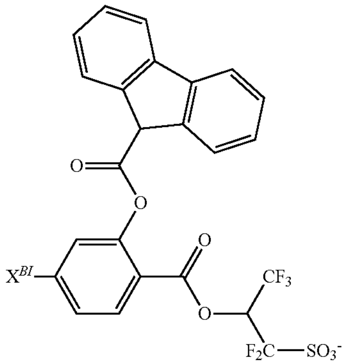
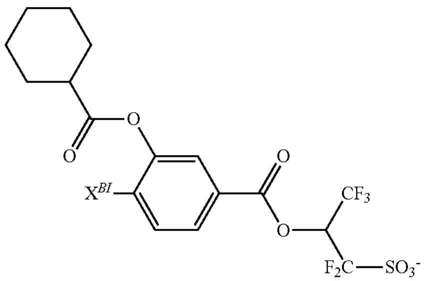
-continued
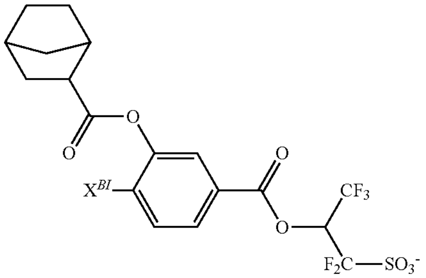
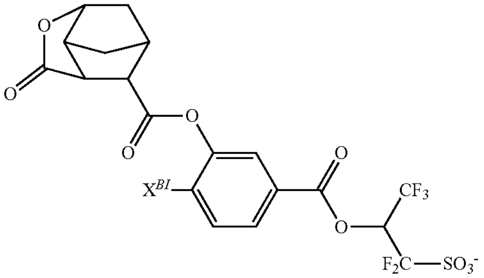
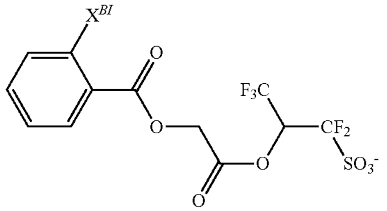
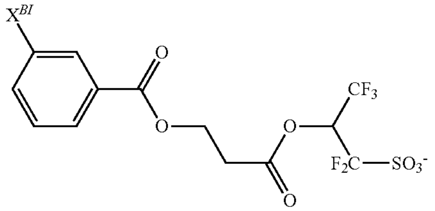
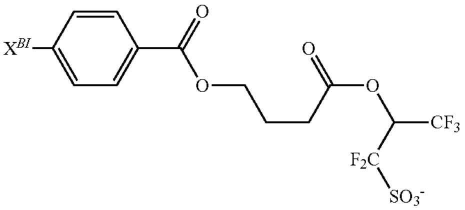
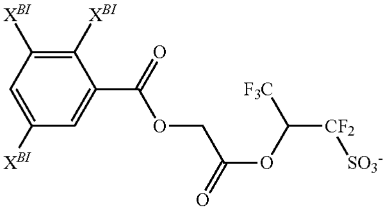
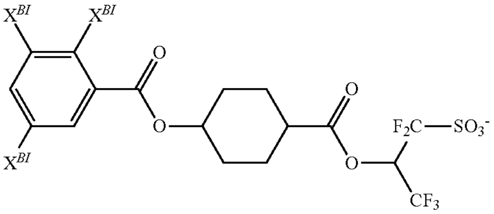

-continued
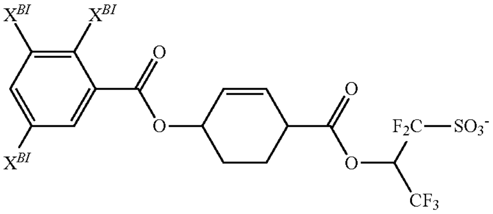
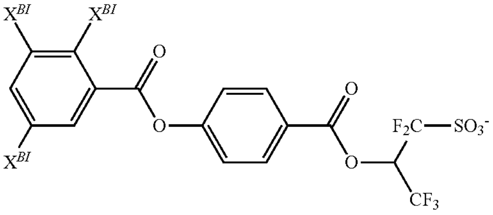
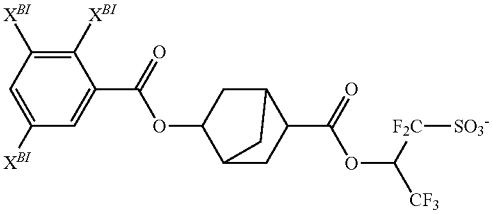
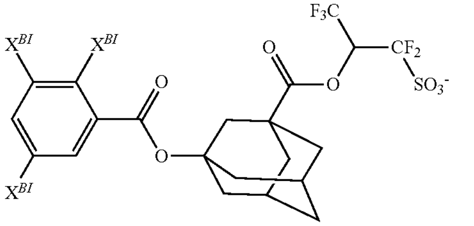
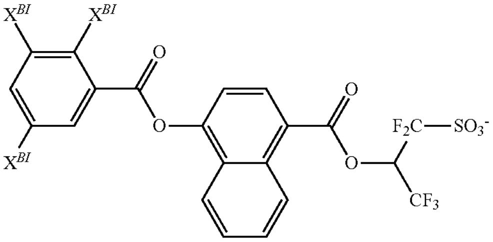
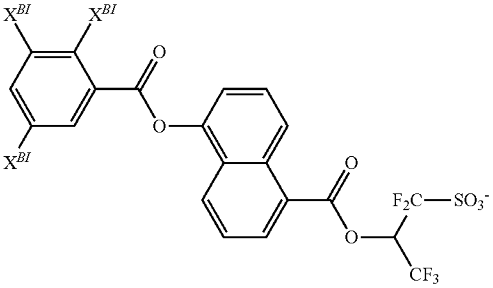
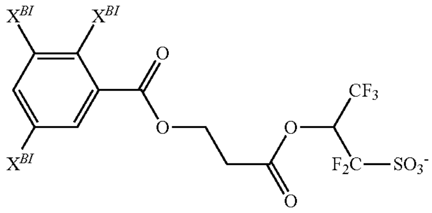
-continued
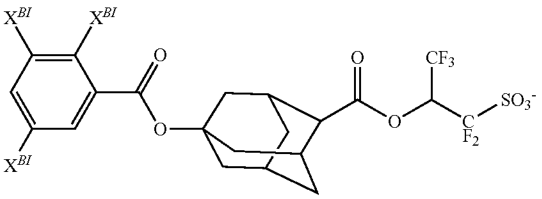
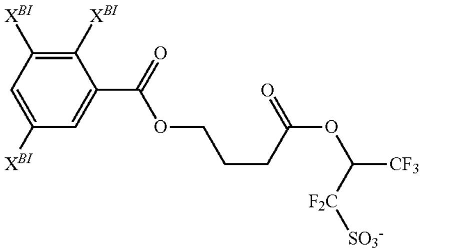
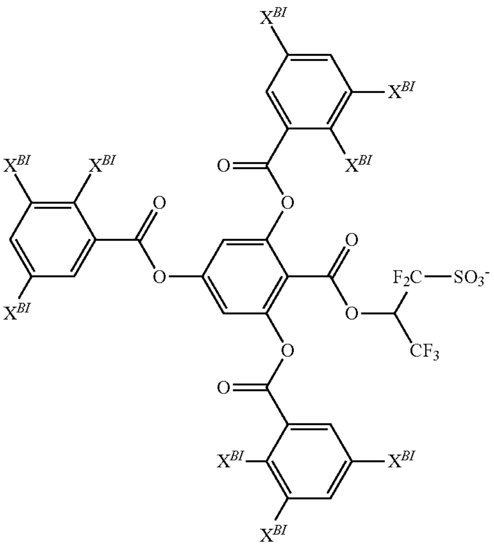
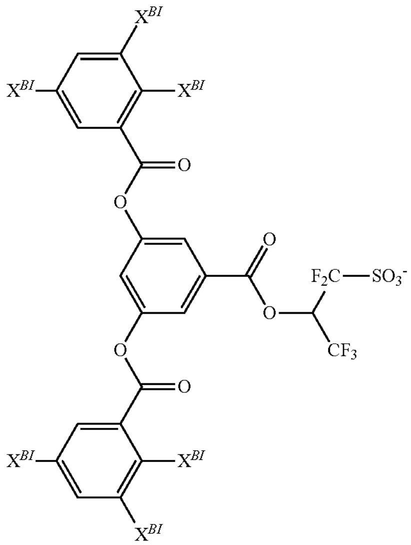

-continued
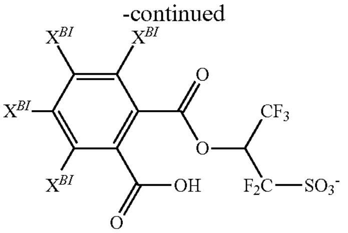
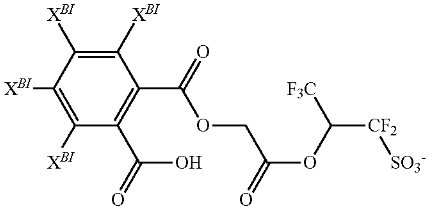
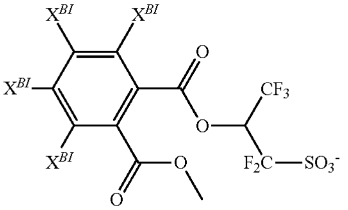
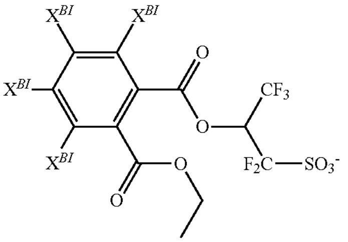
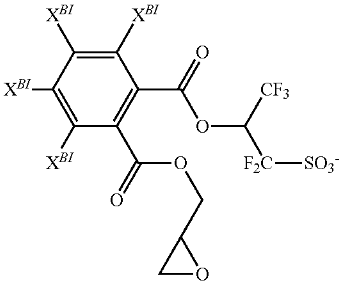
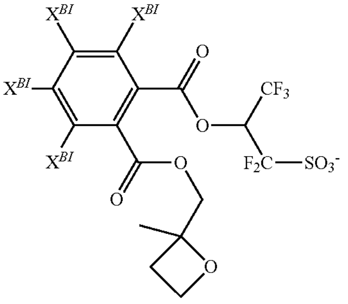
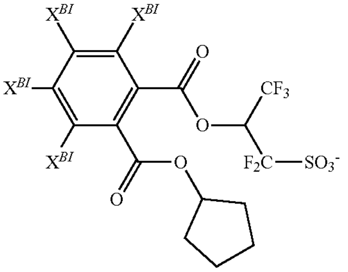
-continued
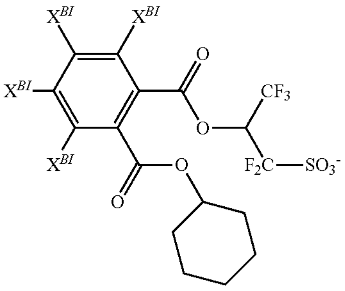
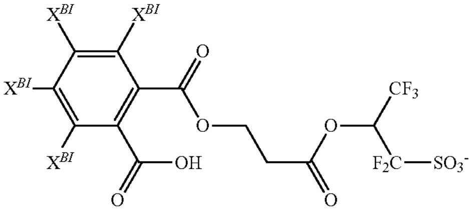
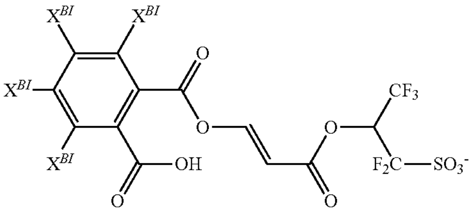
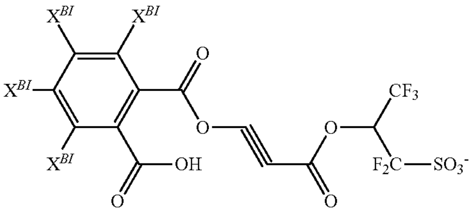
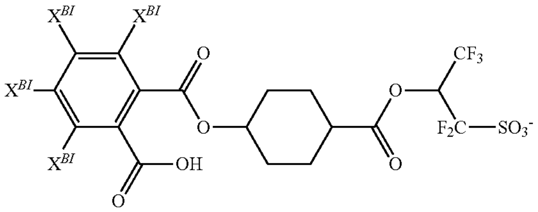
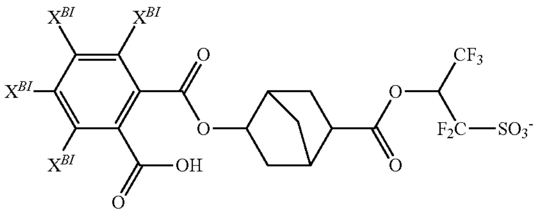
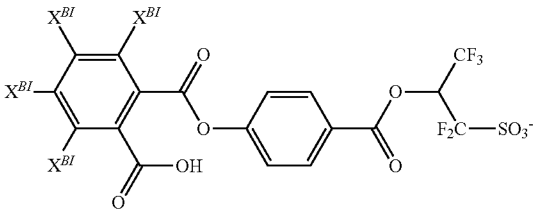

-continued
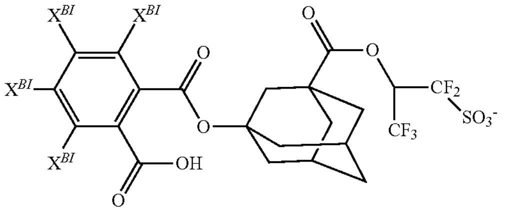
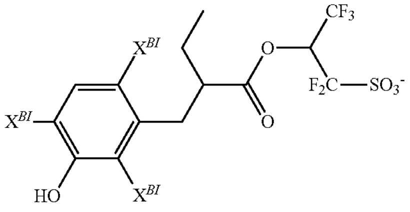
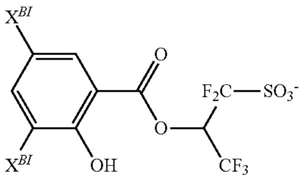
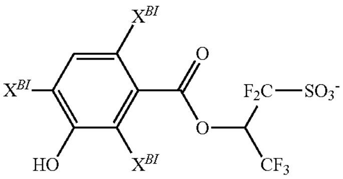
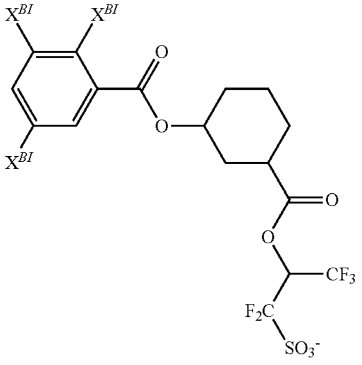
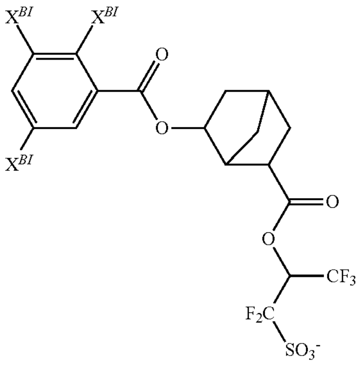
-continued
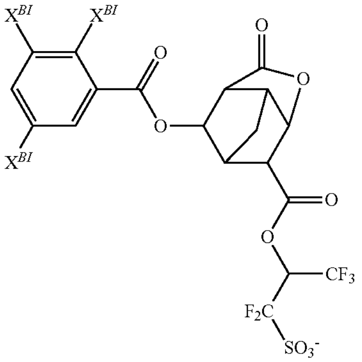
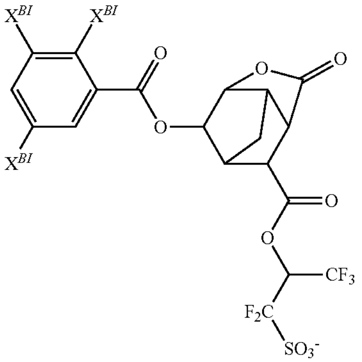
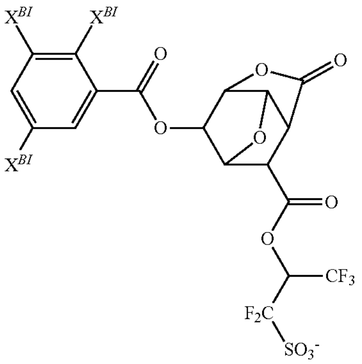
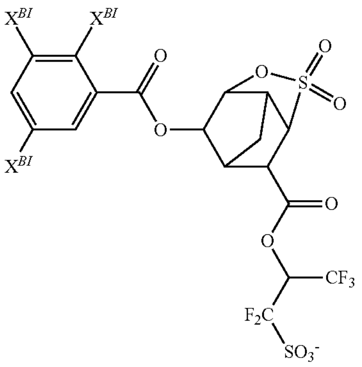

-continued
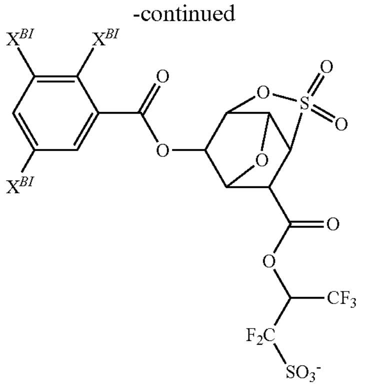
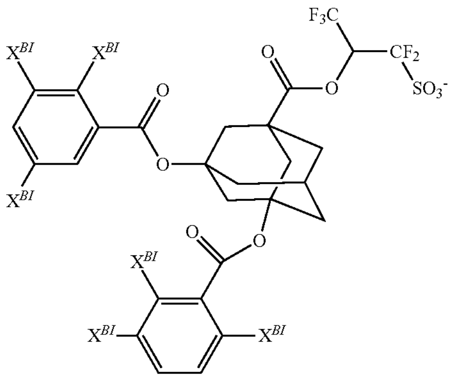
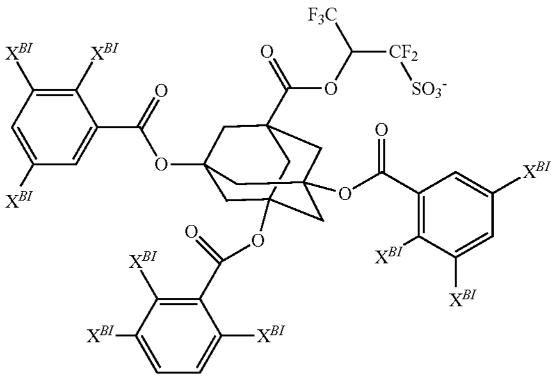
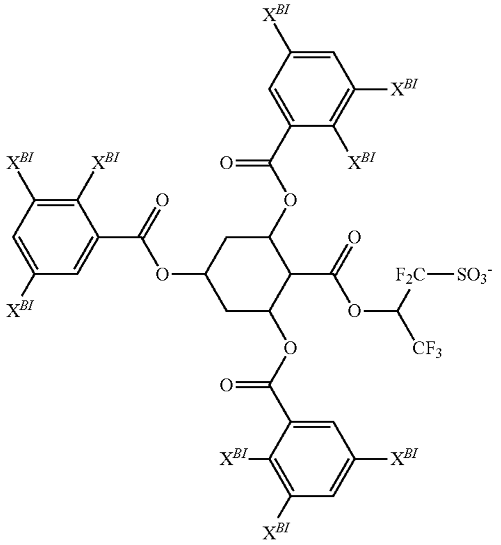
-continued
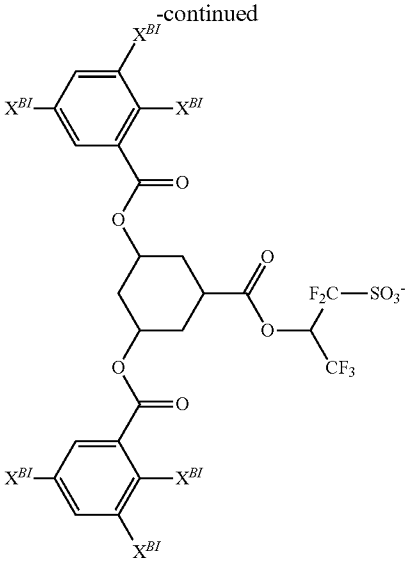
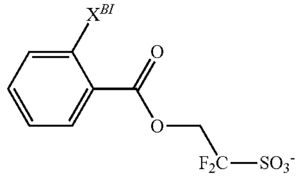
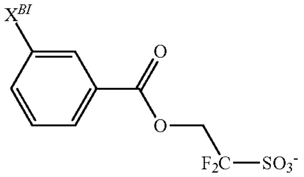
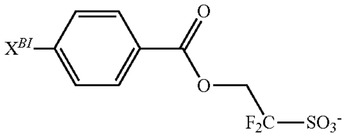
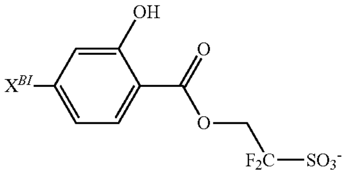
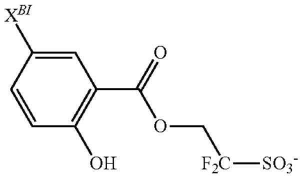
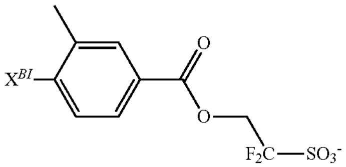
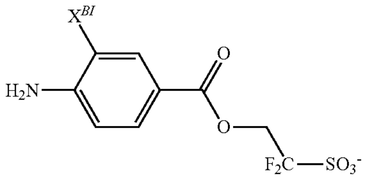

-continued
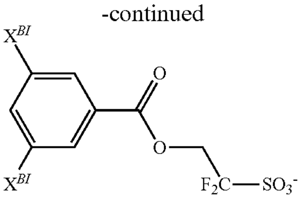
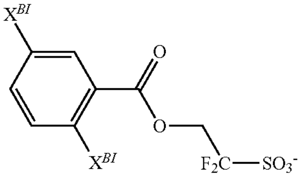
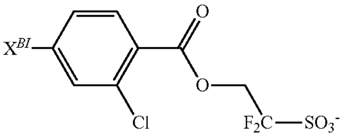
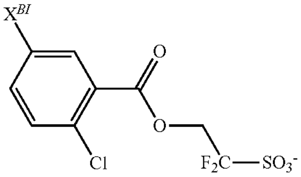
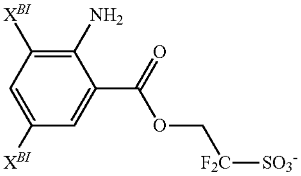
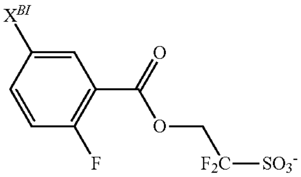
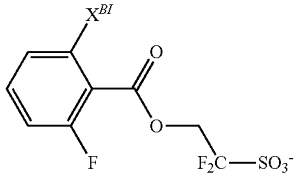
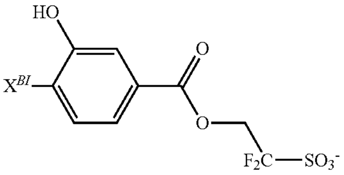
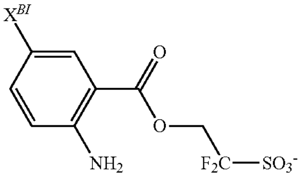
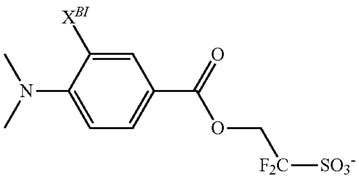
-continued
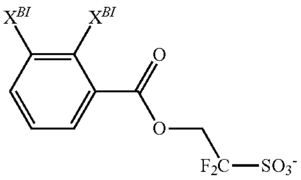
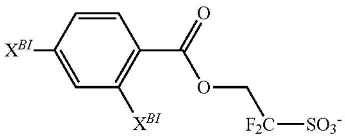
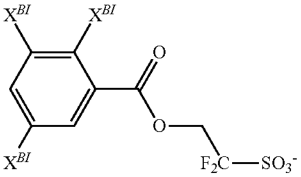
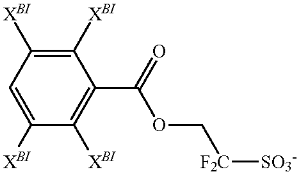
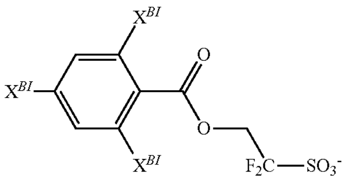
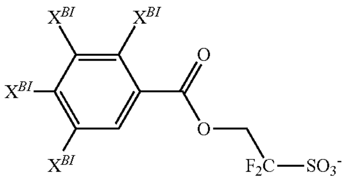
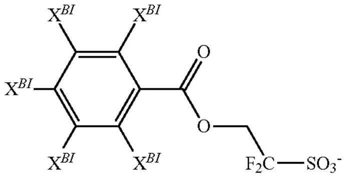
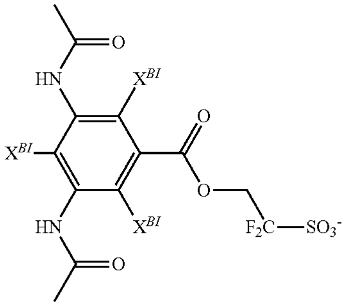

-continued
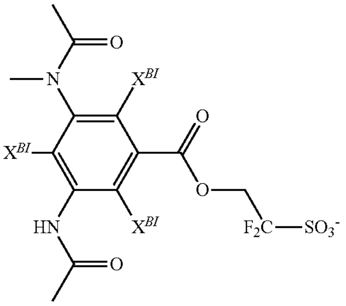
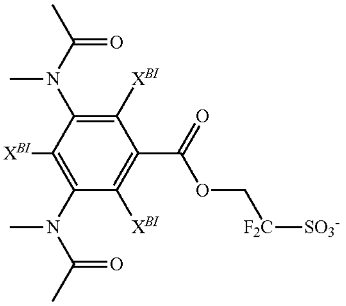
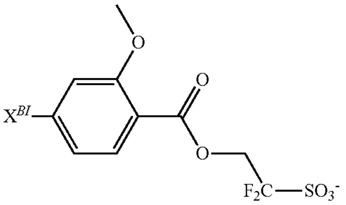
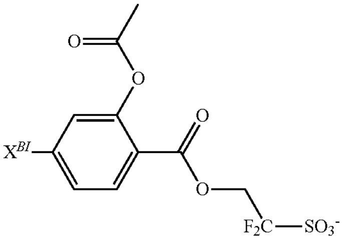
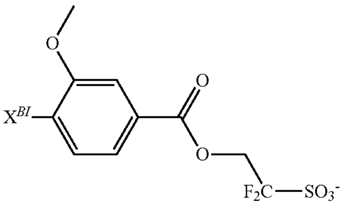
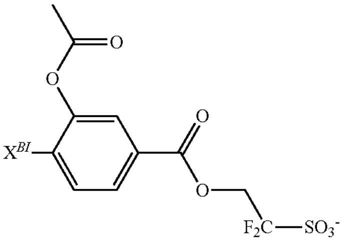
-continued
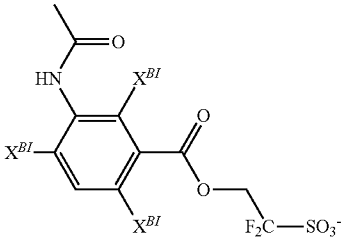
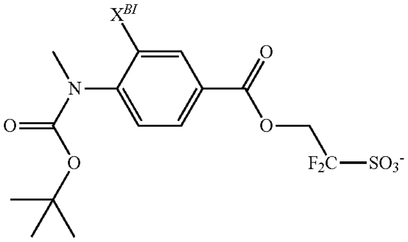
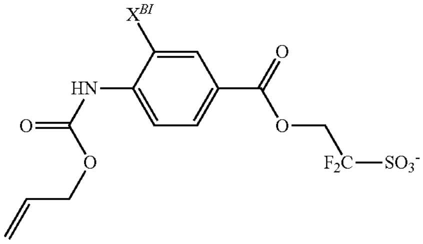
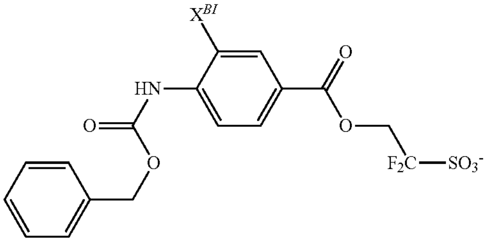
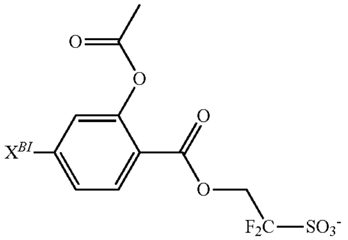
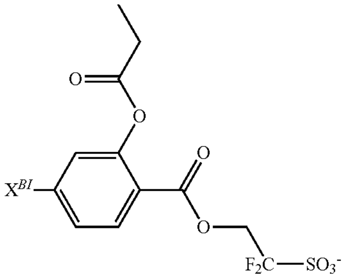

-continued
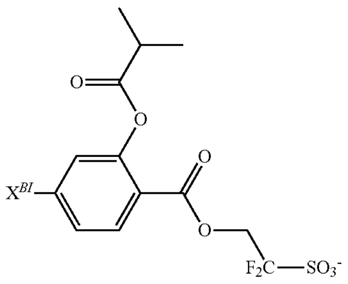
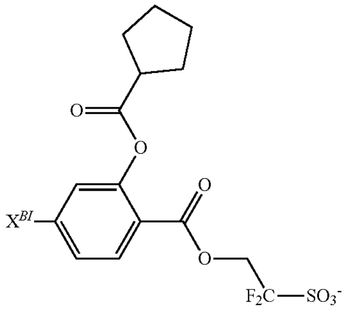
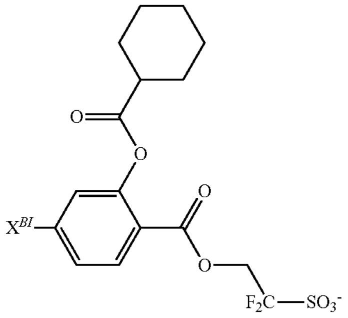
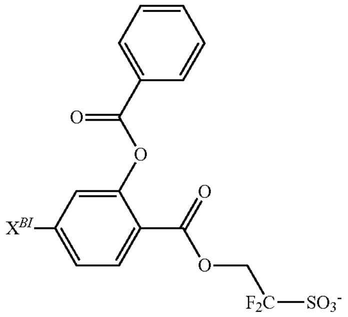
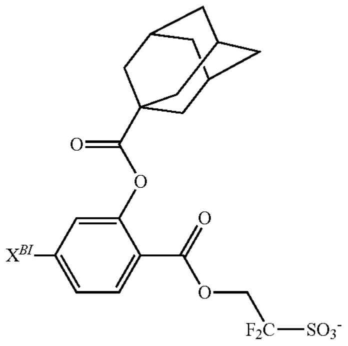
-continued
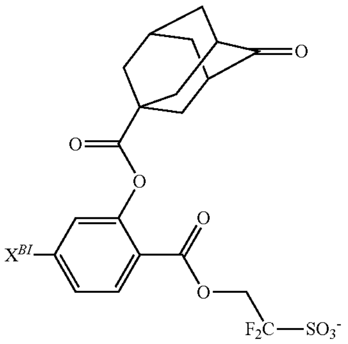
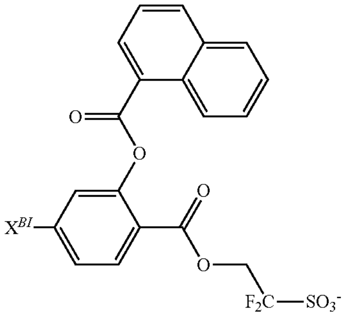
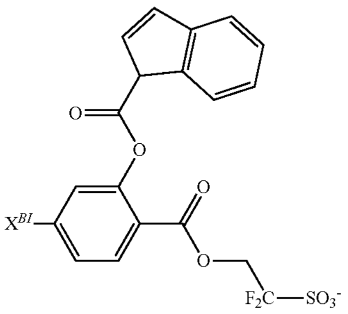
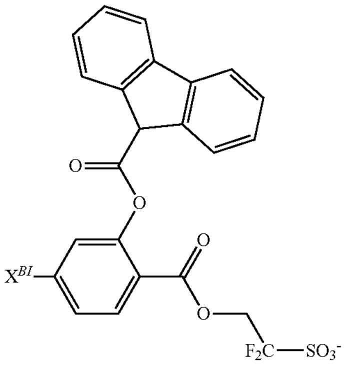
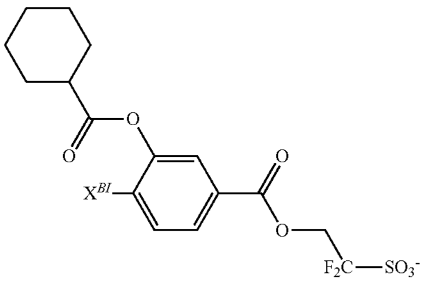

-continued
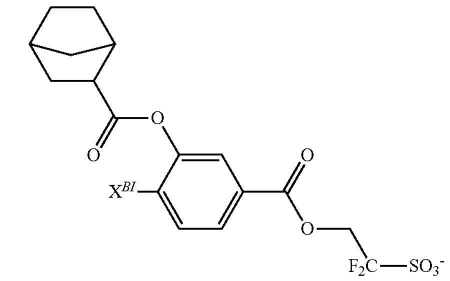
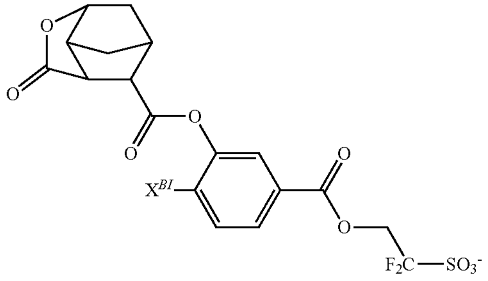
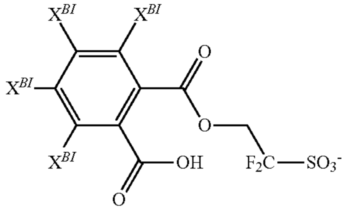
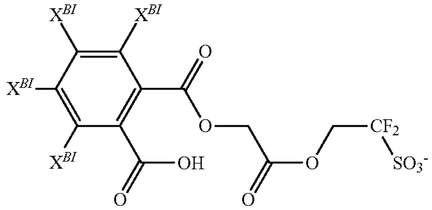
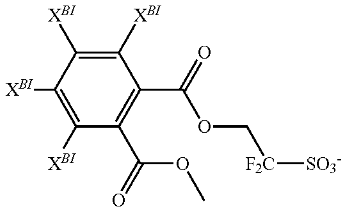
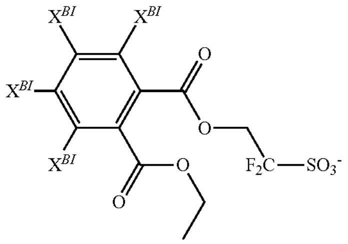
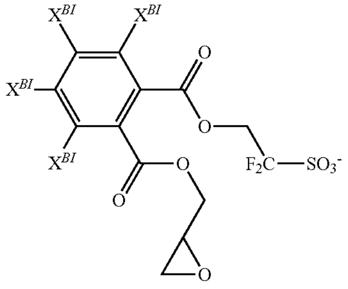
-continued
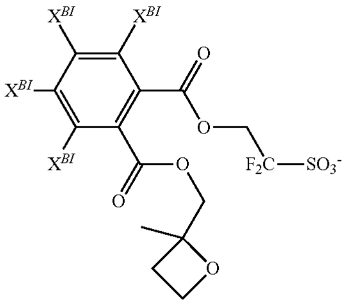
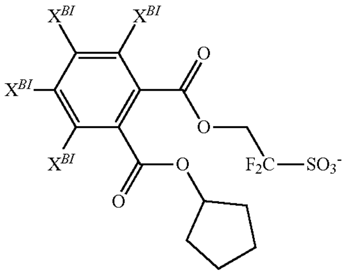
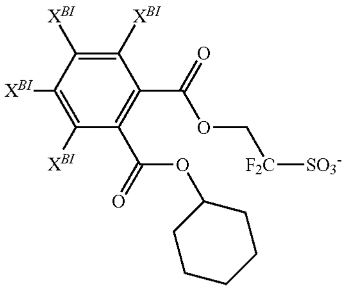
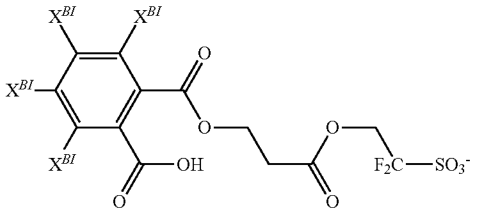
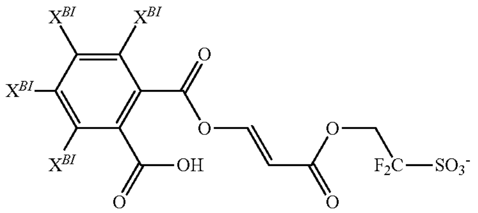
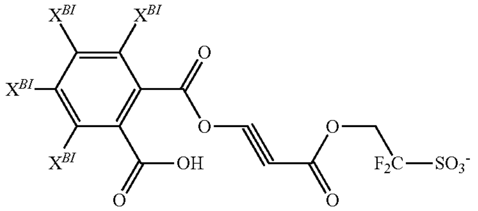
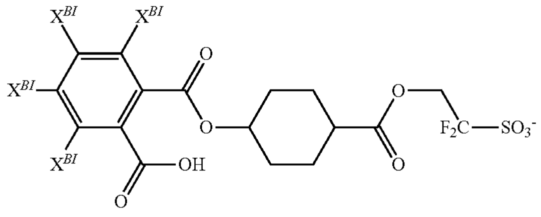

-continued
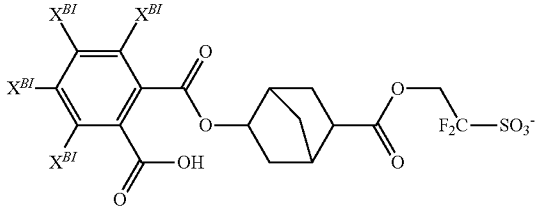
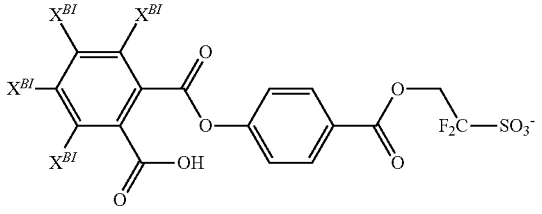
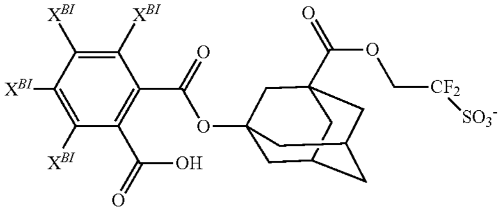
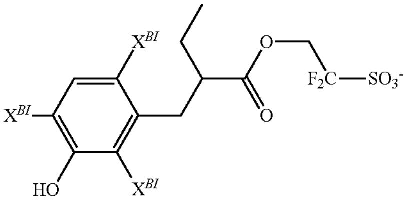
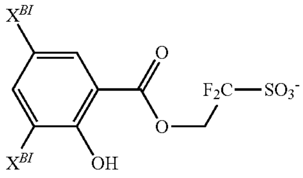
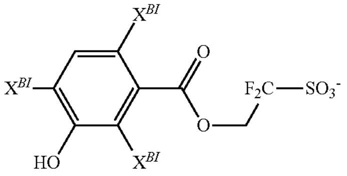
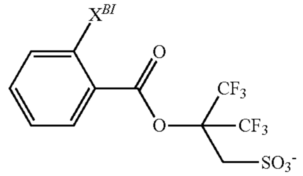
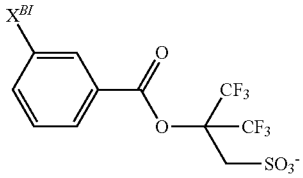
-continued
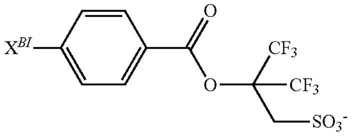
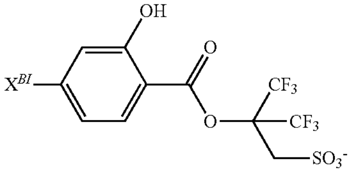
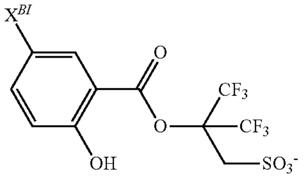
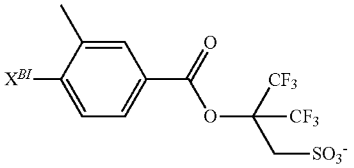
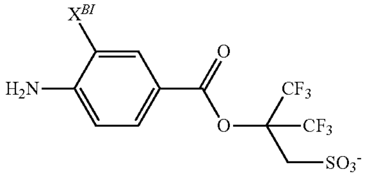
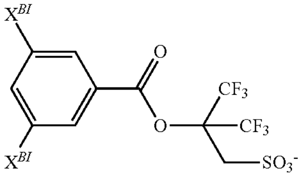
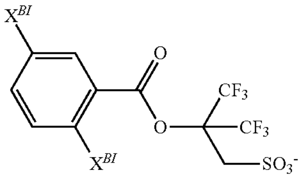
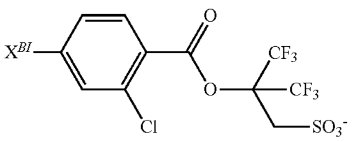
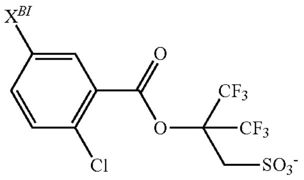
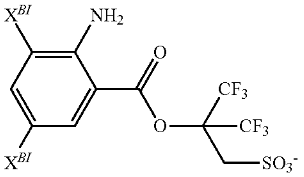

-continued
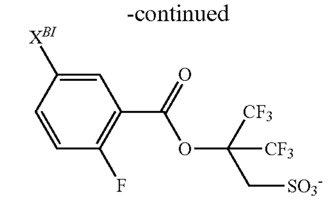
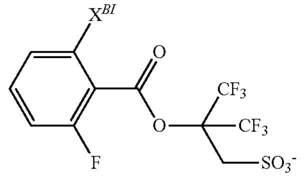
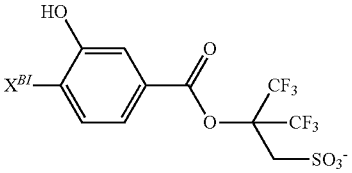
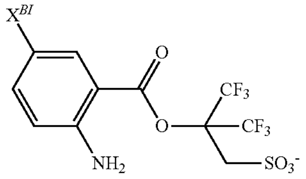
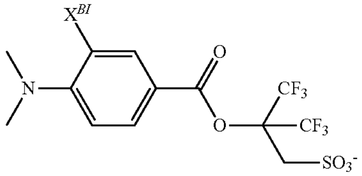
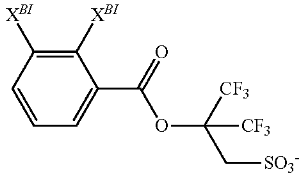
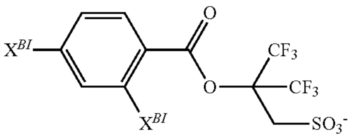
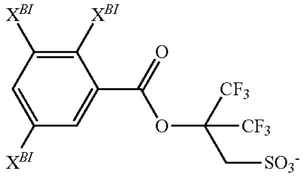
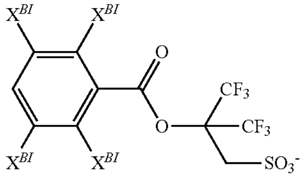
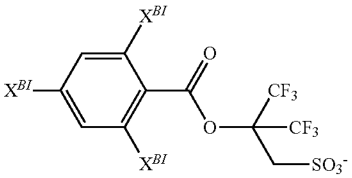
-continued
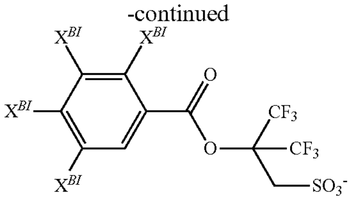
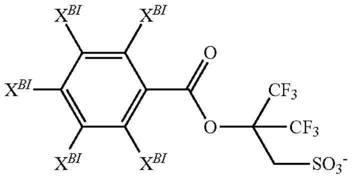
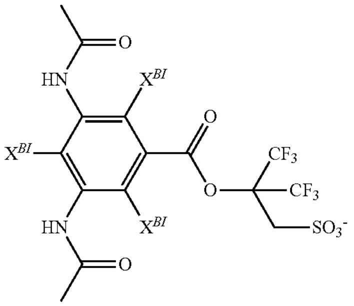
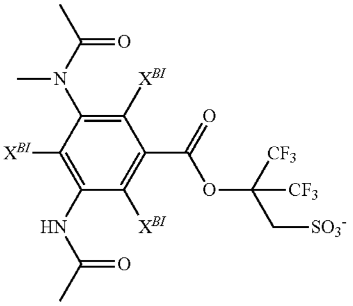
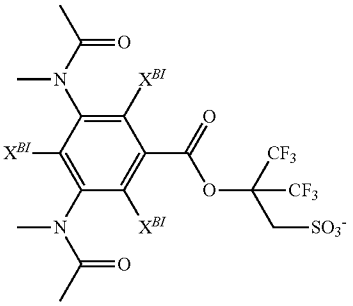
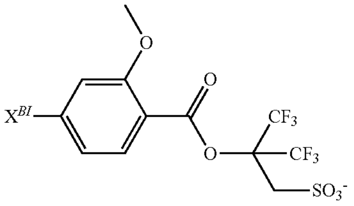
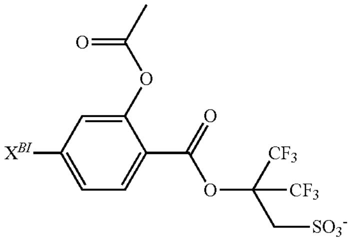

-continued
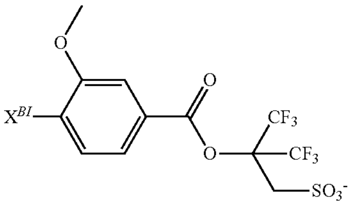
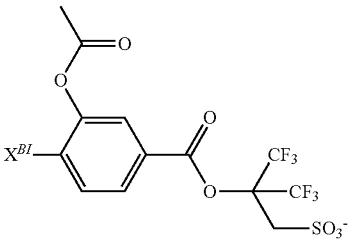
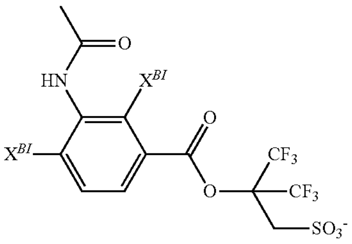
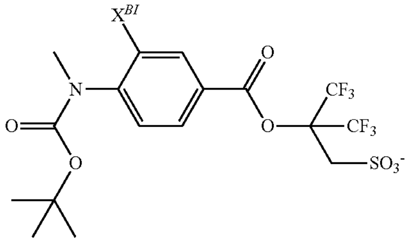
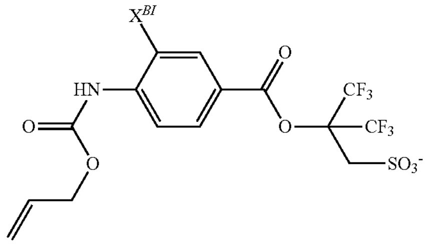
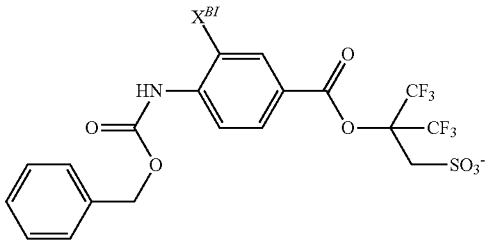
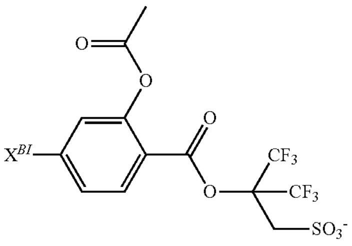
-continued
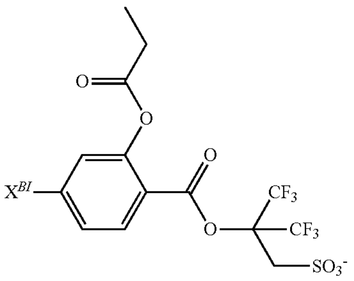
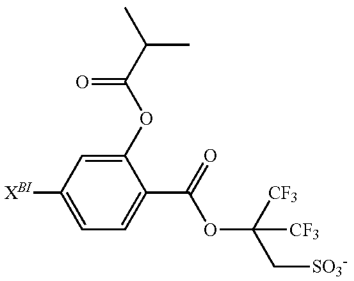
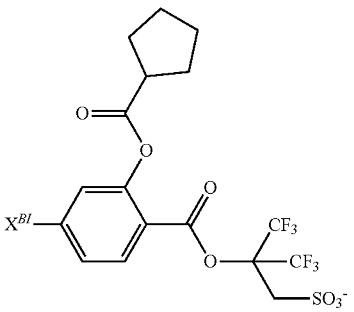
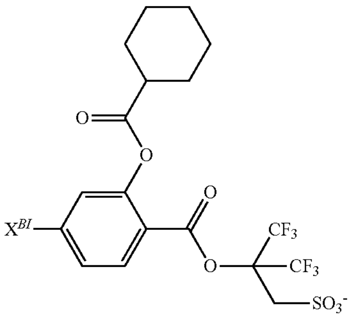
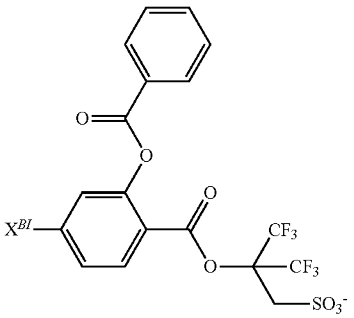

-continued
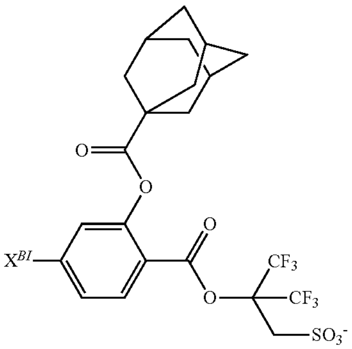
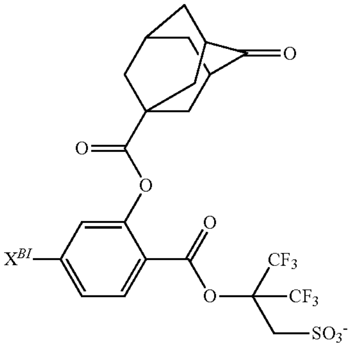
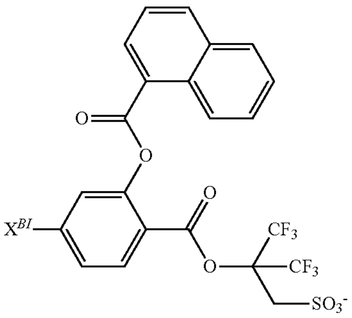
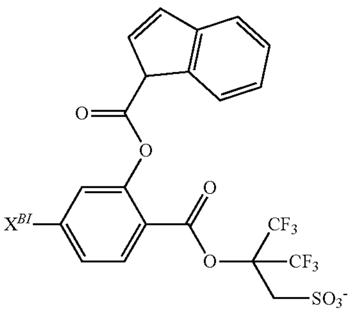
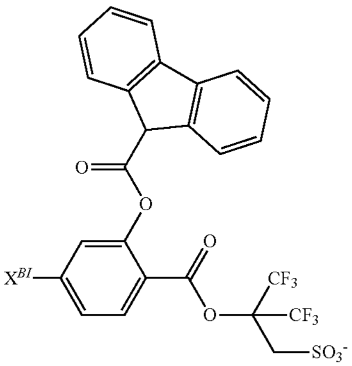
-continued
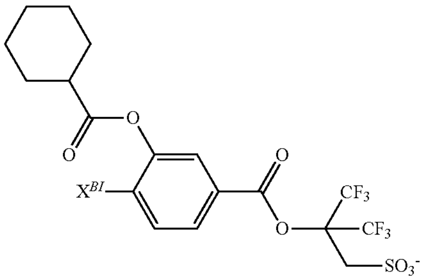
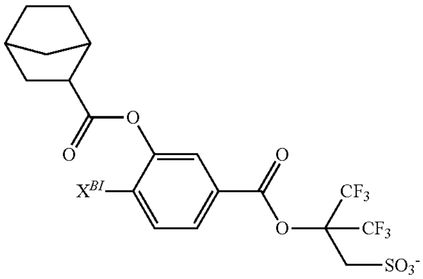
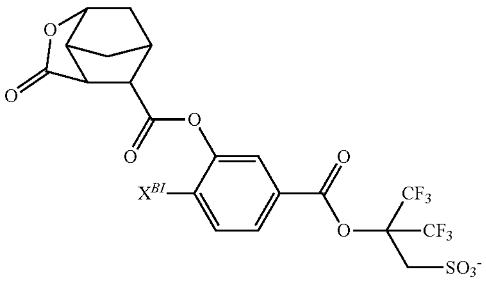
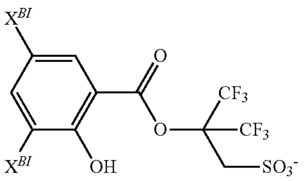
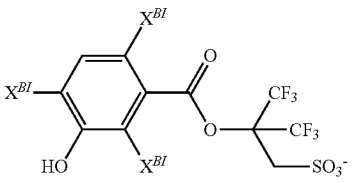
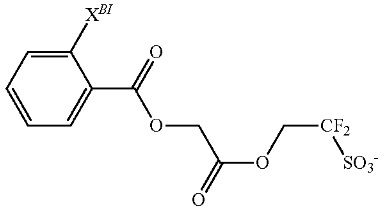
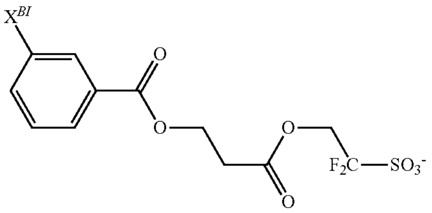

-continued
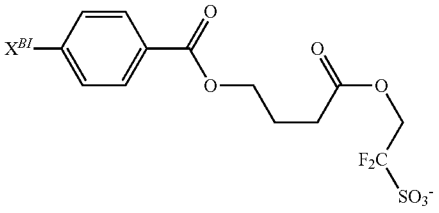
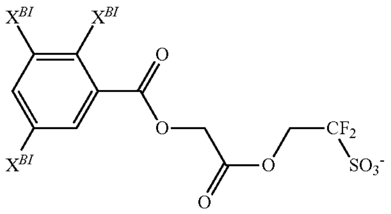
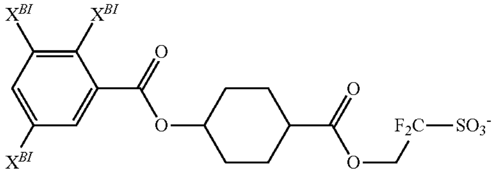
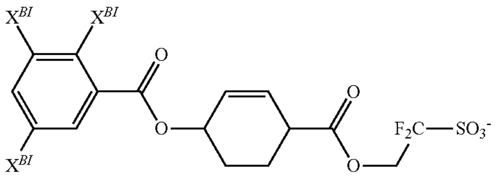
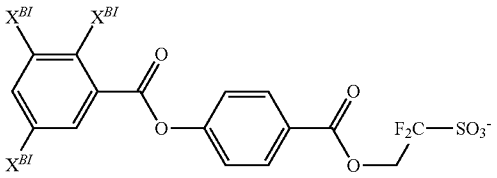
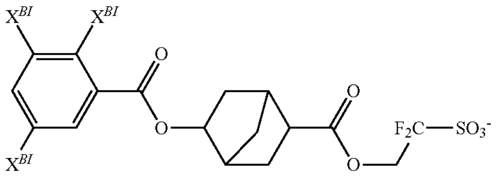
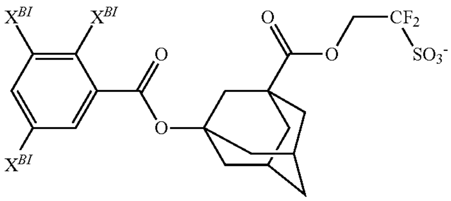
-continued
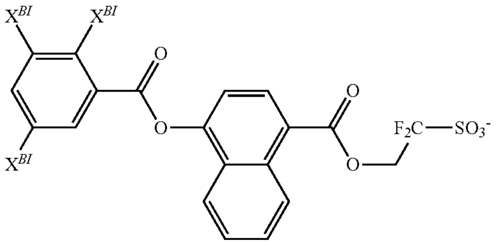
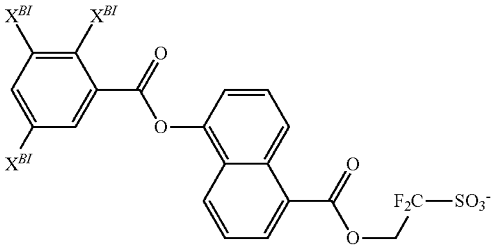
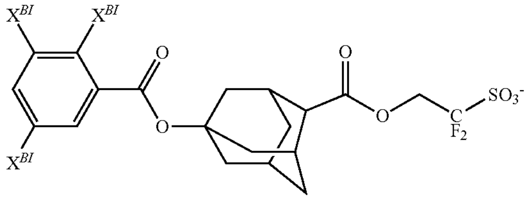
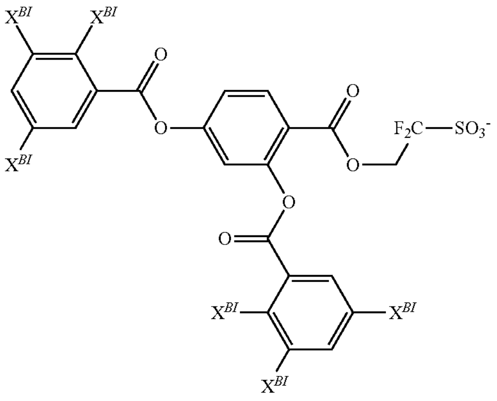
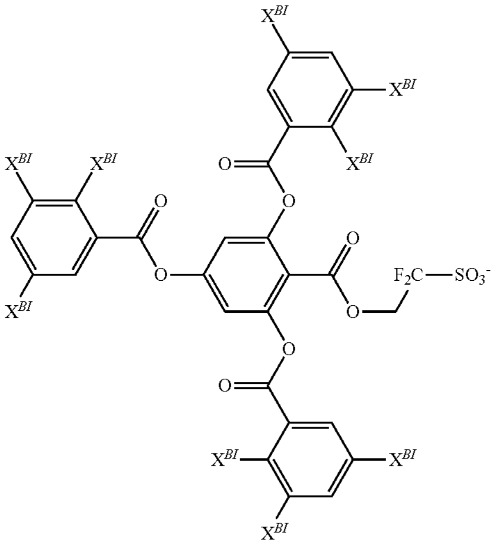

-continued
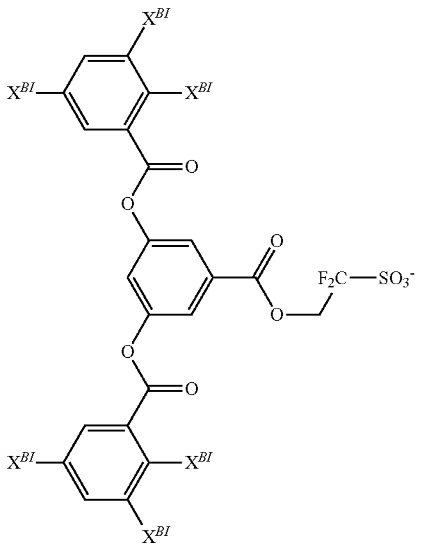
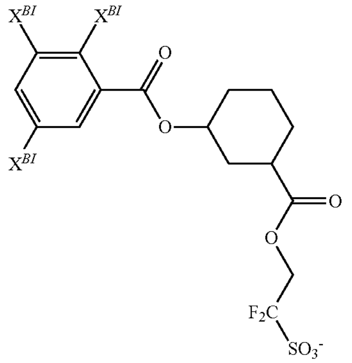
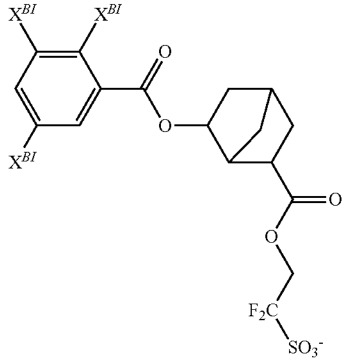
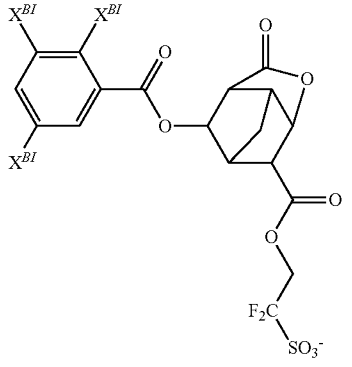
-continued
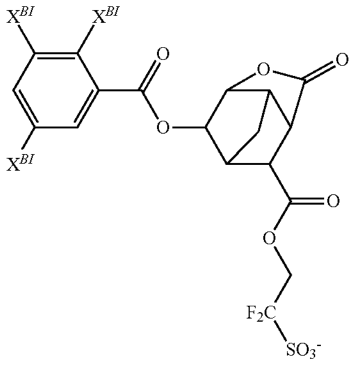
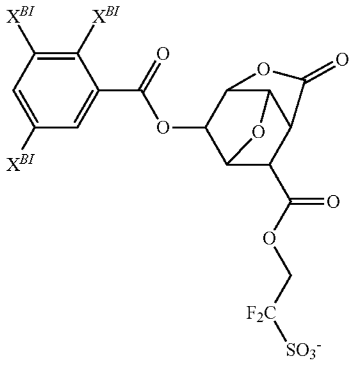
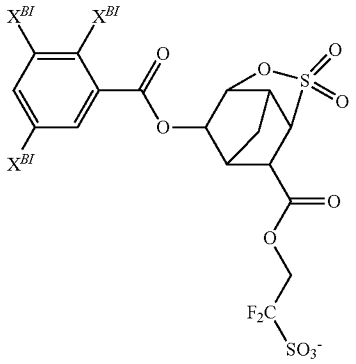
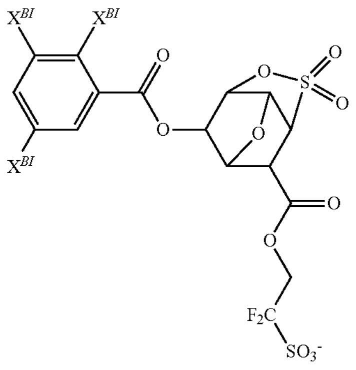

-continued
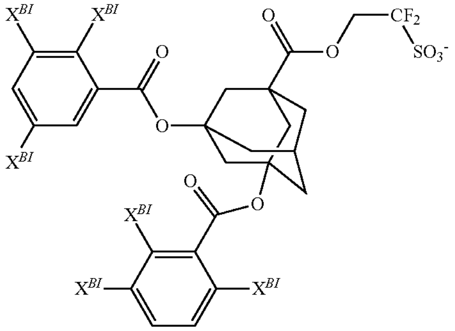
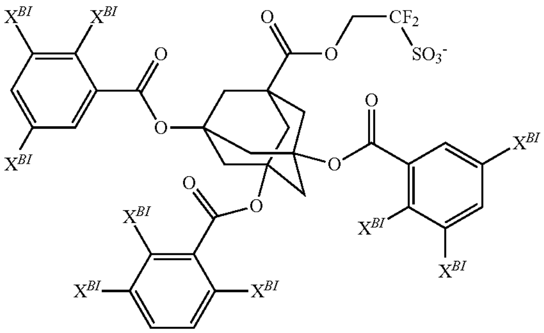
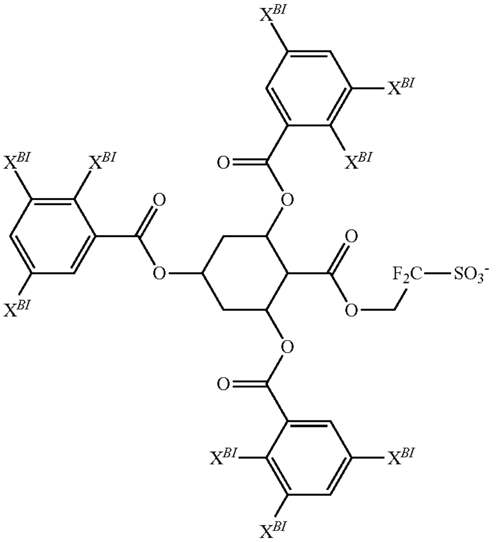
-continued
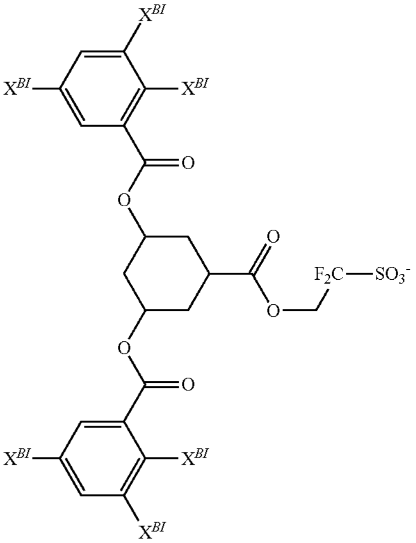
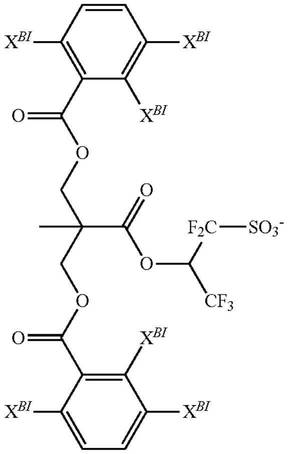
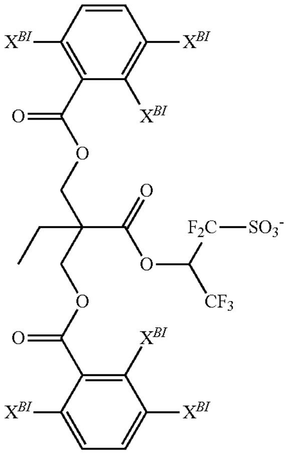

-continued
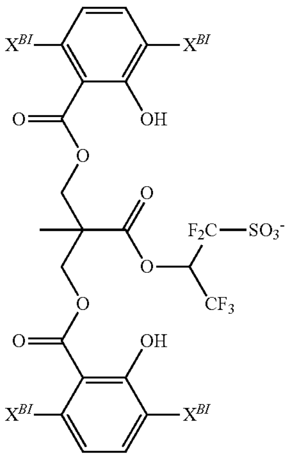
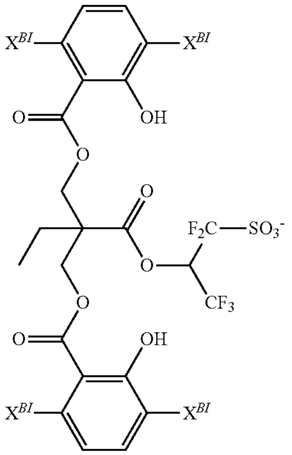
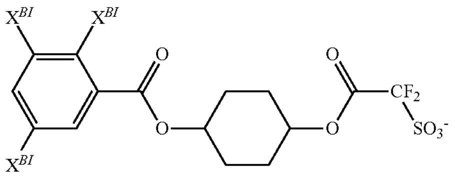
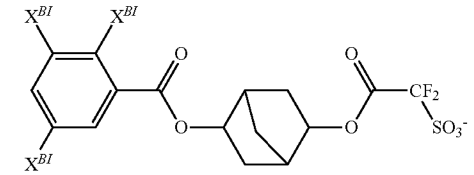
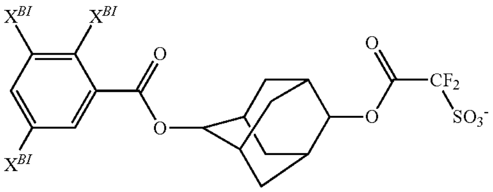
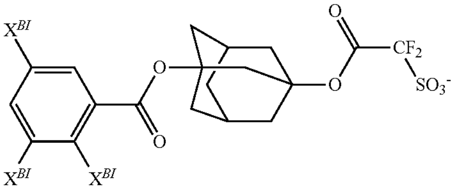
-continued
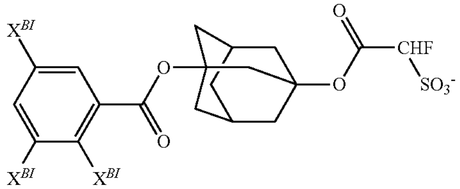
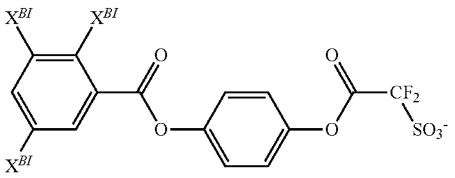
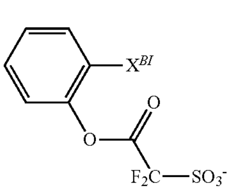
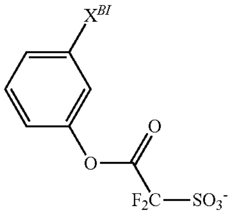
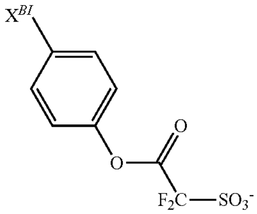
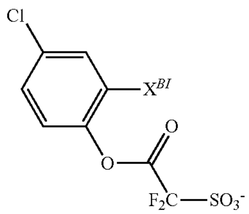
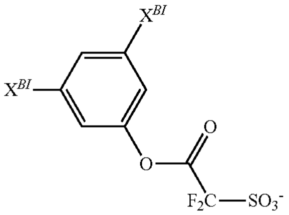
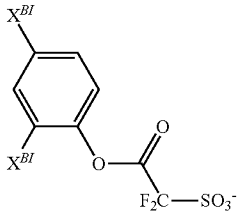
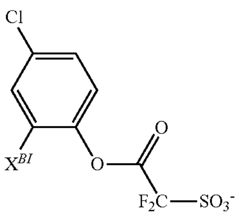
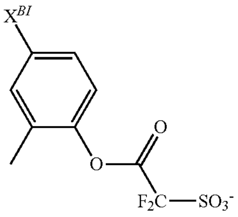
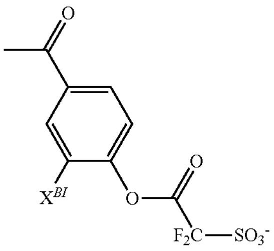
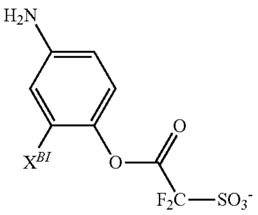

-continued
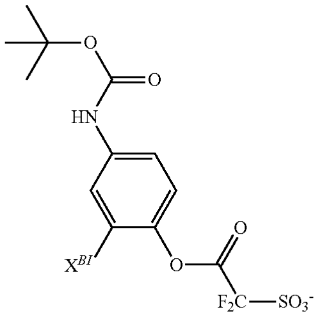
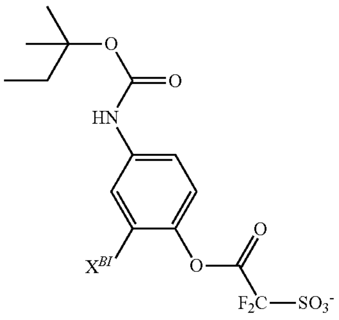
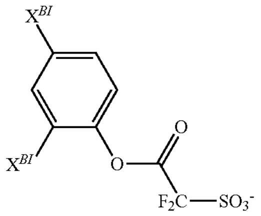
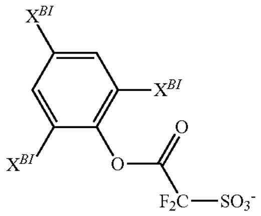
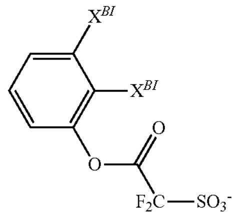
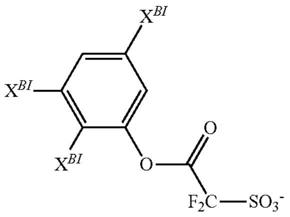
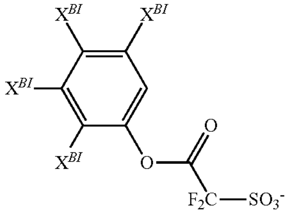
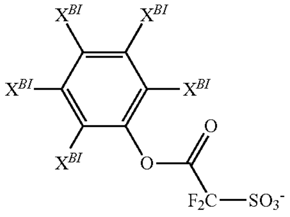
-continued
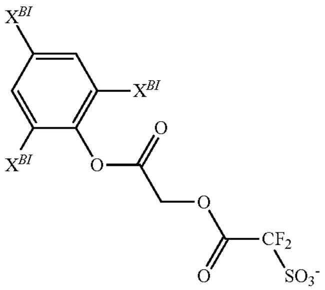
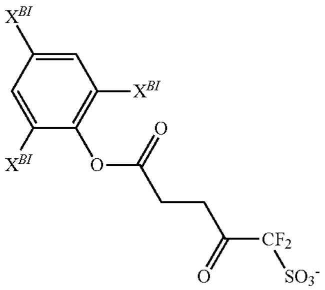
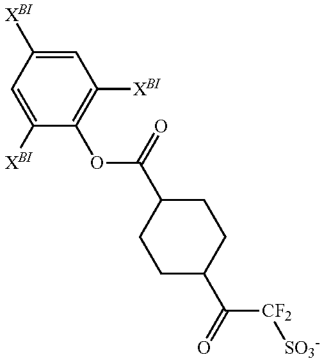
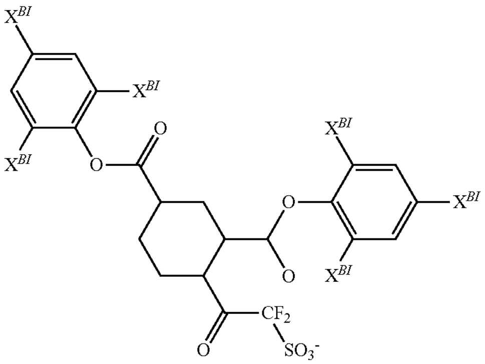
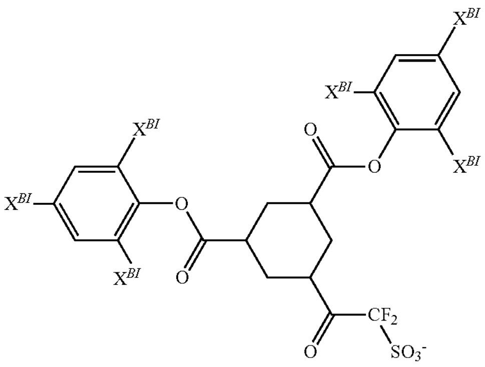

-continued
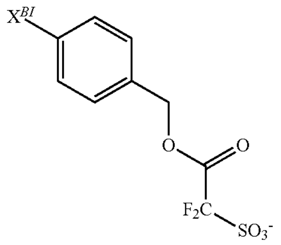
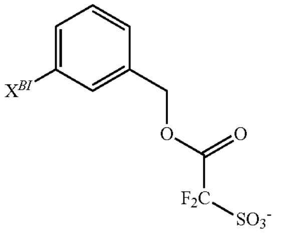
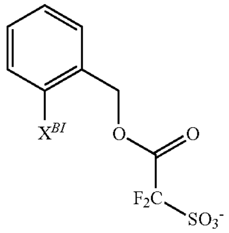
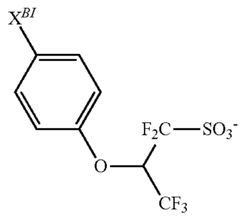
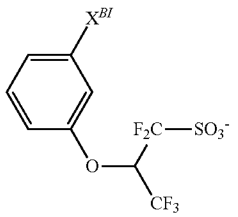
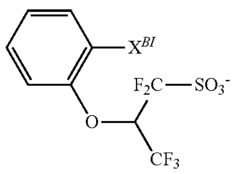
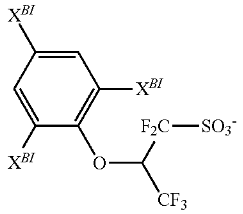
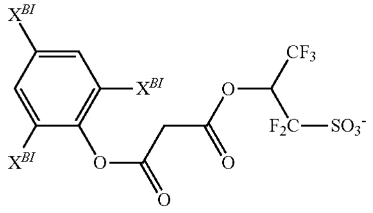
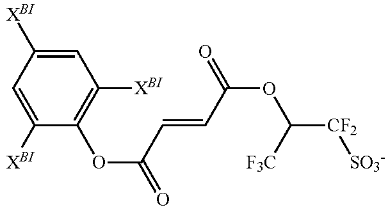
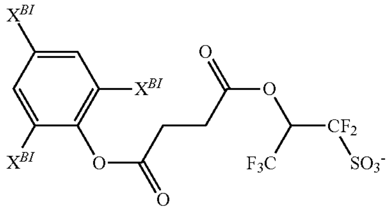
-continued
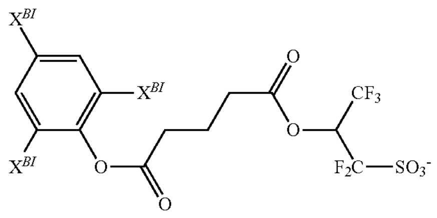
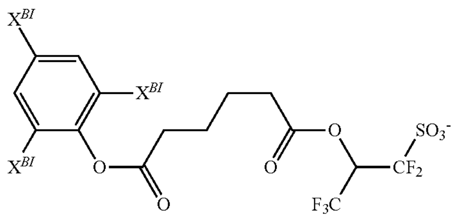
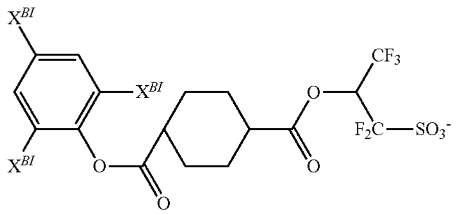
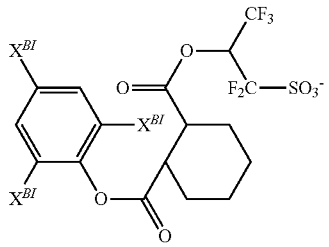
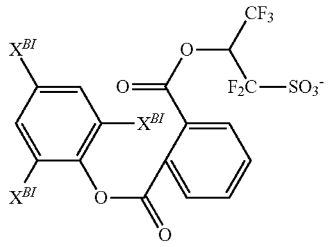
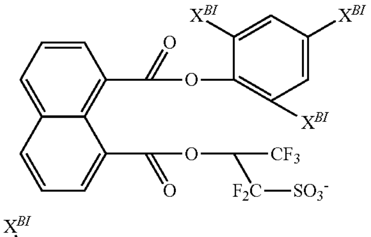
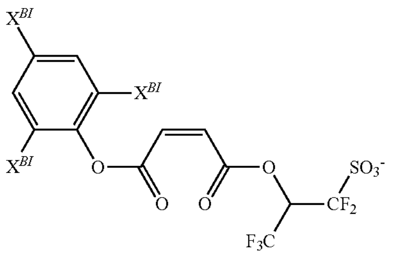

-continued
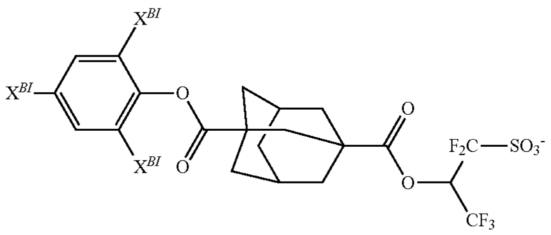
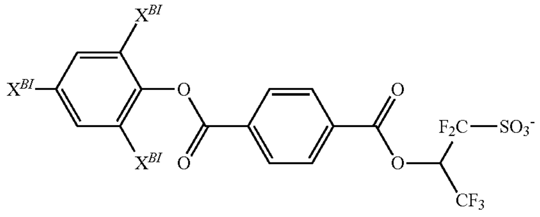
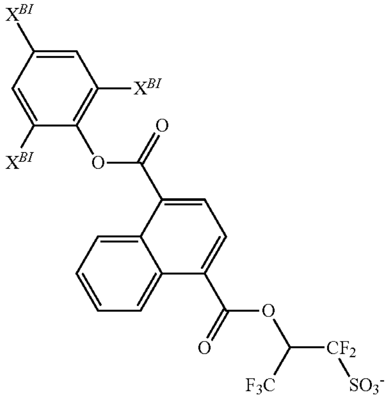
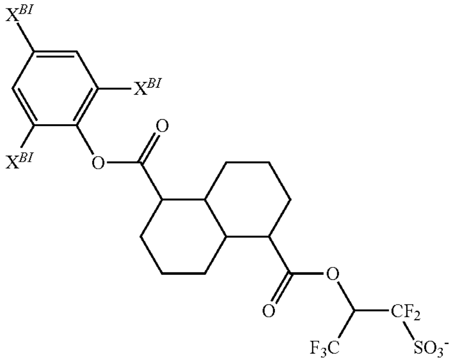
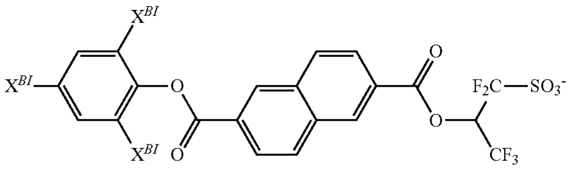
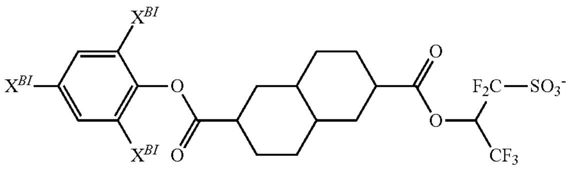
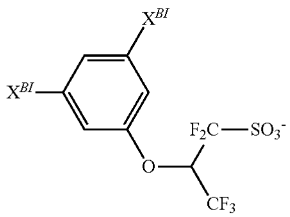
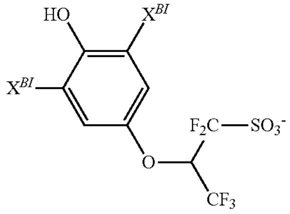
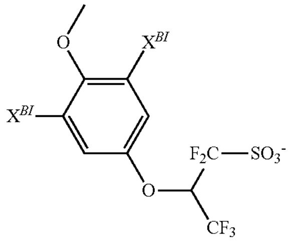
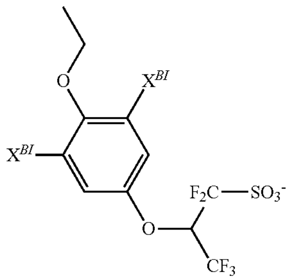
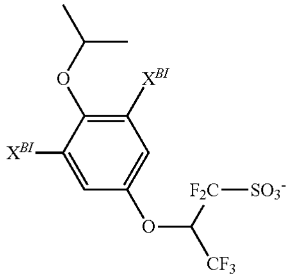
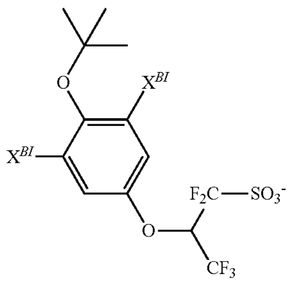

-continued
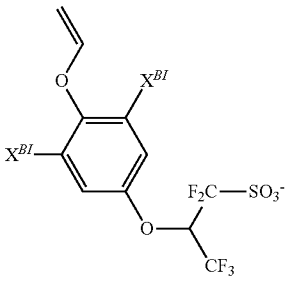
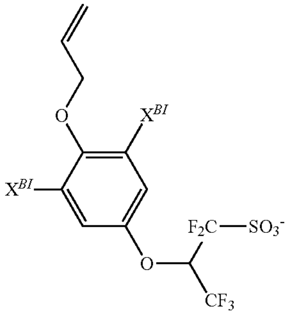
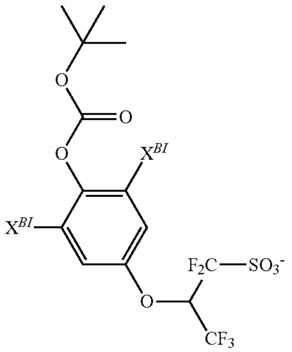
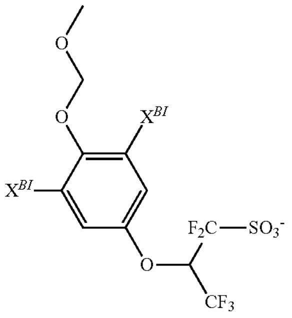
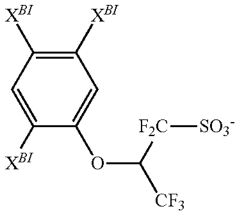
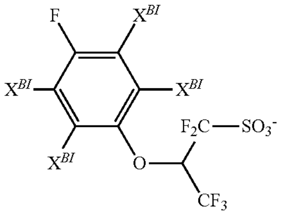
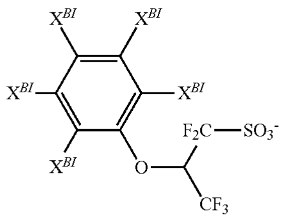
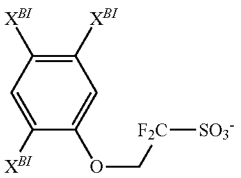
-continued
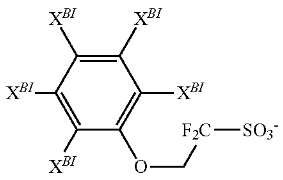
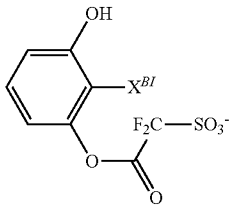
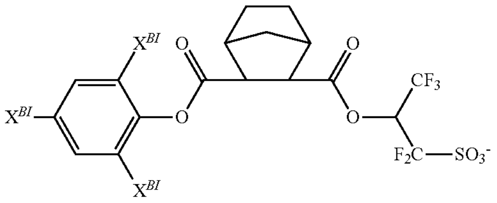
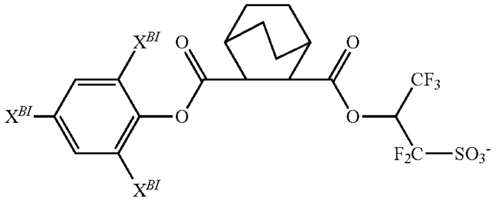
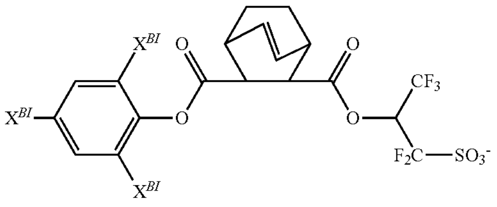
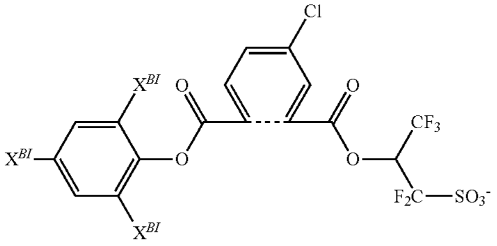
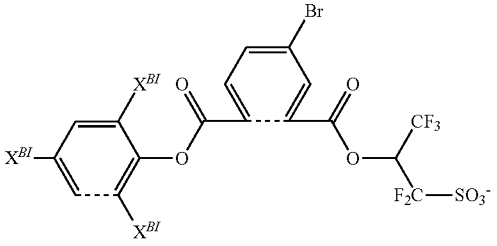
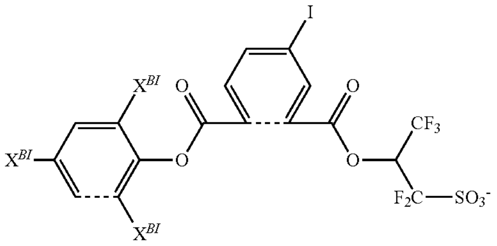

-continued
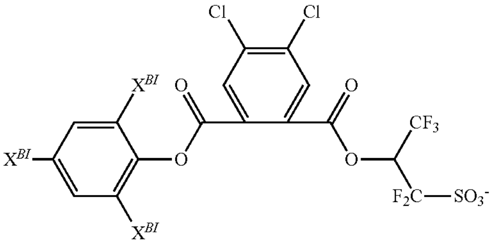
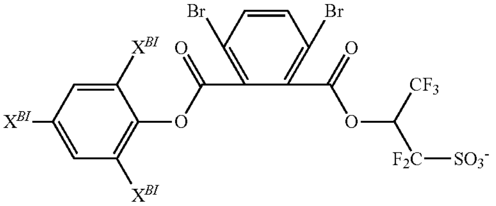
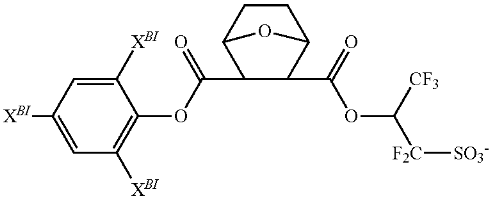
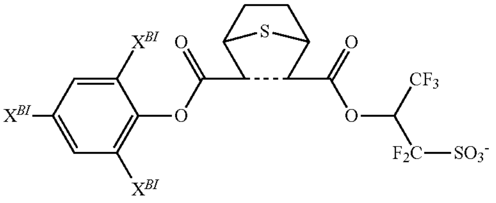
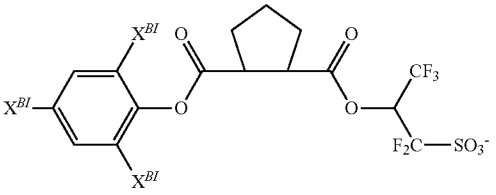
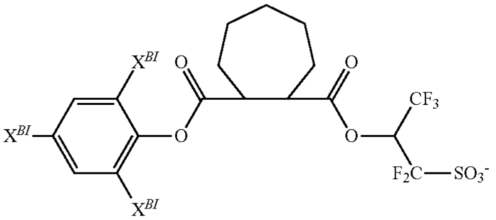
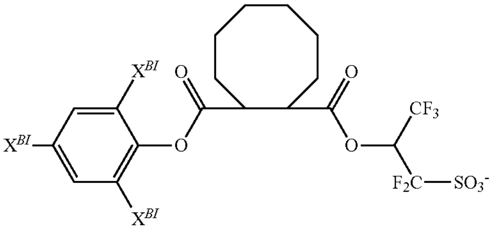
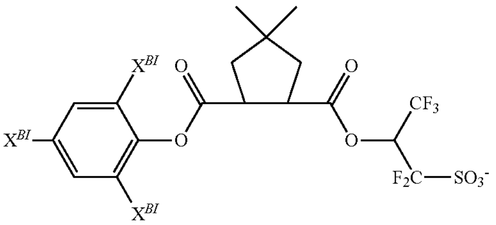
-continued
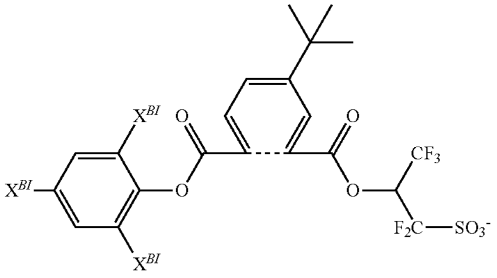
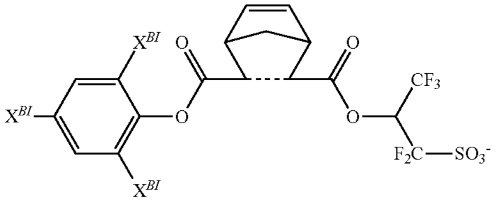
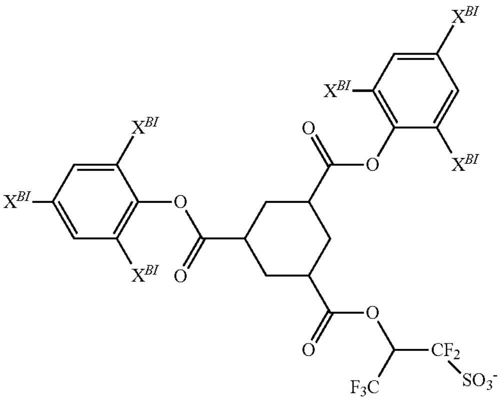
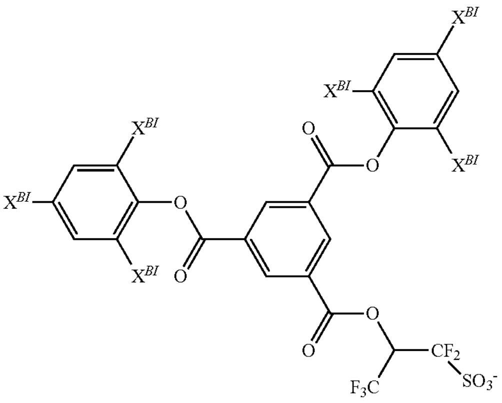

-continued
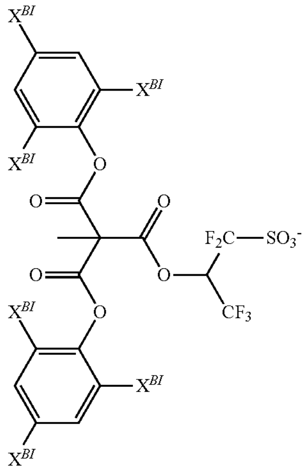
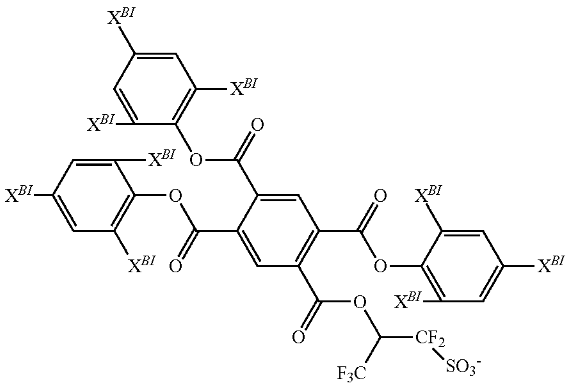
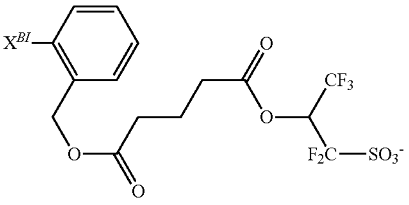
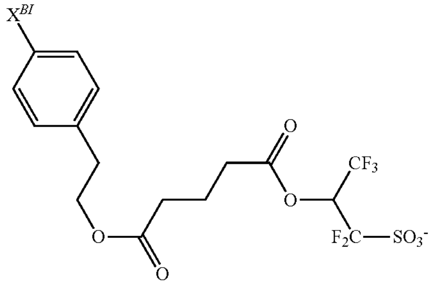
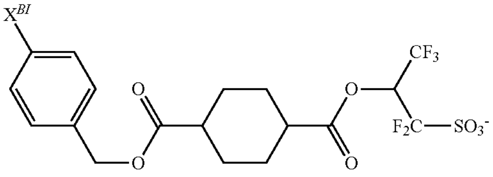
-continued
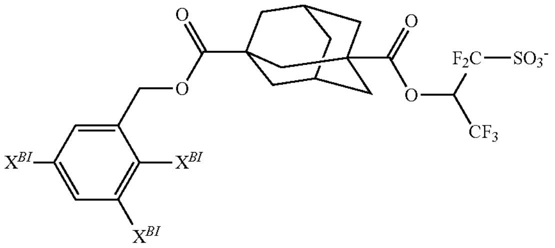
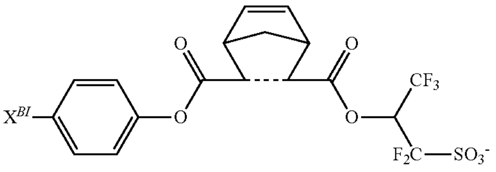
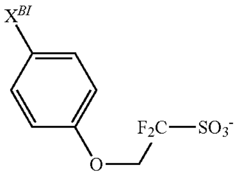
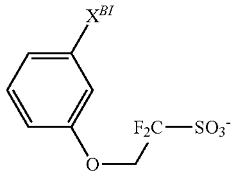
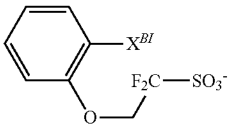
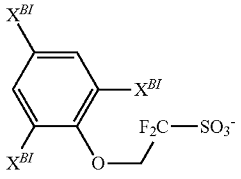
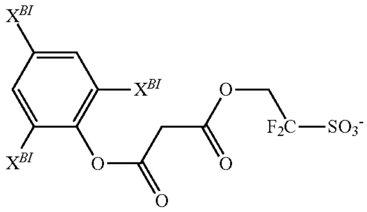
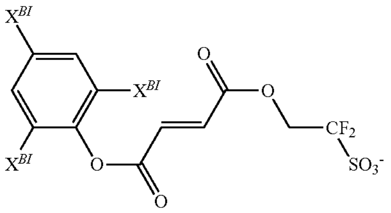
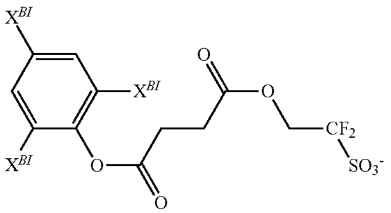
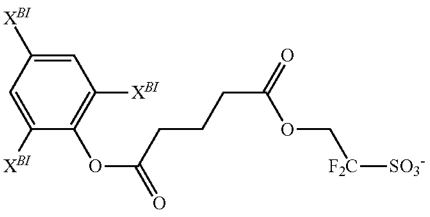

-continued
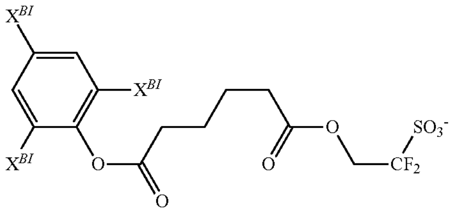
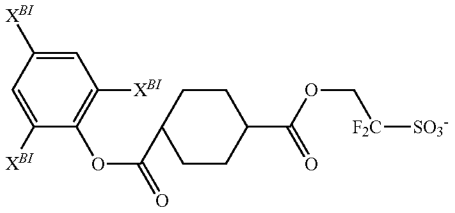
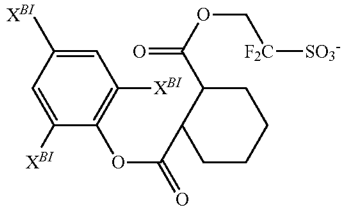
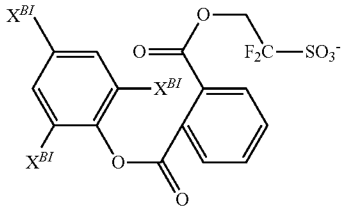
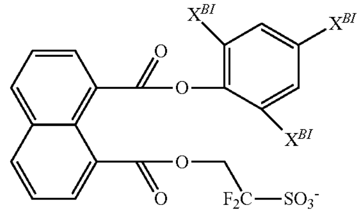
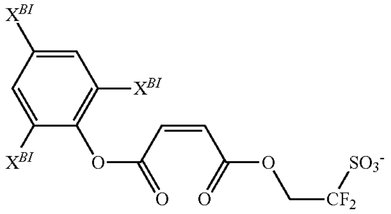
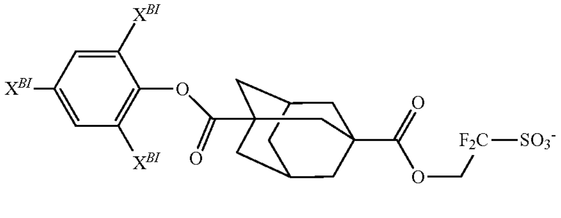
-continued
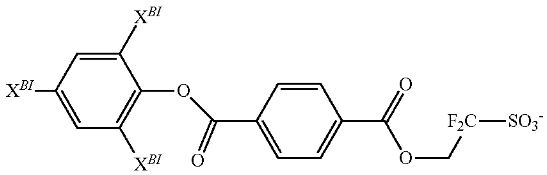
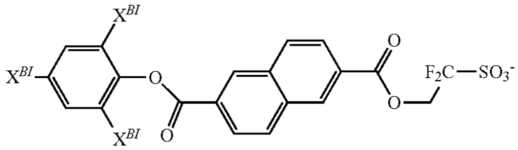
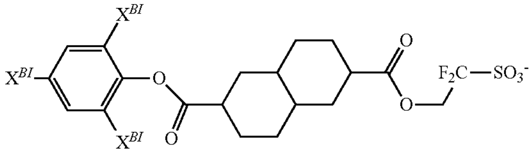
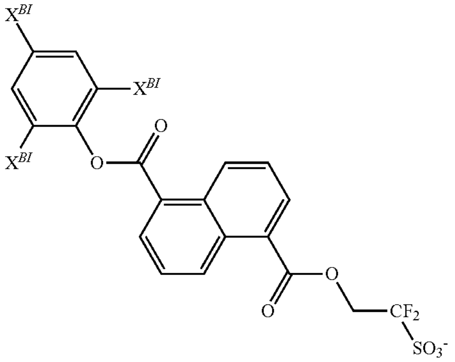
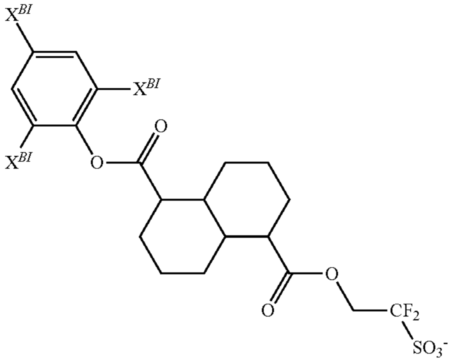
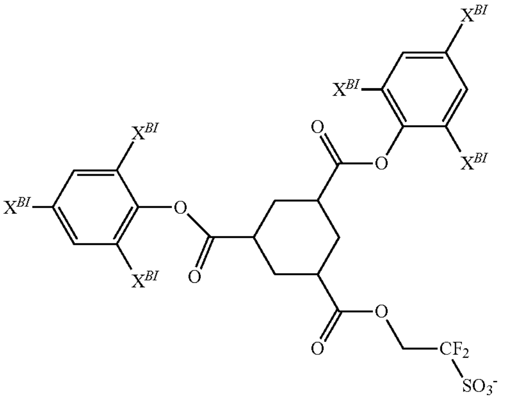

-continued
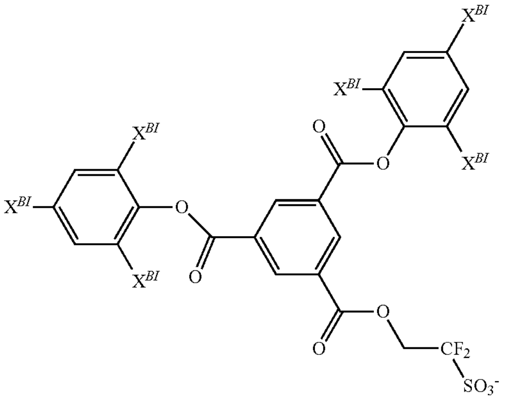
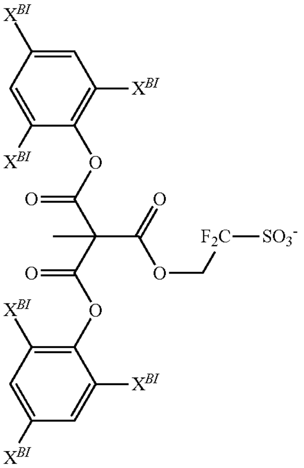
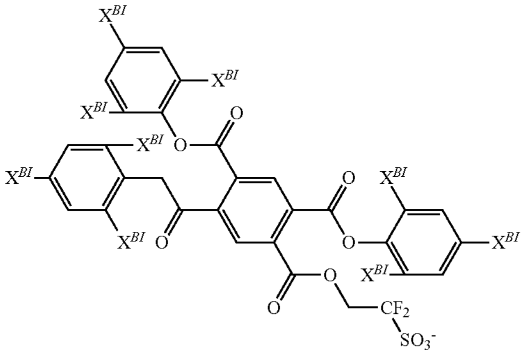
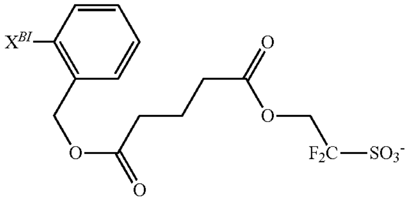
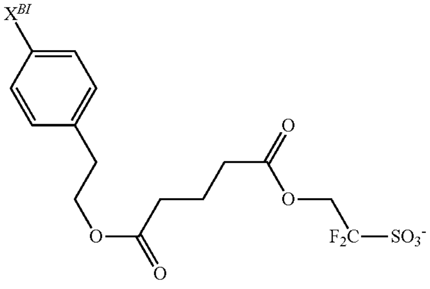
-continued
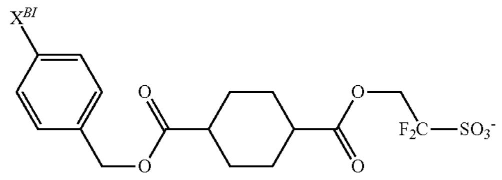
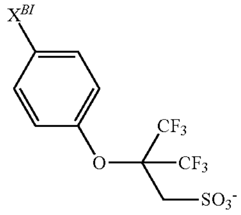
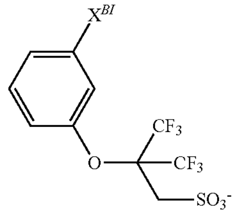
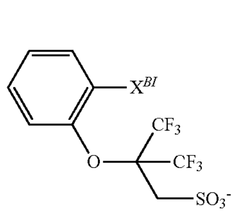
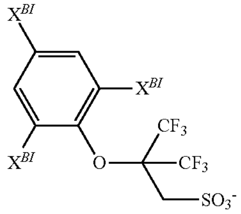
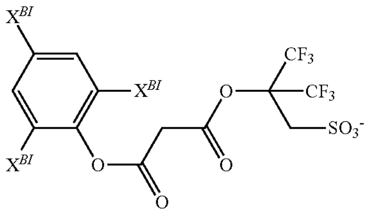
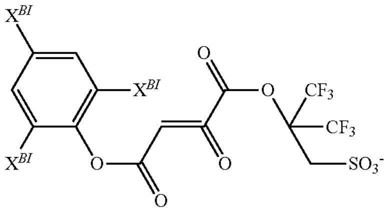
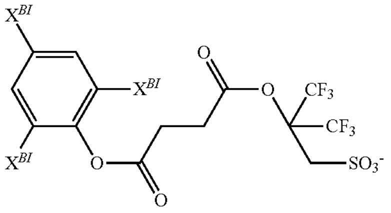
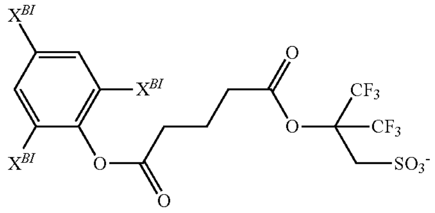
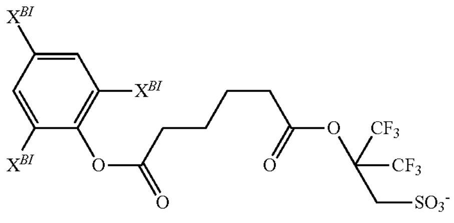

-continued
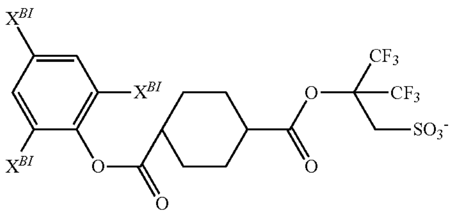
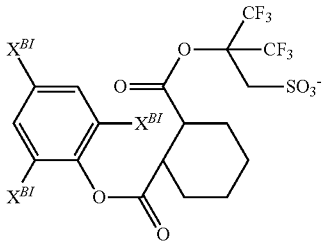
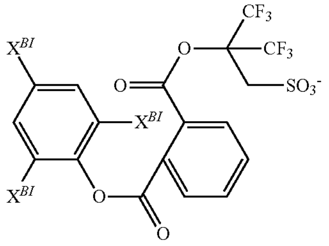
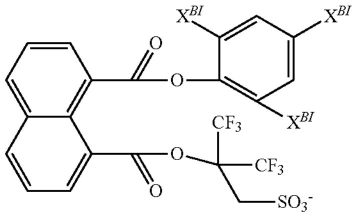
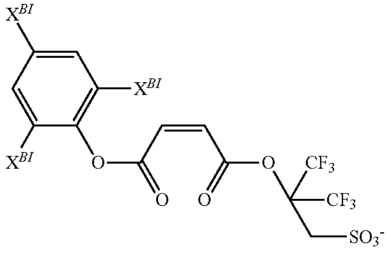
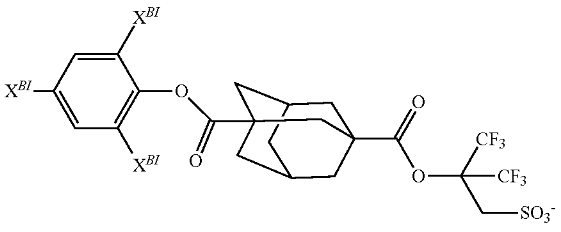
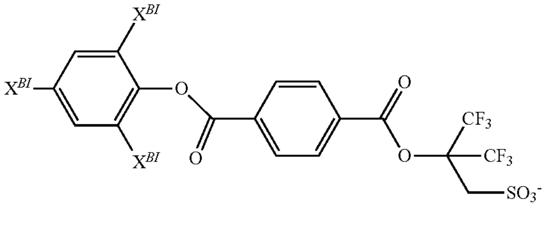
-continued
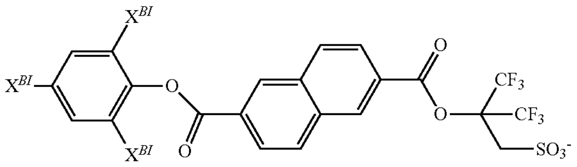
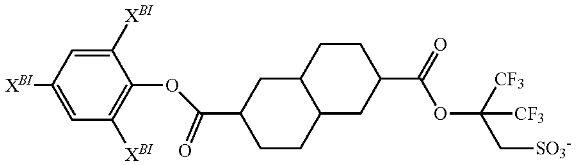
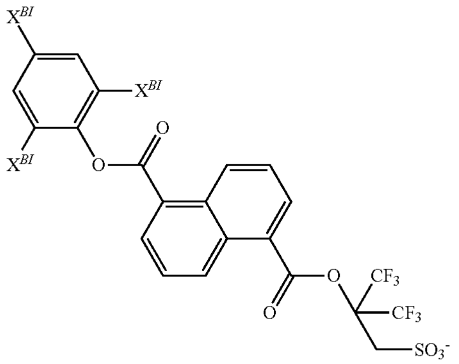
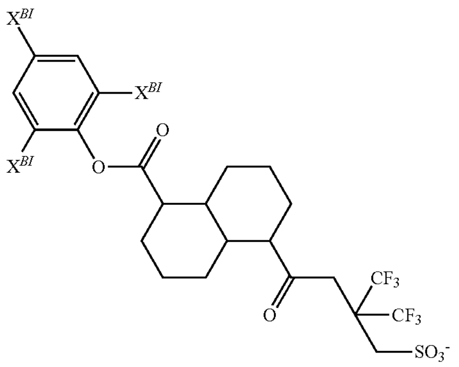
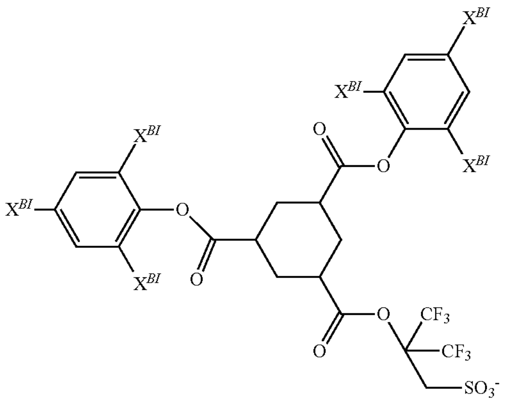

-continued

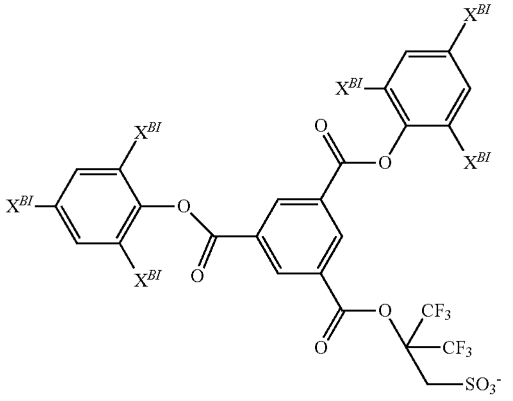

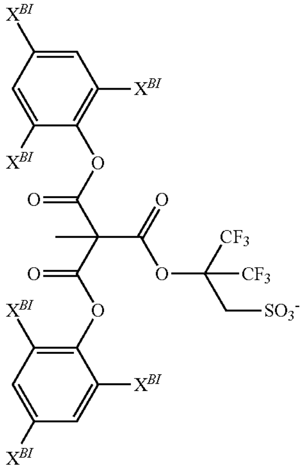

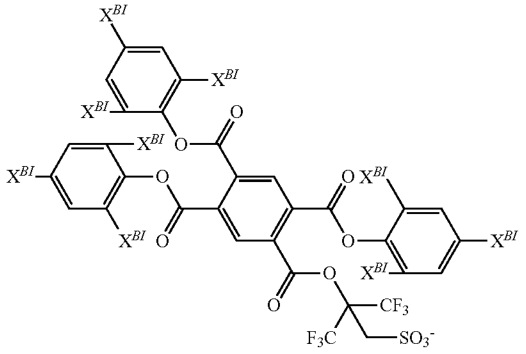

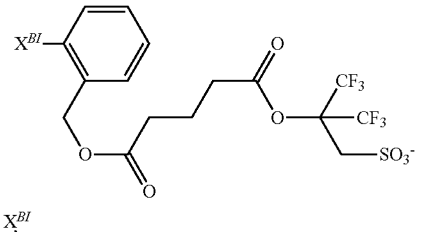

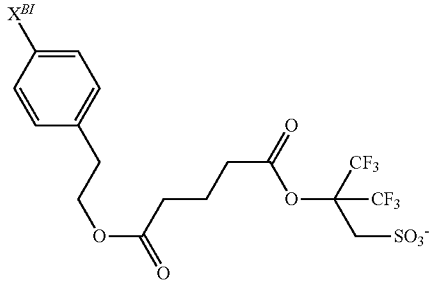

-continued

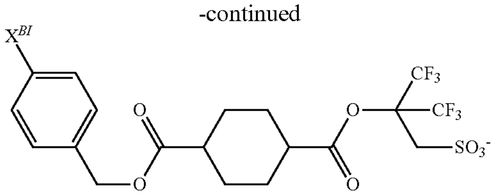

When the resist composition contains the acid generator of addition type, its content is preferably 0.1 to 50 parts by weight, and more preferably 1 to 40 parts by weight per 100 parts by weight of the base polymer. When the base polymer contains repeat units (f) and/or the resist composition contains the acid generator of addition type the resist composition functions as a chemically amplified resist composition.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether: esters such as propylene glycol monomethyl ether acetate (PGMEA), propylene glycol monoethyl ether acetate, ethyl lactate (including L, D and DL-ethyl lactate), ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a quencher other than salt compound A, surfactant, dissolution inhibitor, crosslinker, water repellency improver, and acetylene alcohol may be blended in the resist composition.

The other quencher is typically selected from conventional basic compounds. Conventional basic compounds include primary, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid or carboxylic acid are released by salt exchange with an α-non-fluorinated onium salt. An α-non-fluorinated sulfonic acid and carboxylic acid function as a quencher because they do not induce deprotection reaction. In the exposed region, the quencher of onium salt type is photo-decomposed to lose its quencher function so that the acid may turn more active, leading to an improved contrast.

While salt compound A has a very high acid diffusion controlling effect not only in the unexposed region, but also in the exposed region, it is less effective for improving contrast. By combining salt compound A with a quencher of onium salt type, low acid diffusion and high contrast can be achieved in good balance.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. The dissolution inhibitor which can be used herein is a compound having at least two phenolic hydroxy groups on the molecule, in which an average of from 0 to 100 mol % of all the hydrogen atoms on the phenolic hydroxy groups are replaced by acid labile groups or a compound having at least one carboxy group on the molecule, in which an average of 50 to 100 mol % of all the hydrogen atoms on the carboxy groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxy or carboxy group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

In the case of negative resist compositions, a negative pattern may be formed by adding a crosslinker to reduce the dissolution rate of a resist film in exposed area. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamnine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer. The crosslinker may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as repeat units may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer. The water repellency improver may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohol may be used alone or in admixture.

Pattern Forming Process

The resist composition is used in the fabrication of various integrated circuits. Pattern formation using the resist composition may be performed by well-known lithography processes. The process generally involves the steps of applying the resist composition to form a resist film on a substrate, exposing the resist film to high-energy radiation, and developing the exposed resist film in a developer. If necessary, any additional steps may be added.

Specifically, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μn thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 $\mu C/cm^2$. When EB is used as the high-energy radiation, the resist film is exposed thereto directly or through a mask having a desired pattern in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate or in an oven at 50 to 150° C. for 10 seconds to 30 minutes, preferably at 60 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In the case of positive resist, the resist film in the exposed area is dissolved in the developer whereas the resist film in the unexposed area is not dissolved. In this way, the desired positive pattern is formed on the substrate. Inversely in the case of negative resist, the exposed area of resist film is insolubilized whereas the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol. 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Quenchers Q-1 to Q-46, an amine compound (designated Amine-1) and a fluorinated 1,3-diketone compound (designated F-AcAc-1) used in resist compositions have the structure shown below.

Q-1

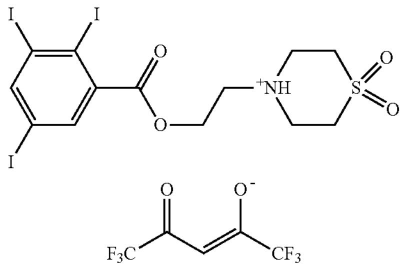

Q-2

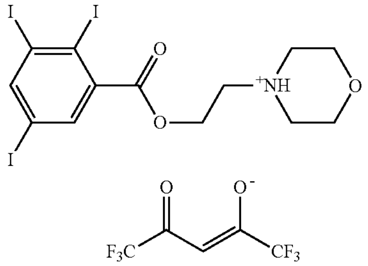

Q-3

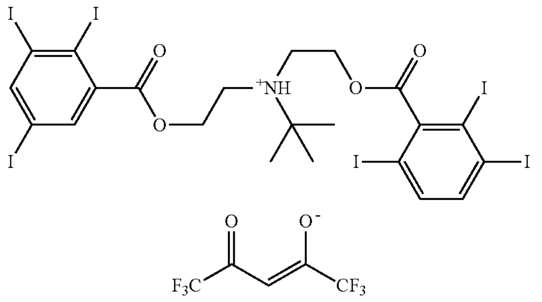

Q-4

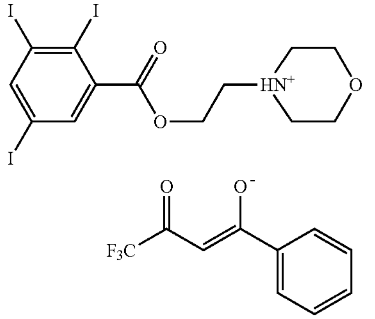

-continued

Q-5

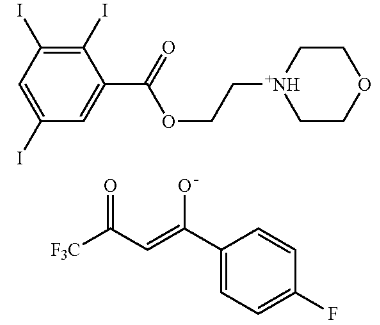

Q-6

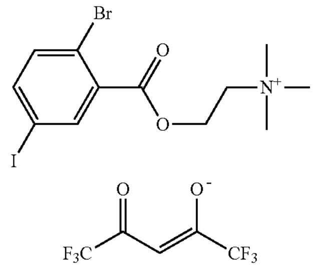

Q-7

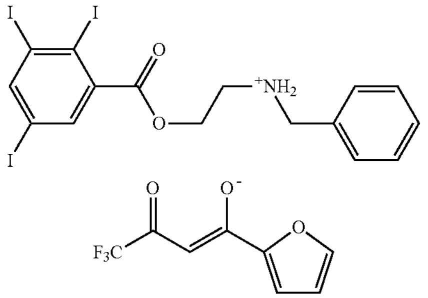

Q-8

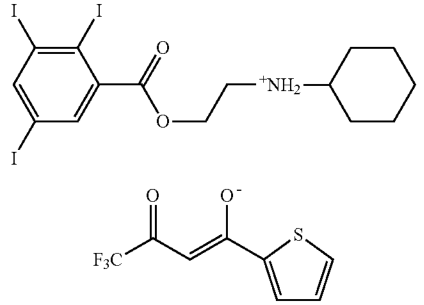

Q-9

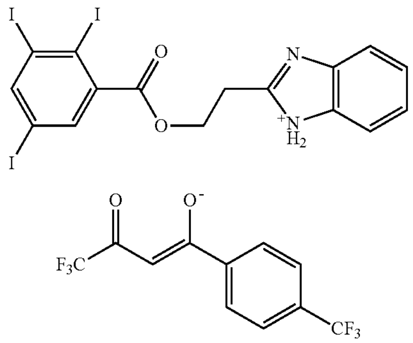

-continued
Q-10
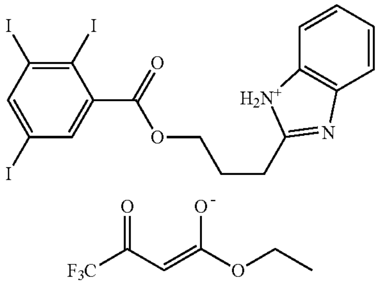
Q-11
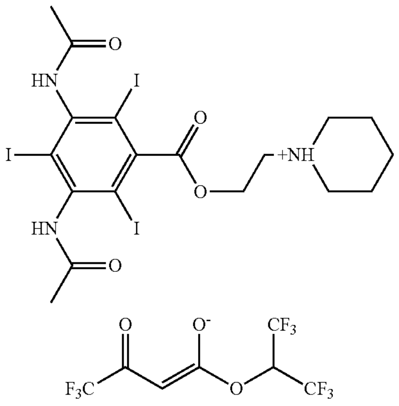
Q-12
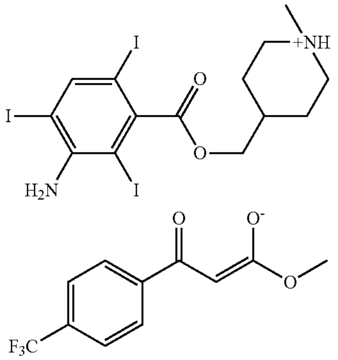
Q-13
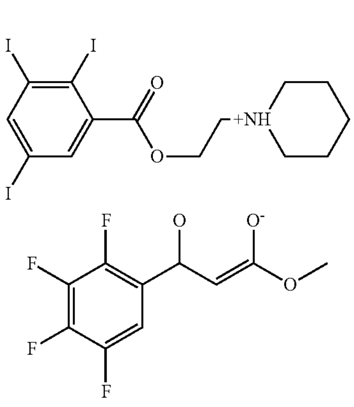
-continued
Q-14
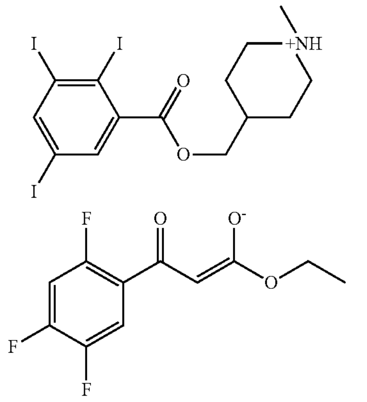
Q-15
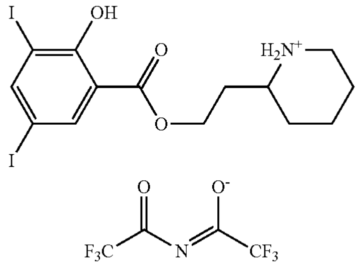
Q-16
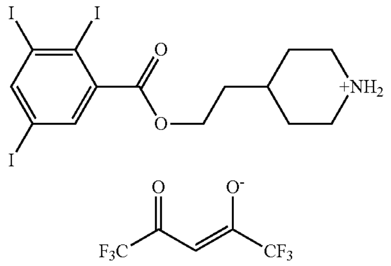
Q-17
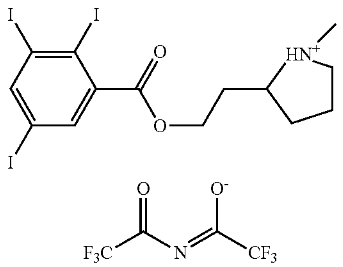
Q-18
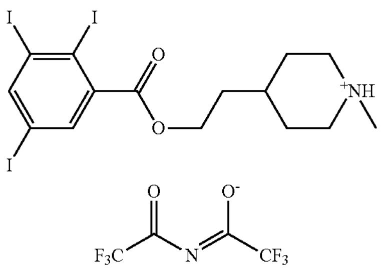

-continued
Q-19
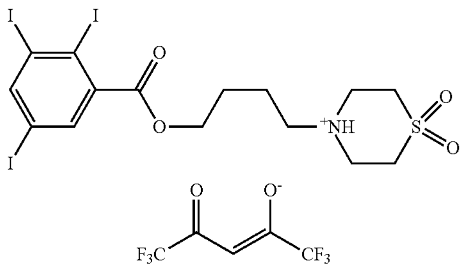
Q-20
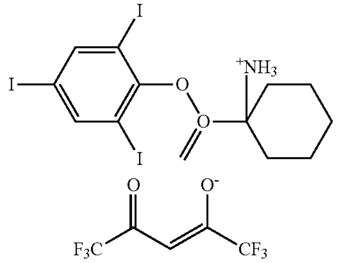
Q-21
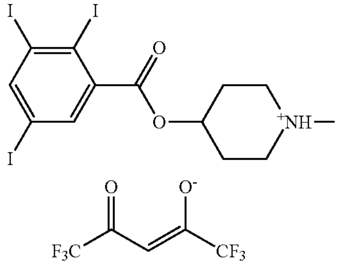
Q-22
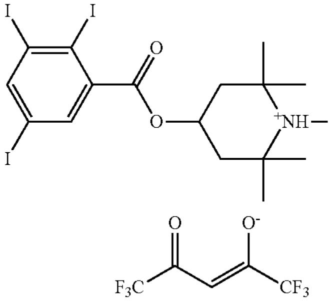
Q-23
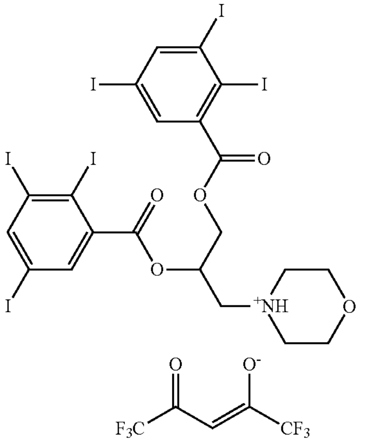
-continued
Q-24
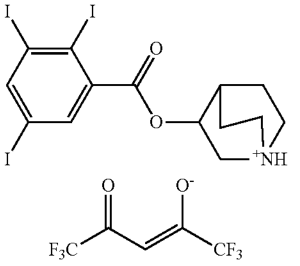
Q-25
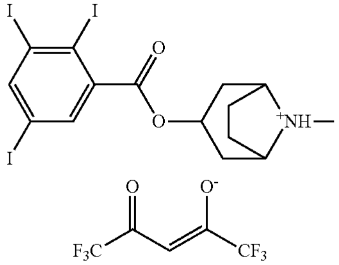
Q-26
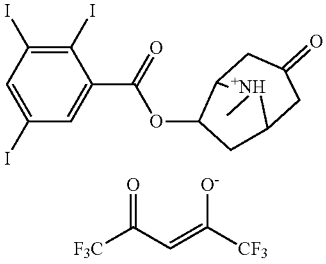
Q-27
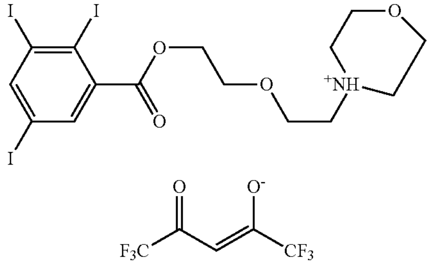
Q-28
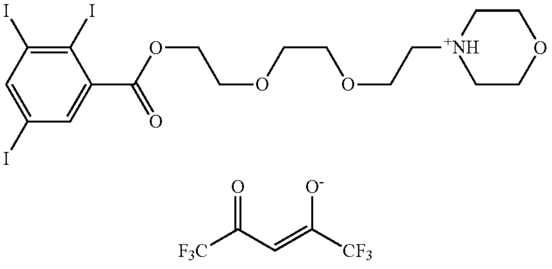

-continued
Q-29
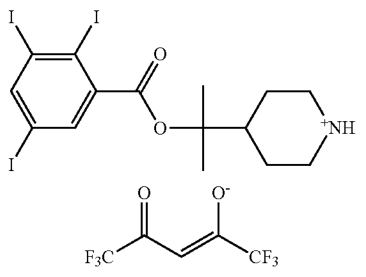
Q-30
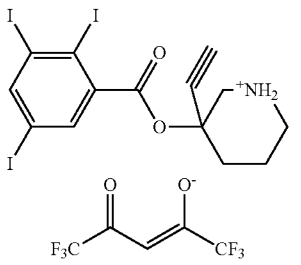
Q-31
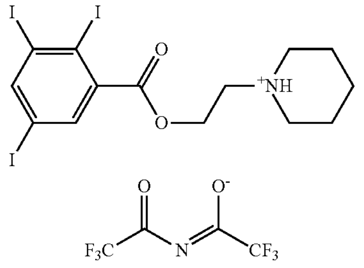
Q-32
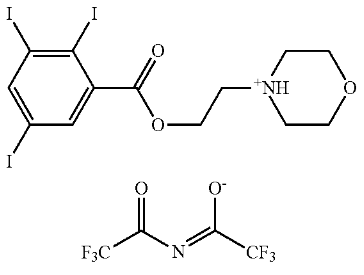
Q-33
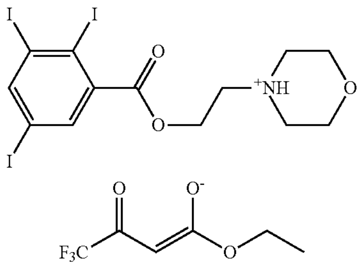
-continued
Q-34
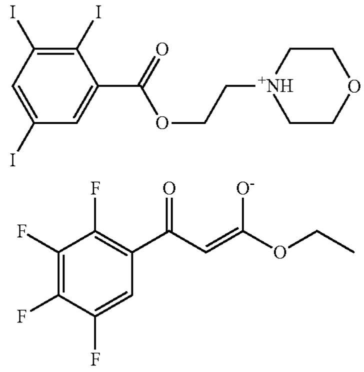
Q-35
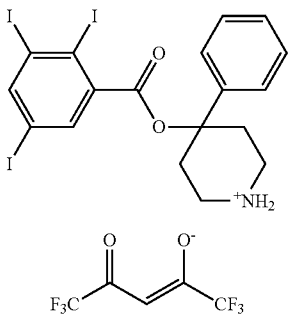
Q-36
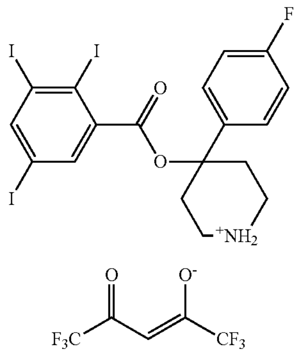
Q-37
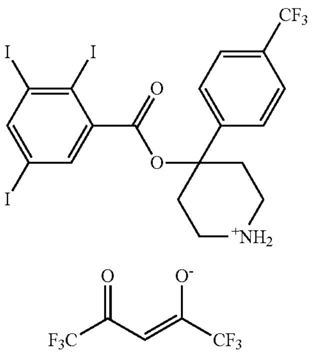

-continued
Q-38
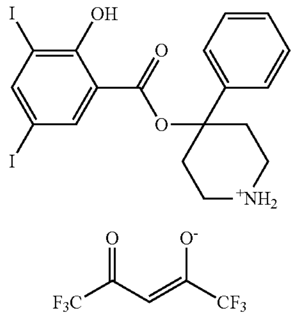
Q-39
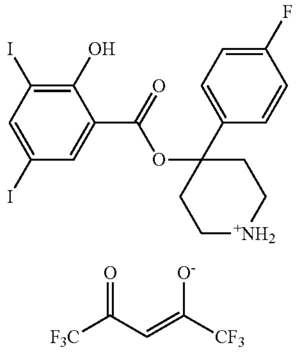
Q-40
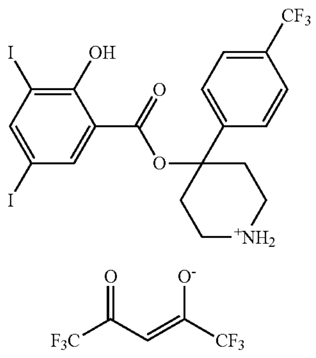
Q-41
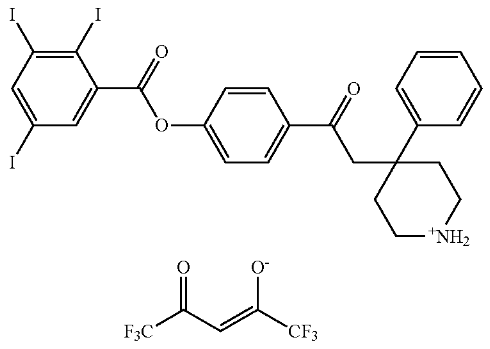
-continued
Q-42
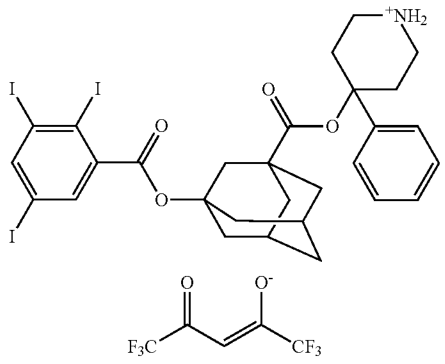
Q-43
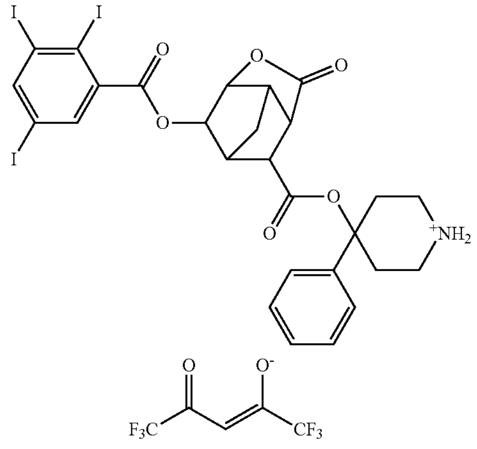
Q-44
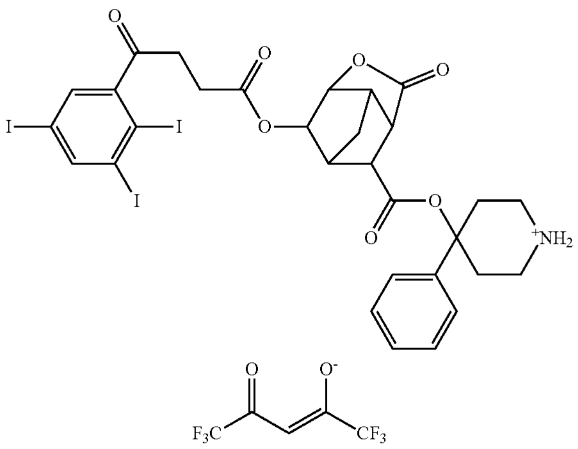

-continued

Q-45

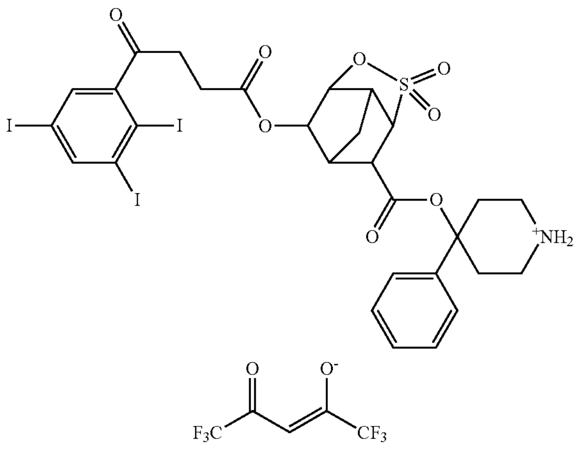

Q-46

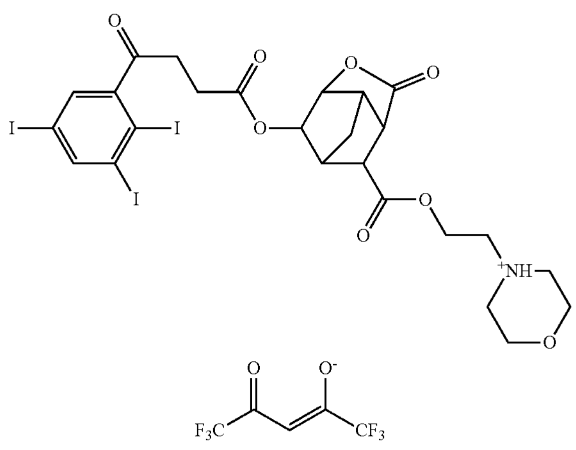

Amine-1

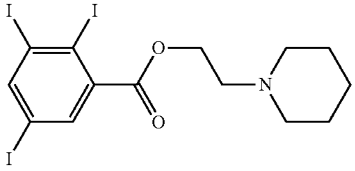

F-AcAc-1

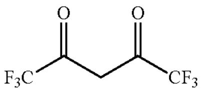

Synthesis Example

Synthesis of Base Polymers P-1 to P-4

Each of base polymers P-1 to P-4 was prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymer was analyzed for composition by $^1$H-NMR spectroscopy, and for Mw and Mw/Mn by GPC versus polystyrene standards using THF solvent.

P-1

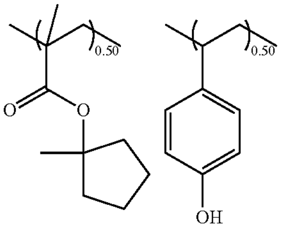

Mw = 4,600
Mw/Mn = 1.44

P-2

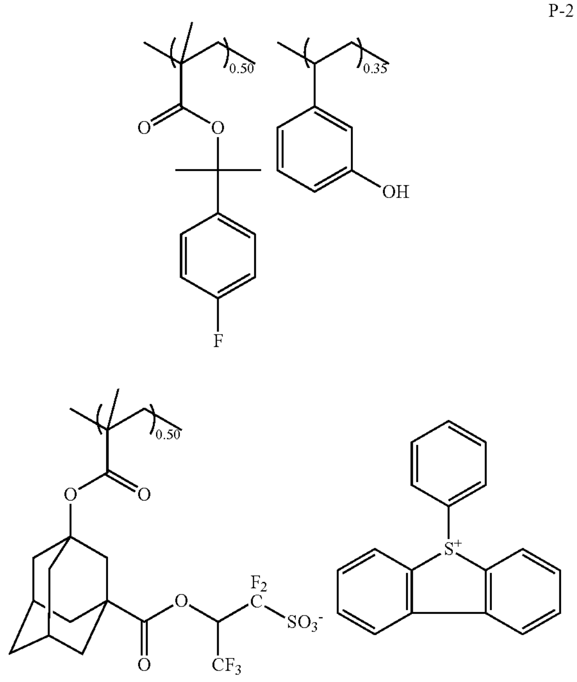

Mw = 8,300
Mw/Mn = 1.81

P-3

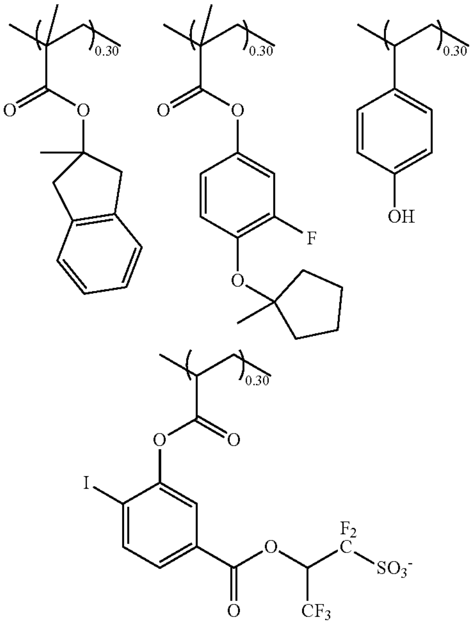

-continued

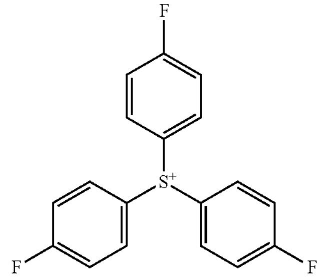

Mw = 7,9000
Mw/Mn = 1.76

P-4

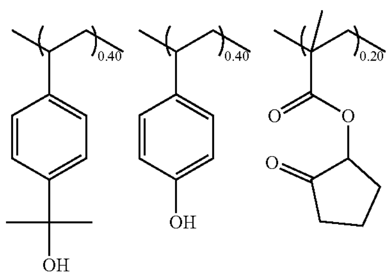

Mw = 5,900
Mw/Mn = 1.59

Examples 1 to 53 and Comparative Examples 1 to 6

(1) Preparation of Resist Compositions

Resist compositions were prepared by dissolving various components in a solvent in accordance with the recipe shown in Tables 1 to 4, and filtering through a filter having a pore size of 0.2 μm. The resist compositions of Examples 1 to 21, 23 to 53 and Comparative Examples 1 to 5 are of positive tone, and the resist compositions of Example 22 and Comparative Example 6 are of negative tone.

The components in Tables 1 to 4 are as identified below.

Organic Solvent:

PGMEA (propylene glycol monomethyl ether acetate)

DAA (diacetone alcohol)

EL (DL form ethyl lactate)

Acid generators: PAG-1 to PAG-4 of the following structural formulae

PAG-1

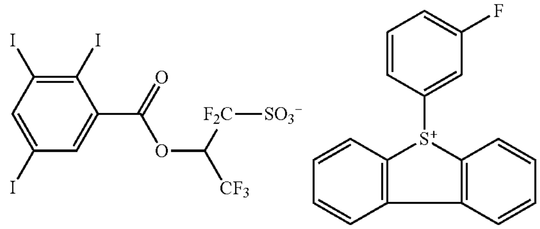

-continued

PAG-2

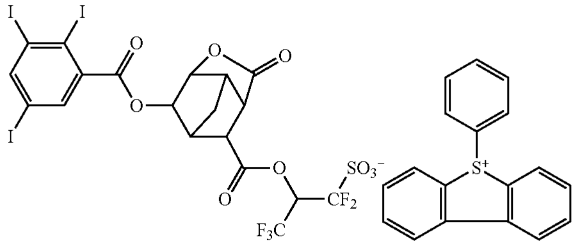

PAG-3

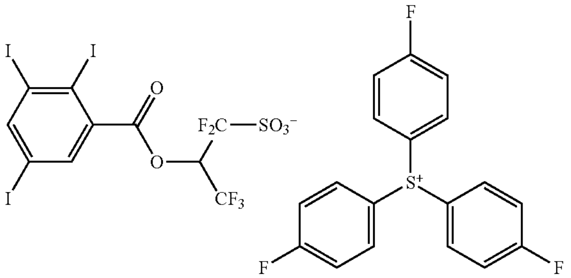

PAG-4

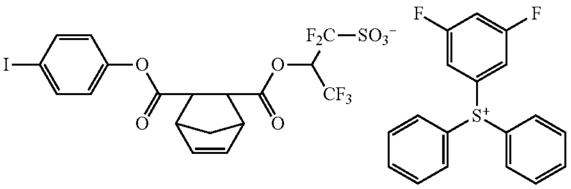

Comparative Quenchers: cQ-1 to cQ-6 of the following structural formulae cQ-1

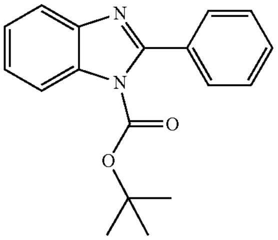

cQ-2

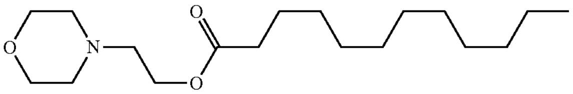

cQ-3

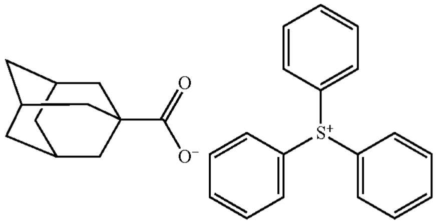

-continued cQ-4

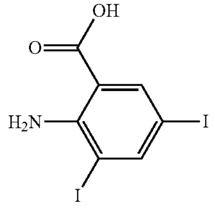

cQ-5

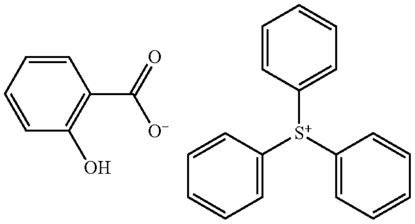

cQ-6

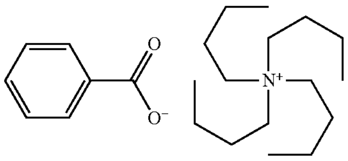

Blend Quenchers: bQ-1 and bQ-2 of the following structural formulae bQ-1

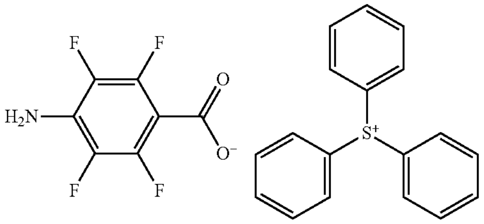

-continued bQ-2

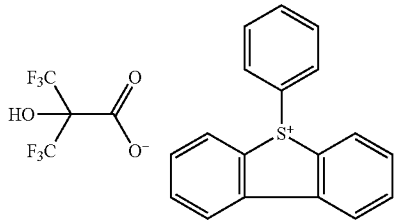

(2) Evaluation by EUV Lithography

Each of the resist compositions in Tables 1 to 4 was spin coated on a silicon substrate having a 20-nm coating of silicon-containing spin-on hard mask SHB-A940 (Shin-Etsu Chemical Co., Ltd., Si content 43 wt %) and prebaked on a hotplate at 100° C. for 60 seconds to form a resist film of 50 nm thick Using an EUV scanner NXE3400 (ASML, NA 0.33, σ 0.9/0.6, quadrupole illumination), the resist film was exposed to EUV through a mask bearing a hole pattern at a pitch 44 nm (on-wafer size) and +20% bias. The resist film was baked (PEB) on a hotplate at the temperature shown in Tables 1 to 4 for 60 seconds and developed in a 2.38 wt % TMAH aqueous solution for 30 seconds to form a hole pattern having a size of 22 nm in Examples 1 to 21, 23 to 53 and Comparative Examples 1 to 5 and a dot pattern having a size of 22 nm in Example 22 and Comparative Example 6.

The resist pattern was observed under CD-SEM (CG6300, Hitachi High-Technologies Corp.). The exposure dose that provides a hole or dot pattern having a size of 22 nm is reported as sensitivity. The size of 50 holes or dots was measured, from which a 3-fold value (3σ) of standard deviation (σ) was computed and reported as size variation or CDU.

The resist composition is shown in Tables 1 to 4 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | P-1 (100) | PAG-1 (30) | Q-1 (8.69) | PGMEA (3,000) DAA (500) | 85 | 36 | 3.5 |
| | 2 | P-1 (100) | PAG-2 (30) | Q-2 (8.21) | PGMEA (3,000) DAA (500) | 85 | 35 | 3.4 |
| | 3 | P-1 (100) | PAG-2 (30) | Q-3 (12.78) | PGMEA (3,000) DAA (500) | 85 | 34 | 3.5 |
| | 4 | P-1 (100) | PAG-2 (30) | Q-4 (8.43) | PGMEA (3,000) DAA (500) | 85 | 32 | 3.4 |
| | 5 | P-1 (100) | PAG-2 (30) | Q-5 (7.36) | PGMEA (3,000) DAA (500) | 85 | 35 | 3.5 |
| | 6 | P-1 (100) | PAG-2 (30) | Q-6 (6.20) | PGMEA (3,000) DAA (500) | 85 | 34 | 3.5 |
| | 7 | P-1 (100) | PAG-2 (30) | Q-7 (8.39) | PGMEA (3,000) DAA (500) | 85 | 36 | 3.4 |
| | 8 | P-1 (100) | PAG-2 (30) | Q-8 (8.47) | PGMEA (3,000) DAA (500) | 85 | 36 | 3.5 |
| | 9 | P-1 (100) | PAG-2 (30) | Q-9 (9.28) | PGMEA (3,000) DAA (500) | 85 | 34 | 3.6 |
| | 10 | P-1 (100) | PAG-2 (30) | Q-10 (8.42) | PGMEA (3,000) DAA (500) | 85 | 36 | 3.5 |
| | 11 | P-1 (100) | PAG-2 (30) | Q-11 (10.31) | PGMEA (3,000) DAA (500) | 85 | 34 | 3.6 |
| | 12 | P-1 (100) | PAG-2 (30) | Q-12 (8.72) | PGMEA (3,000) DAA (500) | 85 | 36 | 3.4 |

TABLE 1-continued

| | Polymer (pbw) | Acid generator (pbw) | Quencher (pbw) | Organic solvent (pbw) | PEB temp. (° C.) | Sensitivity (mJ/cm²) | CDU (nm) |
|---|---|---|---|---|---|---|---|
| 13 | P-1 (100) | PAG-2 (30) | Q-13 (8.61) | PGMEA (3,000) DAA (500) | 85 | 34 | 3.5 |
| 14 | P-1 (100) | PAG-2 (30) | Q-14 (8.57) | PGMEA (3,000) DAA (500) | 85 | 35 | 3.3 |
| 15 | P-1 (100) | PAG-2 (30) | Q-15 (7.10) | PGMEA (3,000) DAA (500) | 85 | 34 | 3.3 |
| 16 | P-1 (100) | PAG-2 (30) | Q-16 (8.19) | PGMEA (3,000) DAA (500) | 85 | 34 | 3.6 |
| 17 | P-1 (100) | PAG-2 (30) | Q-17 (8.19) | PGMEA (3,000) DAA (500) | 85 | 34 | 3.4 |
| 18 | P-2 (100) | — | Q-2 (8-21) | PGMEA (3,000) DAA (500) | 90 | 34 | 3.1 |
| 19 | P-3 (100) | — | Q-2 (8.21) | PGMEA (3,000) DAA (500) | 90 | 30 | 3.0 |
| 20 | P-3 (100) | PAG-3 (4) | Q-2 (8.21) | PGMEA (3,000) DAA (500) | 90 | 27 | 3.2 |
| 21 | P-3 (100) | PAG-4 (4) | Q-2 (8-21) | PGMEA (3,000) DAA (500) | 90 | 28 | 3.1 |
| 22 | P-4 (100) | PAG-2 (20) | Q-2 (8.21) | PGMEA (3,000) DAA (500) | 110 | 39 | 4.6 |

TABLE 2

| | | Polymer (pbw) | Acid generator (pbw) | Quencher (pbw) | Organic solvent (pbw) | PEB temp. (° C.) | Sensitivity (mJ/cm²) | CDU (nm) |
|---|---|---|---|---|---|---|---|---|
| Example | 23 | P-1 (100) | PAG-2 (30) | Q-18 (8.19) | PGMEA (3,000) DAA (500) | 85 | 33 | 3.4 |
| | 24 | P-1 (100) | PAG-2 (30) | Q-19 (8.97) | PGMEA (3,000) DAA (500) | 85 | 34 | 3.5 |
| | 25 | P-1 (100) | PAG-2 (30) | Q-20 (8.05) | PGMEA (3,000) DAA (500) | 85 | 35 | 3.4 |
| | 26 | P-1 (100) | PAG-2 (30) | Q-21 (8.05) | PGMEA (3,000) DAA (500) | 85 | 35 | 3.6 |
| | 27 | P-1 (100) | PAG-2 (30) | Q-22 (8.61) | PGMEA (3,000) DAA (500) | 85 | 35 | 3.2 |
| | 28 | P-1 (100) | PAG-2 (30) | Q-23 (13.32) | PGMEA (3,000) DAA (500) | 85 | 35 | 3.3 |
| | 29 | P-1 (100) | PAG-2 (30) | Q-24 (8.17) | PGMEA (3,000) DAA (500) | 85 | 36 | 3.4 |
| | 30 | P-1 (100) | PAG-2 (30) | Q-25 (8.31) | PGMEA (3,000) DAA (500) | 85 | 34 | 3.4 |
| | 31 | P-1 (100) | PAG-2 (30) | Q-26 (8.45) | PGMEA (3,000) DAA (500) | 85 | 36 | 3.5 |
| | 32 | P-1 (100) | PAG-2 (30) | Q-27 (8-65) | PGMEA (3,000) DAA (500) | 85 | 36 | 3.6 |
| | 33 | P-1 (100) | PAG-2 (30) | Q-28 (9.09) | PGMEA (3,000) DAA (500) | 85 | 36 | 3.5 |
| | 34 | P-1 (100) | PAG-2 (30) | Q-29 (8.33) | PGMEA (3,000) DAA (500) | 85 | 36 | 3.5 |
| | 35 | P-1 (100) | PAG-2 (30) | Q-30 (8.15) | PGMEA (3,000) DAA (500) | 85 | 35 | 3.3 |
| | 36 | P-1 (100) | PAG-2 (30) | Q-31 (8.20) | PGMEA (3,000) DAA (500) | 85 | 34 | 3.4 |
| | 37 | P-1 (100) | PAG-2 (30) | Amine-1 (6.11) F-AcAc-1 (2.08) | PGMEA (3,000) DAA (500) | 85 | 34 | 3.4 |
| | 38 | P-1 (100) | PAG-2 (30) | Q-2 (4.11) bQ-1 (2.35) | PGMEA (3,000) DAA (500) | 85 | 31 | 2.9 |
| | 39 | P-1 (100) | PAG-2 (30) | Q-32 (4.11) bQ-1 (2.35) | PGMEA (3,000) DAA (500) | 85 | 32 | 2.9 |
| | 40 | P-1 (100) | PAG-2 (30) | Q-33 (3.99) bQ-1 (2.35) | PGMEA (3,000) DAA (500) | 85 | 33 | 3.0 |
| | 41 | P-1 (100) | PAG-2 (30) | Q-34 (4.38) bQ-1 (2.35) | PGMEA (3,000) DAA (500) | 85 | 33 | 3.0 |
| | 42 | P-1 (100) | PAG-2 (30) | Q-35 (4.33) bQ-1 (2.35) | PGMEA (3,000) DAA (500) | 85 | 32 | 3.1 |
| | 43 | P-1 (100) | PAG-2 (30) | Q-36 (4.42) bQ-1 (2.35) | PGMEA (3,000) DAA (500) | 85 | 34 | 3.2 |
| | 44 | P-1 (100) | PAG-2 (30) | Q-37 (4.67) bQ-1 (2.35) | PGMEA (3,000) DAA (500) | 85 | 32 | 3.3 |
| | 45 | P-1 (100) | PAG-2 (30) | Q-38 (3.78) bQ-1 (2.35) | PGMEA (3,000) DAA (500) | 85 | 33 | 3.1 |
| | 46 | P-1 (100) | PAG-2 (30) | Q-39 (3.87) bQ-1 (2.35) | PGMEA (3,000) DAA (500) | 85 | 34 | 3.3 |

TABLE 2-continued

| | Polymer (pbw) | Acid generator (pbw) | Quencher (pbw) | Organic solvent (pbw) | PEB temp. (° C.) | Sensitivity ($mJ/cm^2$) | CDU (nm) |
|---|---|---|---|---|---|---|---|
| 47 | P-1 (100) | PAG-2 (30) | Q-40 (4.12) bQ-1 (2.35) | EL (3,500) | 85 | 32 | 3.4 |
| 48 | P-1 (100) | PAG-2 (30) | Q-41 (4.93) bQ-2 (2.35) | EL (3,000) DAA (500) | 85 | 34 | 3.3 |
| 49 | P-1 (100) | PAG-2 (30) | Q-42 (5.22) bQ-2 (2.35) | EL (3,000) DAA (500) | 85 | 33 | 3.2 |
| 50 | P-1 (100) | PAG-2 (30) | Q-43 (5.23) bQ-2 (2.35) | PGMEA (2,000) EL (1,500) | 85 | 33 | 3.2 |

TABLE 3

| | | Polymer (pbw) | Acid generator (pbw) | Quencher (pbw) | Organic solvent (pbw) | PEB temp. (° C.) | Sensitivity ($mJ/cm^2$) | CDU (nm) |
|---|---|---|---|---|---|---|---|---|
| Example | 51 | P-1 (100) | PAG-2 (30) | Q-44 (5.52) bQ-2 (2.35) | PGMEA (2,000) EL (1,500) | 85 | 33 | 3.2 |
| | 52 | P-1 (100) | PAG-2 (30) | Q-45 (5.70) bQ-2 (2.35) | PGMEA (2,000) EL (1,500) | 85 | 35 | 3.2 |
| | 53 | P-1 (100) | PAG-2 (30) | Q-46 (5.78) bQ-2 (2.35) | PGMEA (2,000) EL (1,500) | 85 | 36 | 3.3 |

TABLE 4

| | | Polymer (pbw) | Acid generator (pbw) | Quencher (pbw) | Organic solvent (pbw) | PEB temp. (° C.) | Sensitivity ($mJ/cm^2$) | CDU (nm) |
|---|---|---|---|---|---|---|---|---|
| Comparative Example | 1 | P-1 (100) | PAG-2 (30) | cQ-1 (2.64) | PGMEA (3,000) DAA (500) | 85 | 37 | 4.5 |
| | 2 | P-1 (100) | PAG-2 (30) | cQ-2 (3.13) | PGMEA (3,000) DAA (500) | 85 | 38 | 4.2 |
| | 3 | P-1 (100) | PAG-2 (30) | cQ-3 (4.42) | PGMEA (3,000) DAA (500) | 85 | 39 | 4.3 |
| | 4 | P-1 (100) | PAG-2 (30) | cQ-4 (3.88) | PGMEA (3,000) DAA (500) | 85 | 37 | 4.0 |
| | 5 | P-1 (100) | PAG-2 (30) | cQ-5 (4.00) | PGMEA (3,000) DAA (500) | 85 | 36 | 4.0 |
| | 6 | P-4 (100) | PAG-1 (20) | cQ-6 (3.63) | PGMEA (3,000) DAA (500) | 110 | 44 | 5.1 |

It is evident from Tables 1 to 4 that the inventive resist compositions comprising salt compound A exhibit a high sensitivity and improved CDU.

Japanese Patent Application No. 2021-171611 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, said quencher comprising a salt compound obtained from a nitrogen-containing compound having an iodine-substituted aromatic ring bonded to the nitrogen atom via a $C_1$-$C_{20}$ hydrocarbon group which may contain at least one bond selected from an ester bond and an ether bond and at least one compound selected from a fluorinated 1,3-diketone compound, fluorinated β-keto ester compound, and fluorinated imide compound.

2. The resist composition of claim 1 wherein said salt compound has the formula (A):

(A)

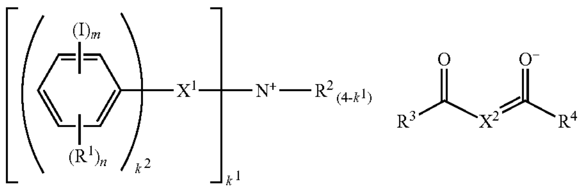

wherein m is an integer of 1 to 5, n is an integer of 0 to 4, m+n is from 1 to 5, $k^1$ is an integer of 1 to 3, $k^2$ is 1 or 2, $X^1$ is a $C_1$-$C_{20}$ ($k^2$+1)-valent hydrocarbon group which may contain at least one bond selected from an ester bond and an ether bond, $R^1$ is hydroxy, a $C_1$-$C_6$ saturated hydrocarbyl group, $C_1$-$C_6$ saturated hydrocarbyloxy group, $C_2$-$C_6$ saturated hydrocarbylcarbonyloxy group, fluorine, chlorine, bromine, amino, —N($R^{1A}$)—C(=O)—$R^{1B}$ or —N($R^{1A}$)—C(═O)—O—$R^{1B}$, $R^{1A}$ is hydrogen or a $C_1$-$C_6$ saturated hydrocarbyl group, $R^{1B}$ is a $C_1$-$C_6$ saturated hydrocarbyl group, $C_2$-$C_8$ unsaturated aliphatic hydrocarbyl group, $C_6$-$C_{12}$ aryl group or $C_7$-$C_{13}$ aralkyl group, $R^2$ is hydrogen, nitro, or a $C_1$-$C_{20}$ hydrocarbyl group which may contain at least one moiety selected from hydroxy, carboxy, thiol, ether bond, ester bond, nitro, cyano, halogen and amino, in case of $k^1$=1 or 2, two groups R may bond together to form a ring with the nitrogen atom to which they are attached, the ring optionally containing a double bond, oxygen, sulfur or nitrogen, or $R^2$ and $X^1$ may bond together to form a ring with the nitrogen atom to which they are attached, the ring optionally containing a double bond, oxygen, sulfur or nitrogen, $R^3$ and $R^4$ are each independently a $C_1$-$C_{16}$ hydrocarbyl group, $C_1$-$C_{16}$ fluorinated hydrocarbyl group, $C_1$-$C_{16}$ hydrocarbyloxy group or $C_1$-$C_{16}$ fluorinated hydrocarbyloxy group, at least one of $R^3$ and $R^4$ being a $C_1$-$C_{16}$ fluorinated hydrocarbyl group or $C_1$-$C_{16}$ fluorinated hydrocarbyloxy group, and in the foregoing groups, some or all of the hydrogen atoms may be substituted by at least one moiety selected from cyano, nitro, hydroxy, and halogen other than fluorine, and some constituent —$CH_2$— may be replaced by at least one moiety selected from an ether bond, ester bond and thioether bond, and $X^2$ is —C(H)═ or —N═.

3. The resist composition of claim 1, further comprising an acid generator capable of generating a sulfonic acid, imide acid or methide acid.

4. The resist composition of claim 1, further comprising an organic solvent.

5. The resist composition of claim 1 wherein the base polymer comprises repeat units having the formula (a1) or repeat units having the formula (a2):

(a1)

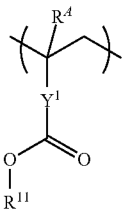

(a2)

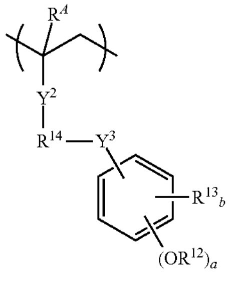

wherein $R^A$ each independently hydrogen or methyl, $Y^1$ is a single bond phenylene, naphthylene, or a $C_1$-$C_{12}$ linking group containing an ester bond and/or lactone ring, $Y^2$ is a single bond or ester bond, $Y^3$ is a single bond, ether bond or ester bond, $R^{11}$ and $R^{12}$ are each independently an acid labile group, $R^{13}$ is fluorine, trifluoromethyl, cyano, a $C_1$-$C_6$ saturated hydrocarbyl group, $C_1$-$C_6$ saturated hydrocarbyloxy group, $C_2$-$C_7$ saturated hydrocarbylcarbonyl group, $C_2$-$C_7$ saturated hydrocarbylcarbonyloxy group, or $C_2$-$C_7$ saturated hydrocarbyloxycarbonyl group, $R^{14}$ is a single bond or a $C_1$-$C_6$ alkanediyl group in which some constituent —$CH_2$— may be replaced by an ether bond or ester bond, a is 1 or 2, b is an integer of 0 to 4, and a+b is from 1 to 5.

6. The resist composition of claim 5 which is a chemically amplified positive resist composition.

7. The resist composition of claim 1 wherein the base polymer is free of an acid labile group.

8. The resist composition of claim 7 which is a chemically amplified negative resist composition.

9. The resist composition of claim 1, further comprising a surfactant.

10. The resist composition of claim 1 wherein the base polymer comprises repeat units of at least one type selected from repeat units having the formulae (f1) to (f3):

(f1)

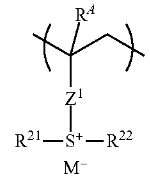

(f2)

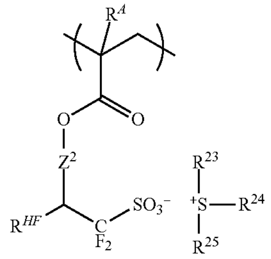

(f3)

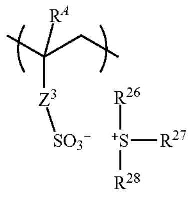

wherein $R^A$ is each independently hydrogen or methyl, $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(═O)—O—$Z^{11}$— or —C(═O)—NH—$Z^{11}$—$Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxy moiety, $Z^2$ is a single bond, —$Z^{21}$—C(═O)—O—, —$Z^{21}$—O— or —$Z^{21}$—O—C(═O)—, $Z^{21}$ is a $C_1$-$C_{12}$ saturated hydrocarbylene group which may contain a carbonyl moiety, ester bond or ether bond, $Z^3$ is a single bond, methylene, ethylene, phenylene, fluorinated phenylene, trifluoromethyl-substituted phenylene group, —O—$Z^{31}$—, —C(═O)—O—$Z^{31}$—, or —C(═O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety, $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, $R^{HF}$ is hydrogen or trifluoromethyl, and $M^-$ is a non-nucleophilic counter ion.

11. A pattern forming process comprising the steps of applying the resist composition of claim 1 to form a resist film on a substrate, exposing the resist film to high-energy radiation, and developing the exposed resist film in a developer.

12. The process of claim 11 wherein the high-energy radiation is ArF excimer laser of wavelength 193 nm, KrF excimer laser of wavelength 248 nm, EB or EUV of wavelength 3 to 15 nm.

* * * * *